US012715923B2

(12) United States Patent
Bujotzek et al.

(10) Patent No.: US 12,715,923 B2
(45) Date of Patent: Aug. 25, 2026

(54) ANTIBODIES BINDING TO GPRC5D

(71) Applicant: Hoffmann-La Roche Inc., Little Falls, NJ (US)

(72) Inventors: Alexander Bujotzek, Munich (DE); Tony Christopeit, Schliersee (DE); Tanja Fauti, Zurich (CH); Georg Fertig, Penzberg (DE); Hélène Cécile Haegel, Illkirch-Graffenstaden (FR); Christian Klein, Bonstetten (CH); Thomas Kraft, Munich (DE); Stefan Lorenz, Penzberg (DE); Maud Léa Mayoux, Zürich (CH); Anneliese Schneider, Feldafing (DE)

(73) Assignee: Hoffmann-La Roche Inc., Branchburg, NJ (US)

( * ) Notice: Subject to any disclaimer, the term of this patent is extended or adjusted under 35 U.S.C. 154(b) by 1215 days.

(21) Appl. No.: 17/586,977

(22) Filed: Jan. 28, 2022

(65) Prior Publication Data

US 2022/0259318 A1 Aug. 18, 2022

Related U.S. Application Data

(63) Continuation of application No. PCT/EP2020/071182, filed on Jul. 28, 2020.

(30) Foreign Application Priority Data

Jul. 31, 2019 (EP) .................................... 19189255

(51) Int. Cl.

| | |
|---|---|
| ***C07K 16/28*** | (2006.01) |
| ***A61K 39/00*** | (2006.01) |
| ***A61P 35/00*** | (2006.01) |
| ***A61P 35/02*** | (2006.01) |
| ***A61P 37/00*** | (2006.01) |
| ***C07K 16/46*** | (2006.01) |
| *C07K 16/42* | (2006.01) |

(52) U.S. Cl.

CPC .......... *C07K 16/2866* (2013.01); *A61P 35/00* (2018.01); *A61P 35/02* (2018.01); *C07K 16/2809* (2013.01); *C07K 16/468* (2013.01); *A61K 2039/505* (2013.01); *C07K 2317/24* (2013.01); *C07K 2317/31* (2013.01); *C07K 2317/33* (2013.01); *C07K 2317/524* (2013.01); *C07K 2317/526* (2013.01); *C07K 2317/55* (2013.01); *C07K 2317/64* (2013.01); *C07K 2317/66* (2013.01); *C07K 2317/71* (2013.01); *C07K 2317/75* (2013.01); *C07K 2317/77* (2013.01); *C07K 2317/92* (2013.01); *C07K 2319/33* (2013.01)

(58) Field of Classification Search

None

See application file for complete search history.

(56) References Cited

U.S. PATENT DOCUMENTS

| | | | |
|---|---|---|---|
| 4,676,980 | A | 6/1987 | Segal et al. |
| 5,571,894 | A | 11/1996 | Wels et al. |
| 5,587,458 | A | 12/1996 | King et al. |
| 5,591,828 | A | 1/1997 | Bosslet et al. |
| 5,731,168 | A | 3/1998 | Carter et al. |
| 5,869,046 | A | 2/1999 | Presta et al. |
| 6,248,516 | B1 | 6/2001 | Winter et al. |
| 6,737,056 | B1 | 5/2004 | Presta |
| 7,332,581 | B2 | 2/2008 | Presta |
| 7,695,936 | B2 | 4/2010 | Carter et al. |
| 11,591,397 | B2 | 2/2023 | Freimoser-Grundschober et al. |
| 11,608,376 | B2 | 3/2023 | Georges et al. |
| 11,672,858 | B2 | 6/2023 | Freimoser-Grundschober et al. |
| 11,780,920 | B2 | 10/2023 | Freimoser-Grundschober et al. |
| 12,215,155 | B2 | 2/2025 | Freimoser-Grundschober et al. |
| 12,466,889 | B2 | 11/2025 | Bujotzek et al. |
| 12,473,373 | B2 | 11/2025 | Freimoser-Grundschober et al. |
| 2008/0069820 | A1 | 3/2008 | Fuh et al. |
| 2016/0075785 | A1 | 3/2016 | Ast et al. |
| 2017/0306044 | A1 | 10/2017 | Vu et al. |
| 2018/0037651 | A1 * | 2/2018 | Attar .................. A61K 39/0011 |
| 2019/0367612 | A1 | 12/2019 | Chaen et al. |
| 2020/0199234 | A1 | 6/2020 | Georges et al. |
| 2020/0270347 | A1 | 8/2020 | Freimoser-Grundschober et al. |
| 2021/0403562 | A1 | 12/2021 | Freimoser-Grundschober et al. |
| 2022/0010014 | A1 | 1/2022 | Freimoser-Grundschober et al. |

(Continued)

FOREIGN PATENT DOCUMENTS

| | | | |
|---|---|---|---|
| CA | 3052938 | A1 | 8/2018 |
| CL | 2020001854 | A1 | 10/2020 |

(Continued)

OTHER PUBLICATIONS

Derksen, "Illegitimate WNT signaling promotes proliferation of multiple myeloma cells," PNAS 101(16):6122-7 (2004).

(Continued)

*Primary Examiner* — Juliet C Switzer

*Assistant Examiner* — Katherine Ann Holtzman

(74) *Attorney, Agent, or Firm* — Roberto K. Rodriguez

(57) ABSTRACT

The present invention generally relates to antibodies that bind to GPRC5D, including bispecific antigen binding molecules e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

39 Claims, 30 Drawing Sheets

Specification includes a Sequence Listing.

(56) References Cited

U.S. PATENT DOCUMENTS

2022/0213199 A1 7/2022 Bujotzek et al.
2022/0259318 A1 8/2022 Bujotzek et al.
2023/0159642 A1 5/2023 Bujotzek et al.
2023/0277662 A1 9/2023 Freimoser-Grundschober et al.
2023/0416365 A1 12/2023 Georges et al.
2023/0416411 A1 12/2023 Bruenker et al.
2024/0042022 A1 2/2024 Freimoser-Grundschober et al.
2024/0043535 A1 2/2024 Amann et al.
2024/0132590 A1 4/2024 Freimoser-Grundschober et al.
2025/0277035 A1 9/2025 Freimoser-Grundschober et al.

FOREIGN PATENT DOCUMENTS

CN 104936986 A 9/2015
CN 105143270 A 12/2015
EP 0404097 B1 9/1996
EP 1870459 B1 6/2016
EP 2992012 B1 * 7/2019 ............. A61P 27/02
EP 3581651 A1 12/2019
EP 3749692 A1 12/2020
JP 2017-536341 A 12/2017
JP 2018-504890 A 2/2018
TW 201936641 A 9/2019
TW I829667 B 1/2024
WO WO-93/01161 A1 1/1993
WO WO-93/16185 A2 8/1993
WO WO-96/27011 A1 9/1996
WO WO-98/50431 A2 11/1998
WO WO-98/50431 A3 1/1999
WO WO-01/77342 A1 10/2001
WO WO-2004/106381 A1 12/2004
WO WO-2005/061547 A2 7/2005
WO WO-2007/042261 A2 4/2007
WO WO-2007/110205 A2 10/2007
WO WO-2007/147901 A1 12/2007
WO WO-2008/024715 A2 2/2008
WO WO-2008/119567 A2 10/2008
WO WO-2009/080251 A1 7/2009
WO WO-2009/080252 A1 7/2009
WO WO-2009/080253 A1 7/2009
WO WO-2009/089004 A1 7/2009
WO WO-2010/112193 A1 10/2010
WO WO-2010/115589 A1 10/2010
WO WO-2010/129304 A2 11/2010
WO WO-2010/136172 A1 12/2010
WO WO-2010/145792 A1 12/2010
WO WO-2010/129304 A3 2/2011
WO WO-2011/034605 A2 3/2011
WO WO-2011/090754 A1 7/2011
WO WO-2011/090762 A1 7/2011
WO WO-2011/143545 A1 11/2011
WO WO-2012/058768 A1 5/2012
WO WO-2012/058768 A8 6/2012
WO WO-2012/130831 A1 10/2012
WO WO-2013/026831 A1 2/2013
WO WO-2013/026833 A1 2/2013
WO WO-2013/026839 A1 2/2013
WO WO-2013/096291 A2 6/2013
WO WO-2013/157953 A1 10/2013
WO WO-2013/157954 A1 10/2013
WO WO-2014/131694 A1 9/2014
WO WO-2014/131712 A1 9/2014
WO WO-2015/095539 A1 6/2015
WO WO-2015/150447 A1 10/2015
WO WO-2016/005593 A1 1/2016
WO WO-2016/016299 A1 2/2016
WO WO-2016/020309 A1 2/2016
WO WO-2016/055593 A1 4/2016
WO WO-2016/062734 A1 4/2016
WO WO-2016/090329 A2 6/2016
WO WO-2016/166629 A1 10/2016
WO WO-2016/172485 A2 10/2016
WO WO-2018/017786 A2 1/2018
WO WO-2018/060301 A1 4/2018
WO WO-2018147245 A1 * 8/2018 ............. A61P 35/00
WO WO-2019/086497 A2 5/2019
WO WO-2019/122046 A1 6/2019
WO WO-2019/122060 A1 6/2019
WO WO-2019154890 A1 * 8/2019 ............. C07K 16/28
WO WO-2019/220368 A1 11/2019
WO WO-2020/092854 A2 5/2020
WO WO-2020/127618 A1 6/2020
WO WO-2020127619 A1 * 6/2020 ......... C07K 16/2809
WO WO-2020148677 A1 7/2020
WO WO-2021018859 A2 2/2021
WO WO-2021/255138 A1 12/2021
WO WO-2021/255143 A1 12/2021
WO WO-2021/255146 A1 12/2021
WO WO-2022079138 A1 * 4/2022 ............. C07K 16/28
WO WO2014110601 A1 7/2024

OTHER PUBLICATIONS

Dirks, “Brain Tumor Stem Cells: Bringing Order to the Chaos of Brain Cancer,” Journal of Clinical Oncology. 26(17):2916-2924 (2008).

López-Lázaro, “The migration ability of stem cells can explain the existence of cancer of unknown primary site. Rethinking metastasis,” Oncoscience. 2(5):467-75 (2015).

Tran, “Survival comparison between glioblastoma multiforme and other incurable cancers,” Journal of Clinical Neuroscience. 17(4):417-21 (2010).

U.S. Appl. No. 19/000,912, Hoffmann-La Roche Inc.

“Human GPRC5D APC-conjugated Antibody,” R&D Systems, retrieved from<https://resources.rndsystems.com/pdfs/datasheets/fab6300a.pdf>, revised Feb. 6, 2018 (2015) (1 page).

Atamaniuk et al., “Overexpression of G protein-coupled receptor 5D in the bone marrow is associated with poor prognosis in patients with multiple myeloma,” Eur J Clin Invest. 42(9):953-60 (2012).

Atwell et al., “Stable heterodimers from remodeling the domain interface of a homodimer using a phage display library,” J Mol Biol. 270(1):26-35 (1997).

Bacac et al., “CEA TCB, a novel T-cell bispecific antibody with potent in vitro and in vivo antitumor activity against solid tumors,” AACR 106th Annual Meeting, Apr. 18-22, Philadelphia, PA. 75(15) Abstract 2481 (2015) (4 pages).

Brennan et al., “Preparation of bispecific antibodies by chemical recombination of monoclonal immunoglobulin $G_1$ fragments,” Science. 229(4708):81-3 (1985).

Bräuner-Osborne et al., “Cloning and characterization of a human orphan family C G-protein coupled receptor GPRC5D,” Biochim Biophys Acta. 1518(3):237-48 (2001).

Carter, “Bispecific human IgG by design,” J Immunol Methods. 248(1-2):7-15 (2001).

Cohen et al., “GPRC5D is a promising marker for monitoring the tumor load and to target multiple myeloma cells,” Hematology. 18(6):348-51 (2013) (5 pages).

Gao et al., “Comparative Transcriptome Analysis of Fetal Skin Reveals Key Genes Related to Hair Follicle Morphogenesis in Cashmere Goats,” PLoS One. 11(3):e0151118, retrieved from <https://www.ncbi.nlm.nih.gov/pmc/articles/PMC4784850/> Apr. 5, 2022 (2016) (26 pages).

Gruber et al., “Efficient Tumor Cell Lysis Mediated by a Bispecific Single Chain Antibody Expressed in *Escherichia coli*,” J Immunol. 152(11):5368-74 (1994) (9 pages).

Heeley et al., “Mutations Flanking the Polyglutamine Repeat in the Modulatory Domain of Rat Glucocorticoid Receptor Lead to an Increase in Affinity for Hormone,” Endocr Res. 28(3):217-229 (2002).

Holliger et al., “‘Diabodies’: Small bivalent and bispecific antibody fragments,” Proc Natl Acad Sci U S A. 90(14):6444-48 (1993).

Holliger et al., “Specific killing of lymphoma cells by cytotoxic T-cells mediated by a bispecific diabody,” Protein Eng. 9(3):299-305 (1996).

Hudson et al., “Engineered Antibodies,” *Nat Med.* 9(1):129-134 (2003).

(56) References Cited

OTHER PUBLICATIONS

Inoue et al., "The RAIG Family Member, GPRC5D, Is Associated with Hard-Keratinized Structures," J Invest Dermatol. 122(3):565-73 (2004).
Johnson et al., "Effector Cell Recruitment with Novel Fv-based Dual-affinity Re-targeting Protein Leads to Potent Tumor Cytolysis and in Vivo B-cell Depletion," J Mol Biol. 399(3):436-49, retrieved from <https://sciencedirect.com/science/article/abs/pii/S0022283610003529?via%3Dihub> Apr. 5, 2022 (2010) (8 pages) (Abstract Only).
Kipriyanov et al., "Bispecific tandem diabody for tumor therapy with improved antigen binding and pharmacokinetics," J Mol Biol. 293(1):41-56 (1999).
Klein et al., "The use of CrossMAb technology for the generation of bi- and multispecific antibodies," MAbs. 8(6):1010-20 (2016).
Kodama et al., "Anti-GPRC5D/CD3 Bispecific T-Cell-Redirecting Antibody for the Treatment of Multiple Myeloma," Mol Cancer Ther. 18(9):1555-64, retrieved from <https://aacrjournals.org/mct/article/18/9/1555/92691/Anti-GPRCD-CD3_Bispecific_T_Cell Redirection> on Apr. 5, 2022 (2019) (25 pages).
Kostelny et al., "Formation of a bispecific antibody by the use of leucine zippers," J Immunol. 148(5):1547-53 (1992).
Liljeblad et al., "Analysis of agalacto-IgG in rheumatoid arthritis using surface plasmon resonance," Glycoconj J. 17(5):323-9 (2000).
Lombardi et al., "Molecular characterization of human multiple myeloma cell lines by integrative genomics: insights into the biology of the disease," Genes Chromosomes Cancer. 46(3):226-38 (2007).
Milstein et al., "Hybrid Hybridomas and Their Use in Immunohistochemistry," Nature. 305(5934):537-40 (1983).
Moreau et al., "Multiple myeloma—translation of trial results into reality," Lancet. 388(10040):111-3 (2016).
Nagorsen et al., "Immunomodulatory therapy of cancer with T cell-engaging BiTE antibody blinatumomab," Exp Cell Res. 317(9):1255-60 (2011).
Pillarisetti et al., "A T-cell redirecting bispecific G-protein-coupled receptor class 5 member D x CD3 antibody to treat multiple myeloma," Blood. 135(15):1232-43, retrieved from <https://www.ncbi.nlm.nih.gov/pmc/articles/PMC7146017/> Apr. 5, 2022 (2020) (20 pages).
Plückthun, "Chapter 11: Antibodies from *Escherichia coli," The Pharmacology of Monoclonal Antibodies*. Martin Rosenberg and Gordon P. Moore. 113:269-315 (1994).
Ridgway et al., "'Knobs-into-holes' engineering of antibody $C_H3$ domains for heavy chain heterodimerization," Protein Eng. 9(7):617-21 (1996).
Schaefer et al., "Immunoglobulin domain crossover as a generic approach for the production of bispecific IgG antibodies," Proc Natl Acad Sci U S A. 108(27):11187-92 (2011).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Smith et al., "GPRC5D is a target for the immunotherapy of multiple myeloma with rationally designed CAR T cells," available in PMC Sep. 22, 2020, published in final edited form as: Sci Transl Med. 11(485): eaau7746, retrieved from <https://www.ncbi.nlm.nih.gov/pmc/articles/PMC7508042/> Apr. 6, 2022 (2019) (22 pages).
Spiess et al., "Alternative molecular formats and therapeutic applications for bispecific antibodies," Mol Immunol. 67(2 Pt A):95-106, retrieved from <https://www.sciencedirect.com/science/article/pii/S016158901500005X?via%3Dihub> Apr. 5, 2022 (2015) (42 pages).
Tai et al., "Targeting B-cell maturation antigen in multiple myeloma," Immunotherapy. 7(11):1187-99, retrieved from <https://ncbi.nlm.nih.gov/pmc/articles/PMC4976846/> Apr. 5, 2022 (2015) (17 pages).
Tutt et al., "Trispecific $F(ab')_3$ derivatives that use cooperative signaling via the TCR/CD3 complex and CD2 to activate and redirect resting cytotoxic T cells," J Immunol. 147(1):60-9 (1991).
International Preliminary Report on Patentability for International Application No. PCT/EP2020/071182, issued Feb. 1, 2022 (13 pages).
International Search Report and Written Opinion for International Application No. PCT/EP2020/071182, mailed Aug. 4, 2021 (23 pages).
Bacac et al. "CEA TCB: A novel head-to-tail 2:1 T cell bispecific antibody for treatment of CEA-positive solid tumors," Oncoimmunology. 5(8 Suppl e1203498) (2016) (3 pages).

* cited by examiner

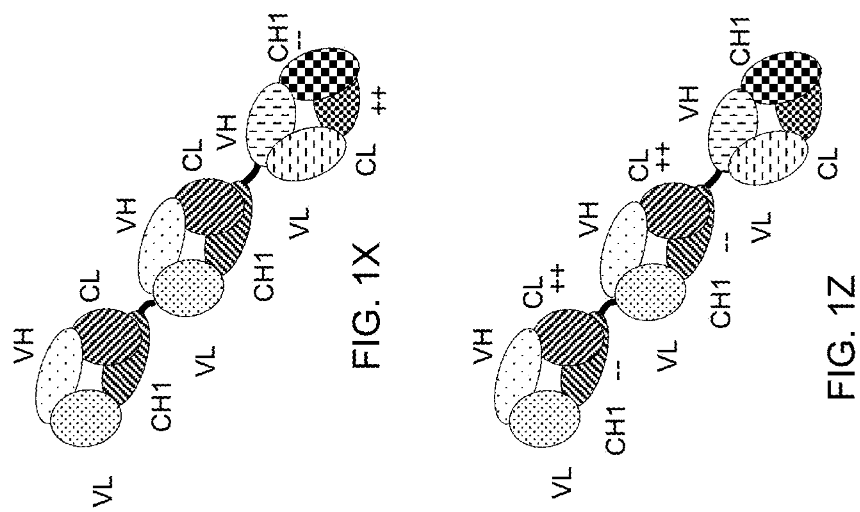
FIG. 1X
FIG. 1Z
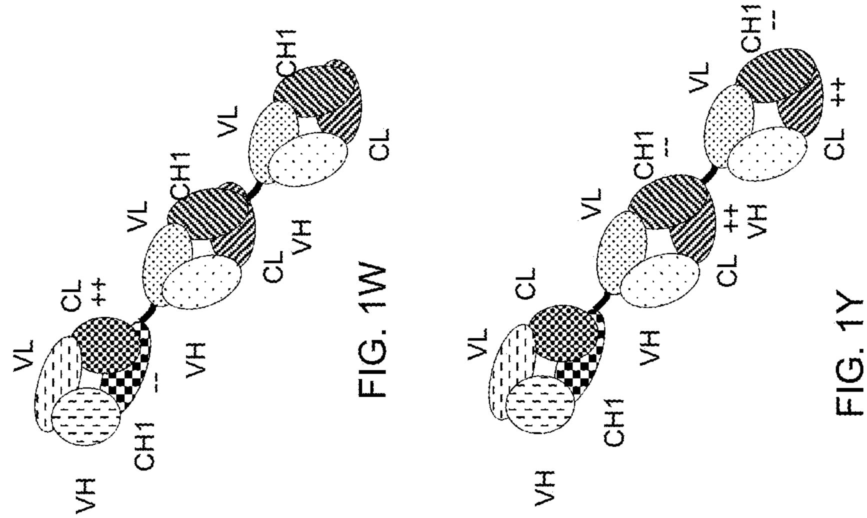
FIG. 1W
FIG. 1Y

ET-150-5-TCB
mean fluorescence intensity
40000
30000
20000
10000
0
$10^{-2}$
$10^{-1}$
$10^{0}$
$10^{1}$
Concentration (µg/ml)

5E11-TCB
mean fluorescence intensity
8000
6000
4000
2000
0
$10^{-2}$
$10^{-1}$
$10^{0}$
$10^{1}$
Concentration (µg/ml)

5F11-TCB
AMO-1
L636
NCI-H929
RPMI-8226
OPM-2
WSU-DLCL2
mean fluorescence intensity
25000
20000
15000
10000
5000
0
$10^{-2}$
$10^{-1}$
$10^{0}$
$10^{1}$
Concentration (µg/ml)

AMO-1
Lactate Desygrogenase release (LDH)
Concentration (μg/ml)

NCI-H929
Lactate Desygrogenase release (LDH)
Concentration (μg/ml)
5E11-TCB
5F11-TCB
DP47-TCB
ET-150-5-TCB RPMI-8226
Lactate Desygrogenase release (LDH)
Concentration (μg/ml)

L363
Lactate Desygrogenase release (LDH)
Concentration (μg/ml)

WSU-DLCL2
Lactate Desygrogenase release (LDH)
Concentration (μg/ml)

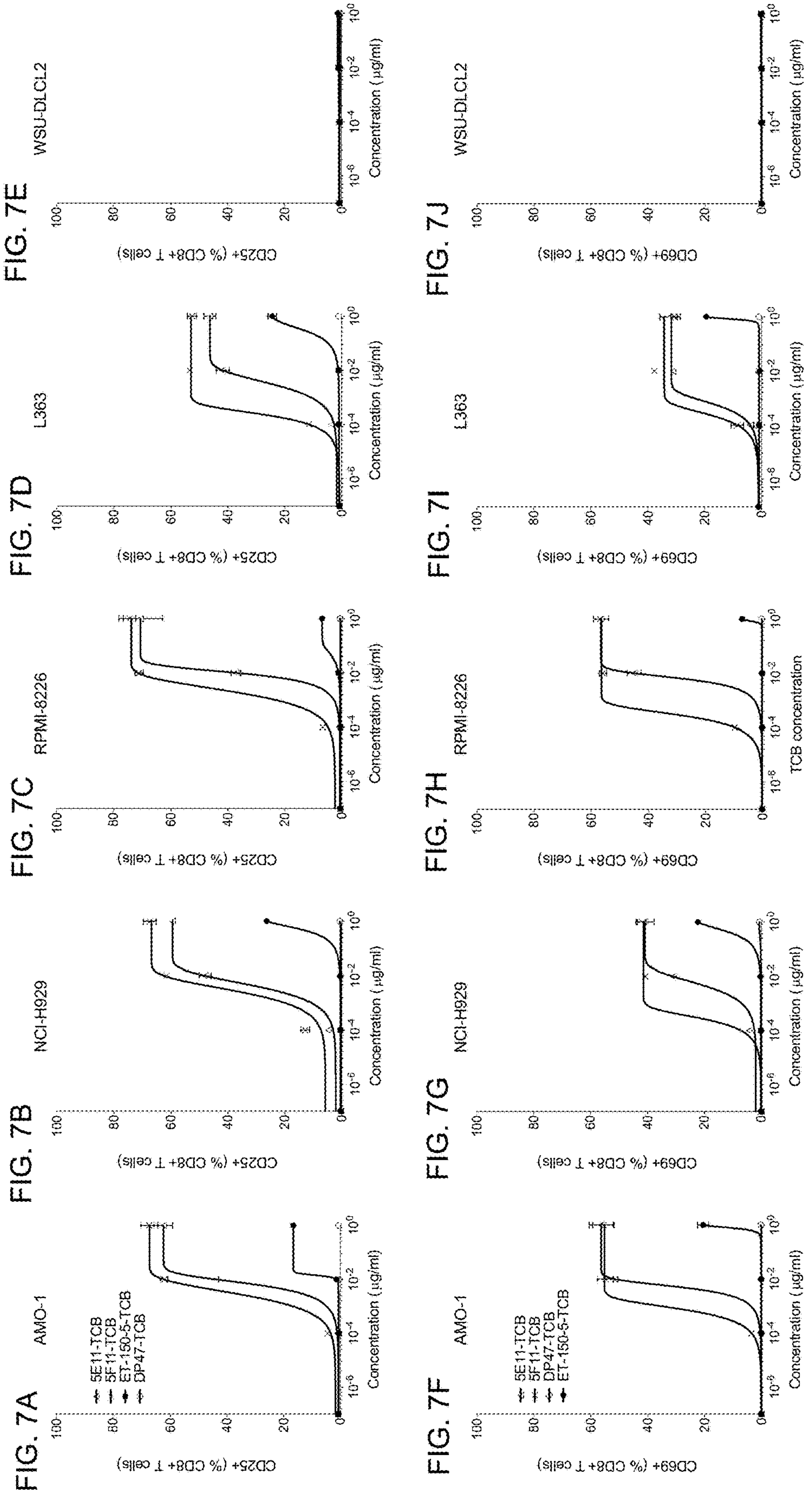
FIG. 7A
AMO-1
5E11-TCB
5F11-TCB
ET-150-5-TCB
DP47-TCB
CD25+ (% CD8+ T cells)
Concentration (μg/ml)
FIG. 7B
NCI-H929
CD25+ (% CD8+ T cells)
Concentration (μg/ml)
FIG. 7C
RPMI-8226
CD25+ (% CD8+ T cells)
Concentration (μg/ml)
FIG. 7D
L363
CD25+ (% CD8+ T cells)
Concentration (μg/ml)
FIG. 7E
WSU-DLCL2
CD25+ (% CD8+ T cells)
Concentration (μg/ml)
FIG. 7F
AMO-1
5E11-TCB
5F11-TCB
DP47-TCB
ET-150-5-TCB
CD69+ (% CD8+ T cells)
Concentration (μg/ml)
FIG. 7G
NCI-H929
CD69+ (% CD8+ T cells)
Concentration (μg/ml)
FIG. 7H
RPMI-8226
CD69+ (% CD8+ T cells)
TCB concentration
FIG. 7I
L363
CD69+ (% CD8+ T cells)
Concentration (μg/ml)
FIG. 7J
WSU-DLCL2
CD69+ (% CD8+ T cells)
Concentration (μg/ml)

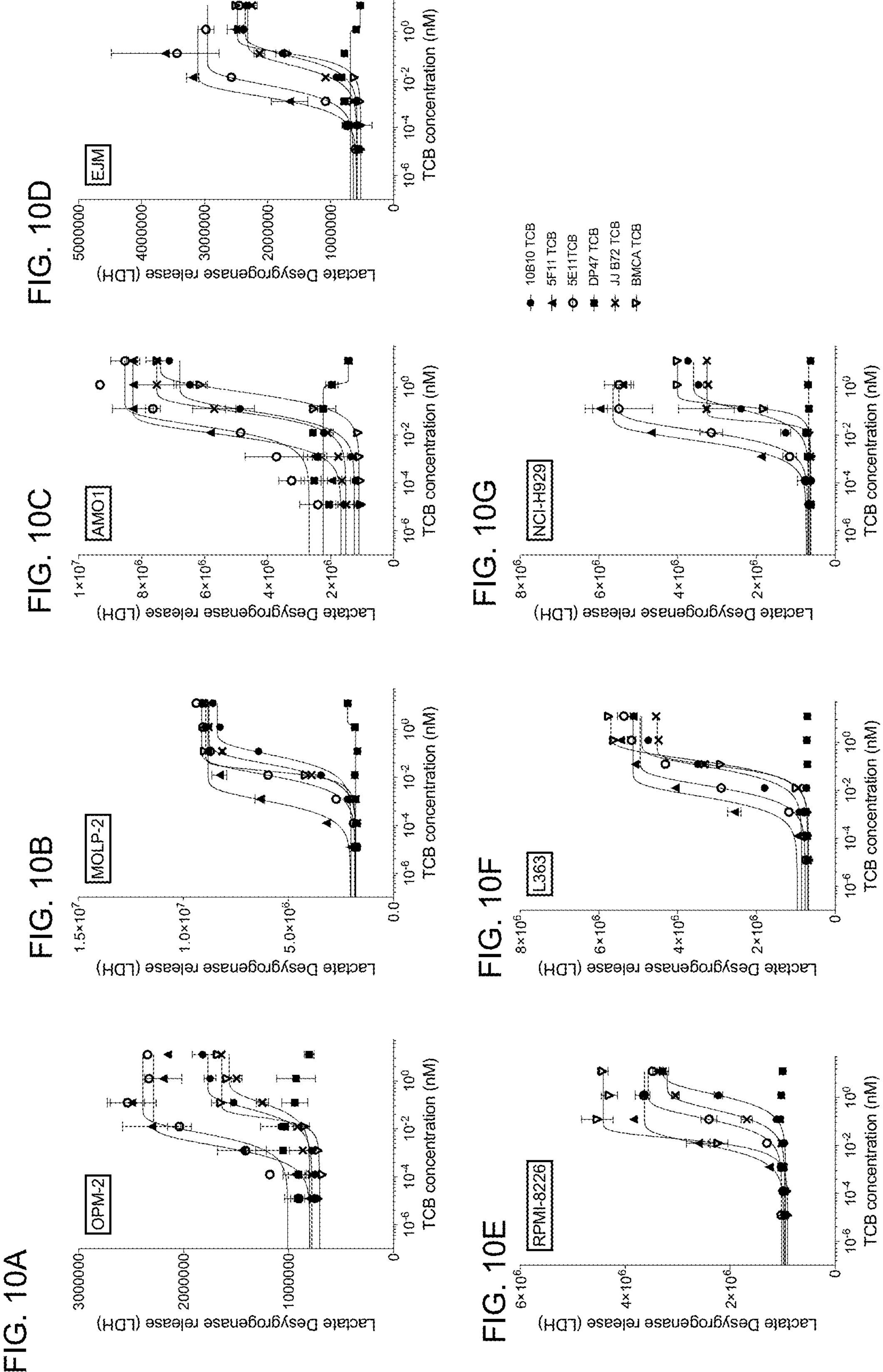
FIG. 10A
OPM-2
Lactate Desygrogenase release (LDH)
TCB concentration (nM)
FIG. 10B
MOLP-2
Lactate Desygrogenase release (LDH)
TCB concentration (nM)
FIG. 10C
AMO1
Lactate Desygrogenase release (LDH)
TCB concentration (nM)
FIG. 10D
EJM
Lactate Desygrogenase release (LDH)
TCB concentration (nM)
FIG. 10E
RPMI-8226
Lactate Desygrogenase release (LDH)
TCB concentration (nM)
FIG. 10F
L363
Lactate Desygrogenase release (LDH)
TCB concentration (nM)
FIG. 10G
NCI-H929
Lactate Desygrogenase release (LDH)
TCB concentration (nM)
10B10 TCB
5F11 TCB
5E11TCB
DP47 TCB
JJ B72 TCB
BMCA TCB 5E11-TCB
CD69, CD4 subset
0.70
CD69, CD8 subset
0.89

5F11-TCB
CD69, CD4 subset
2.89
CD69, CD8 subset
2.65

10B10-TCB
CD69, CD4 subset
1.72
CD69, CD8 subset
2.43

BCMA-TCB
CD69, CD4 subset
3.56
CD69, CD8 subset
3.95

B72-TCB
CD69, CD4 subset
12.2
CD69, CD8 subset
18.5

DP47-TCB
CD69, CD4 subset
1.13
CD69, CD8 subset
1.38
CD4
CD8
CD69

FIG. 13D
Vehicle
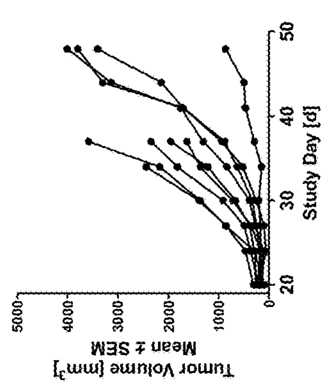
FIG. 13C
B72-TCB
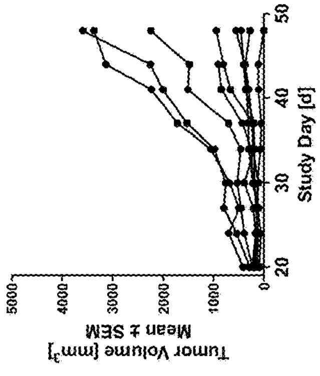
FIG. 13B
BCMA-TCB
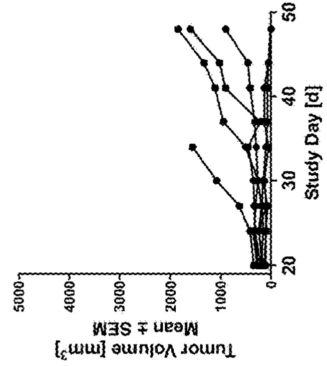
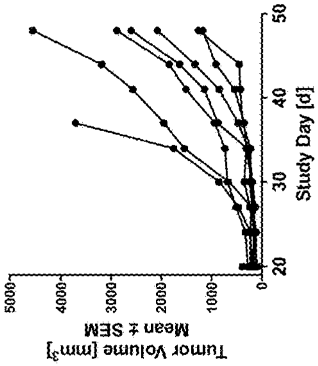
FIG. 13A
5F11-TCB
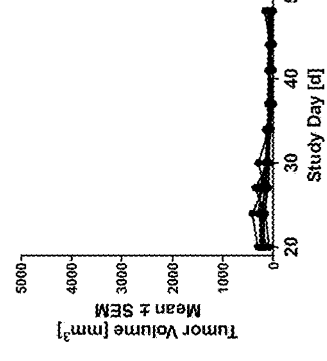
1mg/kg
0.1mg/kg FIG. 14D
Vehicle
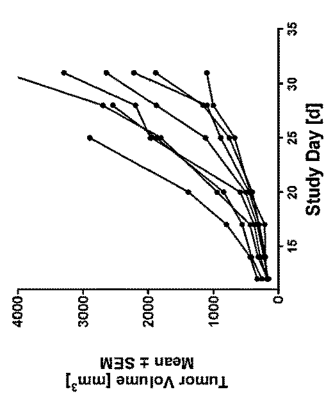
FIG. 14C
B72-TCB
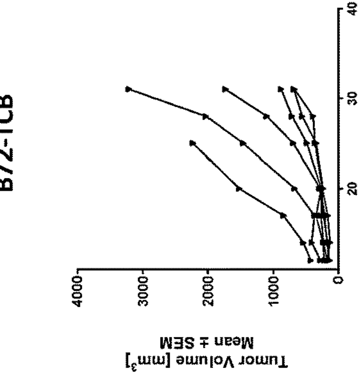
FIG. 14B
5E11-TCB
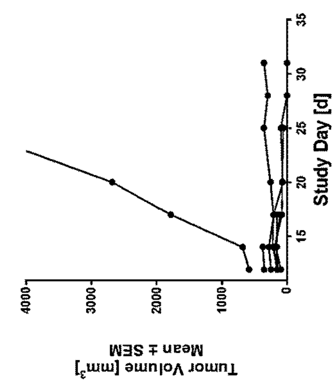
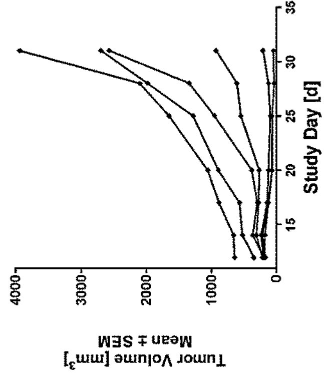
FIG. 14A
5F11-TCB
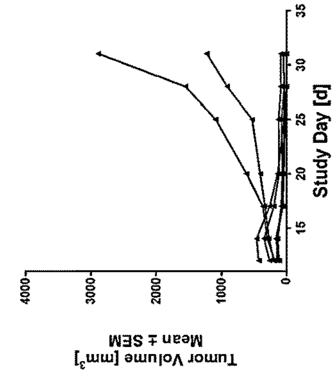
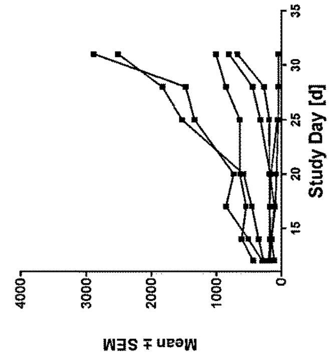
0.1 mg/kg
0.01 mg/kg

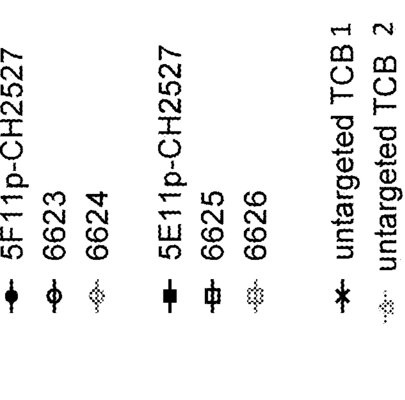
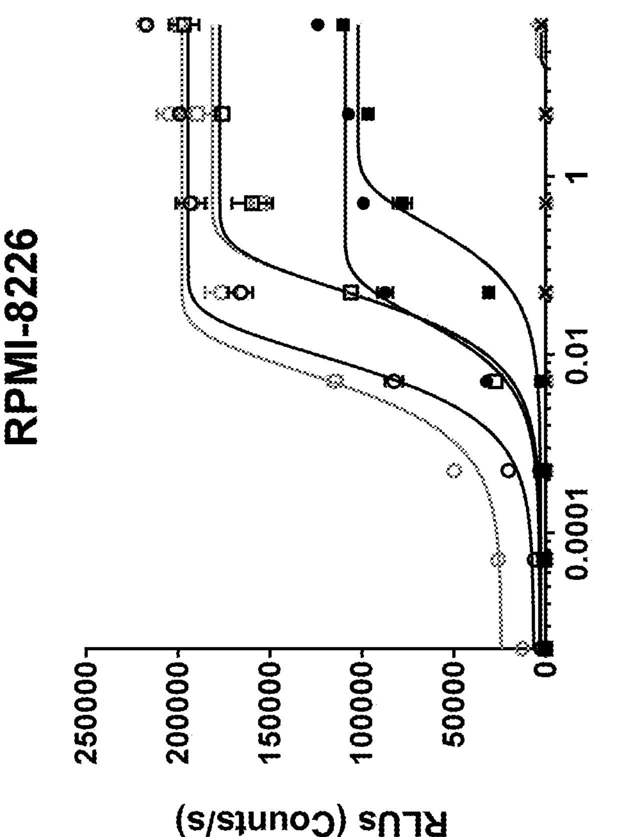
FIG. 17A

AMO-1 (~ 369 630)
RLUs
2×10^7
1.5×10^7
1×10^7
5×10^6
0
0.001
1
1000
1000000
Antibody concentration (pM)

NCI-H929 (~113 200)
RLUs
4000000
3000000
2000000
1000000
0
0.001
1
1000
1000000
Antibody concentration (pM)

LP-1 (~ 18 050)
RLUs
4000000
3000000
2000000
1000000
0
0.001
1
1000
1000000
Antibody concentration (pM)

IM-9 (~ 5840)
RLUs
2500000
2000000
1500000
1000000
500000
0
0.001
1
1000
1000000
Antibody concentration (pM)
GPRC5D-TCB
untargeted TCB
B72
BCMA-TCB

SEQUENCE LISTING

<160> NUMBER OF SEQ ID NOS: 136

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

```
Gly Phe Thr Phe Ser Lys Tyr Ala Met Ala
1               5                   10
```

<210> SEQ ID NO 2
<211> LENGTH: 15
<212> TYPE: PRT
<213> ORGANISM: Artificial Sequence
<220> FEATURE:
<223> OTHER INFORMATION: Synthetic Construct

<400> SEQUENCE: 2

```
Ser Thr Gly Gly Val Asn Thr Tyr Tyr Arg Asp Ser Val Lys Ala
1               5                   10                  15
```

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

```
His Thr Gly Asp Tyr Phe Asp Tyr
1               5
```

<210> SEQ ID NO 4
<211> LENGTH: 14
<212> TYPE: PRT
<213> ORGANISM: Artificial Sequence
<220> FEATURE:
<223> OTHER INFORMATION: Synthetic Construct

<400> SEQUENCE: 4

```
Ala Ser Gln Ser Val Ser Ile Ser Gly Ile Asn Leu Met Asn
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

```
His Ala Ser Ile Leu Ala Ser
1               5
```

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

```
Gln Gln Thr Arg Glu Ser Pro Leu Thr
1               5
```

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Gly Phe Ser Phe Ser Asn Tyr Gly Met Ala
1 5 10

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Ser Thr Gly Gly Gly Asn Thr Tyr Tyr Arg Asp Ser Val Lys Gly
1 5 10 15

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

His Asp Arg Gly Gly Leu Tyr
1 5

<210> SEQ ID NO 10
<211> LENGTH: 16
<212> TYPE: PRT
<213> ORGANISM: Artificial Sequence
<220> FEATURE:
<223> OTHER INFORMATION: Synthetic Construct

<400> SEQUENCE: 10

Arg Ser Ser Lys Ser Leu Leu His Ser Asn Gly Ile Thr Tyr Val Tyr
1 5 10 15

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Arg Met Ser Asn Leu Ala Ser
1 5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gly Gln Leu Leu Glu Asn Pro Tyr Thr
1 5

<210> SEQ ID NO 13
<211> LENGTH: 117
<212> TYPE: PRT
<213> ORGANISM: Artificial Sequence
<220> FEATURE:
<223> OTHER INFORMATION: Synthetic Construct

<400> SEQUENCE: 13

```
Glu Leu Gln Leu Glu Gln Ser Gly Gly Gly Leu Val Gln Pro Gly Gly
1               5                   10                  15

Ser Leu Thr Leu Ser Cys Ala Ala Ser Gly Phe Thr Phe Ser Lys Tyr
            20                  25                  30

Ala Met Ala Trp Val Arg Gln Ala Pro Thr Lys Gly Leu Glu Trp Val
        35                  40                  45

Ala Ser Ile Ser Thr Gly Gly Val Asn Thr Tyr Tyr Arg Asp Ser Val
    50                  55                  60

Lys Ala Arg Phe Thr Ile Ser Arg Asp Asn Ala Lys Asn Thr Gln Tyr
65                  70                  75                  80

Leu Gln Met Asp Ser Leu Arg Ser Glu Asp Thr Ala Thr Tyr Tyr Cys
                85                  90                  95

Ala Thr His Thr Gly Asp Tyr Phe Asp Tyr Trp Gly Gln Gly Val Met
            100                 105                 110

Val Thr Val Ser Ser
        115
```

<210> SEQ ID NO 14
<211> LENGTH: 110
<212> TYPE: PRT
<213> ORGANISM: Artificial Sequence
<220> FEATURE:
<223> OTHER INFORMATION: Synthetic Construct

<400> SEQUENCE: 14

```
Asp Ile Val Leu Thr Gln Ser Pro Ala Leu Ala Val Ser Pro Gly Gln
1               5                   10                  15

Arg Ala Thr Ile Ser Cys Arg Ala Ser Gln Ser Val Ser Ile Ser Gly
            20                  25                  30

Ile Asn Leu Met Asn Trp Tyr Gln Gln Lys Pro Gly Gln Gln Pro Lys
        35                  40                  45

Leu Leu Ile Tyr His Ala Ser Ile Leu Ala Ser Gly Ile Pro Thr Arg
    50                  55                  60

Phe Ser Gly Ser Gly Ser Gly Thr Asp Phe Thr Leu Thr Ile Asp Pro
65                  70                  75                  80

Val Gln Ala Asp Asp Ile Ala Thr Tyr Tyr Cys Gln Gln Thr Arg Glu
                85                  90                  95

Ser Pro Leu Thr Phe Gly Ser Gly Thr Asn Leu Glu Ile Lys
            100                 105                 110
```

<210> SEQ ID NO 15
<211> LENGTH: 116
<212> TYPE: PRT
<213> ORGANISM: Artificial Sequence
<220> FEATURE:
<223> OTHER INFORMATION: Synthetic Construct

<400> SEQUENCE: 15

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Ser Phe Ser Asn Tyr
```

```
            20                  25                  30

Gly Met Ala Trp Val Arg Gln Ala Ala Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Ile Val Ser Arg Asp Asn Ala Lys Asn Thr Gln Tyr
65                  70                  75                  80

Leu Gln Met Asp Ser Leu Arg Ser Glu Asp Thr Ala Thr Tyr Tyr Cys
                85                  90                  95

Thr Arg His Asp Arg Gly Gly Leu Tyr Trp Gly Gln Gly Val Met Val
            100                 105                 110

Thr Val Ser Ser
        115


<210> SEQ ID NO 16
<211> LENGTH: 112
<212> TYPE: PRT
<213> ORGANISM: Artificial Sequence
<220> FEATURE:
<223> OTHER INFORMATION: Synthetic Construct

<400> SEQUENCE: 16

Asp Ile Val Met Thr Gln Ala Pro Leu Ser Val Ser Val Thr Pro Gly
1               5                   10                  15

Glu Ser Ala Ser Ile Ser Cys Arg Ser Ser Lys Ser Leu Leu His Ser
            20                  25                  30

Asn Gly Ile Thr Tyr Val Tyr Trp Tyr Phe Gln Lys Pro Gly Lys Ser
        35                  40                  45

Pro Gln Val Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Val Gly Ile Tyr His Cys Gly Gln Leu
                85                  90                  95

Leu Glu Asn Pro Tyr Thr Phe Gly Ala Gly Thr Glu Leu Glu Leu Lys
            100                 105                 110


<210> SEQ ID NO 17
<211> LENGTH: 217
<212> TYPE: PRT
<213> ORGANISM: Artificial Sequence
<220> FEATURE:
<223> OTHER INFORMATION: Synthetic Construct

<400> SEQUENCE: 17

Asp Ile Val Leu Thr Gln Ser Pro Ala Leu Ala Val Ser Pro Gly Gln
1               5                   10                  15

Arg Ala Thr Ile Ser Cys Arg Ala Ser Gln Ser Val Ser Ile Ser Gly
            20                  25                  30

Ile Asn Leu Met Asn Trp Tyr Gln Gln Lys Pro Gly Gln Gln Pro Lys
        35                  40                  45

Leu Leu Ile Tyr His Ala Ser Ile Leu Ala Ser Gly Ile Pro Thr Arg
    50                  55                  60

Phe Ser Gly Ser Gly Ser Gly Thr Asp Phe Thr Leu Thr Ile Asp Pro
65                  70                  75                  80

Val Gln Ala Asp Asp Ile Ala Thr Tyr Tyr Cys Gln Gln Thr Arg Glu
                85                  90                  95
```

```
Ser Pro Leu Thr Phe Gly Ser Gly Thr Asn Leu Glu Ile Lys Arg Thr
            100                 105                 110

Val Ala Ala Pro Ser Val Phe Ile Phe Pro Pro Ser Asp Arg Lys Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 18
<211> LENGTH: 232
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 19
<211> LENGTH: 447
<212> TYPE: PRT
<213> ORGANISM: Artificial Sequence
<220> FEATURE:
<223> OTHER INFORMATION: Synthetic Construct

<400> SEQUENCE: 19

```
Glu Leu Gln Leu Glu Gln Ser Gly Gly Gly Leu Val Gln Pro Gly Gly
1               5                   10                  15

Ser Leu Thr Leu Ser Cys Ala Ala Ser Gly Phe Thr Phe Ser Lys Tyr
            20                  25                  30

Ala Met Ala Trp Val Arg Gln Ala Pro Thr Lys Gly Leu Glu Trp Val
        35                  40                  45

Ala Ser Ile Ser Thr Gly Gly Val Asn Thr Tyr Tyr Arg Asp Ser Val
    50                  55                  60

Lys Ala Arg Phe Thr Ile Ser Arg Asp Asn Ala Lys Asn Thr Gln Tyr
65                  70                  75                  80

Leu Gln Met Asp Ser Leu Arg Ser Glu Asp Thr Ala Thr Tyr Tyr Cys
                85                  90                  95

Ala Thr His Thr Gly Asp Tyr Phe Asp Tyr Trp Gly Gln Gly Val Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365
```

```
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 20
<211> LENGTH: 672
<212> TYPE: PRT
<213> ORGANISM: Artificial Sequence
<220> FEATURE:
<223> OTHER INFORMATION: Synthetic Construct

<400> SEQUENCE: 20

Glu Leu Gln Leu Glu Gln Ser Gly Gly Gly Leu Val Gln Pro Gly Gly
1               5                   10                  15

Ser Leu Thr Leu Ser Cys Ala Ala Ser Gly Phe Thr Phe Ser Lys Tyr
            20                  25                  30

Ala Met Ala Trp Val Arg Gln Ala Pro Thr Lys Gly Leu Glu Trp Val
        35                  40                  45

Ala Ser Ile Ser Thr Gly Gly Val Asn Thr Tyr Tyr Arg Asp Ser Val
    50                  55                  60

Lys Ala Arg Phe Thr Ile Ser Arg Asp Asn Ala Lys Asn Thr Gln Tyr
65                  70                  75                  80

Leu Gln Met Asp Ser Leu Arg Ser Glu Asp Thr Ala Thr Tyr Tyr Cys
                85                  90                  95

Ala Thr His Thr Gly Asp Tyr Phe Asp Tyr Trp Gly Gln Gly Val Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Gly Gly Gly
    210                 215                 220

Gly Ser Gly Gly Gly Gly Ser Gln Ala Val Val Thr Gln Glu Pro Ser
225                 230                 235                 240

Leu Thr Val Ser Pro Gly Gly Thr Val Thr Leu Thr Cys Gly Ser Ser
                245                 250                 255

Thr Gly Ala Val Thr Thr Ser Asn Tyr Ala Asn Trp Val Gln Glu Lys
            260                 265                 270

Pro Gly Gln Ala Phe Arg Gly Leu Ile Gly Gly Thr Asn Lys Arg Ala
        275                 280                 285
```

```
Pro Gly Thr Pro Ala Arg Phe Ser Gly Ser Leu Leu Gly Gly Lys Ala
    290                 295                 300

Ala Leu Thr Leu Ser Gly Ala Gln Pro Glu Asp Glu Ala Glu Tyr Tyr
305                 310                 315                 320

Cys Ala Leu Trp Tyr Ser Asn Leu Trp Val Phe Gly Gly Gly Thr Lys
                325                 330                 335

Leu Thr Val Leu Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Lys Asp Tyr Phe Pro Glu Pro Val Thr Val Ser Trp Asn
    370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Lys Lys Val Glu Pro Lys Ser Cys Asp Lys Thr
        435                 440                 445

His Thr Cys Pro Pro Cys Pro Ala Pro Glu Ala Ala Gly Gly Pro Ser
    450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala
            500                 505                 510

Lys Thr Lys Pro Arg Glu Glu Gln Tyr Asn Ser Thr Tyr Arg Val Val
        515                 520                 525

Ser Val Leu Thr Val Leu His Gln Asp Trp Leu Asn Gly Lys Glu Tyr
    530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Cys Arg Asp Glu Leu Thr Lys Asn Gln Val Ser Leu Trp Cys
            580                 585                 590

Leu Val Lys Gly Phe Tyr Pro Ser Asp Ile Ala Val Glu Trp Glu Ser
        595                 600                 605

Asn Gly Gln Pro Glu Asn Asn Tyr Lys Thr Thr Pro Pro Val Leu Asp
    610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Lys
            660                 665                 670
```

<210> SEQ ID NO 21
<211> LENGTH: 219
<212> TYPE: PRT
<213> ORGANISM: Artificial Sequence
<220> FEATURE:
<223> OTHER INFORMATION: Synthetic Construct

<400> SEQUENCE: 21

```
Asp Ile Val Met Thr Gln Ala Pro Leu Ser Val Ser Val Thr Pro Gly
1               5                   10                  15

Glu Ser Ala Ser Ile Ser Cys Arg Ser Ser Lys Ser Leu Leu His Ser
            20                  25                  30

Asn Gly Ile Thr Tyr Val Tyr Trp Tyr Phe Gln Lys Pro Gly Lys Ser
        35                  40                  45

Pro Gln Val Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Val Gly Ile Tyr His Cys Gly Gln Leu
                85                  90                  95

Leu Glu Asn Pro Tyr Thr Phe Gly Ala Gly Thr Glu Leu Glu Leu Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 22
<211> LENGTH: 232
<212> TYPE: PRT
<213> ORGANISM: Artificial Sequence
<220> FEATURE:
<223> OTHER INFORMATION: Synthetic Construct

<400> SEQUENCE: 22

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125
```

```
Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 23
<211> LENGTH: 446
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Ser Phe Ser Asn Tyr
            20                  25                  30

Gly Met Ala Trp Val Arg Gln Ala Ala Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Ile Val Ser Arg Asp Asn Ala Lys Asn Thr Gln Tyr
65                  70                  75                  80

Leu Gln Met Asp Ser Leu Arg Ser Glu Asp Thr Ala Thr Tyr Tyr Cys
                85                  90                  95

Thr Arg His Asp Arg Gly Gly Leu Tyr Trp Gly Gln Gly Val Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 24
<211> LENGTH: 671
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Ser Phe Ser Asn Tyr
            20                  25                  30

Gly Met Ala Trp Val Arg Gln Ala Ala Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Ile Val Ser Arg Asp Asn Ala Lys Asn Thr Gln Tyr
65                  70                  75                  80

Leu Gln Met Asp Ser Leu Arg Ser Glu Asp Thr Ala Thr Tyr Tyr Cys
                85                  90                  95

Thr Arg His Asp Arg Gly Gly Leu Tyr Trp Gly Gln Gly Val Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
    290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
                325                 330                 335

Thr Val Leu Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430

Thr Lys Val Asp Lys Lys Val Glu Pro Lys Ser Cys Asp Lys Thr His
        435                 440                 445

Thr Cys Pro Pro Cys Pro Ala Pro Glu Ala Ala Gly Gly Pro Ser Val
    450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
        515                 520                 525

Val Leu Thr Val Leu His Gln Asp Trp Leu Asn Gly Lys Glu Tyr Lys
    530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Cys Arg Asp Glu Leu Thr Lys Asn Gln Val Ser Leu Trp Cys Leu
            580                 585                 590

Val Lys Gly Phe Tyr Pro Ser Asp Ile Ala Val Glu Trp Glu Ser Asn
```

```
        595                 600                 605

Gly Gln Pro Glu Asn Asn Tyr Lys Thr Thr Pro Pro Val Leu Asp Ser
    610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670


<210> SEQ ID NO 25
<211> LENGTH: 216
<212> TYPE: PRT
<213> ORGANISM: Artificial Sequence
<220> FEATURE:
<223> OTHER INFORMATION: Synthetic Construct

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Val Gly Gly Asn
            20                  25                  30

Tyr Val Phe Trp Tyr Gln Gln Val Pro Gly Ala Thr Pro Lys Leu Leu
        35                  40                  45

Ile Tyr Arg Ser Asn Gln Arg Pro Ser Gly Val Pro Asp Arg Phe Ala
    50                  55                  60

Gly Ser Lys Ser Gly Ser Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Phe Val Phe Gly Thr Gly Thr Lys Val Thr Val Leu Gly Gln
            100                 105                 110

Pro Lys Ala Ala Pro Ser Val Thr Leu Phe Pro Pro Ser Ser Lys Lys
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 26
<211> LENGTH: 232
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 27
<211> LENGTH: 447
<212> TYPE: PRT
<213> ORGANISM: Artificial Sequence
<220> FEATURE:
<223> OTHER INFORMATION: Synthetic Construct

<400> SEQUENCE: 27

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Lys Ala Tyr Asp Gln Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

```
Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 28
<211> LENGTH: 672
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60
```

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Lys Ala Tyr Asp Gln Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Gly Gly Gly
    210                 215                 220

Gly Ser Gly Gly Gly Gly Ser Gln Ala Val Val Thr Gln Glu Pro Ser
225                 230                 235                 240

Leu Thr Val Ser Pro Gly Gly Thr Val Thr Leu Thr Cys Gly Ser Ser
                245                 250                 255

Thr Gly Ala Val Thr Thr Ser Asn Tyr Ala Asn Trp Val Gln Glu Lys
            260                 265                 270

Pro Gly Gln Ala Phe Arg Gly Leu Ile Gly Gly Thr Asn Lys Arg Ala
        275                 280                 285

Pro Gly Thr Pro Ala Arg Phe Ser Gly Ser Leu Leu Gly Gly Lys Ala
    290                 295                 300

Ala Leu Thr Leu Ser Gly Ala Gln Pro Glu Asp Glu Ala Glu Tyr Tyr
305                 310                 315                 320

Cys Ala Leu Trp Tyr Ser Asn Leu Trp Val Phe Gly Gly Gly Thr Lys
                325                 330                 335

Leu Thr Val Leu Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Lys Asp Tyr Phe Pro Glu Pro Val Thr Val Ser Trp Asn
    370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Lys Lys Val Glu Pro Lys Ser Cys Asp Lys Thr
        435                 440                 445

His Thr Cys Pro Pro Cys Pro Ala Pro Glu Ala Ala Gly Gly Pro Ser
    450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
```

```
                485                 490                 495

Glu Val Lys Phe Asn Trp Tyr Val Asp Gly Val Glu Val His Asn Ala
            500                 505                 510

Lys Thr Lys Pro Arg Glu Glu Gln Tyr Asn Ser Thr Tyr Arg Val Val
        515                 520                 525

Ser Val Leu Thr Val Leu His Gln Asp Trp Leu Asn Gly Lys Glu Tyr
    530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Cys Arg Asp Glu Leu Thr Lys Asn Gln Val Ser Leu Trp Cys
            580                 585                 590

Leu Val Lys Gly Phe Tyr Pro Ser Asp Ile Ala Val Glu Trp Glu Ser
        595                 600                 605

Asn Gly Gln Pro Glu Asn Asn Tyr Lys Thr Thr Pro Pro Val Leu Asp
    610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Lys
            660                 665                 670


<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Thr Tyr Ala Met Asn
1               5


<210> SEQ ID NO 30
<211> LENGTH: 19
<212> TYPE: PRT
<213> ORGANISM: Artificial Sequence
<220> FEATURE:
<223> OTHER INFORMATION: Synthetic Construct

<400> SEQUENCE: 30

Arg Ile Arg Ser Lys Tyr Asn Asn Tyr Ala Thr Tyr Tyr Ala Asp Ser
1               5                   10                  15

Val Lys Gly


<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

His Gly Asn Phe Gly Asn Ser Tyr Val Ser Trp Phe Ala Tyr
1               5                   10


<210> SEQ ID NO 32
<211> LENGTH: 14
```

<212> TYPE: PRT
<213> ORGANISM: Artificial Sequence
<220> FEATURE:
<223> OTHER INFORMATION: Synthetic Construct

<400> SEQUENCE: 32

```
Gly Ser Ser Thr Gly Ala Val Thr Thr Ser Asn Tyr Ala Asn
1               5                   10
```

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

```
Gly Thr Asn Lys Arg Ala Pro
1               5
```

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

```
Ala Leu Trp Tyr Ser Asn Leu Trp Val
1               5
```

<210> SEQ ID NO 35
<211> LENGTH: 125
<212> TYPE: PRT
<213> ORGANISM: Artificial Sequence
<220> FEATURE:
<223> OTHER INFORMATION: Synthetic Construct

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 36
<211> LENGTH: 109
<212> TYPE: PRT
<213> ORGANISM: Artificial Sequence
<220> FEATURE:
<223> OTHER INFORMATION: Synthetic Construct

<400> SEQUENCE: 36

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105


<210> SEQ ID NO 37
<211> LENGTH: 107
<212> TYPE: PRT
<213> ORGANISM: Artificial Sequence
<220> FEATURE:
<223> OTHER INFORMATION: Synthetic Construct

<400> SEQUENCE: 37

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 38
<211> LENGTH: 105
<212> TYPE: PRT
<213> ORGANISM: Artificial Sequence
<220> FEATURE:
<223> OTHER INFORMATION: Synthetic Construct

<400> SEQUENCE: 38

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
```

```
                85                  90                  95

Lys Thr Val Ala Pro Thr Glu Cys Ser
            100                 105


<210> SEQ ID NO 39
<211> LENGTH: 328
<212> TYPE: PRT
<213> ORGANISM: Artificial Sequence
<220> FEATURE:
<223> OTHER INFORMATION: Synthetic Construct

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

```
<210> SEQ ID NO 40
<211> LENGTH: 207
<212> TYPE: PRT
<213> ORGANISM: Homo sapiens

<400> SEQUENCE: 40

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205


<210> SEQ ID NO 41
<211> LENGTH: 198
<212> TYPE: PRT
<213> ORGANISM: Macaca fascicularis

<400> SEQUENCE: 41

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Leu Val Tyr Tyr Trp Ser Lys
```

```
    130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
        195


<210> SEQ ID NO 42
<211> LENGTH: 225
<212> TYPE: PRT
<213> ORGANISM: Artificial Sequence
<220> FEATURE:
<223> OTHER INFORMATION: Synthetic Construct

<400> SEQUENCE: 42

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225


<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43
```

```
Gly Gly Gly Gly Ser Gly Gly Gly Gly Ser
1               5                   10


<210> SEQ ID NO 44
<211> LENGTH: 11
<212> TYPE: PRT
<213> ORGANISM: Artificial Sequence
<220> FEATURE:
<223> OTHER INFORMATION: Synthetic Construct

<400> SEQUENCE: 44

Asp Gly Gly Gly Gly Ser Gly Gly Gly Gly Ser
1               5                   10


<210> SEQ ID NO 45
<211> LENGTH: 345
<212> TYPE: PRT
<213> ORGANISM: Homo sapiens

<400> SEQUENCE: 45

Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
            20                  25                  30

Gly Ile Val Val Thr Ile Leu Leu Leu Leu Ala Phe Leu Phe Leu Met
        35                  40                  45

Arg Lys Ile Gln Asp Cys Ser Gln Trp Asn Val Leu Pro Thr Gln Leu
    50                  55                  60

Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

Gly Val Leu Phe Ala Leu Cys Phe Ser Cys Leu Leu Ala His Ala Ser
            100                 105                 110

Asn Leu Val Lys Leu Val Arg Gly Cys Val Ser Phe Ser Trp Thr Thr
        115                 120                 125

Ile Leu Cys Ile Ala Ile Gly Cys Ser Leu Leu Gln Ile Ile Ile Ala
    130                 135                 140

Thr Glu Tyr Val Thr Leu Ile Met Thr Arg Gly Met Met Phe Val Asn
145                 150                 155                 160

Met Thr Pro Cys Gln Leu Asn Val Asp Phe Val Val Leu Leu Val Tyr
                165                 170                 175

Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ile
        195                 200                 205

Thr Val Leu Phe Ser Ile Ile Ile Trp Val Val Trp Ile Ser Met Leu
    210                 215                 220

Leu Arg Gly Asn Pro Gln Phe Gln Arg Gln Pro Gln Trp Asp Asp Pro
225                 230                 235                 240

Val Val Cys Ile Ala Leu Val Thr Asn Ala Trp Val Phe Leu Leu Leu
                245                 250                 255

Tyr Ile Val Pro Glu Leu Cys Ile Leu Tyr Arg Ser Cys Arg Gln Glu
            260                 265                 270

Cys Pro Leu Gln Gly Asn Ala Cys Pro Val Thr Ala Tyr Gln His Ser
        275                 280                 285

Phe Gln Val Glu Asn Gln Glu Leu Ser Arg Ala Arg Asp Ser Asp Gly
```

```
    290                 295                 300

Ala Glu Glu Asp Val Ala Leu Thr Ser Tyr Gly Thr Pro Ile Gln Pro
305                 310                 315                 320

Gln Thr Val Asp Pro Thr Gln Glu Cys Phe Ile Pro Gln Ala Lys Leu
                325                 330                 335

Ser Pro Gln Gln Asp Ala Gly Gly Val
            340                 345


<210> SEQ ID NO 46
<211> LENGTH: 117
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ala Trp Val Arg Gln Ala Pro Gly Lys Gly Leu Glu Trp Val
        35                  40                  45

Ala Ser Ile Ser Thr Gly Gly Val Asn Thr Tyr Tyr Arg Asp Ser Val
    50                  55                  60

Lys Ala Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Thr Gly Asp Tyr Phe Asp Tyr Trp Gly Gln Gly Thr Met
            100                 105                 110

Val Thr Val Ser Ser
        115


<210> SEQ ID NO 47
<211> LENGTH: 117
<212> TYPE: PRT
<213> ORGANISM: Artificial Sequence
<220> FEATURE:
<223> OTHER INFORMATION: Synthetic Construct

<400> SEQUENCE: 47

Glu Leu Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ala Trp Val Arg Gln Ala Pro Gly Lys Gly Leu Glu Trp Val
        35                  40                  45

Ala Ser Ile Ser Thr Gly Gly Val Asn Thr Tyr Tyr Arg Asp Ser Val
    50                  55                  60

Lys Ala Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Thr Gly Asp Tyr Phe Asp Tyr Trp Gly Gln Gly Thr Met
            100                 105                 110

Val Thr Val Ser Ser
        115
```

```
<210> SEQ ID NO 48
<211> LENGTH: 117
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ala Trp Val Arg Gln Ala Pro Gly Lys Gly Leu Glu Trp Val
        35                  40                  45

Ala Ser Ile Ser Thr Gly Gly Val Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Thr Gly Asp Tyr Phe Asp Tyr Trp Gly Gln Gly Thr Met
            100                 105                 110

Val Thr Val Ser Ser
        115


<210> SEQ ID NO 49
<211> LENGTH: 117
<212> TYPE: PRT
<213> ORGANISM: Artificial Sequence
<220> FEATURE:
<223> OTHER INFORMATION: Synthetic Construct

<400> SEQUENCE: 49

Glu Leu Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ala Trp Val Arg Gln Ala Pro Gly Lys Gly Leu Glu Trp Val
        35                  40                  45

Ala Ser Ile Ser Thr Gly Gly Val Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Thr Gly Asp Tyr Phe Asp Tyr Trp Gly Gln Gly Thr Met
            100                 105                 110

Val Thr Val Ser Ser
        115


<210> SEQ ID NO 50
<211> LENGTH: 111
<212> TYPE: PRT
<213> ORGANISM: Artificial Sequence
<220> FEATURE:
<223> OTHER INFORMATION: Synthetic Construct

<400> SEQUENCE: 50

Asp Ile Val Met Thr Gln Ser Pro Asp Ser Leu Ala Val Ser Leu Gly
```

```
1               5                   10                  15

Glu Arg Ala Thr Ile Asn Cys Arg Ala Ser Gln Ser Val Ser Ile Ser
            20                  25                  30

Gly Ile Asn Leu Met Asn Trp Tyr Gln Gln Lys Pro Gly Gln Gln Pro
        35                  40                  45

Lys Leu Leu Ile Tyr His Ala Ser Ile Leu Ala Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

Glu Ser Pro Leu Thr Phe Gly Gln Gly Thr Arg Leu Glu Ile Lys
            100                 105                 110


<210> SEQ ID NO 51
<211> LENGTH: 111
<212> TYPE: PRT
<213> ORGANISM: Artificial Sequence
<220> FEATURE:
<223> OTHER INFORMATION: Synthetic Construct

<400> SEQUENCE: 51

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Ile Ser
            20                  25                  30

Gly Ile Asn Leu Met Asn Trp Tyr Gln Gln Lys Pro Gly Gln Gln Pro
        35                  40                  45

Lys Leu Leu Ile Tyr His Ala Ser Ile Leu Ala Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

Glu Ser Pro Leu Thr Phe Gly Gln Gly Thr Arg Leu Glu Ile Lys
            100                 105                 110


<210> SEQ ID NO 52
<211> LENGTH: 111
<212> TYPE: PRT
<213> ORGANISM: Artificial Sequence
<220> FEATURE:
<223> OTHER INFORMATION: Synthetic Construct

<400> SEQUENCE: 52

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ile Ser
            20                  25                  30

Gly Ile Asn Leu Met Asn Trp Tyr Gln Gln Lys Pro Gly Gln Gln Pro
        35                  40                  45

Arg Leu Leu Ile Tyr His Ala Ser Ile Leu Ala Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Arg
                85                  90                  95
```

```
Glu Ser Pro Leu Thr Phe Gly Gln Gly Thr Arg Leu Glu Ile Lys
            100                 105                 110


<210> SEQ ID NO 53
<211> LENGTH: 111
<212> TYPE: PRT
<213> ORGANISM: Artificial Sequence
<220> FEATURE:
<223> OTHER INFORMATION: Synthetic Construct

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ile Ser
            20                  25                  30

Gly Ile Asn Leu Met Asn Trp Tyr Gln Gln Lys Pro Gly Gln Gln Pro
        35                  40                  45

Lys Leu Leu Ile Tyr His Ala Ser Ile Leu Ala Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Arg
                85                  90                  95

Glu Ser Pro Leu Thr Phe Gly Gln Gly Thr Arg Leu Glu Ile Lys
            100                 105                 110


<210> SEQ ID NO 54
<211> LENGTH: 111
<212> TYPE: PRT
<213> ORGANISM: Artificial Sequence
<220> FEATURE:
<223> OTHER INFORMATION: Synthetic Construct

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Gly Ile Asn Leu Met Asn Trp Tyr Gln Gln Lys Pro Gly Lys Gln Pro
        35                  40                  45

Lys Leu Leu Ile Tyr His Ala Ser Ile Leu Ala Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Thr Arg
                85                  90                  95

Glu Ser Pro Leu Thr Phe Gly Gln Gly Thr Arg Leu Glu Ile Lys
            100                 105                 110


<210> SEQ ID NO 55
<211> LENGTH: 111
<212> TYPE: PRT
<213> ORGANISM: Artificial Sequence
<220> FEATURE:
<223> OTHER INFORMATION: Synthetic Construct

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
```

```
            20                  25                  30

Gly Ile Asn Leu Met Asn Trp Tyr Gln Gln Lys Pro Gly Gln Gln Pro
        35                  40                  45

Lys Leu Leu Ile Tyr His Ala Ser Ile Leu Ala Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Thr Arg
                85                  90                  95

Glu Ser Pro Leu Thr Phe Gly Gln Gly Thr Arg Leu Glu Ile Lys
            100                 105                 110


<210> SEQ ID NO 56
<211> LENGTH: 116
<212> TYPE: PRT
<213> ORGANISM: Artificial Sequence
<220> FEATURE:
<223> OTHER INFORMATION: Synthetic Construct

<400> SEQUENCE: 56

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Asp Arg Gly Gly Leu Tyr Trp Gly Gln Gly Thr Met Val
            100                 105                 110

Thr Val Ser Ser
        115


<210> SEQ ID NO 57
<211> LENGTH: 116
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Thr Arg His Asp Arg Gly Gly Leu Tyr Trp Gly Gln Gly Thr Met Val
            100                 105                 110

Thr Val Ser Ser
        115


<210> SEQ ID NO 58
<211> LENGTH: 116
<212> TYPE: PRT
<213> ORGANISM: Artificial Sequence
<220> FEATURE:
<223> OTHER INFORMATION: Synthetic Construct

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Asp Arg Gly Gly Leu Tyr Trp Gly Gln Gly Thr Met Val
            100                 105                 110

Thr Val Ser Ser
        115


<210> SEQ ID NO 59
<211> LENGTH: 116
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Asp Arg Gly Gly Leu Tyr Trp Gly Gln Gly Thr Met Val
            100                 105                 110

Thr Val Ser Ser
        115


<210> SEQ ID NO 60
<211> LENGTH: 116
<212> TYPE: PRT
<213> ORGANISM: Artificial Sequence
```

<220> FEATURE:
<223> OTHER INFORMATION: Synthetic Construct

<400> SEQUENCE: 60

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Asp Arg Gly Gly Leu Tyr Trp Gly Gln Gly Thr Met Val
            100                 105                 110

Thr Val Ser Ser
        115
```

<210> SEQ ID NO 61
<211> LENGTH: 116
<212> TYPE: PRT
<213> ORGANISM: Artificial Sequence
<220> FEATURE:
<223> OTHER INFORMATION: Synthetic Construct

<400> SEQUENCE: 61

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Asp Arg Gly Gly Leu Tyr Trp Gly Gln Gly Thr Met Val
            100                 105                 110

Thr Val Ser Ser
        115
```

<210> SEQ ID NO 62
<211> LENGTH: 112
<212> TYPE: PRT
<213> ORGANISM: Artificial Sequence
<220> FEATURE:
<223> OTHER INFORMATION: Synthetic Construct

<400> SEQUENCE: 62

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30
```

```
Asn Gly Ile Thr Tyr Val Tyr Trp Tyr Leu Gln Lys Pro Gly Gln Ser
        35                  40                  45

Pro Gln Val Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Gly Gln Leu
                85                  90                  95

Leu Glu Asn Pro Tyr Thr Phe Gly Gln Gly Thr Lys Leu Glu Ile Lys
            100                 105                 110


<210> SEQ ID NO 63
<211> LENGTH: 112
<212> TYPE: PRT
<213> ORGANISM: Artificial Sequence
<220> FEATURE:
<223> OTHER INFORMATION: Synthetic Construct

<400> SEQUENCE: 63

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Val Tyr Trp Tyr Leu Gln Lys Pro Gly Lys Ser
        35                  40                  45

Pro Gln Val Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Gly Gln Leu
                85                  90                  95

Leu Glu Asn Pro Tyr Thr Phe Gly Gln Gly Thr Lys Leu Glu Ile Lys
            100                 105                 110


<210> SEQ ID NO 64
<211> LENGTH: 112
<212> TYPE: PRT
<213> ORGANISM: Artificial Sequence
<220> FEATURE:
<223> OTHER INFORMATION: Synthetic Construct

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Val Tyr Trp Tyr Leu Gln Lys Pro Gly Gln Ser
        35                  40                  45

Pro Gln Leu Leu Ile Tyr Arg Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Gly Gln Leu
                85                  90                  95

Leu Glu Asn Pro Tyr Thr Phe Gly Gln Gly Thr Lys Leu Glu Ile Lys
            100                 105                 110


<210> SEQ ID NO 65
```

<211> LENGTH: 112
<212> TYPE: PRT
<213> ORGANISM: Artificial Sequence
<220> FEATURE:
<223> OTHER INFORMATION: Synthetic Construct

<400> SEQUENCE: 65

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Lys Ser Leu Leu His Ser
            20                  25                  30

Asn Gly Ile Thr Tyr Val Tyr Trp Tyr Gln Gln Lys Pro Gly Gln Pro
        35                  40                  45

Pro Lys Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr His Cys Gly Gln Leu
                85                  90                  95

Leu Glu Asn Pro Tyr Thr Phe Gly Gln Gly Thr Lys Leu Glu Ile Lys
            100                 105                 110
```

<210> SEQ ID NO 66
<211> LENGTH: 112
<212> TYPE: PRT
<213> ORGANISM: Artificial Sequence
<220> FEATURE:
<223> OTHER INFORMATION: Synthetic Construct

<400> SEQUENCE: 66

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Lys Ser Leu Leu His Ser
            20                  25                  30

Asn Gly Ile Thr Tyr Val Tyr Trp Tyr Gln Gln Lys Pro Gly Gln Ala
        35                  40                  45

Pro Arg Leu Leu Ile Tyr Arg Met Ser Asn Leu Ala Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr His Cys Gly Gln Leu
                85                  90                  95

Leu Glu Asn Pro Tyr Thr Phe Gly Gln Gly Thr Lys Leu Glu Ile Lys
            100                 105                 110
```

<210> SEQ ID NO 67
<211> LENGTH: 214
<212> TYPE: PRT
<213> ORGANISM: Artificial Sequence
<220> FEATURE:
<223> OTHER INFORMATION: Synthetic Construct

<400> SEQUENCE: 67

```
Asp Ile Gln Leu Thr Gln Ser Pro His Ser Leu Ser Ala Ser Leu Gly
1               5                   10                  15

Glu Thr Val Ser Ile Glu Cys Leu Ala Ser Glu Gly Ile Ser Asn Tyr
            20                  25                  30

Leu Ala Trp Phe His Gln Lys Pro Gly Lys Ser Pro Gln Leu Leu Ile
        35                  40                  45
```

```
Tyr Tyr Ala Ser Ser Leu Gln Asp Gly Val Pro Ser Arg Phe Ser Gly
    50                  55                  60

Ser Gly Ser Gly Thr Gln Tyr Ser Leu Lys Ile Ser Asn Met Gln Pro
65                  70                  75                  80

Glu Asp Glu Gly Val Tyr Tyr Cys Gln Gln Gly Tyr Lys Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 68
<211> LENGTH: 232
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190
```

```
Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 69
<211> LENGTH: 452
<212> TYPE: PRT
<213> ORGANISM: Artificial Sequence
<220> FEATURE:
<223> OTHER INFORMATION: Synthetic Construct

<400> SEQUENCE: 69

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Thr Asn Phe
            20                  25                  30

Tyr Met Ala Trp Val Arg Gln Ala Pro Thr Lys Ala Leu Glu Trp Val
        35                  40                  45

Ala Ser Ile Asn Thr Gly Gly Gly Tyr Thr Tyr Tyr Arg Asp Ser Val
    50                  55                  60

Lys Gly Arg Phe Thr Val Ser Arg Asp Asn Thr Arg Ser Thr Leu Tyr
65                  70                  75                  80

Leu Gln Met Asp Ser Leu Arg Ser Glu Glu Thr Ala Thr Tyr Tyr Cys
                85                  90                  95

Ala Arg His Leu Thr Tyr Tyr Gly Arg Tyr Tyr Tyr Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Glu Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Glu Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Ala Leu Gly Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 70
<211> LENGTH: 677
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Thr Asn Phe
            20                  25                  30

Tyr Met Ala Trp Val Arg Gln Ala Pro Thr Lys Ala Leu Glu Trp Val
        35                  40                  45

Ala Ser Ile Asn Thr Gly Gly Gly Tyr Thr Tyr Tyr Arg Asp Ser Val
    50                  55                  60

Lys Gly Arg Phe Thr Val Ser Arg Asp Asn Thr Arg Ser Thr Leu Tyr
65                  70                  75                  80

Leu Gln Met Asp Ser Leu Arg Ser Glu Glu Thr Ala Thr Tyr Tyr Cys
                85                  90                  95

Ala Arg His Leu Thr Tyr Tyr Gly Arg Tyr Tyr Tyr Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Glu Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Glu Lys Val Glu Pro Lys Ser
    210                 215                 220
```

```
Cys Asp Gly Gly Gly Gly Ser Gly Gly Gly Gly Ser Gln Ala Val Val
225                 230                 235                 240

Thr Gln Glu Pro Ser Leu Thr Val Ser Pro Gly Gly Thr Val Thr Leu
                245                 250                 255

Thr Cys Gly Ser Ser Thr Gly Ala Val Thr Thr Ser Asn Tyr Ala Asn
            260                 265                 270

Trp Val Gln Glu Lys Pro Gly Gln Ala Phe Arg Gly Leu Ile Gly Gly
        275                 280                 285

Thr Asn Lys Arg Ala Pro Gly Thr Pro Ala Arg Phe Ser Gly Ser Leu
    290                 295                 300

Leu Gly Gly Lys Ala Ala Leu Thr Leu Ser Gly Ala Gln Pro Glu Asp
305                 310                 315                 320

Glu Ala Glu Tyr Tyr Cys Ala Leu Trp Tyr Ser Asn Leu Trp Val Phe
                325                 330                 335

Gly Gly Gly Thr Lys Leu Thr Val Leu Ser Ser Ala Ser Thr Lys Gly
            340                 345                 350

Pro Ser Val Phe Pro Leu Ala Pro Ser Ser Lys Ser Thr Ser Gly Gly
        355                 360                 365

Thr Ala Ala Leu Gly Cys Leu Val Lys Asp Tyr Phe Pro Glu Pro Val
    370                 375                 380

Thr Val Ser Trp Asn Ser Gly Ala Leu Thr Ser Gly Val His Thr Phe
385                 390                 395                 400

Pro Ala Val Leu Gln Ser Ser Gly Leu Tyr Ser Leu Ser Ser Val Val
                405                 410                 415

Thr Val Pro Ser Ser Ser Leu Gly Thr Gln Thr Tyr Ile Cys Asn Val
            420                 425                 430

Asn His Lys Pro Ser Asn Thr Lys Val Asp Lys Lys Val Glu Pro Lys
        435                 440                 445

Ser Cys Asp Lys Thr His Thr Cys Pro Pro Cys Pro Ala Pro Glu Ala
    450                 455                 460

Ala Gly Gly Pro Ser Val Phe Leu Phe Pro Pro Lys Pro Lys Asp Thr
465                 470                 475                 480

Leu Met Ile Ser Arg Thr Pro Glu Val Thr Cys Val Val Val Asp Val
                485                 490                 495

Ser His Glu Asp Pro Glu Val Lys Phe Asn Trp Tyr Val Asp Gly Val
            500                 505                 510

Glu Val His Asn Ala Lys Thr Lys Pro Arg Glu Glu Gln Tyr Asn Ser
        515                 520                 525

Thr Tyr Arg Val Val Ser Val Leu Thr Val Leu His Gln Asp Trp Leu
    530                 535                 540

Asn Gly Lys Glu Tyr Lys Cys Lys Val Ser Asn Lys Ala Leu Gly Ala
545                 550                 555                 560

Pro Ile Glu Lys Thr Ile Ser Lys Ala Lys Gly Gln Pro Arg Glu Pro
                565                 570                 575

Gln Val Tyr Thr Leu Pro Pro Cys Arg Asp Glu Leu Thr Lys Asn Gln
            580                 585                 590

Val Ser Leu Trp Cys Leu Val Lys Gly Phe Tyr Pro Ser Asp Ile Ala
        595                 600                 605

Val Glu Trp Glu Ser Asn Gly Gln Pro Glu Asn Asn Tyr Lys Thr Thr
    610                 615                 620

Pro Pro Val Leu Asp Ser Asp Gly Ser Phe Phe Leu Tyr Ser Lys Leu
625                 630                 635                 640

Thr Val Asp Lys Ser Arg Trp Gln Gln Gly Asn Val Phe Ser Cys Ser
```

```
                645                 650                 655

Val Met His Glu Ala Leu His Asn His Tyr Thr Gln Lys Ser Leu Ser
            660                 665                 670

Leu Ser Pro Gly Lys
        675


<210> SEQ ID NO 71
<211> LENGTH: 214
<212> TYPE: PRT
<213> ORGANISM: Artificial Sequence
<220> FEATURE:
<223> OTHER INFORMATION: Synthetic Construct

<400> SEQUENCE: 71

Asp Val Gln Met Thr Gln Ser Pro Tyr Asn Leu Ala Ala Ser Pro Gly
1               5                   10                  15

Glu Ser Val Ser Ile Asn Cys Lys Ala Ser Lys Ser Ile Ser Lys Tyr
            20                  25                  30

Leu Ala Trp Tyr Gln Gln Lys Pro Gly Lys Ala Asn Lys Leu Leu Ile
        35                  40                  45

Tyr Asp Gly Ser Thr Leu Gln Ser Gly Ile Pro Ser Arg Phe Ser Gly
    50                  55                  60

Ser Gly Ser Gly Thr Asp Phe Thr Leu Thr Ile Arg Ser Leu Glu Pro
65                  70                  75                  80

Glu Asp Phe Gly Leu Tyr Tyr Cys Gln Gln His Asn Glu Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 72
<211> LENGTH: 454
<212> TYPE: PRT
<213> ORGANISM: Artificial Sequence
<220> FEATURE:
<223> OTHER INFORMATION: Synthetic Construct

<400> SEQUENCE: 72

Gln Val Thr Leu Lys Glu Ser Gly Pro Gly Ile Leu Gln Pro Ser His
1               5                   10                  15

Thr Leu Ser Leu Thr Cys Ser Phe Ser Gly Phe Ser Leu Ser Thr Tyr
            20                  25                  30

Gly Met Gly Val Asn Trp Ile Arg Gln Pro Ser Gly Lys Gly Leu Glu
        35                  40                  45
```

```
Trp Leu Ala Ser Ile Trp Trp Asn Gly Asn Thr Tyr Asn Asn Pro Ser
    50                  55                  60

Leu Lys Ser Arg Leu Thr Val Ser Lys Asp Thr Ser Asn Asn Gln Ala
65                  70                  75                  80

Phe Leu Lys Val Thr Ser Val Asp Thr Ala Asp Thr Ala Thr Tyr Tyr
                85                  90                  95

Cys Val His Thr Arg Gly Ile Ile Arg Gly Arg Gly Leu Phe Phe Asp
            100                 105                 110

Tyr Trp Gly Gln Gly Val Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Gly
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 73
<211> LENGTH: 441
<212> TYPE: PRT
<213> ORGANISM: Artificial Sequence
<220> FEATURE:
<223> OTHER INFORMATION: Synthetic Construct

<400> SEQUENCE: 73

Gln Thr Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Leu Trp Val Phe Gly Gly Gly Thr Lys Leu Thr Val Leu Ser Ser Ala
100 105 110

Ser Thr Lys Gly Pro Ser Val Phe Pro Leu Ala Pro Ser Ser Lys Ser
115 120 125

Thr Ser Gly Gly Thr Ala Ala Leu Gly Cys Leu Val Lys Asp Tyr Phe
130 135 140

Pro Glu Pro Val Thr Val Ser Trp Asn Ser Gly Ala Leu Thr Ser Gly
145 150 155 160

Val His Thr Phe Pro Ala Val Leu Gln Ser Ser Gly Leu Tyr Ser Leu
165 170 175

Ser Ser Val Val Thr Val Pro Ser Ser Ser Leu Gly Thr Gln Thr Tyr
180 185 190

Ile Cys Asn Val Asn His Lys Pro Ser Asn Thr Lys Val Asp Lys Lys
195 200 205

Val Glu Pro Lys Ser Cys Asp Lys Thr His Thr Cys Pro Pro Cys Pro
210 215 220

Ala Pro Glu Ala Ala Gly Gly Pro Ser Val Phe Leu Phe Pro Pro Lys
225 230 235 240

Pro Lys Asp Thr Leu Met Ile Ser Arg Thr Pro Glu Val Thr Cys Val
245 250 255

Val Val Asp Val Ser His Glu Asp Pro Glu Val Lys Phe Asn Trp Tyr
260 265 270

Val Asp Gly Val Glu Val His Asn Ala Lys Thr Lys Pro Arg Glu Glu
275 280 285

Gln Tyr Asn Ser Thr Tyr Arg Val Val Ser Val Leu Thr Val Leu His
290 295 300

Gln Asp Trp Leu Asn Gly Lys Glu Tyr Lys Cys Lys Val Ser Asn Lys
305 310 315 320

Ala Leu Gly Ala Pro Ile Glu Lys Thr Ile Ser Lys Ala Lys Gly Gln
325 330 335

Pro Arg Glu Pro Gln Val Tyr Thr Leu Pro Pro Cys Arg Asp Glu Leu
340 345 350

Thr Lys Asn Gln Val Ser Leu Trp Cys Leu Val Lys Gly Phe Tyr Pro
355 360 365

Ser Asp Ile Ala Val Glu Trp Glu Ser Asn Gly Gln Pro Glu Asn Asn

```
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 74
<211> LENGTH: 232
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 75
<211> LENGTH: 448
<212> TYPE: PRT
<213> ORGANISM: Artificial Sequence
<220> FEATURE:
<223> OTHER INFORMATION: Synthetic Construct

<400> SEQUENCE: 75
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Asn Ser Asp Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Leu Arg Val Ala Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
```

```
            420                 425                 430

Leu His Asn His Tyr Thr Gln Lys Ser Leu Ser Leu Ser Pro Gly Lys
        435                 440                 445


<210> SEQ ID NO 76
<211> LENGTH: 214
<212> TYPE: PRT
<213> ORGANISM: Artificial Sequence
<220> FEATURE:
<223> OTHER INFORMATION: Synthetic Construct

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Ala Thr His
            20                  25                  30

Val Gly Trp Tyr Gln Gln Lys Pro Gly Lys Ala Pro Lys Arg Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Tyr Asn Arg Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 77
<211> LENGTH: 445
<212> TYPE: PRT
<213> ORGANISM: Artificial Sequence
<220> FEATURE:
<223> OTHER INFORMATION: Synthetic Construct

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Ala Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Glu Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Glu Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 78
<211> LENGTH: 215
<212> TYPE: PRT
<213> ORGANISM: Artificial Sequence
<220> FEATURE:
<223> OTHER INFORMATION: Synthetic Construct

<400> SEQUENCE: 78

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Tyr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Arg Trp Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Arg Lys Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 79
<211> LENGTH: 670
<212> TYPE: PRT
<213> ORGANISM: Artificial Sequence
<220> FEATURE:
<223> OTHER INFORMATION: Synthetic Construct

<400> SEQUENCE: 79

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser Ala Ser Thr Lys Gly Pro Ser Val Phe Pro Leu Ala Pro
        115                 120                 125
```

```
Ser Ser Lys Ser Thr Ser Gly Gly Thr Ala Ala Leu Gly Cys Leu Val
    130                 135                 140

Glu Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Glu Lys Val Glu Pro Lys Ser Cys Asp Gly Gly Gly Gly Ser
    210                 215                 220

Gly Gly Gly Gly Ser Gln Ala Val Val Thr Gln Glu Pro Ser Leu Thr
225                 230                 235                 240

Val Ser Pro Gly Gly Thr Val Thr Leu Thr Cys Gly Ser Ser Thr Gly
                245                 250                 255

Ala Val Thr Thr Ser Asn Tyr Ala Asn Trp Val Gln Glu Lys Pro Gly
            260                 265                 270

Gln Ala Phe Arg Gly Leu Ile Gly Gly Thr Asn Lys Arg Ala Pro Gly
        275                 280                 285

Thr Pro Ala Arg Phe Ser Gly Ser Leu Leu Gly Gly Lys Ala Ala Leu
    290                 295                 300

Thr Leu Ser Gly Ala Gln Pro Glu Asp Glu Ala Glu Tyr Tyr Cys Ala
305                 310                 315                 320

Leu Trp Tyr Ser Asn Leu Trp Val Phe Gly Gly Gly Thr Lys Leu Thr
                325                 330                 335

Val Leu Ser Ser Ala Ser Thr Lys Gly Pro Ser Val Phe Pro Leu Ala
            340                 345                 350

Pro Ser Ser Lys Ser Thr Ser Gly Gly Thr Ala Ala Leu Gly Cys Leu
        355                 360                 365

Val Lys Asp Tyr Phe Pro Glu Pro Val Thr Val Ser Trp Asn Ser Gly
    370                 375                 380

Ala Leu Thr Ser Gly Val His Thr Phe Pro Ala Val Leu Gln Ser Ser
385                 390                 395                 400

Gly Leu Tyr Ser Leu Ser Ser Val Val Thr Val Pro Ser Ser Ser Leu
                405                 410                 415

Gly Thr Gln Thr Tyr Ile Cys Asn Val Asn His Lys Pro Ser Asn Thr
            420                 425                 430

Lys Val Asp Lys Lys Val Glu Pro Lys Ser Cys Asp Lys Thr His Thr
        435                 440                 445

Cys Pro Pro Cys Pro Ala Pro Glu Ala Ala Gly Gly Pro Ser Val Phe
    450                 455                 460

Leu Phe Pro Pro Lys Pro Lys Asp Thr Leu Met Ile Ser Arg Thr Pro
465                 470                 475                 480

Glu Val Thr Cys Val Val Val Asp Val Ser His Glu Asp Pro Glu Val
                485                 490                 495

Lys Phe Asn Trp Tyr Val Asp Gly Val Glu Val His Asn Ala Lys Thr
            500                 505                 510

Lys Pro Arg Glu Glu Gln Tyr Asn Ser Thr Tyr Arg Val Val Ser Val
        515                 520                 525

Leu Thr Val Leu His Gln Asp Trp Leu Asn Gly Lys Glu Tyr Lys Cys
    530                 535                 540

Lys Val Ser Asn Lys Ala Leu Gly Ala Pro Ile Glu Lys Thr Ile Ser
```

```
545                 550                 555                 560

Lys Ala Lys Gly Gln Pro Arg Glu Pro Gln Val Tyr Thr Leu Pro Pro
                565                 570                 575

Cys Arg Asp Glu Leu Thr Lys Asn Gln Val Ser Leu Trp Cys Leu Val
            580                 585                 590

Lys Gly Phe Tyr Pro Ser Asp Ile Ala Val Glu Trp Glu Ser Asn Gly
        595                 600                 605

Gln Pro Glu Asn Asn Tyr Lys Thr Thr Pro Pro Val Leu Asp Ser Asp
    610                 615                 620

Gly Ser Phe Phe Leu Tyr Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655

Asn His Tyr Thr Gln Lys Ser Leu Ser Leu Ser Pro Gly Lys
            660                 665                 670


<210> SEQ ID NO 80
<211> LENGTH: 232
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 81
<211> LENGTH: 107
<212> TYPE: PRT
<213> ORGANISM: Artificial Sequence
<220> FEATURE:
<223> OTHER INFORMATION: Synthetic Construct

<400> SEQUENCE: 81

```
Asp Ile Gln Leu Thr Gln Ser Pro His Ser Leu Ser Ala Ser Leu Gly
1               5                   10                  15

Glu Thr Val Ser Ile Glu Cys Leu Ala Ser Glu Gly Ile Ser Asn Tyr
            20                  25                  30

Leu Ala Trp Phe His Gln Lys Pro Gly Lys Ser Pro Gln Leu Leu Ile
        35                  40                  45

Tyr Tyr Ala Ser Ser Leu Gln Asp Gly Val Pro Ser Arg Phe Ser Gly
    50                  55                  60

Ser Gly Ser Gly Thr Gln Tyr Ser Leu Lys Ile Ser Asn Met Gln Pro
65                  70                  75                  80

Glu Asp Glu Gly Val Tyr Tyr Cys Gln Gln Gly Tyr Lys Tyr Pro Leu
                85                  90                  95

Thr Phe Gly Ser Gly Thr Lys Leu Glu Ile Lys
            100                 105
```

<210> SEQ ID NO 82
<211> LENGTH: 122
<212> TYPE: PRT
<213> ORGANISM: Artificial Sequence
<220> FEATURE:
<223> OTHER INFORMATION: Synthetic Construct

<400> SEQUENCE: 82

```
Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Thr Asn Phe
            20                  25                  30

Tyr Met Ala Trp Val Arg Gln Ala Pro Thr Lys Ala Leu Glu Trp Val
        35                  40                  45

Ala Ser Ile Asn Thr Gly Gly Gly Tyr Thr Tyr Tyr Arg Asp Ser Val
    50                  55                  60

Lys Gly Arg Phe Thr Val Ser Arg Asp Asn Thr Arg Ser Thr Leu Tyr
65                  70                  75                  80

Leu Gln Met Asp Ser Leu Arg Ser Glu Glu Thr Ala Thr Tyr Tyr Cys
                85                  90                  95

Ala Arg His Leu Thr Tyr Tyr Gly Arg Tyr Tyr Tyr Phe Asp Tyr Trp
            100                 105                 110

Gly Gln Gly Val Met Val Thr Val Ser Ser
        115                 120
```

<210> SEQ ID NO 83
<211> LENGTH: 10
<212> TYPE: PRT
<213> ORGANISM: Artificial Sequence
<220> FEATURE:
<223> OTHER INFORMATION: Synthetic Construct

<400> SEQUENCE: 83

```
Gly Phe Thr Phe Ser Lys Tyr Ala Met Ala
1               5                   10
```

<210> SEQ ID NO 84

<211> LENGTH: 17
<212> TYPE: PRT
<213> ORGANISM: Artificial Sequence
<220> FEATURE:
<223> OTHER INFORMATION: Synthetic Construct

<400> SEQUENCE: 84

Ser Ile Ser Thr Gly Gly Val Asn Thr Tyr Tyr Arg Asp Ser Val Lys
1 5 10 15

Ala

<210> SEQ ID NO 85
<211> LENGTH: 17
<212> TYPE: PRT
<213> ORGANISM: Artificial Sequence
<220> FEATURE:
<223> OTHER INFORMATION: Synthetic Construct

<400> SEQUENCE: 85

Ser Ile Ser Thr Gly Gly Val Asn Thr Tyr Tyr Ala Asp Ser Val Lys
1 5 10 15

Gly

<210> SEQ ID NO 86
<211> LENGTH: 8
<212> TYPE: PRT
<213> ORGANISM: Artificial Sequence
<220> FEATURE:
<223> OTHER INFORMATION: Synthetic Construct

<400> SEQUENCE: 86

His Thr Gly Asp Tyr Phe Asp Tyr
1 5

<210> SEQ ID NO 87
<211> LENGTH: 15
<212> TYPE: PRT
<213> ORGANISM: Artificial Sequence
<220> FEATURE:
<223> OTHER INFORMATION: Synthetic Construct

<400> SEQUENCE: 87

Arg Ala Ser Gln Ser Val Ser Ile Ser Gly Ile Asn Leu Met Asn
1 5 10 15

<210> SEQ ID NO 88
<211> LENGTH: 7
<212> TYPE: PRT
<213> ORGANISM: Artificial Sequence
<220> FEATURE:
<223> OTHER INFORMATION: Synthetic Construct

<400> SEQUENCE: 88

His Ala Ser Ile Leu Ala Ser
1 5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Gln Gln Thr Arg Glu Ser Pro Leu Thr
1 5

<210> SEQ ID NO 90
<211> LENGTH: 10
<212> TYPE: PRT
<213> ORGANISM: Artificial Sequence
<220> FEATURE:
<223> OTHER INFORMATION: Synthetic Construct

<400> SEQUENCE: 90

Gly Phe Ser Phe Ser Asn Tyr Gly Met Ala
1 5 10

<210> SEQ ID NO 91
<211> LENGTH: 17
<212> TYPE: PRT
<213> ORGANISM: Artificial Sequence
<220> FEATURE:
<223> OTHER INFORMATION: Synthetic Construct

<400> SEQUENCE: 91

Ser Ile Ser Thr Gly Gly Gly Asn Thr Tyr Tyr Arg Asp Ser Val Lys
1 5 10 15

Gly

<210> SEQ ID NO 92
<211> LENGTH: 17
<212> TYPE: PRT
<213> ORGANISM: Artificial Sequence
<220> FEATURE:
<223> OTHER INFORMATION: Synthetic Construct

<400> SEQUENCE: 92

Ser Ile Ser Thr Gly Gly Gly Asn Thr Tyr Tyr Ala Asp Ser Val Lys
1 5 10 15

Gly

<210> SEQ ID NO 93
<211> LENGTH: 7
<212> TYPE: PRT
<213> ORGANISM: Artificial Sequence
<220> FEATURE:
<223> OTHER INFORMATION: Synthetic Construct

<400> SEQUENCE: 93

His Asp Arg Gly Gly Leu Tyr
1 5

<210> SEQ ID NO 94
<211> LENGTH: 16
<212> TYPE: PRT
<213> ORGANISM: Artificial Sequence
<220> FEATURE:
<223> OTHER INFORMATION: Synthetic Construct

<400> SEQUENCE: 94

Arg Ser Ser Lys Ser Leu Leu His Ser Asn Gly Ile Thr Tyr Val Tyr
1 5 10 15

<210> SEQ ID NO 95
<211> LENGTH: 7
<212> TYPE: PRT
<213> ORGANISM: Artificial Sequence
<220> FEATURE:
<223> OTHER INFORMATION: Synthetic Construct

<400> SEQUENCE: 95

Arg Met Ser Asn Leu Ala Ser
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic Construct

<400> SEQUENCE: 96

Arg Met Ser Asn Arg Ala Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Construct

<400> SEQUENCE: 97

Gly Gln Leu Leu Glu Asn Pro Tyr Thr
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic Construct

<400> SEQUENCE: 98

Ser Tyr Ala Met Asn
1               5

<210> SEQ ID NO 99
<211> LENGTH: 19
<212> TYPE: PRT
<213> ORGANISM: Artificial Sequence
<220> FEATURE:
<223> OTHER INFORMATION: Synthetic Construct

<400> SEQUENCE: 99

Arg Ile Arg Ser Lys Tyr Asn Asn Tyr Ala Thr Tyr Tyr Ala Asp Ser
1               5                   10                  15

Val Lys Gly

<210> SEQ ID NO 100
<211> LENGTH: 14
<212> TYPE: PRT
<213> ORGANISM: Artificial Sequence
<220> FEATURE:
<223> OTHER INFORMATION: Synthetic Construct

<400> SEQUENCE: 100

His Thr Thr Phe Pro Ser Ser Tyr Val Ser Tyr Tyr Gly Tyr
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetic Construct

<400> SEQUENCE: 101

Gly Ser Ser Thr Gly Ala Val Thr Thr Ser Asn Tyr Ala Asn
1 5 10

<210> SEQ ID NO 102
<211> LENGTH: 7
<212> TYPE: PRT
<213> ORGANISM: Artificial Sequence
<220> FEATURE:
<223> OTHER INFORMATION: Synthetic Construct

<400> SEQUENCE: 102

Gly Thr Asn Lys Arg Ala Pro
1 5

<210> SEQ ID NO 103
<211> LENGTH: 9
<212> TYPE: PRT
<213> ORGANISM: Artificial Sequence
<220> FEATURE:
<223> OTHER INFORMATION: Synthetic Construct

<400> SEQUENCE: 103

Ala Leu Trp Tyr Ser Asn Leu Trp Val
1 5

<210> SEQ ID NO 104
<211> LENGTH: 125
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Gln Phe Ser Ser Tyr
20 25 30

Ala Met Asn Trp Val Arg Gln Ala Pro Gly Lys Gly Leu Glu Trp Val
35 40 45

Ser Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Val Arg His Thr Thr Phe Pro Ser Ser Tyr Val Ser Tyr Tyr
100 105 110

Gly Tyr Trp Gly Gln Gly Thr Leu Val Thr Val Ser Ser
115 120 125

<210> SEQ ID NO 105
<211> LENGTH: 109
<212> TYPE: PRT
<213> ORGANISM: Artificial Sequence
<220> FEATURE:
<223> OTHER INFORMATION: Synthetic Construct

<400> SEQUENCE: 105

Gln Ala Val Val Thr Gln Glu Pro Ser Leu Thr Val Ser Pro Gly Gly
1 5 10 15

Thr Val Thr Leu Thr Cys Gly Ser Ser Thr Gly Ala Val Thr Thr Ser

```
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105


<210> SEQ ID NO 106
<211> LENGTH: 10
<212> TYPE: PRT
<213> ORGANISM: Artificial Sequence
<220> FEATURE:
<223> OTHER INFORMATION: Synthetic Construct

<400> SEQUENCE: 106

Gly Tyr Ser Phe Thr Gly Tyr Thr Met Asn
1               5                   10


<210> SEQ ID NO 107
<211> LENGTH: 17
<212> TYPE: PRT
<213> ORGANISM: Artificial Sequence
<220> FEATURE:
<223> OTHER INFORMATION: Synthetic Construct

<400> SEQUENCE: 107

Leu Ile Asn Pro Tyr Lys Gly Val Ser Thr Tyr Asn Gln Lys Phe Lys
1               5                   10                  15

Asp


<210> SEQ ID NO 108
<211> LENGTH: 13
<212> TYPE: PRT
<213> ORGANISM: Artificial Sequence
<220> FEATURE:
<223> OTHER INFORMATION: Synthetic Construct

<400> SEQUENCE: 108

Ser Gly Tyr Tyr Gly Asp Ser Asp Trp Tyr Phe Asp Val
1               5                   10


<210> SEQ ID NO 109
<211> LENGTH: 11
<212> TYPE: PRT
<213> ORGANISM: Artificial Sequence
<220> FEATURE:
<223> OTHER INFORMATION: Synthetic Construct

<400> SEQUENCE: 109

Arg Ala Ser Gln Asp Ile Arg Asn Tyr Leu Asn
1               5                   10


<210> SEQ ID NO 110
<211> LENGTH: 7
<212> TYPE: PRT
<213> ORGANISM: Artificial Sequence
<220> FEATURE:
<223> OTHER INFORMATION: Synthetic Construct
```

<400> SEQUENCE: 110

```
Tyr Thr Ser Arg Leu Glu Ser
1               5
```

<210> SEQ ID NO 111
<211> LENGTH: 9
<212> TYPE: PRT
<213> ORGANISM: Artificial Sequence
<220> FEATURE:
<223> OTHER INFORMATION: Synthetic Construct

<400> SEQUENCE: 111

```
Gln Gln Gly Asn Thr Leu Pro Trp Thr
1               5
```

<210> SEQ ID NO 112
<211> LENGTH: 122
<212> TYPE: PRT
<213> ORGANISM: Artificial Sequence
<220> FEATURE:
<223> OTHER INFORMATION: Synthetic Construct

<400> SEQUENCE: 112

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120
```

<210> SEQ ID NO 113
<211> LENGTH: 106
<212> TYPE: PRT
<213> ORGANISM: Artificial Sequence
<220> FEATURE:
<223> OTHER INFORMATION: Synthetic Construct

<400> SEQUENCE: 113

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95
```

```
Thr Phe Gly Gln Gly Thr Lys Val Glu Ile
            100                 105


<210> SEQ ID NO 114
<211> LENGTH: 219
<212> TYPE: PRT
<213> ORGANISM: Artificial Sequence
<220> FEATURE:
<223> OTHER INFORMATION: Synthetic Construct

<400> SEQUENCE: 114

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Val Tyr Trp Tyr Leu Gln Lys Pro Gly Gln Ser
        35                  40                  45

Pro Gln Leu Leu Ile Tyr Arg Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Gly Gln Leu
                85                  90                  95

Leu Glu Asn Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 115
<211> LENGTH: 232
<212> TYPE: PRT
<213> ORGANISM: Artificial Sequence
<220> FEATURE:
<223> OTHER INFORMATION: Synthetic Construct

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gln Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
```

```
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Ser Tyr Val Ser Tyr Tyr
            100                 105                 110

Gly Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 116
<211> LENGTH: 446
<212> TYPE: PRT
<213> ORGANISM: Artificial Sequence
<220> FEATURE:
<223> OTHER INFORMATION: Synthetic Construct

<400> SEQUENCE: 116

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Asp Arg Gly Gly Leu Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 117
<211> LENGTH: 671
<212> TYPE: PRT
<213> ORGANISM: Artificial Sequence
<220> FEATURE:
<223> OTHER INFORMATION: Synthetic Construct

<400> SEQUENCE: 117

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Asp Arg Gly Gly Leu Tyr Trp Gly Gln Gly Thr Met Val
            100                 105                 110

Thr Val Ser Ser Ala Ser Thr Lys Gly Pro Ser Val Phe Pro Leu Ala
```

```
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
    290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
                325                 330                 335

Thr Val Leu Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430

Thr Lys Val Asp Lys Lys Val Glu Pro Lys Ser Cys Asp Lys Thr His
        435                 440                 445

Thr Cys Pro Pro Cys Pro Ala Pro Glu Ala Ala Gly Gly Pro Ser Val
    450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
        515                 520                 525

Val Leu Thr Val Leu His Gln Asp Trp Leu Asn Gly Lys Glu Tyr Lys
    530                 535                 540
```

```
Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Cys Arg Asp Glu Leu Thr Lys Asn Gln Val Ser Leu Trp Cys Leu
            580                 585                 590

Val Lys Gly Phe Tyr Pro Ser Asp Ile Ala Val Glu Trp Glu Ser Asn
        595                 600                 605

Gly Gln Pro Glu Asn Asn Tyr Lys Thr Thr Pro Pro Val Leu Asp Ser
    610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670


<210> SEQ ID NO 118
<211> LENGTH: 219
<212> TYPE: PRT
<213> ORGANISM: Artificial Sequence
<220> FEATURE:
<223> OTHER INFORMATION: Synthetic Construct

<400> SEQUENCE: 118

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Val Tyr Trp Tyr Leu Gln Lys Pro Gly Lys Ser
        35                  40                  45

Pro Gln Val Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Gly Gln Leu
                85                  90                  95

Leu Glu Asn Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 119
```

<211> LENGTH: 232
<212> TYPE: PRT
<213> ORGANISM: Artificial Sequence
<220> FEATURE:
<223> OTHER INFORMATION: Synthetic Construct

<400> SEQUENCE: 119

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gln Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Ser Tyr Val Ser Tyr Tyr
            100                 105                 110

Gly Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 120
<211> LENGTH: 446
<212> TYPE: PRT
<213> ORGANISM: Artificial Sequence
<220> FEATURE:
<223> OTHER INFORMATION: Synthetic Construct

<400> SEQUENCE: 120

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Thr Arg His Asp Arg Gly Gly Leu Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 121
<211> LENGTH: 671
<212> TYPE: PRT
<213> ORGANISM: Artificial Sequence
<220> FEATURE:
<223> OTHER INFORMATION: Synthetic Construct

<400> SEQUENCE: 121

```
Gln Val Gln Leu Val Glu Ser Gly Gly Gly Val Val Gln Pro Gly Arg
```

```
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Asp Arg Gly Gly Leu Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
    290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
                325                 330                 335

Thr Val Leu Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430
```

```
Thr Lys Val Asp Lys Lys Val Glu Pro Lys Ser Cys Asp Lys Thr His
        435                 440                 445

Thr Cys Pro Pro Cys Pro Ala Pro Glu Ala Ala Gly Gly Pro Ser Val
    450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
        515                 520                 525

Val Leu Thr Val Leu His Gln Asp Trp Leu Asn Gly Lys Glu Tyr Lys
    530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Cys Arg Asp Glu Leu Thr Lys Asn Gln Val Ser Leu Trp Cys Leu
            580                 585                 590

Val Lys Gly Phe Tyr Pro Ser Asp Ile Ala Val Glu Trp Glu Ser Asn
        595                 600                 605

Gly Gln Pro Glu Asn Asn Tyr Lys Thr Thr Pro Pro Val Leu Asp Ser
    610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670


<210> SEQ ID NO 122
<211> LENGTH: 218
<212> TYPE: PRT
<213> ORGANISM: Artificial Sequence
<220> FEATURE:
<223> OTHER INFORMATION: Synthetic Construct

<400> SEQUENCE: 122

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ile Ser
            20                  25                  30

Gly Ile Asn Leu Met Asn Trp Tyr Gln Gln Lys Pro Gly Gln Gln Pro
        35                  40                  45

Lys Leu Leu Ile Tyr His Ala Ser Ile Leu Ala Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Arg
                85                  90                  95

Glu Ser Pro Leu Thr Phe Gly Gln Gly Thr Arg Leu Glu Ile Lys Arg
            100                 105                 110

Thr Val Ala Ala Pro Ser Val Phe Ile Phe Pro Pro Ser Asp Arg Lys
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 123
<211> LENGTH: 232
<212> TYPE: PRT
<213> ORGANISM: Artificial Sequence
<220> FEATURE:
<223> OTHER INFORMATION: Synthetic Construct

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gln Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Ser Tyr Val Ser Tyr Tyr
            100                 105                 110

Gly Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 124
<211> LENGTH: 447
<212> TYPE: PRT
<213> ORGANISM: Artificial Sequence
```

<220> FEATURE:
<223> OTHER INFORMATION: Synthetic Construct

<400> SEQUENCE: 124

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Lys Tyr
20 25 30

Ala Met Ala Trp Val Arg Gln Ala Pro Gly Lys Gly Leu Glu Trp Val
35 40 45

Ala Ser Ile Ser Thr Gly Gly Val Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Thr His Thr Gly Asp Tyr Phe Asp Tyr Trp Gly Gln Gly Thr Met
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Glu Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Glu Lys Val Glu Pro Lys Ser Cys Asp Lys Thr His
210 215 220

Thr Cys Pro Pro Cys Pro Ala Pro Glu Ala Ala Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Gly Ala Pro Ile Glu Lys Thr Ile
325 330 335

Ser Lys Ala Lys Gly Gln Pro Arg Glu Pro Gln Val Cys Thr Leu Pro
340 345 350

Pro Ser Arg Asp Glu Leu Thr Lys Asn Gln Val Ser Leu Ser Cys Ala
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

```
Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 125
<211> LENGTH: 672
<212> TYPE: PRT
<213> ORGANISM: Artificial Sequence
<220> FEATURE:
<223> OTHER INFORMATION: Synthetic Construct

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ala Trp Val Arg Gln Ala Pro Gly Lys Gly Leu Glu Trp Val
        35                  40                  45

Ala Ser Ile Ser Thr Gly Gly Val Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Thr Gly Asp Tyr Phe Asp Tyr Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Gly Gly Gly
    210                 215                 220

Gly Ser Gly Gly Gly Gly Ser Gln Ala Val Val Thr Gln Glu Pro Ser
225                 230                 235                 240

Leu Thr Val Ser Pro Gly Gly Thr Val Thr Leu Thr Cys Gly Ser Ser
                245                 250                 255

Thr Gly Ala Val Thr Thr Ser Asn Tyr Ala Asn Trp Val Gln Glu Lys
            260                 265                 270

Pro Gly Gln Ala Phe Arg Gly Leu Ile Gly Gly Thr Asn Lys Arg Ala
        275                 280                 285

Pro Gly Thr Pro Ala Arg Phe Ser Gly Ser Leu Leu Gly Gly Lys Ala
    290                 295                 300

Ala Leu Thr Leu Ser Gly Ala Gln Pro Glu Asp Glu Ala Glu Tyr Tyr
305                 310                 315                 320
```

```
Cys Ala Leu Trp Tyr Ser Asn Leu Trp Val Phe Gly Gly Gly Thr Lys
                325                 330                 335

Leu Thr Val Leu Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Lys Asp Tyr Phe Pro Glu Pro Val Thr Val Ser Trp Asn
    370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Lys Lys Val Glu Pro Lys Ser Cys Asp Lys Thr
        435                 440                 445

His Thr Cys Pro Pro Cys Pro Ala Pro Glu Ala Ala Gly Gly Pro Ser
    450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala
            500                 505                 510

Lys Thr Lys Pro Arg Glu Glu Gln Tyr Asn Ser Thr Tyr Arg Val Val
        515                 520                 525

Ser Val Leu Thr Val Leu His Gln Asp Trp Leu Asn Gly Lys Glu Tyr
    530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Cys Arg Asp Glu Leu Thr Lys Asn Gln Val Ser Leu Trp Cys
            580                 585                 590

Leu Val Lys Gly Phe Tyr Pro Ser Asp Ile Ala Val Glu Trp Glu Ser
        595                 600                 605

Asn Gly Gln Pro Glu Asn Asn Tyr Lys Thr Thr Pro Pro Val Leu Asp
    610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Lys
            660                 665                 670


<210> SEQ ID NO 126
<211> LENGTH: 218
<212> TYPE: PRT
<213> ORGANISM: Artificial Sequence
<220> FEATURE:
<223> OTHER INFORMATION: Synthetic Construct

<400> SEQUENCE: 126

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ile Ser
            20                  25                  30

Gly Ile Asn Leu Met Asn Trp Tyr Gln Gln Lys Pro Gly Gln Gln Pro
        35                  40                  45

Arg Leu Leu Ile Tyr His Ala Ser Ile Leu Ala Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Arg
                85                  90                  95

Glu Ser Pro Leu Thr Phe Gly Gln Gly Thr Arg Leu Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 127
<211> LENGTH: 232
<212> TYPE: PRT
<213> ORGANISM: Artificial Sequence
<220> FEATURE:
<223> OTHER INFORMATION: Synthetic Construct

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gln Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Ser Tyr Val Ser Tyr Tyr
            100                 105                 110

Gly Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160
```

```
Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 128
<211> LENGTH: 447
<212> TYPE: PRT
<213> ORGANISM: Artificial Sequence
<220> FEATURE:
<223> OTHER INFORMATION: Synthetic Construct

<400> SEQUENCE: 128

```
Glu Leu Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ala Trp Val Arg Gln Ala Pro Gly Lys Gly Leu Glu Trp Val
        35                  40                  45

Ala Ser Ile Ser Thr Gly Gly Val Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Thr Gly Asp Tyr Phe Asp Tyr Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 129
<211> LENGTH: 672
<212> TYPE: PRT
<213> ORGANISM: Artificial Sequence
<220> FEATURE:
<223> OTHER INFORMATION: Synthetic Construct

<400> SEQUENCE: 129

Glu Leu Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ala Trp Val Arg Gln Ala Pro Gly Lys Gly Leu Glu Trp Val
        35                  40                  45

Ala Ser Ile Ser Thr Gly Gly Val Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Thr Gly Asp Tyr Phe Asp Tyr Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Glu Lys Val Glu Pro Lys Ser Cys Asp Gly Gly Gly
    210                 215                 220

Gly Ser Gly Gly Gly Gly Ser Gln Ala Val Val Thr Gln Glu Pro Ser
225                 230                 235                 240

Leu Thr Val Ser Pro Gly Gly Thr Val Thr Leu Thr Cys Gly Ser Ser
                245                 250                 255

Thr Gly Ala Val Thr Thr Ser Asn Tyr Ala Asn Trp Val Gln Glu Lys
            260                 265                 270

Pro Gly Gln Ala Phe Arg Gly Leu Ile Gly Gly Thr Asn Lys Arg Ala
        275                 280                 285

Pro Gly Thr Pro Ala Arg Phe Ser Gly Ser Leu Leu Gly Gly Lys Ala
    290                 295                 300

Ala Leu Thr Leu Ser Gly Ala Gln Pro Glu Asp Glu Ala Glu Tyr Tyr
305                 310                 315                 320

Cys Ala Leu Trp Tyr Ser Asn Leu Trp Val Phe Gly Gly Gly Thr Lys
                325                 330                 335

Leu Thr Val Leu Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Lys Asp Tyr Phe Pro Glu Pro Val Thr Val Ser Trp Asn
    370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Lys Lys Val Glu Pro Lys Ser Cys Asp Lys Thr
        435                 440                 445

His Thr Cys Pro Pro Cys Pro Ala Pro Glu Ala Ala Gly Gly Pro Ser
    450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala
            500                 505                 510

Lys Thr Lys Pro Arg Glu Glu Gln Tyr Asn Ser Thr Tyr Arg Val Val
        515                 520                 525

Ser Val Leu Thr Val Leu His Gln Asp Trp Leu Asn Gly Lys Glu Tyr
    530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Cys Arg Asp Glu Leu Thr Lys Asn Gln Val Ser Leu Trp Cys
            580                 585                 590

Leu Val Lys Gly Phe Tyr Pro Ser Asp Ile Ala Val Glu Trp Glu Ser
        595                 600                 605

Asn Gly Gln Pro Glu Asn Asn Tyr Lys Thr Thr Pro Pro Val Leu Asp
    610                 615                 620
```

```
Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Lys
            660                 665                 670


<210> SEQ ID NO 130
<211> LENGTH: 219
<212> TYPE: PRT
<213> ORGANISM: Artificial Sequence
<220> FEATURE:
<223> OTHER INFORMATION: Synthetic Construct

<400> SEQUENCE: 130

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Val Tyr Trp Tyr Leu Gln Lys Pro Gly Lys Ser
        35                  40                  45

Pro Gln Val Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Gly Gln Leu
                85                  90                  95

Leu Glu Asn Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 131
<211> LENGTH: 229
<212> TYPE: PRT
<213> ORGANISM: Artificial Sequence
<220> FEATURE:
<223> OTHER INFORMATION: Synthetic Construct

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45
```

```
Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225
```

<210> SEQ ID NO 132
<211> LENGTH: 446
<212> TYPE: PRT
<213> ORGANISM: Artificial Sequence
<220> FEATURE:
<223> OTHER INFORMATION: Synthetic Construct

<400> SEQUENCE: 132

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Asp Arg Gly Gly Leu Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 133
<211> LENGTH: 669
<212> TYPE: PRT
<213> ORGANISM: Artificial Sequence
<220> FEATURE:
<223> OTHER INFORMATION: Synthetic Construct

<400> SEQUENCE: 133

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met Ala Trp Val Arg Gln Ala Pro Gly Lys Gly Leu Glu Trp Val
        35                  40                  45

Ala Ser Ile Ser Thr Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Thr Arg His Asp Arg Gly Gly Leu Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Asp Ile Gln Met Thr Gln Ser Pro Ser Ser
225                 230                 235                 240

Leu Ser Ala Ser Val Gly Asp Arg Val Thr Ile Thr Cys Arg Ala Ser
                245                 250                 255

Gln Asp Ile Arg Asn Tyr Leu Asn Trp Tyr Gln Gln Lys Pro Gly Lys
            260                 265                 270

Ala Pro Lys Leu Leu Ile Tyr Tyr Thr Ser Arg Leu Glu Ser Gly Val
        275                 280                 285

Pro Ser Arg Phe Ser Gly Ser Gly Ser Gly Thr Asp Tyr Thr Leu Thr
    290                 295                 300

Ile Ser Ser Leu Gln Pro Glu Asp Phe Ala Thr Tyr Tyr Cys Gln Gln
305                 310                 315                 320

Gly Asn Thr Leu Pro Trp Thr Phe Gly Gln Gly Thr Lys Val Glu Ile
                325                 330                 335

Lys Ser Ser Ala Ser Thr Lys Gly Pro Ser Val Phe Pro Leu Ala Pro
            340                 345                 350

Ser Ser Lys Ser Thr Ser Gly Gly Thr Ala Ala Leu Gly Cys Leu Val
        355                 360                 365

Lys Asp Tyr Phe Pro Glu Pro Val Thr Val Ser Trp Asn Ser Gly Ala
    370                 375                 380

Leu Thr Ser Gly Val His Thr Phe Pro Ala Val Leu Gln Ser Ser Gly
385                 390                 395                 400

Leu Tyr Ser Leu Ser Ser Val Val Thr Val Pro Ser Ser Ser Leu Gly
                405                 410                 415

Thr Gln Thr Tyr Ile Cys Asn Val Asn His Lys Pro Ser Asn Thr Lys
            420                 425                 430

Val Asp Lys Lys Val Glu Pro Lys Ser Cys Asp Lys Thr His Thr Cys
        435                 440                 445

Pro Pro Cys Pro Ala Pro Glu Ala Ala Gly Gly Pro Ser Val Phe Leu
    450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
                485                 490                 495

Phe Asn Trp Tyr Val Asp Gly Val Glu Val His Asn Ala Lys Thr Lys
            500                 505                 510
```

```
Pro Arg Glu Glu Gln Tyr Asn Ser Thr Tyr Arg Val Val Ser Val Leu
        515                 520                 525

Thr Val Leu His Gln Asp Trp Leu Asn Gly Lys Glu Tyr Lys Cys Lys
    530                 535                 540

Val Ser Asn Lys Ala Leu Gly Ala Pro Ile Glu Lys Thr Ile Ser Lys
545                 550                 555                 560

Ala Lys Gly Gln Pro Arg Glu Pro Gln Val Tyr Thr Leu Pro Pro Cys
                565                 570                 575

Arg Asp Glu Leu Thr Lys Asn Gln Val Ser Leu Trp Cys Leu Val Lys
            580                 585                 590

Gly Phe Tyr Pro Ser Asp Ile Ala Val Glu Trp Glu Ser Asn Gly Gln
        595                 600                 605

Pro Glu Asn Asn Tyr Lys Thr Thr Pro Pro Val Leu Asp Ser Asp Gly
    610                 615                 620

Ser Phe Phe Leu Tyr Ser Lys Leu Thr Val Asp Lys Ser Arg Trp Gln
625                 630                 635                 640

Gln Gly Asn Val Phe Ser Cys Ser Val Met His Glu Ala Leu His Asn
                645                 650                 655

His Tyr Thr Gln Lys Ser Leu Ser Leu Ser Pro Gly Lys
            660                 665


<210> SEQ ID NO 134
<211> LENGTH: 16
<212> TYPE: PRT
<213> ORGANISM: Artificial Sequence
<220> FEATURE:
<223> OTHER INFORMATION: Synthetic Construct

<400> SEQUENCE: 134

Asp Ala Phe Asp Ile Trp Gly Gln Gly Thr Met Val Thr Val Ser Ser
1               5                   10                  15


<210> SEQ ID NO 135
<211> LENGTH: 12
<212> TYPE: PRT
<213> ORGANISM: Artificial Sequence
<220> FEATURE:
<223> OTHER INFORMATION: Synthetic Construct

<400> SEQUENCE: 135

Ile Thr Phe Gly Gln Gly Thr Arg Leu Glu Ile Lys
1               5                   10


<210> SEQ ID NO 136
<211> LENGTH: 12
<212> TYPE: PRT
<213> ORGANISM: Artificial Sequence
<220> FEATURE:
<223> OTHER INFORMATION: Synthetic Construct

<400> SEQUENCE: 136

Tyr Thr Phe Gly Gln Gly Thr Lys Leu Glu Ile Lys
1               5                   10
```

ANTIBODIES BINDING TO GPRC5D

CROSS REFERENCE TO RELATED APPLICATIONS

This application is a continuation of International Application No. PCT/EP2020/071182, filed Jul. 28, 2020, the entire contents of which is incorporated herein by reference, and which claims benefit to European Patent Application No. 19189255.3, filed Jul. 31, 2019.

SEQUENCE LISTING

The instant application contains a Sequence Listing which has been submitted electronically in ASCII format and is hereby incorporated by reference in its entirety. Said ASCII copy, created on Nov. 25, 2025, is named 51177-042001_Sequence_Listing_1_25_25_ST25.txt and is 216,230 bytes in size.

FIELD OF THE INVENTION

The present invention generally relates to antibodies that bind to GPRC5D, including bispecific antigen binding molecules e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

BACKGROUND

Affecting ~75.000 new patients every year in the EU and US, multiple myeloma (MM) is one of the most common hematological malignancies, which remains a high unmet medical need. Multiple myeloma is characterized by terminally differentiated plasma cells that secrete non-functional monoclonal immunoglobulins. In the short-term, the immunomodulatory drugs such as lenalidomide and pomalidomide, and proteasome inhibitors such as carfilzomib or bortezomib may remain the backbone of 1$^{st}$ line therapy for multiple myeloma (Moreau, P. and S. V. Rajkumar, multiple myeloma-translation of trial results into reality. Lancet, 2016. 388(10040): p. 111-3). However, these drugs do not target specifically the diseased tumor cells e.g. diseased plasma cells (PC). Efforts have been made towards selectively depleting the plasma cells in multiple myeloma. The lack of surface proteins that specifically mark plasma cells has hampered the development of antibodies or cellular therapies for multiple myeloma. So far, there are few cases of successful biologics, including daratumumab (anti-CD38) and elotuzumab (anti-CD319), with the caveat that these two molecules are not uniquely expressed by plasma cells. Therefore, novel targets from plasma cells in multiple myeloma were identified using RNA-sequencing, such as the G protein-coupled receptor class C group 5 member D (GPRC5D). that is differentially expressed by plasma cells in multiple myeloma versus plasma cells form healthy donors. It has been reported that GPRC5D is associated with prognosis and tumour load in multiple myeloma patients (Atamaniuk. J., et al., Overexpression of G protein-coupled receptor 5D in the bone marrow is associated with poor prognosis in patients with multiple myeloma. Eur J Clin Invest, 2012. 42(9): p. 953-60; and Cohen, Y., et al., GPRC5D is a promising marker for monitoring the tumour load and to target multiple myeloma cells. Hematology. 2013. 18(6): p. 348-51). GPRC5D is an orphan receptor with no known ligand and largely unknown biology in men in general and in cancer specifically. The GPRC5D encoding gene, which is mapped on chromosome 12p13.3, contains three exons and spans about 9.6 kb (Brauner-Osborne, H., et al., Cloning and characterization of a human orphan family C G-protein coupled receptor GPRC5D. Biochim Biophys Acta, 2001. 1518(3): p. 237-48). The large first exon encodes the seven-transmembrane domain. It has been shown that GPRC5D is involved in keratin formation in hair follicles in animals (Gao, Y., et al., Comparative Transcriptome Analysis of Fetal Skin Reveals Key Genes Related to Hair Follicle Morphogenesis in Cashmere Goats. PLoS One, 2016. 11(3): p. e0151118; and Inoue, S., T. Nambu, and T. Shimomura, The RAIG family member, GPRC5D, is associated with hard-keratinized structures. J Invest Dermatol, 2004. 122(3): p. 565-73). WO 2018/017786 A2 discloses GPRC5D-specific antibodies or antigen-binding fragments. Given that all standard-of-care treatments are not able to cure multiple myeloma patients, there is a clear need to develop potent and specific new therapies. One of this approaches includes antibodies that bind GPRC5D, in particular bispecific antibodies that bind GPRC5D on target cells and an activating T-cell antigen such as CD3 on T-cells. Upon simultaneous binding of such an antibody to both of its targets, a T-cell synapse will be formed, leading to activation of the (cytotoxic) T cell and subsequent lysis of the target cell.

The present invention provides novel antibodies, including bispecific antibodies that specifically bind human GPRC5D. Particularly, the T-cell bispecific antibodies according to the invention targeting GPRC5D have the potency to treat multiple myeloma.

SUMMARY OF THE INVENTION

The present inventors have developed bispecific antigen binding molecules that bind to GPRC5D and an activating T cell antigen, incorporating the novel GPRC5D antibody.

In a first aspect the present invention provides a bispecific antigen binding molecule, comprising (a) a first antigen binding moiety that binds to a first antigen, wherein the first antigen is GPRC5D and the first antigen binding moiety comprises a (i) a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; (ii) a heavy chain variable region (VH) comprising a heavy chain complementary determining region (HCDR) 1 of SEQ ID NO: 83, a HCDR 2 of SEQ ID NO: 85, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; (iii) a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; (iv) a heavy chain variable region (VH) comprising a heavy chain complementary determining region (HCDR) 1 of SEQ ID NO: 90, a HCDR 2 of SEQ ID NO: 91, and a HCDR 3 of SEQ ID NO:

93, and a light chain variable region (VL) comprising a light chain complementarity determining region (LCDR) 1 of SEQ ID NO: 94, a LCDR 2 of SEQ ID NO: 96 and a LCDR 3 of SEQ ID NO: 97; or (v) a heavy chain variable region (VH) comprising a heavy chain complementary determining region (HCDR) 1 of SEQ ID NO: 90, a HCDR 2 of SEQ ID NO: 92, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; and (b) a second antigen binding moiety that binds to a second antigen, wherein the second antigen is CD3 and the second antigen binding moiety comprises (i) a heavy chain variable region (VH) comprising a heavy chain complementary determining region (HCDR) 1 of SEQ ID NO: 29, a HCDR 2 of SEQ ID NO: 30, and a HCDR 3 of SEQ ID NO: 31, and a light chain variable region (VL) comprising a light chain complementarity determining region (LCDR) 1 of SEQ ID NO: 32, a LCDR 2 of SEQ ID NO: 33 and a LCDR 3 of SEQ ID NO: 34; (i) a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; or (ii) a heavy chain variable region (VH) comprising a heavy chain complementary determining region (HCDR) 1 of SEQ ID NO: 106, a HCDR 2 of SEQ ID NO: 107, and a HCDR 3 of SEQ ID NO: 108, and a light chain variable region (VL) comprising a light chain complementarity determining region (LCDR) 1 of SEQ ID NO: 109, a LCDR 2 of SEQ ID NO: 110 and a LCDR 3 of SEQ ID NO: 111.

In another embodiment, (i) the VH of the first antigen binding moiety comprises an amino acid sequence that is at least about 95%, 96%, 97%, 98%, 99% or 100% identical to the sequence of SEQ ID NO: 13, and the VL of the first antigen binding moiety comprises an amino acid sequence that is at least about 95%, 96%, 97%, 98%, 99% or 100% identical to the amino acid sequence of SEQ ID NO: 14; or (ii) the VH of the first antigen binding moiety comprises an amino acid sequence that is at least about 95%, 96%, 97%, 98%, 99% or 100% identical to the sequence of SEQ ID NO: 15, and the VL of the first antigen binding moiety comprises an amino acid sequence that is at least about 95%, 96%, 97%, 98%, 99% or 100% identical to the amino acid sequence of SEQ ID NO: 16; or (iii) the VH of the first antigen binding moiety comprises an amino acid sequence that is at least about 95%, 96%, 97%, 98%, 99% or 100% identical to the sequence of SEQ ID NO: 48, and the VL of the first antigen binding moiety comprises an amino acid sequence that is at least about 95%, 96%, 97%, 98%, 99% or 100% identical to the amino acid sequence of SEQ ID NO: 53; or (iv) wherein the VH of the first antigen binding moiety comprises an amino acid sequence that is at least about 95%, 96%, 97%, 98%, 99% or 100% identical to the sequence of SEQ ID NO: 49, and wherein the VL of the first antigen binding moiety comprises an amino acid sequence that is at least about 95%, 96%, 97%, 98%, 99% or 100% identical to the amino acid sequence of SEQ ID NO: 52; or (v) the VH of the first antigen binding moiety comprises an amino acid sequence that is at least about 95%, 96%, 97%, 98%, 99% or 100% identical to the sequence of SEQ ID NO: 57, and the VL of the first antigen binding moiety comprises an amino acid sequence that is at least about 95%, 96%, 97%, 98%, 99% or 100% identical to the amino acid sequence of SEQ ID NO: 64; or (vi) the VH of the first antigen binding moiety comprises an amino acid sequence that is at least about 95%, 96%, 97%, 98%, 99% or 100% identical to the sequence of SEQ ID NO: 58, and the VL of the first antigen binding moiety comprises an amino acid sequence that is at least about 95%, 96%, 97%, 98%, 99% or 100% identical to the amino acid sequence of SEQ ID NO: 63. In another embodiment, the VH of the second antigen binding moiety comprises an amino acid sequence (i) that is at least about 95%, 96%, 97%, 98%, 99% or 100% identical to the amino acid sequence of SEQ ID NO: 35, and the VL of the second antigen binding moiety comprises an amino acid sequence that is at least about 95%, 96%, 97%, 98%, 99% or 100% identical to the amino acid sequence of SEQ ID NO: 36; (ii) that is at least about 95%, 96%, 97%, 98%, 99% or 100% identical to the amino acid sequence of SEQ ID NO: 104, and the VL of the second antigen binding moiety comprises an amino acid sequence that is at least about 95%, 96%, 97%, 98%, 99% or 100% identical to the amino acid sequence of SEQ ID NO: 105; or (iii) that is at least about 95%, 96%, 97%, 98%, 99% or 100% identical to the amino acid sequence of SEQ ID NO: 112, and the VL of the second antigen binding moiety comprises an amino acid sequence that is at least about 95%, 96%, 97%, 98%, 99% or 100% identical to the amino acid sequence of SEQ ID NO: 113.

In an embodiment, the first and/or the second antigen binding moiety is a Fab molecule. This means, either the first antigen binding moiety may be a Fab molecule, or the second antigen binding moiety may be a Fab molecule, or the first antigen binding moiety and the second antigen binding moiety may be Fab molecules. In another embodiment, the second antigen binding moiety is a Fab molecule wherein the variable domains VL and VH or the constant domains CL and CH1, particularly the variable domains VL and VH, of the Fab light chain and the Fab heavy chain are replaced by each other. In another embodiment, the first antigen binding moiety is a Fab molecule wherein in the constant domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index). In another embodiment, the first and the second antigen binding moiety are fused to each other, optionally via a peptide linker. In another embodiment, the first and the second antigen binding moiety are each a Fab molecule and wherein either (i) the second antigen binding moiety is fused at the C-terminus of the Fab heavy chain to the N-terminus of the Fab heavy chain of the first antigen binding moiety, or (ii) the first antigen binding moiety is fused at the C-terminus of the Fab heavy chain to the N-terminus of the Fab heavy chain of the second antigen binding moiety. In another embodiment, the bispecific antigen binding molecule comprises a third antigen binding moiety. In another embodiment, the third antigen moiety is identical to the first antigen binding moiety. In another embodiment, the bispecific antigen binding molecule comprises an Fc domain composed of a first and a second subunit. In another embodiment, the first, the second and, where present, the third antigen binding moiety are each a Fab molecule; and wherein either (i) the second antigen binding moiety is fused at the C-terminus of the Fab heavy chain to the N-terminus of the Fab heavy chain of the first antigen binding moiety and the first antigen binding moiety is fused at the C-terminus of the Fab heavy chain to the N-terminus of the first subunit of the Fc domain, or (ii) the first antigen binding moiety is fused at the C-terminus of the Fab heavy chain to the N-terminus of the Fab heavy chain of the second antigen binding moiety and the second antigen binding moiety is fused at the C-terminus of the Fab heavy chain to the N-terminus of the first subunit of the Fc domain; and wherein the third antigen binding moiety, where present, is fused at the C-terminus of the Fab heavy chain to the N-terminus of the second subunit of the Fc domain. In another embodiment, the Fc domain is an IgG Fc domain. In another embodiment, the Fc domain is an IgG1 Fc domain. In yet another embodiment, the Fc domain is a human Fc domain. In another embodiment, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. In another embodiment, the Fc domain comprises one or more amino acid substitution that reduces binding to an Fc receptor and/or effector function.

In another aspect, the invention provides one or more isolated polynucleotide encoding the bispecific antigen binding molecule as described herein. In a further aspect, the invention provides one or more vector, particularly expression vector, comprising the polynucleotide(s) as described herein. In another aspect, the invention provides a host cell comprising the polynucleotide(s) or the vector(s) as described herein.

In another aspect of the invention a method of producing a bispecific antigen binding molecule that binds to GPRC5D, comprising the steps of a) culturing the host cell as described herein under conditions suitable for the expression of the bispecific antigen binding molecule and b) optionally recovering the bispecific antigen binding molecule.

In another aspect, the invention provides a bispecific antigen binding molecule that binds to GPRC5D, produced by the method of claim 21.

In another aspect, the invention provides a pharmaceutical composition comprising the bispecific antigen binding molecule as described herein and a pharmaceutically acceptable carrier.

In another aspect, the invention provides a bispecific antigen binding molecule as disclosed herein or a pharmaceutical composition as disclosed herein for use as a medicament.

In another aspect, the invention provides a bispecific antigen binding molecule as disclosed herein or a pharmaceutical composition as disclosed herein for use in the treatment of a disease.

In another aspect, the invention provides a bispecific antigen binding molecule or pharmaceutical composition as disclosed herein, wherein the disease is cancer or an autoimmune disease.

In another aspect, the invention provides a bispecific antigen binding molecule or pharmaceutical composition as disclosed herein, wherein the disease is multiple myeloma.

In a further aspect, the invention provides use of a bispecific antigen binding molecule as discloser herein in the manufacture of a medicament for the treatment of a disease.

In another aspect the invention relates to a method of treating a disease, particularly cancer, more particularly multiple myeloma, in an individual, comprising administering to said individual a therapeutically effective amount of a composition comprising a bispecific antigen binding molecule as described herein in a pharmaceutically acceptable form. Alternatively, the disease is an autoimmune disease, such as systemic lupus erythematosus and/or rheumatoid arthritis. In any of the above embodiments the individual preferably is a mammal, particularly a human.

BRIEF DESCRIPTION OF THE DRAWINGS

FIG. 1A-FIG. 1Z. Exemplary configurations of the bispecific antigen binding molecules of the invention. (FIG. 1A, FIG. 1D) Illustration of the "1+1 CrossMab" molecule. (FIG. 1B, FIG. 1E) Illustration of the "2+1 IgG Crossfab" molecule with alternative order of Crossfab and Fab components ("inverted"). (FIG. 1C, FIG. 1F) Illustration of the "2+1 IgG Crossfab" molecule. (FIG. 1W, FIG. 1Y) Illustration of the "Fab-$(Crossfab)_2$" molecule. (FIG. 1X, FIG. 1Z) Illustration of the "$(Crossfab)_2$-Fab" molecule. Black dot: optional modification in the Fc domain promoting heterodimerization. ++, −−: amino acids of opposite charges optionally introduced in the CH1 and CL domains. Crossfab molecules are depicted as comprising an exchange of VH and VL regions, but may—in embodiments wherein no charge modifications are introduced in CH1 and CL domains—alternatively comprise an exchange of the CH1 and CL domains.

FIG. 7A-FIG. 7J. T-cell activation, as determined by up-regulation of CD25 on CD8+ T-cells, upon incubation of T-cells with increasing concentrations of GPRCSD-TCBs or negative control DP47-TCB in presence of AMO-1 (FIG. 7A), NCI-H929 (FIG. 7B), RPMI-8226 (FIG. 7C), L363 (FIG. 7D) and WSU-DLCL2 (FIG. 7E); and as determined by up-regulation of CD69 on CD8+ T-cells upon incubation of T-cells with increasing concentrations of GPRCSD-TCBs or negative control DP47-TCB in presence of either AMO-1 (FIG. 7F), NCI-H929 (FIG. 7G), RPMI-8226 (FIG. 7H), L363 (FIG. 7I) and WSU-DLCL2 (FIG. 7J).

FIG. 10A-FIG. 10G. T-cell mediated lysis of various Multiple Myeloma (MM) cell lines induced by different GPRC5D- or BCMA-targeting T-cell bispecific molecules (FIG. 10A-FIG. 10G) during 20 hours of co-incubation (E:T=10:1, human pan T cells). Depicted are duplicates with SD.

FIG. 13A-FIG. 13D. In vivo efficacy induced by different GPRC5D-targeting T-cell bispecific molecules (5F11-TCB in FIG. 13A; BCMA-TCB in FIG. 13B; B72-TCB in FIG. 13C; Vehicle in FIG. 13D), as depicted by tumor growth kinetics over time in a model of humanized NSG mice, engrafted with NCI-H929 tumor cells. Plotted are spider graphs with each line referring to a single mouse.

FIG. 14A-FIG. 14D. In vivo efficacy induced by different GPRC5D-targeting T-cell bispecific molecules (5F11-TCB in FIG. 14A; 5E11-TCB in FIG. 14B; B72-TCB in FIG. 14C; vehicle in FIG. 14D), as depicted by tumor growth kinetics over time in a model of humanized NSG mice, engrafted with OPM-2 tumor cells. Plotted are spider graphs with each line referring to a single mouse.

FIG. 17A-FIG. 17G. Jurkat-NFAT activation assay in presence of different GPRC5D×CD3 bispecific TCB molecules (FIG. 17A-FIG. 17G) versus untargeted control TCBs, as indicated.

FIG. 23C; 6623: FIG. 23D; 6624: FIG. 23E, 6625: FIG. 23F, 6626: FIG. 23G).

DETAILED DESCRIPTION OF THE INVENTION

Definitions

Figures 1A, 1B, 1C, 1D, 1E, 1F:
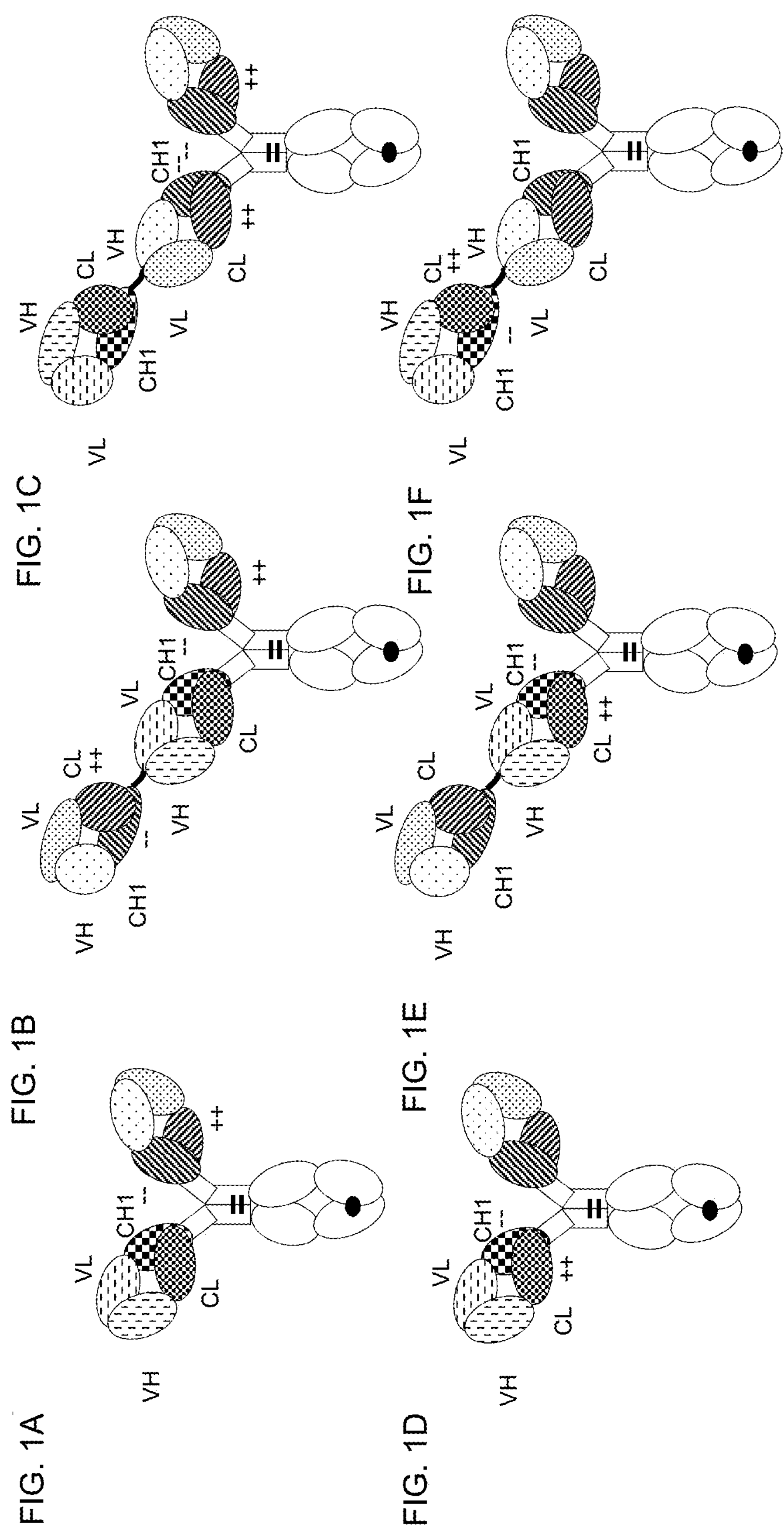

Terms are used herein as generally used in the art, unless otherwise defined in the following.

As used herein, the term "antigen binding molecule" refers in its broadest sense to a molecule that specifically binds an antigenic determinant. Examples of antigen binding molecules are immunoglobulins and derivatives, e.g. fragments, thereof.

The term "bispecific" means that the antigen binding molecule is able to specifically bind to at least two distinct antigenic determinants. Typically, a bispecific antigen binding molecule comprises two antigen binding sites, each of which is specific for a different antigenic determinant.

In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites; a Fab molecule typically has a single antigen binding site.

As used herein, the term "antigen binding moiety" refers to a polypeptide molecule that specifically binds to an antigenic determinant. In one embodiment, an antigen binding moiety is able to direct the entity to which it is attached (e.g. a second antigen binding moiety) to a target site, for example to a specific type of tumor cell bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: $\alpha$, $\delta$, $\varepsilon$, $\gamma$, or $\mu$. Useful light chain constant regions include any of the two isotypes: $\kappa$ and $\lambda$.

As used herein, the term "antigenic determinant" is synonymous with "antigen" and "epitope", and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g. GPRC5D, CD3) can be any native form of the proteins from any vertebrate source, including mammals such as primates (e.g. humans), non-human primates (e.g. cynomolgus monkeys) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants. An exemplary human protein useful as antigen is CD3, particularly the epsilon subunit of CD3 (see UniProt no. P07766 (version 185), NCBI RefSeq no. NP_000724.1, SEQ ID NO: 40 for the human sequence; or UniProt no. Q95LI5 (version 69), NCBI GenBank no. BAB71849.1, SEQ ID NO: 41 for the cynomolgus [*Macaca fascicularis*] sequence), or GPRC5D (see UniProt no. Q9NZD1 (version 115); NCBI RefSeq no. NP_061124.1, SEQ ID NO: 45 for the human sequence). In certain embodiments the antibody or bispecific antigen binding molecule of the invention binds to an epitope of CD3 or GPRC5D that is conserved among the CD3 or GPRC5D antigens from different species. In particular embodiments, the antibody or bispecific antigen binding molecule of the invention binds to human GPRC5D.

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed e.g. on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR.

In certain embodiments, an antigen binding moiety that binds to the antigen, or an antigen binding molecule comprising that antigen binding moiety, has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$M to $10^{-13}$ M, e.g., from $10^{-9}$ M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

An "activating T cell antigen" as used herein refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular embodiment the activating T cell antigen is CD3, particularly the epsilon subunit of CD3 (see UniProt no. P07766 (version 144), NCBI RefSeq no. NP_000724.1, SEQ ID NO: 40 for the human sequence; or UniProt no. Q95LI5 (version 49), NCBI GenBank no. BAB71849.1, SEQ ID NO: 41 for the cynomolgus [*Macaca fascicularis*] sequence).

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art and described herein.

A "target cell antigen" as used herein refers to an antigenic determinant presented on the surface of a target cell, for example a cell in a tumor such as a cancer cell or a cell of the tumor stroma. In a particular embodiment, the target cell antigen is GPRC5D, particularly human GPRC5D according to SEQ ID NO: 45.

As used herein, the terms "first", "second" or "third" with respect to Fab molecules etc., are used for convenience of distinguishing when there is more than one of each type of moiety. Use of these terms is not intended to confer a specific order or orientation of the bispecific antigen binding molecule unless explicitly so stated.

By "fused" is meant that the components (e.g. a Fab molecule and an Fc domain subunit) are linked by peptide bonds, either directly or via one or more peptide linkers.

A "Fab molecule" refers to a protein consisting of the VH and CH1 domain of the heavy chain (the "Fab heavy chain") and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The term "immunoglobulin molecule" refers to a protein having the structure of a naturally occurring antibody. For example, immunoglobulins of the IgG class are heterotetrameric glycoproteins of about 150,000 Daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called $\alpha$ (IgA), $\delta$ (IgD), $\varepsilon$ (IgE), $\gamma$ (IgG), or $\mu$ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an immunoglobulin may be assigned to one of two types, called kappa (u) and lambda (a), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

The term "monoclonal antibody" as used herein refers to an antibody obtained from a population of substantially homogeneous antibodies, i.e. the individual antibodies comprised in the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "isolated" antibody is one which has been separated from a component of its natural environment, i.e. that is not in its natural milieu. No particular level of purification is required. For example, an isolated antibody can be removed from its native or natural environment.

Recombinantly produced antibodies expressed in host cells are considered isolated for the purpose of the invention, as are native or recombinant antibodies which have been separated, fractionated, or partially or substantially purified by any suitable technique. As such, the antibodies and bispecific antigen binding molecules of the present invention are isolated. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al., *J. Chromatogr. B* 848:79-87 (2007). The terms "full length antibody," "intact antibody," and "whole antibody" are used herein interchangeably to refer to an antibody having a structure substantially similar to a native antibody structure.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 64446448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, $6^{th}$ ed., W.H. Freeman and Co., page 91 (2007). A single VH or VL domain may be sufficient to confer antigen-binding specificity. As used herein in connection with variable region sequences, "Kabat numbering" refers to the numbering system set forth by Kabat et al., *Sequences of Proteins of Immunological Interest,* 5th Ed. Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, MD (1991)) is used for the light chain constant domain CL of kappa and lambda isotype and the Kabat EU index numbering system (see pages 661-723) is used for the heavy chain constant domains (CH1, Hinge, CH2 and CH3), which is herein further clarified by referring to "numbering according to Kabat EU index" in this case.

The term "hypervariable region" or "HVR", as used herein, refers to each of the regions of an antibody variable domain which are hypervariable in sequence ("complementarity determining regions" or "CDRs"; CDRs of the heavy chain variable region/domain are abbreviated e.g. as HCDR1, HCDR2 and HCDR3; CDRs of the light chain variable region/domain are abbreviated e.g. as LCDR1, LCDR2 and LCDR3) and/or form structurally defined loops ("hypervariable loops") and/or contain the antigen-contacting residues ("antigen contacts"). Generally, antibodies comprise six HVRs; three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following order in VH (or VL): FR1-H1(L1)-FR2-H2(L2)-FR3-H3(L3)-FR4.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. In some embodiments, some FR residues in a humanized antibody are substituted with corresponding residues from a non-human antibody (e.g., the antibody from which the HVR residues are derived), e.g., to restore or improve antibody specificity or affinity. A "humanized form" of an antibody, e.g. of a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain embodiments, a human antibody is derived from a non-human transgenic mammal, for example a mouse, a rat, or a rabbit. In certain embodiments, a human antibody is derived from a hybridoma cell line. Antibodies or antibody fragments isolated from human antibody libraries are also considered human antibodies or human antibody fragments herein.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Amino acid sequences of heavy chains including Fc domains (or a subunit of an Fc domain as defined herein) are denoted herein without C-terminal glycine-lysine dipeptide if not indicated otherwise. In one embodiment of the invention, a heavy chain including a subunit of an Fc domain as specified herein, comprised in an antibody or bispecific antigen binding molecule according to the invention, comprises an additional C-terminal glycine-lysine dipeptide (G446 and K447, numbering according to EU index of Kabat). In one embodiment of the invention, a heavy chain including a subunit of an Fc domain as specified herein, comprised in an antibody or bispecific antigen binding molecule according to the invention, comprises an additional C-terminal glycine residue (G446, numbering according to EU index of Kabat). Compositions of the invention, such as the pharmaceutical compositions described herein, comprise a population of antibodies or bispecific antigen binding molecules of the invention. The population of antibodies or bispecific antigen binding molecules may comprise molecules having a full-length heavy chain and molecules having a cleaved variant heavy chain. The population of antibodies or bispecific antigen binding molecules may consist of a mixture of molecules having a full-length heavy chain and molecules having a cleaved variant heavy chain, wherein at least 50%, at least 60%, at least 70%, at least 80% or at least 90% of the antibodies or bispecific antigen binding molecules have a cleaved variant heavy chain. In one embodiment of the invention a composition comprising a population of antibodies or bispecific antigen binding molecules of the invention comprises an antibody or bispecific antigen binding molecule comprising a heavy chain including a subunit of an Fc domain as specified herein with an additional C-terminal glycine-lysine dipeptide (G446 and K447, numbering according to EU index of Kabat). In one embodiment of the invention a composition comprising a population of antibodies or bispecific antigen binding molecules of the invention comprises an antibody or bispecific antigen binding molecule comprising a heavy chain including a subunit of an Fc domain as specified herein with an additional C-terminal glycine residue (G446, numbering according to EU index of Kabat). In one embodiment of the invention such a composition comprises a population of antibodies or bispecific antigen binding molecules comprised of molecules comprising a heavy chain including a subunit of an Fc domain as specified herein; molecules comprising a heavy chain including a subunit of a Fc domain as specified herein with an additional C-terminal glycine residue (G446, numbering according to EU index of Kabat); and molecules comprising a heavy chain including a subunit of an Fc domain as specified herein with an additional C-terminal glycine-lysine dipeptide (G446 and K447, numbering according to EU index of Kabat). Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain. The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. For purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36, and is publicly available from http://fasta.bioch.virginia.edu/fasta_www2/fasta_down.shtml. Alternatively, a public server accessible at http://fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms.

Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

"Isolated polynucleotide (or nucleic acid) encoding [e.g. an antibody or bispecific antigen binding molecule of the invention]" refers to one or more polynucleotide molecules encoding antibody heavy and light chains (or fragments thereof), including such polynucleotide molecule(s) in a single vector or separate vectors, and such nucleic acid molecule(s) present at one or more locations in a host cell.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette comprises polynucleotide sequences that encode antibodies or bispecific antigen binding molecules of the invention or fragments thereof.

The term "vector" or "expression vector" refers to a DNA molecule that is used to introduce and direct the expression of a specific gene to which it is operably associated in a cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the cell, the ribonucleic acid molecule or protein that is encoded by the gene is produced by the cellular transcription and/or translation machinery. In one embodiment, the expression vector of the invention comprises an expression cassette that comprises polynucleotide sequences that encode antibodies or bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies or bispecific antigen binding molecules of the present invention.

Host cells include cultured cells, e.g. mammalian cultured cells, such as HEK cells, CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example, the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or bispecific antigen binding molecules of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

DETAILED DESCRIPTION OF THE EMBODIMENTS

The invention provides antibodies and bispecific antigen binding molecules that bind GPRC5D, particularly human GPRC5D. In addition, the molecules have other favorable properties for therapeutic application, e.g. with respect to efficacy and/or safety as well as producibility.

GPRC5D Antibody

In a first aspect the present invention provides an antibody that binds to GPRC5D, wherein the antibody comprises (i) a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; (ii) a heavy chain variable region (VH) comprising a heavy chain complementary determining region (HCDR) 1 of SEQ ID NO: 83, a HCDR 2 of SEQ ID NO: 85, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; (iii) a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; (iv) a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 96 and a LCDR 3 of SEQ ID NO: 97; or (v) a heavy chain variable region (VH) comprising a heavy chain complementary determining region (HCDR) 1 of SEQ ID NO: 90, a HCDR 2 of SEQ ID NO: 92, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97.

In some embodiments, the antibody is a humanized antibody. In one embodiment, the VH is a humanized VH and/or the VL is a humanized VL. In one embodiment, the antibody comprises CDRs as in any of the above embodiments, and further comprises an acceptor human framework, e.g. a human immunoglobulin framework or a human consensus framework.

In a particular embodiment, (i) the VH comprises an amino acid sequence that is at least about 95%, 96%, 97%, 98%, 99% or 100% identical to the sequence of SEQ ID NO: 13, and the VL comprises an amino acid sequence that is at least about 95%, 96%, 97%, 98%, 99% or 100% identical to the amino acid sequence of SEQ ID NO: 14; or (ii) the VH comprises an amino acid sequence that is at least about 95%, 96%, 97%, 98%, 99% or 100% identical to the sequence of SEQ ID NO: 15, and the VL comprises an amino acid sequence that is at least about 95%, 96%, 97%, 98%, 99% or 100% identical to the amino acid sequence of SEQ ID NO: 16; or (iii) the VH comprises an amino acid sequence that is at least about 95%, 96%, 97%, 98%, 99% or 100% identical to the sequence of SEQ ID NO: 48, and the VL comprises an amino acid sequence that is at least about 95%, 96%, 97%, 98%, 99% or 100% identical to the amino acid sequence of SEQ ID NO: 53; or (iv) the VH comprises an amino acid sequence that is at least about 95%, 96%, 97%, 98%, 99% or 100% identical to the sequence of SEQ ID NO: 49, and the VL comprises an amino acid sequence that is at least about 95%, 96%, 97%, 98%, 99% or 100% identical to the amino acid sequence of SEQ ID NO: 52; or (v) the VH comprises an amino acid sequence that is at least about 95%, 96%, 97%, 98%, 99% or 100% identical to the sequence of SEQ ID NO: 57, and the VL comprises an amino acid sequence that is at least about 95%, 96%, 97%, 98%, 99% or 100% identical to the amino acid sequence of SEQ ID NO: 64; or (vi) the VH comprises an amino acid sequence that is at least about 95%, 96%, 97%, 98%, 99% or 100% identical to the sequence of SEQ ID NO: 58, and the VL comprises an amino acid sequence that is at least about 95%, 96%, 97%, 98%, 99% or 100% identical to the amino acid sequence of SEQ ID NO: 63.

In a particular embodiment, the antibody comprises (i) a VH that is at least about 95%, 96%, 97%, 98%, 99% or 100% identical to an amino acid sequence of SEQ ID NO: 13, and a VL that is at least about 95%, 96%, 97%, 98%, 99% or 100% identical to the amino acid sequence of SEQ ID NO: 14; or (ii) a VH that is at least about 95%, 96%, 97%, 98%, 99% or 100% identical to the amino acid sequence of SEQ ID NO: 15, and a VL that is at least about 95%, 96%, 97%, 98%, 99% or 100% identical to the amino acid sequence of SEQ ID NO: 16; or (iii) a VH that is at least about 95%, 96%, 97%, 98%, 99% or 100% identical to the amino acid sequence of SEQ ID NO: 48, and the VL is at least about 95%, 96%, 97%, 98%, 99% or 100% identical to the amino acid sequence of SEQ ID NO: 53; or (iv) the VH is at least about 95%, 96%, 97%, 98%, 99% or 100% identical to the sequence of SEQ ID NO: 49, and the VL is at least about 95%, 96%, 97%, 98%, 99% or 100% identical to the amino acid sequence of SEQ ID NO: 52; or (v) the VH is at least about 95%, 96%, 97%, 98%, 99% or 100% identical to the sequence of SEQ ID NO: 57, and the VL is at least about 95%, 96%, 97%, 98%, 99% or 100% identical to the amino acid sequence of SEQ ID NO: 64; or (vi) the VH is at least about 95%, 96%, 97%, 98%, 99% or 100% identical to the sequence of SEQ ID NO: 58, and the VL is at least about 95%, 96%, 97%, 98%, 99% or 100% identical to the amino acid sequence of SEQ ID NO: 63.

In another embodiment, the antibody is an IgG, particularly an IgG1, antibody. In one embodiment, the antibody is a full-length antibody. In another embodiment, the antibody is an antibody fragment selected from the group of an Fv molecule, a scFv molecule, a Fab molecule, and a F(ab')2 molecule. In one embodiment, the antibody is a multispecific antibody.

In certain embodiments, a VH or VL sequence having at least 95%, 96%, 97%, 98%, or 99% identity contains substitutions (e.g., conservative substitutions), insertions, or deletions relative to the reference sequence, but an antibody comprising that sequence retains the ability to bind to GPRCSD. In certain embodiments, a total of 1 to 10 amino acids have been substituted, inserted and/or deleted in SEQ ID NO: 13 and/or a total of 1 to 10 amino acids have been substituted, inserted and/or deleted in SEQ ID NO: 14 and/or a total of 1 to 10 amino acids have been substituted, inserted and/or deleted in SEQ ID NO: 15 and/or a total of 1 to 10 amino acids have been substituted, inserted and/or deleted in SEQ ID NO: 16 and/or a total of 1 to 10 amino acids have been substituted, inserted and/or deleted in SEQ ID NO: 48 and/or a total of 1 to 10 amino acids have been substituted, inserted and/or deleted in SEQ ID NO: 53 and/or a total of 1 to 10 amino acids have been substituted, inserted and/or deleted in SEQ ID NO: 49 and/or a total of 1 to 10 amino acids have been substituted, inserted and/or deleted in SEQ ID NO: 52 and/or a total of 1 to 10 amino acids have been substituted, inserted and/or deleted in SEQ ID NO: 57 and/or a total of 1 to 10 amino acids have been substituted, inserted and/or deleted in SEQ ID NO: 64 and/or a total of 1 to 10 amino acids have been substituted, inserted and/or deleted in SEQ ID NO: 58 and/or a total of 1 to 10 amino acids have been substituted, inserted and/or deleted in SEQ ID NO: 63.

In certain embodiments, substitutions, insertions, or deletions occur in regions outside the HVRs (i.e., in the FRs). Optionally, the antibody comprises the VH sequence in SEQ ID NO: 13 and/or the VL sequence in SEQ ID NO: 14, including post-translational modifications of that sequence. Optionally, the antibody comprises the VH sequence in SEQ ID NO: 15 and/or the VL sequence in SEQ ID NO: 16, including post-translational modifications of that sequence. Optionally, the antibody comprises the VH sequence in SEQ ID NO: 448 and/or the VL sequence in SEQ ID NO: 53, including post-translational modifications of that sequence. Optionally, the antibody comprises the VH sequence in SEQ ID NO: 49 and/or the VL sequence in SEQ ID NO: 52, including post-translational modifications of that sequence. Optionally, the antibody comprises the VH sequence in SEQ ID NO: 57 and/or the VL sequence in SEQ ID NO: 64, including post-translational modifications of that sequence. Optionally, the antibody comprises the VH sequence in SEQ ID NO: 58 and/or the VL sequence in SEQ ID NO: 63, including post-translational modifications of that sequence.

In one embodiment, the antibody comprises a VH comprising an amino acid sequence selected from the group of SEQ ID NO: 13 and SEQ ID NO: 15, and a VL comprising the amino acid sequence of SEQ ID NO: 14.

In one embodiment, the antibody comprises a VH sequence selected from the group of SEQ ID NO: 13 and SEQ ID NO: 12, and the VL sequence of SEQ ID NO: 16.

In a particular embodiment, the antibody comprises a VH comprising the amino acid sequence of SEQ ID NO: 13 and a VL comprising the amino acid sequence of SEQ ID NO: 14. In a particular embodiment, the antibody comprises the VH sequence of SEQ ID NO: 13 and the VL sequence of SEQ ID NO: 14.

In a particular embodiment, the antibody comprises a VH comprising the amino acid sequence of SEQ ID NO: 15 and a VL comprising the amino acid sequence of SEQ ID NO: 16. In a particular embodiment, the antibody comprises the VH sequence of SEQ ID NO: 15 and the VL sequence of SEQ ID NO: 16.

In a particular embodiment, the antibody comprises a VH comprising the amino acid sequence of SEQ ID NO: 48 and a VL comprising the amino acid sequence of SEQ ID NO: 53. In a particular embodiment, the antibody comprises the VH sequence of SEQ ID NO: 48 and the VL sequence of SEQ ID NO: 53.

In a particular embodiment, the antibody comprises a VH comprising the amino acid sequence of SEQ ID NO: 49 and a VL comprising the amino acid sequence of SEQ ID NO: 52. In a particular embodiment, the antibody comprises the VH sequence of SEQ ID NO: 49 and the VL sequence of SEQ ID NO: 52.

In a particular embodiment, the antibody comprises a VH comprising the amino acid sequence of SEQ ID NO: 57 and a VL comprising the amino acid sequence of SEQ ID NO: 64. In a particular embodiment, the antibody comprises the VH sequence of SEQ ID NO: 57 and the VL sequence of SEQ ID NO: 64.

In a particular embodiment, the antibody comprises a VH comprising the amino acid sequence of SEQ ID NO: 58 and a VL comprising the amino acid sequence of SEQ ID NO: 63. In a particular embodiment, the antibody comprises the VH sequence of SEQ ID NO: 58 and the VL sequence of SEQ ID NO: 63.

In one embodiment, the antibody comprises a human constant region. In one embodiment, the antibody is an immunoglobulin molecule comprising a human constant region, particularly an IgG class immunoglobulin molecule comprising a human CH1, CH2, CH3 and/or CL domain.

Exemplary sequences of human constant domains are given in SEQ ID NOs 37 and 38 (human kappa and lambda CL domains, respectively) and SEQ ID NO: 39 (human IgG1 heavy chain constant domains CH1-CH2-CH3). In some embodiments, the antibody comprises a light chain constant region comprising an amino acid sequence that is at least about 95%, 96%, 97%, 98%, 99% or 100% identical to the amino acid sequence of SEQ ID NO: 37 or SEQ ID NO: 39, particularly the amino acid sequence of SEQ ID NO: 38. In some embodiments, the antibody comprises a heavy chain constant region comprising an amino acid sequence that is at least about 95%, 96%, 97%, 98%, 99% or 100% identical to the amino acid sequence of SEQ ID NO: 39.

Particularly, the heavy chain constant region may comprise amino acid mutations in the Fc domain as described herein.

In one embodiment, the antibody is a monoclonal antibody.

In one embodiment, the antibody is an IgG, particularly an $IgG_1$, antibody. In one embodiment, the antibody is a full-length antibody.

In one embodiment, the antibody comprises an Fc domain, particularly an IgG Fc domain, more particularly an $IgG_1$ Fc domain. In one embodiment the Fc domain is a human Fc domain. The Fc domain of the antibody may incorporate any of the features, singly or in combination, described herein in relation to the Fc domain of the bispecific antigen binding molecule of the invention.

In another embodiment, the antibody is an antibody fragment selected from the group of an Fv molecule, a scFv molecule, a Fab molecule, and a F(ab')2 molecule; particularly a Fab molecule.

In another embodiment, the antibody fragment is a diabody, a triabody or a tetrabody.

In a further aspect, the antibody according to any of the above embodiments may incorporate any of the features, singly or in combination, as described in the sections below.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one embodiment, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. Arch. Biochem. Biophys. 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. Biotech. Bioeng. 87:614-622 (2004); Kanda, Y. et al., Biotechnol. Bioeng., 94(4):680-688 (2006); and WO2003/085107), or cells with reduced or abolished activity of a GDP-fucose synthesis or transporter protein (see, e.g., US2004259150, US2005031613, US2004132140, US2004110282).

In a further embodiment, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. No. 7,521,541, 8,30,930, 7,855,275, 9,000,130, or WO2016040856.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Immunoconjugates

The invention also provides immunoconjugates comprising an anti-GPRC5D antibody as described herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in Pharmacol Review 68:3-19 (2016).

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $p^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

Multispecific Antibodies

In certain embodiments, an antibody provided herein is a multispecific antibody, e.g. a bispecific antibody. Multispecific antibodies are monoclonal antibodies that have binding specificities for at least two different sites, i.e., different epitopes on different antigens or different epitopes on the same antigen. In certain embodiments, the multispecific antibody has three or more binding specificities. In certain embodiments, one of the binding specificities is for GPRC5D and the other (two or more) specificity is for any other antigen. In certain embodiments, bispecific antibodies may bind to two (or more) different epitopes of GPRC5D. Multispecific (e.g., bispecific) antibodies may also be used to localize cytotoxic agents or cells to cells which express GPRC5D. Multispecific antibodies can be prepared as full length antibodies or antibody fragments.

Techniques for making multispecific antibodies include, but are not limited to, recombinant co-expression of two immunoglobulin heavy chain-light chain pairs having different specificities (see multispecific antibody, particularly a bispecific antibody, wherein one of the binding specificities is for GPRC5D and the other is for CD3.

Examples of bispecific antibody formats that may be useful for this purpose include, but are not limited to, the so-called "BiTE" (bispecific T cell engager) molecules wherein two scFv molecules are fused by a flexible linker (see, e.g., WO2004/106381, WO2005/061547, WO2007/042261, and WO2008/119567, Nagorsen and Bluerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO2013/026839, WO 2016/020309; Bacac et al., Oncoimmunology 5(8) (2016) e1203498.

Bispecific Antigen Binding Molecules that Bind to GPRC5D and a Second Antigen

The invention also provides a bispecific antigen binding molecule, i.e. an antigen binding molecule that comprises at least two antigen binding moieties capable of specific binding to two distinct antigenic determinants (a first and a second antigen).

According to particular embodiments of the invention, the antigen binding moieties comprised in the bispecific antigen binding molecule are Fab molecules (i.e. antigen binding domains composed of a heavy and a light chain, each comprising a variable and a constant domain). In one embodiment, the first and/or the second antigen binding moiety is a Fab molecule. In one embodiment, said Fab molecule is human. In a particular embodiment, said Fab molecule is humanized. In yet another embodiment, said Fab molecule comprises human heavy and light chain constant domains.

Preferably, at least one of the antigen binding moieties is a crossover Fab molecule. Such modification reduces mispairing of heavy and light chains from different Fab molecules, thereby improving the yield and purity of the bispecific antigen binding molecule of the invention in recombinant production. In a particular crossover Fab molecule useful for the bispecific antigen binding molecule of the invention, the variable domains of the Fab light chain and the Fab heavy chain (VL and VH, respectively) are exchanged. Even with this domain exchange, however, the preparation of the bispecific antigen binding molecule may comprise certain side products due to a so-called Bence Jones-type interaction between misspaired heavy and light chains (see Schaefer et al, PNAS, 108 (2011) 11187-11191). To further reduce mispairing of heavy and light chains from different Fab molecules and thus increase the purity and yield of the desired bispecific antigen binding molecule, charged amino acids with opposite charges may be introduced at specific amino acid positions in the CH1 and CL domains of either the Fab molecule(s) binding to the first antigen (GPRC5D), or the Fab molecule binding to the second antigen (e.g. an activating T cell antigen such as CD3), as further described herein. Charge modifications are made either in the conventional Fab molecule(s) comprised in the bispecific antigen binding molecule (such as shown e.g. in FIG. 1A-FIG. 1C and FIG. 1G-FIG. 1J), or in the VH/VL crossover Fab molecule(s) comprised in the bispecific antigen binding molecule (such as shown e.g. in FIG. 1D-FIG. 1F and FIG. 1K-FIG. 1N) (but not in both). In particular embodiments, the charge modifications are made in the conventional Fab molecule(s) comprised in the bispecific antigen binding molecule (which in particular embodiments bind(s) to the first antigen, i.e. GPRC5D).

In a particular embodiment according to the invention, the bispecific antigen binding molecule is capable of simultaneous binding to the first antigen (i.e. GPRC5D), and the second antigen (e.g. an activating T cell antigen, particularly CD3). In one embodiment, the bispecific antigen binding molecule is capable of crosslinking a T cell and a target cell by simultaneous binding GPRC5D and an activating T cell antigen. In an even more particular embodiment, such simultaneous binding results in lysis of the target cell, particularly a GPRC5D expressing tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the bispecific antigen binding molecule to the activating T cell antigen, particularly CD3, without simultaneous binding to GPRC5D does not result in T cell activation. In one embodiment, the bispecific antigen binding molecule is capable of re-directing cytotoxic activity of a T cell to a target cell. In a particular embodiment, said re-direction is independent of MHC-mediated peptide antigen presentation by the target cell and/or specificity of the T cell. Particularly, a T cell according to any of the embodiments of the invention is a cytotoxic T cell. In some embodiments the T cell is a $CD4^+$ or a $CD8^+$ T cell, particularly a $CD8^+$ T cell.

First Antigen Binding Moiety

The bispecific antigen binding molecule of the invention comprises at least one antigen binding moiety, particularly a Fab molecule, that binds to GPRC5D (first antigen). In certain embodiments, the bispecific antigen binding molecule comprises two antigen binding moieties, particularly Fab molecules, which bind to GPRC5D. In a particular such embodiment, each of these antigen binding moieties binds to the same antigenic determinant. In an even more particular embodiment, all of these antigen binding moieties are identical, i.e. they comprise the same amino acid sequences including the same amino acid substitutions in the CH1 and CL domain as described herein (if any). In one embodiment, the bispecific antigen binding molecule comprises not more than two antigen binding moieties, particularly Fab molecules, which bind to GPRC5D.

In particular embodiments, the antigen binding moiety(ies) which bind to GPRC5D is/are a conventional Fab molecule. In such embodiments, the antigen binding moiety(ies) that binds to a second antigen is a crossover Fab molecule as described herein, i.e. a Fab molecule wherein the variable domains VH and VL or the constant domains CH1 and CL of the Fab heavy and light chains are exchanged/replaced by each other.

In alternative embodiments, the antigen binding moiety(ies)which bind to GPRC5D is/are a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) that binds a second antigen is a conventional Fab molecule.

The GPRC5D binding moiety is able to direct the bispecific antigen binding molecule to a target site, for example to a specific type of tumor cell that expresses GPRC5D.

The first antigen binding moiety of the bispecific antigen binding molecule may incorporate any of the features, singly or in combination, described herein in relation to the antibody that binds GPRC5D, unless scientifically clearly unreasonable or impossible.

Thus, in one aspect, the invention provides a bispecific antigen binding molecule, comprising (a) a first antigen binding moiety that binds to a first antigen, wherein the first antigen is GPRC5D and the first antigen binding moiety comprises a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89, and (b) a second antigen binding moiety that binds to a second antigen. In another aspect, the invention provides a bispecific antigen binding molecule, comprising (a) a first antigen binding moiety that binds to a first antigen, wherein the first antigen is GPRC5D and the first antigen binding moiety comprises a heavy chain variable region (VH) comprising a heavy chain complementary determining region (HCDR) 1 of SEQ ID NO: 83, a HCDR 2 of SEQ ID NO: 85, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89, and (b) a second antigen binding moiety that binds to a second antigen. In another aspect, the invention provides a bispecific antigen binding molecule, comprising (a) a first antigen binding moiety that binds to a first antigen, wherein the first antigen is GPRC5D and the first antigen binding moiety comprises a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97, and (b) a second antigen binding moiety that binds to a second antigen. In another aspect, the invention provides a bispecific antigen binding molecule, comprising (a) a first antigen binding moiety that binds to a first antigen, wherein the first antigen is GPRC5D and the first antigen binding moiety comprises a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 96 and a LCDR 3 of SEQ ID NO: 97, and (b) a second antigen binding moiety that binds to a second antigen. In another aspect, the invention provides a bispecific antigen binding molecule, comprising (a) a first antigen binding moiety that binds to a first antigen, wherein the first antigen is GPRC5D and the first antigen binding moiety comprises a heavy chain variable region (VH) comprising a heavy chain complementary determining region (HCDR) 1 of SEQ ID NO: 90, a HCDR 2 of SEQ ID NO: 92, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97, and (b) a second antigen binding moiety that binds to a second antigen. In another aspect, the invention provides a bispecific antigen binding molecule, comprising (a) a first antigen binding moiety that binds to a first antigen, wherein the first antigen is GPRC5D and the first antigen binding moiety comprises a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6, and (b) a second antigen binding moiety that binds to a second antigen. In another aspect, the invention provides a bispecific antigen binding molecule, comprising (a) a first antigen binding moiety that binds to a first antigen, wherein the first antigen is GPRC5D and the first antigen binding moiety comprises a heavy chain variable region (VH) comprising a heavy chain complementary determining region (HCDR) 1 of SEQ ID NO: 7, a HCDR 2 of SEQ ID NO: 8, and a HCDR 3 of SEQ ID NO: 9, and a light chain variable region (VL) comprising a light chain complementarity determining region (LCDR) 1 of SEQ ID NO: 10, a LCDR 2 of SEQ ID NO: 11 and a LCDR 3 of SEQ ID NO: 12, and (b) a second antigen binding moiety that binds to a second antigen.

In some embodiments, the first antigen binding moiety is (derived from) a humanized antibody. In one embodiment, the VH is a humanized VH and/or the VL is a humanized VL. In one embodiment, the first antigen binding moiety comprises CDRs as in any of the above embodiments, and further comprises an acceptor human framework, e.g. a human immunoglobulin framework or a human consensus framework.

In one embodiment, the VH of the first antigen binding moiety comprises an amino acid sequence that is at least about 95%, 96%, 97%, 98%, 99% or 100% identical to an amino acid sequence selected from the group of SEQ ID NO: 13, SEQ ID NO: 15, SEQ ID NO: 48, SEQ ID NO: 49, SEQ ID NO: 57 and SEQ ID NO: 58, and the VL of the first antigen binding moiety comprises an amino acid sequence that is at least about 95%, 96%, 97%, 98%, 99% or 100% identical to an amino acid sequence selected from the group of SEQ ID NO: 14, SEQ ID NO: 16, SEQ ID NO: 52, SEQ ID NO: 53, SEQ ID NO: 63 and SEQ ID NO: 64.

In one embodiment, the first antigen binding moiety comprises a VH sequence that is at least about 95%, 96%, 97%, 98%, 99% or 100% identical to an amino acid sequence selected from the group of SEQ ID NO: 13, SEQ ID NO: 15. SEQ ID NO: 48, SEQ ID NO: 49, SEQ ID NO: 57 and SEQ ID NO: 58, and a VL sequence that is at least about 95%, 96%, 97%, 98%, 99% or 100% identical to the amino acid sequence selected from the group of SEQ ID NO: 14, SEQ ID NO: 16, SEQ ID NO: 52, SEQ ID NO: 53, SEQ ID NO: 63 and SEQ ID NO: 64.

In one embodiment, the first antigen binding moiety comprises a VH comprising an amino acid sequence selected from the group of SEQ ID NO: 13, SEQ ID NO: 15, SEQ ID NO: 48, SEQ ID NO: 49, SEQ ID NO: 57 and SEQ ID NO: 58, and a VL comprising the amino acid sequence selected from the group of SEQ ID NO: 14, SEQ ID NO: 16, SEQ ID NO: 52, SEQ ID NO: 53, SEQ ID NO: 63 and SEQ ID NO: 64.

In one embodiment, the first antigen binding moiety comprises a VH sequence selected from the group of SEQ ID NO: 13, SEQ ID NO: 15, SEQ ID NO: 48, SEQ ID NO: 49, SEQ ID NO: 57 and SEQ ID NO: 58, and the VL sequence selected from the group of SEQ ID NO: 14, SEQ ID NO: 16, SEQ ID NO: 52, SEQ ID NO: 53, SEQ ID NO: 63 and SEQ ID NO: 64.

In a particular embodiment, the first antigen binding moiety comprises a VH comprising the amino acid sequence of SEQ ID NO: 13 and a VL comprising the amino acid sequence of SEQ ID NO: 14. In a particular embodiment, the first antigen binding moiety comprises the VH sequence of SEQ ID NO: 13 and the VL sequence of SEQ ID NO: 14.

In a particular embodiment, the first antigen binding moiety comprises a VH comprising the amino acid sequence of SEQ ID NO: 15 and a VL comprising the amino acid sequence of SEQ ID NO: 16. In a particular embodiment, the first antigen binding moiety comprises the VH sequence of SEQ ID NO: 15 and the VL sequence of SEQ ID NO: 16.

In a particular embodiment, the first antigen binding moiety comprises a VH comprising the amino acid sequence of SEQ ID NO: 48 and a VL comprising the amino acid sequence of SEQ ID NO: 53. In a particular embodiment, the first antigen binding moiety comprises the VH sequence of SEQ ID NO: 48 and the VL sequence of SEQ ID NO: 53.

In a particular embodiment, the first antigen binding moiety comprises a VH comprising the amino acid sequence of SEQ ID NO: 49 and a VL comprising the amino acid sequence of SEQ ID NO: 52. In a particular embodiment, the first antigen binding moiety comprises the VH sequence of SEQ ID NO: 49 and the VL sequence of SEQ ID NO: 52.

In a particular embodiment, the first antigen binding moiety comprises a VH comprising the amino acid sequence of SEQ ID NO: 57 and a VL comprising the amino acid sequence of SEQ ID NO: 64. In a particular embodiment, the first antigen binding moiety comprises the VH sequence of SEQ ID NO: 57 and the VL sequence of SEQ ID NO: 64.

In a particular embodiment, the first antigen binding moiety comprises a VH comprising the amino acid sequence of SEQ ID NO: 58 and a VL comprising the amino acid sequence of SEQ ID NO: 63. In a particular embodiment, the first antigen binding moiety comprises the VH sequence of SEQ ID NO: 58 and the VL sequence of SEQ ID NO: 63. In one embodiment, the first antigen binding moiety comprises a human constant region. In one embodiment, the first antigen binding moiety is a Fab molecule comprising a human constant region, particularly a human CH1 and/or CL domain. Exemplary sequences of human constant domains are given in SEQ ID NOs 37 and 38 (human kappa and lambda CL domains, respectively) and SEQ ID NO: 39 (human $IgG_1$ heavy chain constant domains CH1-CH2-CH3). In some embodiments, the first antigen binding moiety comprises a light chain constant region comprising an amino acid sequence that is at least about 95%, 96%, 97%, 98%, 99% or 100% identical to the amino acid sequence of SEQ ID NO: 37 or SEQ ID NO: 38, particularly the amino acid sequence of SEQ ID NO: 37. Particularly, the light chain constant region may comprise amino acid mutations as described herein under "charge modifications" and/or may comprise deletion or substitutions of one or more (particularly two)N-terminal amino acids if in a crossover Fab molecule. In some embodiments, the first antigen binding moiety comprises a heavy chain constant region comprising an amino acid sequence that is at least about 95%, 96%, 97%, 98%, 99% or 100% identical to the CH1 domain sequence comprised in the amino acid sequence of SEQ ID NO: 39. Particularly, the heavy chain constant region (specifically CH1 domain) may comprise amino acid mutations as described herein under "charge modifications".

Second Antigen Binding Moiety

The bispecific antigen binding molecule of the invention comprises at least one antigen binding moiety, particularly a Fab molecule that binds to a second antigen (different from GPRC5D).

In particular embodiments, the antigen binding moiety that binds the second antigen is a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) that binds to the first antigen (i.e. GPRC5D) is preferably a conventional Fab molecule. In embodiments where there is more than one antigen binding moiety, particularly Fab molecule, that binds to GPRC5D comprised in the bispecific antigen binding molecule, the antigen binding moiety that binds to the second antigen preferably is a crossover Fab molecule and the antigen binding moieties that bind to GPRC5D are conventional Fab molecules.

In alternative embodiments, the antigen binding moiety that binds to the second antigen is a conventional Fab molecule. In such embodiments, the antigen binding moiety(ies) that binds to the first antigen (i.e. GPRC5D) is a crossover Fab molecule as described herein, i.e. a Fab molecule wherein the variable domains VH and VL or the constant domains CH1 and CL of the Fab heavy and light chains are exchanged/replaced by each other. In embodiments where there is more than one antigen binding moiety, particularly Fab molecule, that binds to a second antigen comprised in the bispecific antigen binding molecule, the antigen binding moiety that binds to GPRC5D preferably is a crossover Fab molecule and the antigen binding moieties that bind to the second antigen are conventional Fab molecules.

In some embodiments, the second antigen is an activating T cell antigen (also referred to herein as an "activating T cell antigen binding moiety, or activating T cell antigen binding Fab molecule").

In a particular embodiment, the bispecific antigen binding molecule comprises not more than one antigen binding moiety capable of specific binding to an activating T cell antigen. In one embodiment the bispecific antigen binding molecule provides monovalent binding to the activating T cell antigen.

In particular embodiments, the second antigen is CD3, particularly human CD3 (SEQ ID NO: 40) or cynomolgus CD3 (SEQ ID NO: 41), most particularly human CD3. In one embodiment the NO: 101, a LCDR 2 of SEQ ID NO: 102 and a LCDR 3 of SEQ ID NO: 103. In some embodiments, the second antigen binding moiety is (derived from) a humanized antibody. In one embodiment, the VH is a humanized VH and/or the VL is a humanized VL. In one embodiment, the second antigen binding moiety comprises CDRs as in any of the above embodiments, and further comprises an acceptor human framework, e.g. a human immunoglobulin framework or a human consensus framework. In one embodiment, the second antigen binding moiety comprises a VH sequence that is at least about 95%, 96%, 97%, 98%, 99% or 100% identical to the amino acid sequence of SEQ ID NO: 104. In one embodiment, the second antigen binding moiety comprises a VL sequence that is at least about 95%, 96%, 97%, 98%, 99% or 100% identical to the amino acid sequence of SEQ ID NO: 105. In one embodiment, the second antigen binding moiety comprises a VH sequence that is at least about 95%, 96%, 97%, 98%, 99% or 100% identical to the amino acid sequence of SEQ ID NO: 104, and a VL sequence that is at least about 95%, 96%, 97%, 98%, 99% or 100% identical to the amino acid sequence of SEQ ID NO: 105. In one embodiment, the VH of the second antigen binding moiety comprises an amino acid sequence that is at least about 95%, 96%, 97%, 98%, 99% or 100% identical to the amino acid sequence of SEQ ID NO: 104, and the VL of the second antigen binding moiety comprises an amino acid sequence that is at least about 95%, 96%, 97%, 98%, 99% or 100% identical to the amino acid sequence of SEQ ID NO: 105. In one embodiment, the second antigen binding moiety comprises a VH comprising the amino acid sequence of SEQ ID NO: 104, and a VL comprising the amino acid sequence of SEQ ID NO: 105. In one embodiment, the second antigen binding moiety comprises the VH sequence of SEQ ID NO: 104, and the VL sequence of SEQ ID NO: 105.

In one embodiment, the second antigen binding moiety comprises a HCDR 1 of SEQ ID NO: 106, a HCDR 2 of SEQ ID NO: 107, a HCDR 3 of SEQ ID NO: 108, a LCDR 1 of SEQ ID NO: 109, a LCDR 2 of SEQ ID NO: 110 and a LCDR 3 of SEQ ID NO: 111. In one embodiment, the second antigen binding moiety comprises a VH comprising a HCDR 1 of SEQ ID NO: 106, a HCDR 2 of SEQ ID NO: 107, and a HCDR 3 of SEQ ID NO: 108, and a VL comprising a LCDR 1 of SEQ ID NO: 109, a LCDR 2 of SEQ ID NO: 110 and a LCDR 3 of SEQ ID NO: 111.

In some embodiments, the second antigen binding moiety is (derived from) a humanized antibody. In one embodiment, the VH is a humanized VH and/or the VL is a humanized VL. In one embodiment, the second antigen binding moiety comprises CDRs as in any of the above embodiments, and further comprises an acceptor human framework, e.g. a human immunoglobulin framework or a human consensus framework. In one embodiment, the second antigen binding moiety comprises a VH sequence that is at least about 95%, 96%, 97%, 98%, 99% or 100% identical to the amino acid sequence of SEQ ID NO: 112. In one embodiment, the second antigen binding moiety comprises a VL sequence that is at least about 95%, 96%, 97%, 98%, 99% or 100% identical to the amino acid sequence of SEQ ID NO: 113. In one embodiment, the second antigen binding moiety comprises a VH sequence that is at least about 95%, 96%, 97%, 98%, 99% or 100% identical to the amino acid sequence of SEQ ID NO: 112, and a VL sequence that is at least about 95%, 96%, 97%, 98%, 99% or 100% identical to the amino acid sequence of SEQ ID NO: 113. In one embodiment, the VH of the second antigen binding moiety comprises an amino acid sequence that is at least about 95%, 96%, 97%, 98%, 99% or 100% identical to the amino acid sequence of SEQ ID NO: 112, and the VL of the second antigen binding moiety comprises an amino acid sequence that is at least about 95%, 96%, 97%, 98%, 99% or 100% identical to the amino acid sequence of SEQ ID NO: 113. In one embodiment, the second antigen binding moiety comprises a VH comprising the amino acid sequence of SEQ ID NO: 112, and a VL comprising the amino acid sequence of SEQ ID NO: 113. In one embodiment, the second antigen binding moiety comprises the VH sequence of SEQ ID NO: 112, and the VL sequence of SEQ ID NO: 113.

In one embodiment, the second antigen binding moiety comprises a human constant region. In one embodiment, the second antigen binding moiety is a Fab molecule comprising a human constant region, particularly a human CH1 and/or CL domain. Exemplary sequences of human constant domains are given in SEQ ID NOs 37 and 38 (human kappa and lambda CL domains, respectively) and SEQ ID NO: 39 (human $IgG_1$ heavy chain constant domains CH1-CH2-CH3). In some embodiments, the second antigen binding moiety comprises a light chain constant region comprising an amino acid sequence that is at least about 95%, 96%, 97%, 98%, 99% or 100% identical to the amino acid sequence of SEQ ID NO: 37 or SEQ ID NO: 38, particularly the amino acid sequence of SEQ ID NO: 37. Particularly, the light chain constant region may comprise amino acid mutations as described herein under "charge modifications" and/or may comprise deletion or substitutions of one or more (particularly two)N-terminal amino acids if in a crossover Fab molecule. In some embodiments, the second antigen binding moiety comprises a heavy chain constant region comprising an amino acid sequence that is at least about 95%, 96%, 97%, 98%, 99% or 100% identical to the CH1 domain sequence comprised in the amino acid sequence of SEQ ID NO: 39. Particularly, the heavy chain constant region (specifically CH1 domain) may comprise amino acid mutations as described herein under "charge modifications".

In some embodiments, the second antigen binding moiety is a Fab molecule wherein the variable domains VL and VH or the constant domains CL and CH1, particularly the variable domains VL and VH, of the Fab light chain and the Fab heavy chain are replaced by each other (i.e. according to such embodiment, the second antigen binding moiety is a crossover Fab molecule wherein the variable or constant domains of the Fab light chain and the Fab heavy chain are exchanged). In one such embodiment, the first (and the third, if any) antigen binding moiety is a conventional Fab molecule.

In one embodiment, not more than one antigen binding moiety that binds to the second antigen (e.g. an activating T cell antigen such as CD3) is present in the bispecific antigen binding molecule (i.e. the bispecific antigen binding molecule provides monovalent binding to the second antigen).

Charge Modifications

The bispecific antigen binding molecules of the invention may comprise amino acid substitutions in Fab molecules comprised therein which are particularly efficient in reducing mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety). The ratio of a desired bispecific antigen binding molecule compared to undesired side products, in particular Bence Jones-type side products occurring in bispecific antigen binding molecules with a VH/VL domain exchange in one of their binding arms, can be improved by the introduction of charged amino acids with opposite charges at specific amino acid positions in the CH1 and CL domains (sometimes referred to herein as "charge modifications").

Accordingly, in some embodiments wherein the first and the second antigen binding moiety of the bispecific antigen binding molecule are both Fab molecules, and in one of the antigen binding moieties (particularly the second antigen binding moiety) the variable domains VL and VH of the Fab light chain and the Fab heavy chain are replaced by each other, i) in the constant domain CL of the first antigen binding moiety the amino acid at position 124 is substituted by a positively charged amino acid (numbering according to Kabat), and wherein in the constant domain CH1 of the first antigen binding moiety the amino acid at position 147 or the amino acid at position 213 is substituted by a negatively charged amino acid (numbering according to Kabat EU index); or ii) in the constant domain CL of the second antigen binding moiety the amino acid at position 124 is substituted by a positively charged amino acid (numbering according to Kabat), and wherein in the constant domain CH1 of the second antigen binding moiety the amino acid at position 147 or the amino acid at position 213 is substituted by a negatively charged amino acid (numbering according to Kabat EU index).

The bispecific antigen binding molecule does not comprise both modifications mentioned under i) and ii). The constant domains CL and CH1 of the antigen binding moiety having the VH/VL exchange are not replaced by each other (i.e. remain unexchanged).

In a more specific embodiment, i) in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index); or ii) in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In one such embodiment, in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index).

In a further embodiment, in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 is substituted independently by glutamic acid (E), or aspartic acid (D) (numbering according to Kabat EU index).

In a particular embodiment, in the constant domain CL of the first antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first antigen binding moiety the amino acid at position 124 is substituted by lysine (K) (numbering according to Kabat) and the amino acid at position 123 is substituted by lysine (K) (numbering according to Kabat), and in the constant domain CH1 of the first antigen binding moiety the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first antigen binding moiety the amino acid at position 124 is substituted by lysine (K) (numbering according to Kabat) and the amino acid at position 123 is substituted by arginine (R) (numbering according to Kabat), and in the constant domain CH1 of the first antigen binding moiety the amino acid at position 147 is substituted by glutamic acid (E) (numbering according to Kabat EU index) and the amino acid at position 213 is substituted by glutamic acid (E) (numbering according to Kabat EU index).

In particular embodiments, if amino acid substitutions according to the above embodiments are made in the constant domain CL and the constant domain CH1 of the first antigen binding moiety, the constant domain CL of the first antigen binding moiety is of kappa isotype.

Alternatively, the amino acid substitutions according to the above embodiments may be made in the constant domain CL and the constant domain CH1 of the second antigen binding moiety instead of in the constant domain CL and the constant domain CH1 of the first antigen binding moiety. In particular such embodiments, the constant domain CL of the second antigen binding moiety is of kappa isotype.

Accordingly, in one embodiment, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In a further embodiment, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index).

In still another embodiment, in the constant domain CL of the second antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one embodiment, in the constant domain CL of the second antigen binding moiety the amino acid at position 124 is substituted by lysine (K) (numbering according to Kabat) and the amino acid at position 123 is substituted by lysine (K) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In another embodiment, in the constant domain CL of the second antigen binding moiety the amino acid at position 124 is substituted by lysine (K) (numbering according to Kabat) and the amino acid at position 123 is substituted by arginine (R) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In a particular embodiment, the bispecific antigen binding molecule of the invention comprises (a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89, and (b) a second antigen binding moiety that binds to a second antigen, wherein the second antigen binding moiety is a Fab molecule wherein the variable domains VL and VH of the Fab light chain and the Fab heavy chain are replaced by each other;

wherein in the constant domain CL of the first antigen binding moiety the amino acid at position 124 is substituted independently by lysine (K), arginine (R) or histidine (H) (numbering according to Kabat) (in a particular embodiment independently by lysine (K) or arginine (R)) and the amino acid at position 123 is substituted independently by lysine (K), arginine (R) or histidine (H) (numbering according to Kabat) (in a particular embodiment independently by lysine (K) or arginine (R)), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a particular embodiment, the bispecific antigen binding molecule of the invention comprises (a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 85, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89, and (b) a second antigen binding moiety that binds to a second antigen, wherein the second antigen binding moiety is a Fab molecule wherein the variable domains VL and VH of the Fab light chain and the Fab heavy chain are replaced by each other;

wherein in the constant domain CL of the first antigen binding moiety the amino acid at position 124 is substituted independently by lysine (K), arginine (R) or histidine (H) (numbering according to Kabat) (in a particular embodiment independently by lysine (K) or arginine (R)) and the amino acid at position 123 is substituted independently by lysine (K), arginine (R) or histidine (H) (numbering according to Kabat) (in a particular embodiment independently by lysine (K) or arginine (R)), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a particular embodiment, the bispecific antigen binding molecule of the invention comprises (a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97, and (b) a second antigen binding moiety that binds to a second antigen, wherein the second antigen binding moiety is a Fab molecule wherein the variable domains VL and VH of the Fab light chain and the Fab heavy chain are replaced by each other;

wherein in the constant domain CL of the first antigen binding moiety the amino acid at position 124 is substituted independently by lysine (K), arginine (R) or histidine (H) (numbering according to Kabat) (in a particular embodiment independently by lysine (K) or arginine (R)) and the amino acid at position 123 is substituted independently by lysine (K), arginine (R) or histidine (H) (numbering according to Kabat) (in a particular embodiment independently by lysine (K) or arginine (R)), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a particular embodiment, the bispecific antigen binding molecule of the invention comprises (a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 96 and a LCDR 3 of SEQ ID NO: 97, and (b) a second antigen binding moiety that binds to a second antigen, wherein the second antigen binding moiety is a Fab molecule wherein the variable domains VL and VH of the Fab light chain and the Fab heavy chain are replaced by each other;

wherein in the constant domain CL of the first antigen binding moiety the amino acid at position 124 is substituted independently by lysine (K), arginine (R) or histidine (H) (numbering according to Kabat) (in a particular embodiment independently by lysine (K) or arginine (R)) and the amino acid at position 123 is substituted independently by lysine (K), arginine (R) or histidine (H) (numbering according to Kabat) (in a particular embodiment independently by lysine (K) or arginine (R)), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a particular embodiment, the bispecific antigen binding molecule of the invention comprises at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a particular embodiment, the bispecific antigen binding molecule of the invention comprises (a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 7, a HCDR 2 of SEQ ID NO: 8, and a HCDR 3 of SEQ ID NO: 9, and a light chain variable region (VL) comprising a light chain complementarity determining region (LCDR) 1 of SEQ ID NO: 10, a LCDR 2 of SEQ ID NO: 11 and a LCDR 3 of SEQ ID NO: 12, and (b) a second antigen binding moiety that binds to a second antigen, wherein the second antigen binding moiety is a Fab molecule wherein the variable domains VL and VH of the Fab light chain and the Fab heavy chain are replaced by each other;

wherein in the constant domain CL of the first antigen binding moiety the amino acid at position 124 is substituted independently by lysine (K), arginine (R) or histidine (H) (numbering according to Kabat) (in a particular embodiment independently by lysine (K) or arginine (R)) and the amino acid at position 123 is substituted independently by lysine (K), arginine (R) or histidine (H) (numbering according to Kabat) (in a particular embodiment independently by lysine (K) or arginine (R)), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

Bispecific Antigen Binding Molecule Formats

The components of the bispecific antigen binding molecule according to the present invention can be fused to each other in a variety of configurations. Exemplary configurations are depicted in FIG. 1A-FIG. 1Z.

In particular embodiments, the antigen binding moieties comprised in the bispecific antigen binding molecule are Fab molecules. In such embodiments, the first, second, third etc. antigen binding moiety may be referred to herein as first, second, third etc. Fab molecule, respectively. In one embodiment, the first and the second antigen binding moiety of the bispecific antigen binding molecule are fused to each other, optionally via a peptide linker. In particular embodiments, the first and the second antigen binding moiety are each a Fab molecule. In one such embodiment, the second antigen binding moiety is fused at the C-terminus of the Fab heavy chain to the N-terminus of the Fab heavy chain of the first antigen binding moiety. In another such embodiment, the first antigen binding moiety is fused at the C-terminus of the Fab heavy chain to the N-terminus of the Fab heavy chain of the second antigen binding moiety. In embodiments wherein either (i) the second antigen binding moiety is fused at the C-terminus of the Fab heavy chain to the N-terminus of the Fab heavy chain of the first antigen binding moiety or (ii) the first antigen binding moiety is fused at the C-terminus of the Fab heavy chain to the N-terminus of the Fab heavy chain of the second antigen binding moiety, additionally the Fab light chain of the first antigen binding moiety and the Fab light chain of the second antigen binding moiety may be fused to each other, optionally via a peptide linker.

A bispecific antigen binding molecule with a single antigen binding moiety (such as a Fab molecule) capable of specific binding to a target cell antigen such as GPRC5D (for example as shown in FIG. 1A, FIG. 1D, FIG. 1G, FIG. 1H, FIG. 1K, FIG. 1L) is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In other cases, however, it will be advantageous to have a bispecific antigen binding molecule comprising two or more antigen binding moieties (such as Fab molecules) specific for a target cell antigen (see examples shown in FIG. 1B, FIG. 1C, FIG. 1E, FIG. 1F, FIG. 1I, FIG. 1J, FIG. 1M or FIG. 1N), for example to optimize targeting to the target site or to allow crosslinking of target cell antigens.

Accordingly, in particular embodiments, the bispecific antigen binding molecule according to the present invention comprises a third antigen binding moiety.

In one embodiment, the third antigen binding moiety binds to the first antigen, i.e. GPRC5D. In one embodiment, the third antigen binding moiety is a Fab molecule.

In one embodiment, the third antigen moiety is identical to the first antigen binding moiety.

The third antigen binding moiety of the bispecific antigen binding molecule may incorporate any of the features, singly or in combination, described herein in relation to the first antigen binding moiety and/or the antibody that binds GPRC5D, unless scientifically clearly unreasonable or impossible.

In one embodiment, the third antigen binding moiety comprises a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86, and a light chain variable region embodiment, the third antigen binding moiety comprises CDRs as in any of the above embodiments, and further comprises an acceptor human framework, e.g. a human immunoglobulin framework or a human consensus framework.

In one embodiment, the VH of the third antigen binding moiety comprises an amino acid sequence that is at least about 95%, 96%, 97%, 98%, 99% or 100% identical to an amino acid sequence selected from the group of SEQ ID NO: 13, SEQ ID NO: 15, SEQ ID NO: 48, SEQ ID NO: 49, SEQ ID NO: 57 and SEQ ID NO: 58, and the VL of the third antigen binding moiety comprises an amino acid sequence that is at least about 95%, 96%, 97%, 98%, 99% or 100% identical to the amino acid sequence selected from the group of SEQ ID NO: 14, SEQ ID NO: 16, SEQ ID NO: 52, SEQ ID NO: 53, SEQ ID NO: 63 and SEQ ID NO: 64.

In one embodiment, the third antigen binding moiety comprises a VH sequence that is at least about 95%, 96%, 97%, 98%, 99% or 100% identical to an amino acid sequence selected from the group of SEQ ID NO: 13, SEQ ID NO: 15 SEQ ID NO: 48, SEQ ID NO: 49, SEQ ID NO: 57 and SEQ ID NO: 58, and a VL sequence that is at least about 95%, 96%, 97%, 98%, 99% or 100% identical to the amino acid sequence selected from the group of SEQ ID NO: 14, SEQ ID NO: 16, SEQ ID NO: 52, SEQ ID NO: 53, SEQ ID NO: 63 and SEQ ID NO: 64.

In one embodiment, the third antigen binding moiety comprises a VH comprising an amino acid sequence selected from the group of SEQ ID NO: 13, SEQ ID NO: 15 SEQ ID NO: 48, SEQ ID NO: 49, SEQ ID NO: 57 and SEQ ID NO: 58, and a VL comprising the amino acid sequence selected from the group of SEQ ID NO: 14, SEQ ID NO: 16, SEQ ID NO: 52, SEQ ID NO: 53, SEQ ID NO: 63 and SEQ ID NO: 64.

In one embodiment, the third antigen binding moiety comprises a VH sequence selected from the group of SEQ ID NO: 13, SEQ ID NO: 15 SEQ ID NO: 48, SEQ ID NO: 49, SEQ ID NO: 57 and SEQ ID NO: 58, and the VL sequence selected from the group of SEQ ID NO: 14, SEQ ID NO: 16, SEQ ID NO: 52, SEQ ID NO: 53, SEQ ID NO: 63 and SEQ ID NO: 64.

In a particular embodiment, the third antigen binding moiety comprises a VH comprising the amino acid sequence of SEQ ID NO: 13 and a VL comprising the amino acid sequence of SEQ ID NO: 14. In a particular embodiment, the third antigen binding moiety comprises the VH sequence of SEQ ID NO: 13 and the VL sequence of SEQ ID NO: 14.

In a particular embodiment, the third antigen binding moiety comprises a VH comprising the amino acid sequence of SEQ ID NO: 15 and a VL comprising the amino acid sequence of SEQ ID NO: 16. In a particular embodiment, the third antigen binding moiety comprises the VH sequence of SEQ ID NO: 15 and the VL sequence of SEQ ID NO: 16.

In a particular embodiment, the third antigen binding moiety comprises a VH comprising the amino acid sequence of SEQ ID NO: 48 and a VL comprising the amino acid sequence of SEQ ID NO: 53. In a particular embodiment, the third antigen binding moiety comprises the VH sequence of SEQ ID NO: 48 and the VL sequence of SEQ ID NO: 53.

In a particular embodiment, the third antigen binding moiety comprises a VH comprising the amino acid sequence of SEQ ID NO: 49 and a VL comprising the amino acid sequence of SEQ ID NO: 52. In a particular embodiment, the third antigen binding moiety comprises the VH sequence of SEQ ID NO: 49 and the VL sequence of SEQ ID NO: 52.

In a particular embodiment, the third antigen binding moiety comprises a VH comprising the amino acid sequence of SEQ ID NO: 57 and a VL comprising the amino acid sequence of SEQ ID NO: 64. In a particular embodiment, the third antigen binding moiety comprises the VH sequence of SEQ ID NO: 57 and the VL sequence of SEQ ID NO: 64.

In a particular embodiment, the third antigen binding moiety comprises a VH comprising the amino acid sequence of SEQ ID NO: 58 and a VL comprising the amino acid sequence of SEQ ID NO: 63. In a particular embodiment, the third antigen binding moiety comprises the VH sequence of SEQ ID NO: 58 and the VL sequence of SEQ ID NO: 63.

In one embodiment, the third antigen binding moiety comprises a human constant region. In one embodiment, the third antigen binding moiety is a Fab molecule comprising a human constant region, particularly a human CH1 and/or CL domain. Exemplary sequences of human constant domains are given in SEQ ID NOs 37 and 38 (human kappa and lambda CL domains, respectively) and SEQ ID NO: 39 (human $IgG_1$ heavy chain constant domains CH1-CH2-CH3). In some embodiments, the third antigen binding moiety comprises a light chain constant region comprising an amino acid sequence that is at least about 95%, 96%, 97%, 98%, 99% or 100% identical to the amino acid sequence of SEQ ID NO: 37 or SEQ ID NO: 38, particularly the amino acid sequence of SEQ ID NO: 37. Particularly, the light chain constant region may comprise amino acid mutations as described herein under "charge modifications" and/or may comprise deletion or substitutions of one or more (particularly two)N-terminal amino acids if in a crossover Fab molecule. In some embodiments, the third antigen binding moiety comprises a heavy chain constant region comprising an amino acid sequence that is at least about 95%, 96%, 97%, 98%, 99% or 100% identical to the CH1 domain sequence comprised in the amino acid sequence of SEQ ID NO: 39. Particularly, the heavy chain constant region (specifically CH1 domain) may comprise amino acid mutations as described herein under "charge modifications".

In particular embodiments, the third and the first antigen binding moiety are each a Fab molecule and the third antigen binding moiety is identical to the first antigen binding moiety. Thus, in these embodiments the first and the third antigen binding moiety comprise the same heavy and light chain amino acid sequences and have the same arrangement of domains (i.e. conventional or crossover)). Furthermore, in these embodiments, the third antigen binding moiety comprises the same amino acid substitutions, if any, as the first antigen binding moiety. For example, the amino acid substitutions described herein as "charge modifications" will be made in the constant domain CL and the constant domain CH1 of each of the first antigen binding moiety and the third antigen binding moiety. Alternatively, said amino acid substitutions may be made in the constant domain CL and the constant domain CH1 of the second antigen binding moiety (which in particular embodiments is also a Fab molecule), but not in the constant domain CL and the constant domain CH1 of the first antigen binding moiety and the third antigen binding moiety.

Like the first antigen binding moiety, the third antigen binding moiety particularly is a conventional Fab molecule. Embodiments wherein the first and the third antigen binding moieties are crossover Fab molecules (and the second antigen binding moiety is a conventional Fab molecule) are, however, also contemplated. Thus, in particular embodiments, the first and the third antigen binding moieties are each a conventional Fab molecule, and the second antigen binding moiety is a crossover Fab molecule as described herein, i.e. a Fab molecule wherein the variable domains VH and VL or the constant domains CL and CH1 of the Fab heavy and light chains are exchanged/replaced by each other. In other embodiments, the first and the third antigen binding moieties are each a crossover Fab molecule and the second antigen binding moiety is a conventional Fab molecule.

If a third antigen binding moiety is present, in a particular embodiment the first and the third antigen moiety bind to GPRC5D, and the second antigen binding moiety binds to a second antigen, particularly an activating T cell antigen, more particularly CD3, most particularly CD3 epsilon.

In particular embodiments, the bispecific antigen binding molecule comprises an Fc domain composed of a first and a second subunit. The first and the second subunit of the Fc domain are capable of stable association.

The bispecific antigen binding molecule according to the invention can have different configurations, i.e. the first, second (and optionally third) antigen binding moiety may be fused to each other and to the Fc domain in different ways. The components may be fused to each other directly or, preferably, via one or more suitable peptide linkers. Where fusion of a Fab molecule is to the N-terminus of a subunit of the Fc domain, it is typically via an immunoglobulin hinge region.

In some embodiments, the first and the second antigen binding moiety are each a Fab molecule and the second antigen binding moiety is fused at the C-terminus of the Fab heavy chain to the N-terminus of the first or the second subunit of the Fc domain. In such embodiments, the first antigen binding moiety may be fused at the C-terminus of the Fab heavy chain to the N-terminus of the Fab heavy chain of the second antigen binding moiety or to the N-terminus of the other one of the subunits of the Fc domain. In particular such embodiments, said first antigen binding moiety is a conventional Fab molecule, and the second antigen binding moiety is a crossover Fab molecule as described herein, i.e. a Fab molecule wherein the variable domains VH and VL or the constant domains CL and CH1 of the Fab heavy and light chains are exchanged/replaced by each other. In other such embodiments, said first Fab molecule is a crossover Fab molecule and the second Fab molecule is a conventional Fab molecule.

Figures 1G, 1H, 1I, 1J, 1K, 1L, 1M, 1N:
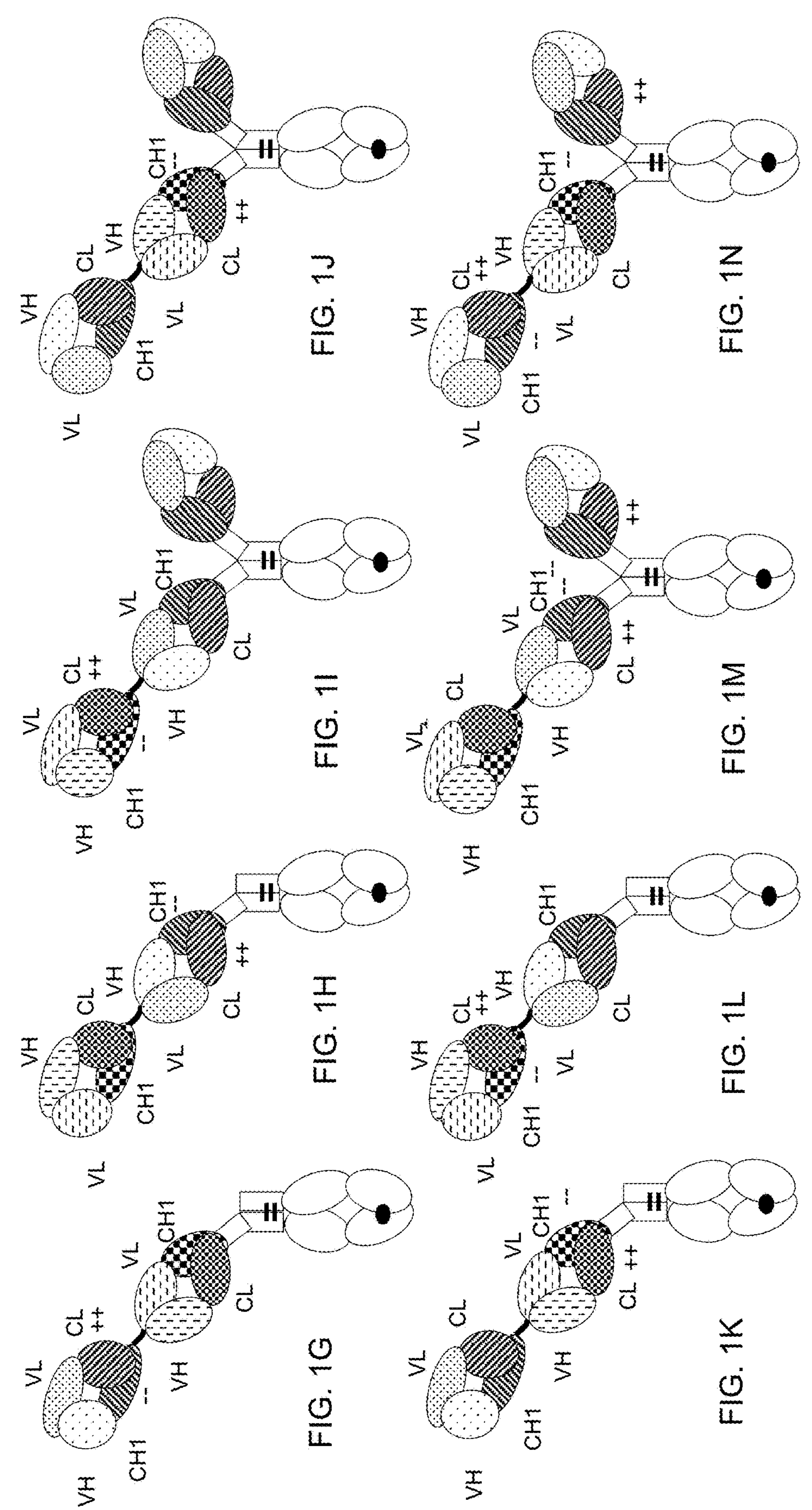
(FIG. 1G, FIG. 1K) Illustration of the "1+1 IgG Crossfab" molecule with alternative order of Crossfab and Fab components ("inverted").
(FIG. 1H, FIG. 1L) Illustration of the "1+1 IgG Crossfab" molecule.
(FIG. 1I, FIG. 1M) Illustration of the "2+1 IgG Crossfab" molecule with two CrossFabs.
(FIG. 1J, FIG. 1N) Illustration of the "2+1 IgG Crossfab" molecule with two CrossFabs and alternative order of Crossfab and Fab components ("inverted").

In one embodiment, the first and the second antigen binding moiety are each a Fab molecule, the second antigen binding moiety is fused at the C-terminus of the Fab heavy chain to the N-terminus of the first or the second subunit of the Fc domain, and the first antigen binding moiety is fused at the C-terminus of the Fab heavy chain to the N-terminus of the Fab heavy chain of the second antigen binding moiety. In a specific embodiment, the bispecific antigen binding molecule essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIG. 1G and FIG. 1K (with the second antigen binding domain in these examples being a VH/VL crossover Fab molecule). Optionally, the Fab light chain of the first Fab molecule and the Fab light chain of the second Fab molecule may additionally be fused to each other.

In another embodiment, the first and the second antigen binding moiety are each a Fab molecule and the first and the second antigen binding moiety are each fused at the C-terminus of the Fab heavy chain to the N-terminus of one of the subunits of the Fc domain. In a specific embodiment, the bispecific antigen binding molecule essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIG. 1A and FIG. 1D (in these examples with the second antigen binding domain being a VH/VL crossover Fab molecule and the first antigen binding moiety being a conventional Fab molecule). The first and the second Fab molecule may be fused to the Fc domain directly or through a peptide linker. In a particular embodiment the first and the the N-terminus of the second subunit of the Fc domain. Such a configuration is schematically depicted in FIG. 1C and FIG. 1F (in these examples with the second antigen binding moiety being a VH/VL crossover Fab molecule, and the first and the third antigen binding moiety being a conventional Fab molecule) and in FIG. 1I and FIG. 1M (in these examples with the second antigen binding moiety being a conventional Fab molecule, and the first and the third antigen binding moiety being a VH/VL crossover Fab molecule). The first and the third Fab molecule may be fused to the Fc domain directly or through a peptide linker. In a particular embodiment the first and the third Fab molecule are each fused to the Fc domain through an immunoglobulin hinge region. In a specific embodiment, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In configurations of the bispecific antigen binding molecule wherein a Fab molecule is fused at the C-terminus of the Fab heavy chain to the N-terminus of each of the subunits of the Fc domain through an immunoglobulin hinge regions, the two Fab molecules, the hinge regions and the Fc domain essentially form an immunoglobulin molecule. In a particular embodiment the immunoglobulin molecule is an IgG class immunoglobulin. In an even more particular embodiment the immunoglobulin is an $IgG_1$ subclass immunoglobulin. In another embodiment the immunoglobulin is an $IgG_4$ subclass immunoglobulin. In a further particular embodiment the immunoglobulin is a human immunoglobulin. In other embodiments the immunoglobulin is a chimeric immunoglobulin or a humanized immunoglobulin. In one embodiment, the immunoglobulin comprises a human constant region, particularly a human Fc region.

In some of the bispecific antigen binding molecule of the invention, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the bispecific antigen binding molecules of the invention.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one embodiment said peptide linker has a length of at least amino acids, in one embodiment a length of 5 to 100, in a further embodiment of 10 to 50 amino acids. In one embodiment said peptide linker is $(GxS)_n$ or $(GXS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one embodiment x=4 and n=2 or 3, in a further embodiment x=4 and n=2. In one embodiment said peptide linker is $(G_4S)_2$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence (D)-$(G_4S)_2$ (SEQ ID NOs 43 and 44). Another suitable such linker comprises the sequence $(G_4S)_4$. Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit ($VL_{(2)}$-$CH1_{(2)}$—CH2-CH3(—CH4)), and a polypeptide wherein the Fab heavy chain of the first Fab molecule shares a carboxy-terminal peptide bond with an Fc domain subunit ($VH_{(1)}$—CH1(1)-CH2-CH3(—CH4)). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In certain embodiments the polypeptides are covalently linked, e.g., by a disulfide bond.

In certain embodiments the bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit ($VH_{(2)}$-$CL_{(2)}$-CH2-CH3(—CH4)), and a polypeptide wherein the Fab heavy chain of the first Fab molecule shares a carboxy-terminal peptide bond with an Fc domain subunit ($VH_{(1)}$—CH1(1)-CH2-CH3(—CH4)). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-CH1(2)) and the Fab light chain polypeptide of the first Fab molecule (VL(j)-CL(j)). In certain embodiments the polypeptides are covalently linked, e.g., by a disulfide bond.

In some embodiments, the bispecific antigen binding molecule comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with an Fc domain subunit ($VL_{(2)}$-$CH1_{(2)}$—$VH_{(1)}$—$CH1_{(1)}$—CH2-CH3(—CH4)). In other embodiments, the bispecific antigen binding molecule comprises a polypeptide wherein the Fab heavy chain of the first Fab molecule shares a carboxy-terminal peptide bond with the Fab light chain variable region of the second Fab molecule which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit ($VH_{(1)}$—$CH1_{(1)}$-$VL_{(2)}$-$CH1_{(2)}$—CH2-CH3 (—CH4)).

In some of these embodiments the bispecific antigen binding molecule further comprises a crossover Fab light chain polypeptide of the second Fab molecule, wherein the Fab heavy chain variable region of the second Fab molecule shares a carboxy-terminal peptide bond with the Fab light chain constant region of the second Fab molecule ($VH_{(2)}$-$CL_{(2)}$), and the Fab light chain polypeptide of the first Fab molecule ($VL_{(1)}$-$CL_{(1)}$). In others of these embodiments the bispecific antigen binding molecule further comprises a polypeptide wherein the Fab heavy chain variable region of the second Fab molecule shares a carboxy-terminal peptide bond with the Fab light chain constant region of the second Fab molecule which in turn shares a carboxy-terminal peptide bond with the Fab light chain polypeptide of the first Fab molecule ($VH_{(2)}$-$CL_{(2)}$-VL(1)-CL(1)), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule (VL(1)-CL(1)-$VH_{(2)}$-$CL_{(2)}$), as appropriate.

The bispecific antigen binding molecule according to these embodiments may further comprise (i) an Fc domain subunit polypeptide (CH2-CH3(—CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(—CH4)) and the Fab light chain polypeptide of a third Fab molecule ($VL_{(3)}$-$CL_{(3)}$). In certain embodiments the polypeptides are covalently linked, e.g., by a disulfide bond.

In some embodiments, the bispecific antigen binding molecule comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with an Fc domain subunit ($VH_{(2)}$-$CL_{(2)}$-VH (1)-CH1(1)-CH2-CH3(—CH4)). In other embodiments, the bispecific antigen binding molecule comprises a polypeptide wherein the Fab heavy chain of the first Fab molecule shares a carboxy-terminal peptide bond with the Fab heavy chain variable region of the second Fab molecule which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit (VH(1)-CH1(1)-$VH_{(2)}$-$CL_{(2)}$-CH2-CH3(—CH4)).

In some of these embodiments the bispecific antigen binding molecule further comprises a crossover Fab light chain polypeptide of the second Fab molecule, wherein the Fab light chain variable region of the second Fab molecule shares a carboxy-terminal peptide bond with the Fab heavy chain constant region of the second Fab molecule ($VL_{(2)}$-$CH1_{(2)}$), and the Fab light chain polypeptide of the first Fab molecule ($VL_{(1)}$-$CL_{(1)}$). In others of these embodiments the bispecific antigen binding molecule further comprises a polypeptide wherein the Fab light chain variable region of the second Fab molecule shares a carboxy-terminal peptide bond with the Fab heavy chain constant region of the second Fab molecule which in turn shares a carboxy-terminal peptide bond with the Fab light chain polypeptide of the first Fab molecule ($VL_{(2)}$-$CH1_{(2)}$-VL(1)-CL(1)), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule (VL(1)-CL(1)-$VL_{(2)}$-$CH1_{(2)}$), as appropriate.

Figures 1O, 1P, 1Q, 1R, 1S, 1T, 1U, 1V:
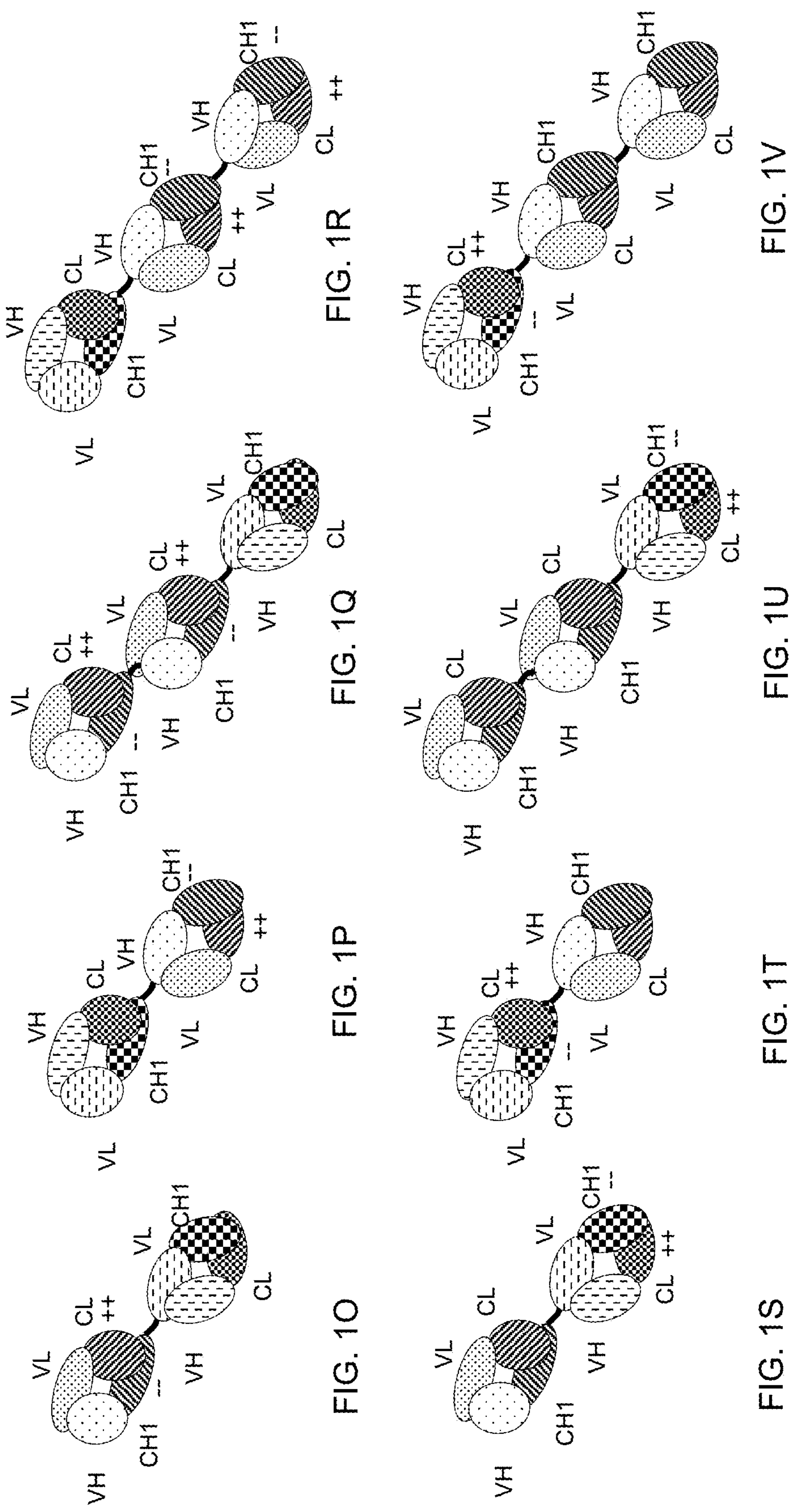
(FIG. 1O, FIG. 1S) Illustration of the "Fab-Crossfab" molecule.
(FIG. 1P, FIG. 1T) Illustration of the "Crossfab-Fab" molecule.
(FIG. 1Q, FIG. 1U) Illustration of the "$(Fab)_2$-Crossfab" molecule.
(FIG. 1R, FIG. 1V) Illustration of the "Crossfab-$(Fab)_2$" molecule.

The bispecific antigen binding molecule according to these embodiments may further comprise (i) an Fc domain subunit polypeptide (CH2-CH3(—CH4)), or (ii) a polypeptide wherein the Fab heavy chain of a third Fab molecule shares a carboxy-terminal peptide bond with an Fc domain subunit depicted in FIG. 1Q and FIG. 1U (in these examples with the second antigen binding domain being a VH/VL crossover Fab molecule and the first and the antigen binding moiety each being a conventional Fab molecule), or FIG. 1X and FIG. 1Z (in these examples with the second antigen binding domain being a conventional Fab molecule and the first and the third antigen binding moiety each being a VH/VL crossover Fab molecule).

In some embodiments, the second Fab molecule is fused at the C-terminus of the Fab heavy chain to the N-terminus of the Fab heavy chain of the first Fab molecule, and the bispecific antigen binding molecule further comprises a third antigen binding moiety, particularly a third Fab molecule, wherein said third Fab molecule is fused at the N-terminus of the Fab heavy chain to the C-terminus of the Fab heavy chain of the first Fab molecule. In certain such embodiments, the bispecific antigen binding molecule essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the N-terminus of the Fab heavy chain to the C-terminus of the Fab heavy chain of the first Fab molecule. Such a configuration is schematically depicted in FIG. 1R and FIG. 1V (in these examples with the second antigen binding domain being a VH/VL crossover Fab molecule and the first and the antigen binding moiety each being a conventional Fab molecule), or FIG. 1W and FIG. 1Y (in these examples with the second antigen binding domain being a conventional Fab molecule and the first and the third antigen binding moiety each being a VH/VL crossover Fab molecule).

In certain embodiments the bispecific antigen binding molecule according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(1)}$—$CH1_{(1)}$-$VL_{(2)}$-CH1(2)). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule (VL(1)-CL(1)).

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-CH1(2)-$VH_{(1)}$-CH1(1)). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule (VL(i)-$CL_{(1)}$).

In certain embodiments the bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(2)}$-$CL_{(2)}$-$VH_{(1)}$—CH1(1)). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule (VL(1)-CL(1)).

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-CH1(2)-$VH_{(1)}$-CH1(1)). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule (VH(2)-CL(2)) and the Fab light chain polypeptide of the first Fab molecule ($VL_{(1)}$-$CL_{(1)}$).

In certain embodiments the bispecific antigen binding molecule according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(3)}$-CH1(3)-VH(1)-CH1(1)-$VL_{(2)}$-$CH1_{(2)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the bispecific antigen binding molecule further comprises the Fab light chain polypeptide of a third Fab molecule ($VL_{(3)}$-$CL_{(3)}$).

In certain embodiments the bispecific antigen binding molecule according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region) (VH(3)-$CH1_{(3)}$-$VH_{(1)}$—CH1(I)-$VH_{(2)}$-$CL_{(2)}$). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-CH1(2)) and the Fab light chain polypeptide of the first Fab molecule (VL(1)-CL(1)). In some embodiments the bispecific antigen binding molecule further comprises the Fab light chain polypeptide of a third Fab molecule ($VL_{(3)}$-$CL_{(3)}$).

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with the Fab heavy chain of a third Fab molecule (VL(2)-$CH1_{(2)}$-$VH_{(1)}$—CH1(I)-$VH_{(3)}$-$CH1_{(3)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule (VL(1)-CL(1)). In some embodiments the bispecific antigen binding molecule further comprises the Fab light chain polypeptide of a third Fab molecule ($VL_{(3)}$-$CL_{(3)}$).

In certain embodiments the bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with the Fab heavy chain of a third Fab molecule ($VH_{(2)}$-$CL_{(2)}$-VH(1)-CH1(1)-$VH_{(3)}$-$CH1_{(3)}$). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the bispecific antigen binding molecule further comprises the Fab light chain polypeptide of a third Fab molecule ($VL_{(3)}$-$CL_{(3)}$).

In certain embodiments the bispecific antigen binding molecule according to the invention comprises a polypeptide wherein the Fab heavy chain of the second Fab molecule shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) ($VH_{(2)}$—$CH1_{(2)}$-$VL_{(1)}$-$CH1_{(1)}$-$VL_{(3)}$-$CH1_{(3)}$). In some embodiments the bispecific antigen binding molecule further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule (VL(2)-$CL_{(2)}$). In some embodiments the bispecific antigen binding molecule further comprises a polypeptide wherein the Fab heavy chain variable region of a third Fab molecule shares a carboxy-terminal peptide bond with the Fab light chain constant region of a third Fab molecule (VH(3)-$CL_{(3)}$).

In certain embodiments the bispecific antigen binding molecule according to the invention comprises a polypeptide wherein the Fab heavy chain of the second Fab molecule shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares chain constant region is replaced by a light chain constant region), which in turn shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule ($VH_{(3)}$-$CL_{(3)}$-$VH_{(1)}$-$CL_{(1)}$-$VH_{(2)}$)-$CH1_{(2)}$). In some embodiments the bispecific antigen binding molecule further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In some embodiments the bispecific antigen binding molecule further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 85, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 96 and a LCDR 3 of SEQ ID NO: 97; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 92, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 7, a HCDR 2 of SEQ ID NO: 8, and a HCDR 3 of SEQ ID NO: 9, and a light chain variable region (VL) comprising a light chain complementarity determining region (LCDR) 1 of SEQ ID NO: 10, a LCDR 2 of SEQ ID NO: 11 and a LCDR 3 of SEQ ID NO: 12; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein (i) the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 85, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3, and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein (i) the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein (i) the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 96 and a LCDR 3 of SEQ ID NO: 97; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein (i) the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 92, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein (i) the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein (i) the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 7, a HCDR 2 of SEQ ID NO: 8, and a HCDR 3 of SEQ ID NO: 9, and a light chain variable region (VL) comprising a light chain complementarity determining region (LCDR) 1 of SEQ ID NO: 10, a LCDR 2 of SEQ ID NO: 11 and a LCDR 3 of SEQ ID NO: 12; b) a second antigen binding moiety that binds to a second antigen, wherein the second antigen is CD3 and the second antigen binding moiety is a Fab molecule wherein the variable domains VL and VH or the constant domains CL and CH1 of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein (i) the first antigen binding moiety under a) and the second antigen binding moiety under b) are each fused at the C-terminus of the Fab heavy chain to the N-terminus of one of the subunits of the Fc domain under c).

In all of the different configurations of the bispecific antigen binding molecule according to the invention, the amino acid substitutions described herein, if present, may either be in the CH1 and CL domains of the first and (if present) the third antigen binding moiety/Fab molecule, or in the CH1 and CL domains of the second antigen binding moiety/Fab molecule. Preferably, they are in the CH1 and CL domains of the first and (if present) the third antigen binding moiety/Fab molecule. In accordance with the concept of the invention, if amino acid substitutions as described herein are made in the first (and, if present, the third) antigen binding moiety/Fab molecule, no such amino acid substitutions are made in the second antigen binding moiety/Fab molecule. Conversely, if amino acid substitutions as described herein are made in the second antigen binding moiety/Fab molecule, no such amino acid substitutions are made in the first (and, if present, the third) antigen binding moiety/Fab molecule. Amino acid substitutions are particularly made in bispecific antigen binding molecules comprising a Fab molecule wherein the variable domains VL and VH1 of the Fab light chain and the Fab heavy chain are replaced by each other.

In particular embodiments of the bispecific antigen binding molecule according to the invention, particularly wherein amino acid substitutions as described herein are made in the first (and, if present, the third) antigen binding moiety/Fab molecule, the constant domain CL of the first (and, if present, the third) Fab molecule is of kappa isotype. In other embodiments of the bispecific antigen binding molecule according to the invention, particularly wherein amino acid substitutions as described herein are made in the second antigen binding moiety/Fab molecule, the constant domain CL of the second antigen binding moiety/Fab molecule is of kappa isotype. In some embodiments, the constant domain CL of the first (and, if present, the third) antigen binding moiety/Fab molecule and the constant domain CL of the second antigen binding moiety/Fab molecule are of kappa isotype.

In one embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86; and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3 and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In one embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 85, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3 and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In one embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; b) a second antigen binding moiety that binds to a second antigen, wherein the second antigen is CD3 and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In one embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 96 and a LCDR 3 of SEQ ID NO: 97; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In one embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 92, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In one embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In one embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 7, a HCDR 2 of SEQ ID NO: 8, and a HCDR 3 of SEQ ID NO: 9, and a light chain variable region (VL) comprising a light chain complementarity determining region (LCDR) 1 of SEQ ID NO: 10, a LCDR 2 of SEQ ID NO: 11 and a LCDR 3 of SEQ ID NO: 12; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 85, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 96 and a LCDR 3 of SEQ ID NO: 97; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 92, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In a particular embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 7, a HCDR 2 of SEQ ID NO: 8, and a HCDR 3 of SEQ ID NO: 9, and a light chain variable region (VL) comprising a light chain complementarity determining region (LCDR) 1 of SEQ ID NO: 10, a LCDR 2 of SEQ ID NO: 11 and a LCDR 3 of SEQ ID NO: 12; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) a third antigen binding moiety that binds to the first antigen and is identical to the first antigen binding moiety; and d) an Fc domain composed of a first and a second subunit; wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 84, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 83, a HCDR 2 of SEQ ID NO: 85, and a HCDR 3 of SEQ ID NO: 86, and a light chain variable region (VL) comprising a light chain complementarity determining region (LCDR) 1 of SEQ ID NO: 87, a LCDR 2 of SEQ ID NO: 88 and a LCDR 3 of SEQ ID NO: 89; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 95 and a LCDR 3 of SEQ ID NO: 97; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 91, and a HCDR 3 of SEQ ID NO: 93, and a light chain variable region (VL) comprising a light chain complementarity determining region (LCDR) 1 of SEQ ID NO: 94, a LCDR 2 of SEQ ID NO: 96 and a LCDR 3 of SEQ ID NO: 97; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 90, a HCDR 2 of SEQ ID NO: 92, and a HCDR 3 of SEQ ID NO: 93, and a light chain variable region (VL) comprising a light chain complementarity determining region (LCDR) 1 of SEQ ID NO: 94, lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein the first antigen binding moiety under a) and the second antigen binding moiety under b) are each fused at the C-terminus of the Fab heavy chain to the N-terminus of one of the subunits of the Fc domain under c).

In another embodiment, the invention provides a bispecific antigen binding molecule comprising a) a first antigen binding moiety that binds to a first antigen, wherein the first antigen is GPRC5D and the first antigen binding moiety is a Fab molecule comprising a heavy chain variable region (VH) comprising a heavy chain complementary determining region (HCDR) 1 of SEQ ID NO: 7, a HCDR 2 of SEQ ID NO: 8, and a HCDR 3 of SEQ ID NO: 9, and a light chain variable region (VL) comprising a light chain complementarity determining region (LCDR) 1 of SEQ ID NO: 10, a LCDR 2 of SEQ ID NO: 11 and a LCDR 3 of SEQ ID NO: 12; b) a second antigen binding moiety that binds to a second antigen, wherein the second antigen is CD3, and the second antigen binding moiety is a Fab molecule wherein the variable domains VL and VH of the Fab light chain and the Fab heavy chain are replaced by each other, and wherein the Fab molecule comprises a heavy chain variable region (VH) comprising a heavy chain complementary determining region (HCDR) 1 of SEQ ID NO: 98, a HCDR 2 of SEQ ID NO: 99, and a HCDR 3 of SEQ ID NO: 100, and a light chain variable region (VL) comprising a light chain complementarity determining region (LCDR) 1 of SEQ ID NO: 101, a LCDR 2 of SEQ ID NO: 102 and a LCDR 3 of SEQ ID NO: 103; c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein the first antigen binding moiety under a) and the second antigen binding moiety under b) are each fused at the C-terminus of the Fab heavy chain to the N-terminus of one of the subunits of the Fc domain under c).

According to any of the above embodiments, components of the bispecific antigen binding molecule (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G4(SG_4)_n$ peptide linkers, wherein n is generally an integer from 1 to 10, typically from 2 to 4.

In a particular aspect, the invention provides a bispecific antigen binding molecule comprising a) a first and a third antigen binding moiety that binds to a first antigen; wherein the first antigen is GPRC5D and wherein the first and the second antigen binding moiety are each a (conventional) Fab molecule comprising a heavy chain variable region comprising the amino acid sequence of SEQ ID NO: 13 and a light chain variable region comprising the amino acid sequence of SEQ ID NO: 14; b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising a heavy chain variable region comprising the amino acid sequence of SEQ ID NO: 35 and a light chain variable region comprising the amino acid sequence of SEQ ID NO: 36; c) an Fc domain composed of a first and a second subunit; wherein in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein further the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In a particular aspect, the invention provides a bispecific antigen binding molecule comprising a) a first and a third antigen binding moiety that binds to a first antigen; wherein the first antigen is GPRC5D and wherein the first and the second antigen binding moiety are each a (conventional) Fab molecule comprising a heavy chain variable region comprising the amino acid sequence of SEQ ID NO: 15 and a light chain variable region comprising the amino acid sequence of SEQ ID NO: 16; b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising a heavy chain variable region comprising the amino acid sequence of SEQ ID NO: 35 and a light chain variable region comprising the amino acid sequence of SEQ ID NO: 36; c) an Fc domain composed of a first and a second subunit; wherein in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein further the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In a particular aspect, the invention provides a bispecific antigen binding molecule comprising a) a first and a third antigen binding moiety that binds to a first antigen; wherein the first antigen is GPRC5D and wherein the first and the second antigen binding moiety are each a (conventional) Fab molecule comprising a heavy chain variable region comprising the amino acid sequence of SEQ ID NO: 57 and a light chain variable region comprising the amino acid sequence of SEQ ID NO: 64; b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising a heavy chain variable region comprising the amino acid sequence of SEQ ID NO: 104 and a light chain variable region comprising the amino acid sequence of SEQ ID NO: 105; c) an Fc domain composed of a first and a second subunit; wherein in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein further the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In a particular aspect, the invention provides a bispecific antigen binding molecule comprising a) a first and a third antigen binding moiety that binds to a first antigen; wherein the first antigen is GPRC5D and wherein the first and the second antigen binding moiety are each a (conventional) Fab molecule comprising a heavy chain variable region comprising the amino acid sequence of SEQ ID NO: 58 and a light chain variable region comprising the amino acid sequence of SEQ ID NO: 63; b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising a heavy chain variable region comprising the amino acid sequence of SEQ ID NO: 104 and a light chain variable region comprising the amino acid sequence of SEQ ID NO: 105; c) an Fc domain composed of a first and a second subunit; wherein in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein further the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In a particular aspect, the invention provides a bispecific antigen binding molecule comprising a) a first and a third antigen binding moiety that binds to a first antigen; wherein the first antigen is GPRC5D and wherein the first and the second antigen binding moiety are each a (conventional) Fab molecule comprising a heavy chain variable region comprising the amino acid sequence of SEQ ID NO: 48 and a light chain variable region comprising the amino acid sequence of SEQ ID NO: 53; b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising a heavy chain variable region comprising the amino acid sequence of SEQ ID NO: 104 and a light chain variable region comprising the amino acid sequence of SEQ ID NO: 105; c) an Fc domain composed of a first and a second subunit; wherein in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein further the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In a particular aspect, the invention provides a bispecific antigen binding molecule comprising a) a first and a third antigen binding moiety that binds to a first antigen; wherein the first antigen is GPRC5D and wherein the first and the second antigen binding moiety are each a (conventional) Fab molecule comprising a heavy chain variable region comprising the amino acid sequence of SEQ ID NO: 49 and a light chain variable region comprising the amino acid sequence of SEQ ID NO: 52; b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising a heavy chain variable region comprising the amino acid sequence of SEQ ID NO: 104 and a light chain variable region comprising the amino acid sequence of SEQ ID NO: 105; c) an Fc domain composed of a first and a second subunit; wherein in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein further the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In a particular aspect, the invention provides a bispecific antigen binding molecule comprising a) a first and a third antigen binding moiety that binds to a first antigen; wherein the first antigen is GPRC5D and wherein the first and the second antigen binding moiety are each a (conventional) Fab molecule comprising a heavy chain variable region comprising the amino acid sequence of SEQ ID NO: 58 and a light chain variable region comprising the amino acid sequence of SEQ ID NO: 63; b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising a heavy chain variable region comprising the amino acid sequence of SEQ ID NO: 104 and a light chain variable region comprising the amino acid sequence of SEQ ID NO: 105; c) an Fc domain composed of a first and a second subunit; wherein in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein further the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In one embodiment according to this aspect of the invention, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

In a further embodiment according to this aspect of the invention, in the first subunit of the Fc domain additionally the serine residue at position 354 is replaced with a cysteine residue (S354C) or the glutamic acid residue at position 356 is replaced with a cysteine residue (E356C) In another specific embodiment, the bispecific antigen binding molecule comprises a polypeptide comprising an amino acid sequence that is at least 95%, 96%, 97%, 98%, or 99% identical to the sequence of SEQ ID NO: 114, a polypeptide comprising an amino acid sequence that is at least 95%, 96%, 97%, 98%, or 99% identical to the sequence of SEQ ID NO: 115, a polypeptide comprising an amino acid sequence that is at least 95%, 96%, 97%, 98%, or 99% identical to the sequence of SEQ ID NO: 116, and a polypeptide comprising an amino acid sequence that is at least 95%, 96%, 97%, 98%, or 99% identical to the sequence of SEQ ID NO: 117. In a further specific embodiment, the bispecific antigen binding molecule comprises a polypeptide comprising the amino acid sequence of SEQ ID NO: 114, a polypeptide comprising the amino acid sequence of SEQ ID NO: 115, a polypeptide comprising the amino acid sequence of SEQ ID NO: 116 and a polypeptide comprising the amino acid sequence of SEQ ID NO: 117.

In another specific embodiment, the bispecific antigen binding molecule comprises a polypeptide comprising an amino acid sequence that is at least 95%, 96%, 97%, 98%, or 99% identical to the sequence of SEQ ID NO: 118, a polypeptide comprising an amino acid sequence that is at least 95%, 96%, 97%, 98%, or 99% identical to the sequence of SEQ ID NO: 119, a polypeptide comprising an amino acid sequence that is at least 95%, 96%, 97%, 98%, or 99% identical to the sequence of SEQ ID NO: 120, and a polypeptide comprising an amino acid sequence that is at least 95%, 96%, 97%, 98%, or 99% identical to the sequence of SEQ ID NO: 121. In a further specific embodiment, the bispecific antigen binding molecule comprises a polypeptide comprising the amino acid sequence of SEQ ID NO: 118, a polypeptide comprising the amino acid sequence of SEQ ID NO: 119, a polypeptide comprising the amino acid sequence of SEQ ID NO: 120 and a polypeptide comprising the amino acid sequence of SEQ ID NO: 121.

In another specific embodiment, the bispecific antigen binding molecule comprises a polypeptide comprising an amino acid sequence that is at least 95%, 96%, 97%, 98%, or 99% identical to the sequence of SEQ ID NO: 122, a polypeptide comprising an amino acid sequence that is at least 95%, 96%, 97%, 98%, or 99% identical to the sequence of SEQ ID NO: 123, a polypeptide comprising an amino acid sequence that is at least 95%, 96%, 97%, 98%, or 99% identical to the sequence of SEQ ID NO: 124, and a polypeptide comprising an amino acid sequence that is at least 95%, 96%, 97%, 98%, or 99% identical to the sequence of SEQ ID NO: 125. In a further specific embodiment, the bispecific antigen binding molecule comprises a polypeptide comprising the amino acid sequence of SEQ ID NO: 122, a polypeptide comprising the amino acid sequence of SEQ ID NO: 123, a polypeptide comprising the amino acid sequence of SEQ ID NO: 124 and a polypeptide comprising the amino acid sequence of SEQ ID NO: 125.

In another specific embodiment, the bispecific antigen binding molecule comprises a polypeptide comprising an amino acid sequence that is at least 95%, 96%, 97%, 98%, or 99% identical to the sequence of SEQ ID NO: 126, a polypeptide comprising an amino acid sequence that is at least 95%, 96%, 97%, 98%, or 99% identical to the sequence of SEQ ID NO: 127, a polypeptide comprising an amino acid sequence that is at least 95%, 96%, 97%, 98%, or 99% identical to the sequence of SEQ ID NO: 128, and a polypeptide comprising an amino acid sequence that is at least 95%, 96%, 97%, 98%, or 99% identical to the sequence of SEQ ID NO: 129. In a further specific embodiment, the bispecific antigen binding molecule comprises a polypeptide comprising the amino acid sequence of SEQ ID NO: 126, a polypeptide comprising the amino acid sequence of SEQ ID NO: 127, a polypeptide comprising the amino acid sequence of SEQ ID NO: 128 and a polypeptide comprising the amino acid sequence of SEQ ID NO: 129.

In another specific embodiment, the bispecific antigen binding molecule comprises a polypeptide comprising an amino acid sequence that is at least 95%, 96%, 97%, 98%, or 99% identical to the sequence of SEQ ID NO: 130, a polypeptide comprising an amino acid sequence that is at least 95%, 96%, 97%, 98%, or 99% identical to the sequence of SEQ ID NO: 131, a polypeptide comprising an amino acid sequence that is at least 95%, 96%, 97%, 98%, or 99% identical to the sequence of SEQ ID NO: 132, and a polypeptide comprising an amino acid sequence that is at least 95%, 96%, 97%, 98%, or 99% identical to the sequence of SEQ ID NO: 133. In a further specific embodiment, the bispecific antigen binding molecule comprises a polypeptide comprising the amino acid sequence of SEQ ID NO: 130, a polypeptide comprising the amino acid sequence of SEQ ID NO: 131, a polypeptide comprising the amino acid sequence of SEQ ID NO: 132 and a polypeptide comprising the amino acid sequence of SEQ ID NO: 133.

Fc Domain

In particular embodiments, the bispecific antigen binding molecule of the invention comprises an Fc domain composed of a first and a second subunit. It is understood, that the features of the Fc domain described herein in relation to the bispecific antigen binding molecule can equally apply to an Fc domain comprised in an antibody of the invention.

The Fc domain of the bispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment, the bispecific antigen binding molecule of the invention comprises not more than one Fc domain.

In one embodiment, the Fc domain of the bispecific antigen binding molecule is an IgG Fc domain. In a particular embodiment, the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat EU index numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)).

In a further particular embodiment, the Fc domain is a human Fc domain. In an even more particular embodiment, the Fc domain is a human $IgG_1$ Fc domain. An exemplary sequence of a human $IgG_1$ Fc region is given in SEQ ID NO: 42.

Fc Domain Modifications Promoting Heterodimerization

Bispecific antigen binding molecules according to the invention comprise different antigen binding moieties, which may be fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of bispecific antigen binding molecules in recombinant production, it will thus be advantageous to introduce in the Fc domain of the bispecific antigen binding molecule a modification promoting the association of the desired polypeptides.

Accordingly, in particular embodiments, the Fc domain of the bispecific antigen binding molecule according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy-light chain modifications (e.g. VH and VL exchange/replacement in one binding arm and the introduction of substitutions of charged amino acids with opposite charges in the CH1/CL interface) in the bispecific antigen binding molecule which reduce heavy/light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific embodiment, in (the CH3 domain of) the first subunit of the Fc domain (the "knobs" subunit) the threonine residue at position 366 is replaced with a tryptophan residue (T366W), and in (the CH3 domain of) the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In a particular embodiment the antigen binding moiety that binds to the second antigen (e.g. an activating T cell antigen) is fused (optionally via the first antigen binding moiety, which binds to GPRC5D, and/or a peptide linker) to the first subunit of the Fc domain (comprising the "knob" modification). Without wishing to be bound by theory, fusion of the antigen binding moiety that binds a second antigen, such as an activating T cell antigen, to the knob-containing subunit of the Fc domain will (further) minimize the generation of antigen binding molecules comprising two antigen binding moieties that bind to an activating T cell antigen (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment, the heterodimerization approach described in EP 1870459, is used alternatively. This approach is based on the introduction of charged amino acids with opposite charges at specific amino acid positions in the CH3/CH3 domain interface between the two subunits of the Fc domain. One preferred embodiment for the bispecific antigen binding molecule of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another embodiment, the bispecific antigen binding molecule of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment, the bispecific antigen binding molecule of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said bispecific antigen binding molecule comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one embodiment, the heterodimerization approach described in WO 2013/157953 is used alternatively. In one embodiment, a first CH3 domain comprises amino acid mutation T366K and a second CH3 domain comprises amino acid mutation L351D (numberings according to Kabat EU index). In a further embodiment, the first CH3 domain comprises further amino acid mutation L351K. In a further embodiment, the second CH3 domain comprises further an amino acid mutation selected from Y349E, Y349D and L368E (preferably L368E) (numberings according to Kabat EU index).

In one embodiment, the heterodimerization approach described in WO 2012/058768 is used alternatively. In one embodiment a first CH3 domain comprises amino acid mutations L351Y, Y407A and a second CH3 domain comprises amino acid mutations T366A, K409F. In a further embodiment the second CH3 domain comprises a further amino acid mutation at position T411, D399, S400, F405, N390, or K392, e.g. selected from a) T411N, T411R, T411Q, T411K, T411 D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further embodiment a first CH3 domain comprises amino acid mutations L351Y, Y407A and a second CH3 domain comprises amino acid mutations T366V, K409F. In a further embodiment, a first CH3 domain comprises amino acid mutation Y407A and a second CH3 domain comprises amino acid mutations T366A, K409F. In a further embodiment, the second CH3 domain further comprises amino acid mutations K392E, T411E, D399R and S400R (numberings according to Kabat EU index).

In one embodiment, the heterodimerization approach described in WO 2011/143545 is used alternatively, e.g. with the amino acid modification at a position selected from the group consisting of 368 and 409 (numbering according to Kabat EU index).

In one embodiment, the heterodimerization approach described in WO 2011/090762, which also uses the knobs-into-holes technology described above, is used alternatively. In one embodiment a first CH3 domain comprises amino acid mutation T366W and a second CH3 domain comprises amino acid mutation Y407A. In one embodiment, a first CH3 domain comprises amino acid mutation T366Y and a second CH3 domain comprises amino acid mutation Y407T (numberings according to Kabat EU index).

In one embodiment, the bispecific antigen binding molecule or its Fc domain is of $IgG_2$ subclass and the heterodimerization approach described in WO 2010/129304 is used alternatively.

In an alternative embodiment, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment, a first CH3 domain comprises amino acid substitution of K392 or N392 with a negatively charged amino acid (e.g. glutamic acid (E), or aspartic acid (D), preferably K392D or N392D) and a second CH3 domain comprises amino acid substitution of D399, E356, D356, or E357 with a positively charged amino acid (e.g. lysine (K) or arginine (R), preferably D399K, E356K, D356K, or E357K, and more preferably D399K and E356K). In a further embodiment, the first CH3 domain further comprises amino acid substitution of K409 or R409 with a negatively charged amino acid (e.g. glutamic acid (E), or aspartic acid (D), preferably K409D or R409D). In a further embodiment the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further embodiment, the heterodimerization approach described in WO 2007/147901 is used alternatively. In one embodiment, a first CH3 domain comprises amino acid mutations K253E, D282K, and K322D and a second CH3 domain comprises amino acid mutations D239K, E240K, and K292D (numberings according to Kabat EU index).

In still another embodiment, the heterodimerization approach described in WO 2007/110205 can be used alternatively.

In one embodiment, the first subunit of the Fc domain comprises amino acid substitutions K392D and K409D, and the second subunit of the Fc domain comprises amino acid substitutions D356K and D399K (numbering according to Kabat EU index).

Fc Domain Modifications Reducing Fc Receptor Binding and/or Effector Function

The Fc domain confers to the bispecific antigen binding molecule (or the antibody) favorable pharmacokinetic properties, including a long serum half-life which contributes to good accumulation in the target tissue and a favorable tissue-blood distribution ratio. At the same time, it may, however, lead to undesirable targeting of the bispecific antigen binding molecule (or the antibody) to cells expressing Fc receptors rather than to the preferred antigen-bearing cells. Moreover, the co-activation of Fc receptor signaling pathways may lead to cytokine release which, in combination with the T cell activating properties (e.g. in embodiments of the bispecific antigen binding molecule wherein the second antigen binding moiety binds to an activating T cell antigen) and the long half-life of the bispecific antigen binding molecule, results in excessive activation of cytokine receptors and severe side effects upon systemic administration. Activation of (Fc receptor-bearing) immune cells other than T cells may even reduce efficacy of the bispecific antigen binding molecule (particularly a bispecific antigen binding molecule wherein the second antigen binding moiety binds to an activating T cell antigen) due to the potential destruction of T cells e.g. by NK cells.

Accordingly, in particular embodiments, the Fc domain of the bispecific antigen binding molecule according to the invention exhibits reduced binding affinity to an Fc receptor and/or reduced effector function, as compared to a native $IgG_1$ Fc domain. In one such embodiment the Fc domain (or the bispecific antigen binding molecule comprising said Fc domain) exhibits less than 50%, preferably less than 20%, more preferably less than 10% and most preferably less than 5% of the binding affinity to an Fc receptor, as compared to a native $IgG_1$ Fc domain (or a bispecific antigen binding molecule comprising a native $IgG_1$ Fc domain), and/or less than 50%, preferably less than 20%, more preferably less than 10% and most preferably less than 5% of the effector function, as compared to a native $IgG_1$ Fc domain (or a bispecific antigen binding molecule comprising a native $IgG_1$ Fc domain). In one embodiment, the Fc domain (or the bispecific antigen binding molecule comprising said Fc domain) does not substantially bind to an Fc receptor and/or induce effector the Fc domain to said receptor, is achieved when the Fc domain (or the bispecific antigen binding molecule comprising said Fc domain) exhibits greater than about 70% of the binding affinity of a non-engineered form of the Fc domain (or the bispecific antigen binding molecule comprising said non-engineered form of the Fc domain) to FcRn. The Fc domain, or bispecific antigen binding molecules of the invention comprising said Fc domain, may exhibit greater than about 80% and even greater than about 90% of such affinity. In certain embodiments, the Fc domain of the bispecific antigen binding molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment, the reduced effector function is one or more selected from the group of reduced CDC, reduced ADCC, reduced ADCP, and reduced cytokine secretion. In a particular embodiment, the reduced effector function is reduced ADCC. In one embodiment the reduced ADCC is less than 20% of the ADCC induced by a non-engineered Fc domain (or a bispecific antigen binding molecule comprising a non-engineered Fc domain).

In one embodiment, the amino acid mutation that reduces the binding affinity of the Fc domain to an Fc receptor and/or effector function is an amino acid substitution. In one embodiment, the Fc domain comprises an amino acid substitution at a position selected from the group of E233, L234, L235, N297, P331 and P329 (numberings according to Kabat EU index). In a more specific embodiment, the Fc domain comprises an amino acid substitution at a position selected from the group of L234, L235 and P329 (numberings according to Kabat EU index). In some embodiments, the Fc domain comprises the amino acid substitutions L234A and L235A (numberings according to Kabat EU index). In one such embodiment, the Fc domain is an $IgG_1$ Fc domain, particularly a human $IgG_1$ Fc domain. In one embodiment, the Fc domain comprises an amino acid substitution at position P329. In a more specific embodiment, the amino acid substitution is P329A or P329G, particularly P329G (numberings according to Kabat EU index). In one embodiment, the Fc domain comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, $IgG_4$ Fc domain comprising the amino acid substitutions S228P, L235E and optionally P329G (numberings according to Kabat EU index).

In certain embodiments, N-glycosylation of the Fc domain has been eliminated. In one such embodiment, the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or bispecific antigen binding molecules comprising an Fc domain for Fc receptors may be evaluated using cell lines known to express particular Fc receptors, such as human NK cells expressing FcγIIIa receptor.

Effector function of an Fc domain, or a bispecific antigen binding molecule comprising an Fc domain, can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTP™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the Fc domain, or the bispecific antigen binding molecule comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

FcRn binding and in vivo clearance/half-life determinations can also be performed using methods known in the art (see, e.g., Petkova, S. B. et al., *Int'l. Immunol.* 18(12):1759-1769 (2006); WO 2013/120929).

Polynucleotides

The invention further provides isolated polynucleotides encoding an antibody or bispecific antigen binding molecule as described herein or a fragment thereof. In some embodiments, said fragment is an antigen binding fragment.

The polynucleotides encoding antibodies or bispecific antigen binding molecules of the invention may be expressed as a single polynucleotide that encodes the entire antibody or bispecific antigen binding molecule or as multiple (e.g., two or more) polynucleotides that are co-expressed. Polypeptides encoded by polynucleotides that are co-expressed may associate through, e.g., disulfide bonds or other means to form a functional antibody or bispecific antigen binding molecule. For example, the light chain portion of an antibody or bispecific antigen binding molecule may be encoded by a separate polynucleotide from the portion of the antibody or bispecific antigen binding molecule comprising the heavy chain of the antibody or bispecific antigen binding molecule. When co-expressed, the heavy chain polypeptides will associate with the light chain polypeptides to form the antibody or bispecific antigen binding molecule. In another example, the portion of the antibody or bispecific antigen binding molecule comprising one of the two Fc domain subunits and optionally (part of) one or more Fab molecules could be encoded by a separate polynucleotide from the portion of the antibody or bispecific antigen binding molecule comprising the other of the two Fc domain subunits and optionally (part of) a Fab molecule. When co-expressed, the Fc domain subunits will associate to form the Fc domain.

In some embodiments, the isolated polynucleotide encodes the entire antibody or bispecific antigen binding molecule according to the invention as described herein. In other embodiments, the isolated polynucleotide encodes a polypeptide comprised in the antibody or bispecific antigen binding molecule according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Antibodies or bispecific antigen binding molecules of the invention may be obtained, for example, by solid-state peptide synthesis (e.g. Merrifield solid phase synthesis) or recombinant production. For recombinant production one or more polynucleotide encoding the antibody or bispecific antigen binding molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of an antibody or bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., Molecular Cloning: A Laboratory Manual, Cold Spring Harbor Laboratory, N.Y. (1989); and Ausubel et al., Current Protocols in Molecular Biology, Greene Publishing Associates and Wiley Interscience, N.Y (1989). The expression vector can be part of a plasmid, virus, or may be a nucleic acid fragment. The expression vector includes an expression cassette into which the polynucleotide encoding the antibody or bispecific antigen binding molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody or bispecific antigen binding molecule is desired, DNA encoding a signal sequence may be placed upstream of the nucleic acid encoding an antibody or bispecific antigen binding molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the antibody or bispecific antigen binding molecule may be included within or at the ends of the antibody or bispecific antigen binding molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) one or more vector comprising one or more polynucleotide that encodes (part of) an antibody or bispecific antigen binding molecule of the invention. As used herein, the term "host cell" refers to any kind of cellular system which can be engineered to generate the antibody or bispecific antigen binding molecule of the invention or fragments thereof. Host cells suitable for replicating and for supporting expression of antibodies or bispecific antigen binding molecules are well known in the art. Such cells may be transfected or transduced as appropriate with the particular expression vector and large quantities of vector containing cells can be grown for seeding large scale fermenters to obtain sufficient quantities of the antibody or bispecific antigen binding molecule for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr$^-$ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing an antibody or bispecific antigen binding molecule according to the invention is provided, wherein the method comprises culturing a host cell comprising a polynucleotide encoding the antibody or bispecific antigen binding molecule, as provided herein, under conditions suitable for expression of the antibody or bispecific antigen binding molecule, and optionally recovering the antibody or bispecific antigen binding molecule from the host cell (or host cell culture medium).

The components of the bispecific antigen binding molecule (or the antibody) of the invention may be genetically fused to each other. The bispecific antigen binding molecule can be designed such that its components are fused directly to each other or indirectly through a linker sequence. The composition and length of the linker may be determined in accordance with methods well known in the art and may be tested for efficacy. Examples of linker sequences between different components of bispecific antigen binding molecules are provided herein. Additional sequences may also be included to incorporate a cleavage site to separate the individual components of the fusion if desired, for example an endopeptidase recognition sequence.

The antibody or bispecific antigen binding molecule of the invention generally comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region may be used in the antibody or bispecific antigen binding molecule of the invention. Non-limiting antibodies, antibody fragments, antigen binding domains or variable regions useful in the present invention can be of murine, primate, or human origin. If the antibody or bispecific antigen binding molecule is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Human antibodies can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolation from human antibody libraries, as described herein.

Antibodies useful in the invention may be isolated by screening combinatorial libraries for antibodies with the desired activity or activities. Methods for screening combinatorial libraries are reviewed, e.g., in Lerner et al. in Nature Reviews 16:498-508 (2016). For example, a variety of methods are known in the art for generating phage display libraries and screening such libraries for antibodies possessing the desired binding characteristics. Such methods are reviewed, e.g., in Frenzel et al. in mAbs 8:1177-1194 (2016); Bazan et al. in Human Vaccines and Immunotherapeutics 8:1817-1828 (2012) and Zhao et al. in *Critical Reviews in Biotechnology* 36:276-289 (2016) as well as in Hoogenboom et al. in *Methods in Molecular Biology* 178: 1-37 (O'Brien et al., ed., Human Press, Totowa, NJ, 2001) and in Marks and Bradbury in *Methods in Molecular Biology* 248:161-175 (Lo, ed., Human Press, Totowa, NJ, 2003).

In certain phage display methods, repertoires of VH and VL genes are separately cloned by polymerase chain reaction (PCR) and recombined randomly in phage libraries, which can then be screened for antigen-binding phage as described in Winter et al. in *Annual Review of Immunology* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. in *EMBO Journal* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in *Journal of Molecular Biology* 227: 381-388 (1992).

Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936. Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in *Methods in Molecular Biology* 503:135-56 (2012) and in Cherf et al. in *Methods in Molecular biology* 1319:155-175 (2015) as well as in the Zhao et al. in *Methods in Molecular Biology* 889:73-84 (2012). Methods for ribosome display are described, e.g., in He et al. in *Nucleic Acids Research* 25:5132-5134 (1997) and in Hanes et al. in *PNAS* 94:4937-4942 (1997).

Antibodies or bispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the antibody or bispecific antigen binding molecule binds. For example, for affinity chromatography purification of antibodies or bispecific antigen binding molecules of the invention, a matrix with protein A or protein G may be used. Sequential Protein A or G affinity chromatography and size exclusion chromatography can be used to isolate an antibody or bispecific antigen binding molecule essentially as described in the Examples. The purity of the antibody or bispecific antigen binding molecule can be determined by any of a variety of well-known analytical methods including gel electrophoresis, high pressure liquid chromatography, and the like.

Assays

Antibodies or bispecific antigen binding molecules provided herein may be identified, screened for, or characterized for their physical/chemical properties and/or biological activities by various assays known in the art.

Affinity Assays

The affinity of the antibody or bispecific antigen binding molecule for an Fc receptor or a target antigen can be determined for example by surface plasmon resonance (SPR), using standard instrumentation such as a BIAcore instrument (GE Healthcare), and receptors or target proteins such as may be obtained by recombinant expression. Alternatively, binding of antibodies or bispecific antigen binding molecules for different receptors or target antigens may be evaluated using cell lines expressing the particular receptor or target antigen, for example by flow cytometry (FACS). A specific illustrative and exemplary embodiment for measuring binding affinity is described in the following.

According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody is diluted with 10 mM sodium acetate, pH 5.0, to 40 μg/ml before injection at a flow rate of 5 μl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the antibody or bispecific antigen binding molecule (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 μl/min for 120 s.

To determine the affinity to the target antigen, antibodies or bispecific antigen binding molecules are captured by an anti-human Fab specific antibody (GE Healthcare) that is immobilized on an activated CM5-sensor chip surface as described for the anti Penta-His antibody. The final amount of coupled protein is approximately 12000 RU. The antibodies or bispecific antigen binding molecules are captured for 90 s at 300 nM. The target antigens are passed through the flow cells for 180 s at a concentration range from 250 to 1000 nM with a flowrate of 30 μl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the bispecific antigen binding molecules (or antibodies) of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

Compositions, Formulations, and Routes of Administration

In a further aspect, the invention provides pharmaceutical compositions comprising any of the antibodies or bispecific antigen binding molecules provided herein, e.g., for use in any of the below therapeutic methods. In one embodiment, a pharmaceutical composition comprises any of the antibodies or bispecific antigen binding molecules provided herein and a pharmaceutically acceptable carrier. In another embodiment, a pharmaceutical composition comprises any of the antibodies or bispecific antigen binding molecules provided herein and at least one additional therapeutic agent, e.g., as described below.

Further provided is a method of producing an antibody or bispecific antigen binding molecule of the invention in a form suitable for administration in vivo, the method comprising (a) obtaining an antibody or bispecific antigen binding molecule according to the invention, and (b) formulating the antibody or bispecific antigen binding molecule with at least one pharmaceutically acceptable carrier, whereby a preparation of antibody or bispecific antigen binding molecule is formulated for administration in vivo.

Pharmaceutical compositions of the present invention comprise a therapeutically effective amount of antibody or bispecific antigen binding molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains an antibody or bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

An immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

Parenteral compositions include those designed for administration by injection, e.g. subcutaneous, intradermal, intralesional, intravenous, intraarterial intramuscular, intrathecal or intraperitoneal injection. For injection, the antibodies or bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the antibodies or bispecific antigen binding molecules may be in powder form for constitution with a suitable vehicle, e.g., sterile pyrogen-free water, before use. Sterile injectable solutions are prepared by incorporating the antibodies or bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the antibodies or bispecific antigen binding molecules may also be formulated as a depot preparation. Such long acting formulations may be administered by implantation (for example subcutaneously or intramuscularly) or by intramuscular injection. Thus, for example, the antibodies or bispecific antigen binding molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antibodies or bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen. The antibodies or bispecific antigen binding molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or systemic lupus erythematosus and/or rheumatoid arthritis. Production of pathogenic autoantibodies by self-reactive plasma cells is a hallmark of autoimmune diseases. Therefore, GPRC5D can be used to target self-reactive plasma cells in autoimmune diseases.

In a further aspect, the invention provides for the use of an antibody or bispecific antigen binding molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of an antibody or bispecific antigen binding molecule of the invention. In one embodiment a composition is administered to said individual, comprising the antibody or bispecific antigen binding molecule of the invention in a pharmaceutically acceptable form. In certain embodiments the disease to be treated is a proliferative disorder. In a particular embodiment the disease is cancer.

In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with an antibody or bispecific antigen binding molecule of the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of an antibody or bispecific antigen binding molecule to induce lysis of a target cell. In one embodiment, an "individual" is a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that may be treated using an antibody or bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of kidney cancer, bladder cancer, skin cancer, lung cancer, colorectal cancer, breast cancer, brain cancer, head and neck cancer and prostate cancer. In one embodiment, the cancer is prostate cancer. A skilled artisan readily recognizes that in many cases the antibody or bispecific antigen binding molecule may not provide a cure but may only provide partial benefit. In some embodiments, a physiological change having some benefit is also considered therapeutically beneficial. Thus, in some embodiments, an amount of antibody or bispecific antigen binding molecule that provides a physiological change is considered an "effective amount" or a "therapeutically effective amount". The subject, patient, or individual in need of treatment is typically a mammal, more specifically a human.

In some embodiments, an effective amount of an antibody or bispecific antigen binding molecule of the invention is administered to a cell. In other embodiments, a therapeutically effective amount of an antibody or bispecific antigen binding molecule of the invention is administered to an individual for the treatment of disease.

For the prevention or treatment of disease, the appropriate dosage of an antibody or bispecific antigen binding molecule of the invention (when used alone or in combination with one or more other additional therapeutic agents) will depend on the type of disease to be treated, the route of administration, the body weight of the patient, the type of antibody or bispecific antigen binding molecule, the severity and course of the disease, whether the antibody or bispecific antigen binding molecule is administered for preventive or therapeutic purposes, previous or concurrent therapeutic interventions, the patient's clinical history and response to the antibody or bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The antibody or bispecific antigen binding molecule is suitably administered to the patient at one time or over a series of treatments. Depending on the type and severity of the disease, about 1 μg/kg to 15 mg/kg (e.g. 0.1 mg/kg-10 mg/kg) of antibody or bispecific antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or bispecific antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody or bispecific antigen binding molecule). An initial higher loading dose, followed by one or more lower doses may be administered. However, other dosage regimens may be useful. The progress of this therapy is easily monitored by conventional techniques and assays.

The antibodies or bispecific antigen binding molecules of the invention will generally be used in an amount effective to achieve the intended purpose. For use to treat or prevent a disease condition, the antibodies or bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the antibodies or bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the antibodies or bispecific antigen binding molecules may not be related to plasma concentration. One having skill in the art will be able to optimize therapeutically effective local dosages without undue experimentation.

A therapeutically effective dose of the antibodies or bispecific antigen binding molecules described herein will generally provide therapeutic benefit without causing substantial toxicity. Toxicity and therapeutic efficacy of an antibody or bispecific antigen binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antibodies or bispecific antigen binding molecules that exhibit large therapeutic indices are preferred. In one embodiment, the antibody or bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with antibodies or bispecific antigen binding molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The antibodies and bispecific antigen binding molecules of the invention may be administered in combination with one or more other agents in therapy. For instance, an antibody or bispecific antigen binding molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent. Such other agents are suitably present in combination in amounts that are effective for the purpose intended. The effective amount of such other agents depends on the amount of antibody or bispecific antigen binding molecule used, the type of disorder or treatment, and other factors discussed above. The antibodies or bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antibody or bispecific antigen binding molecule of the invention can occur prior to, simultaneously, and/or following, administration of the additional therapeutic agent and/or adjuvant. Antibodies or bispecific antigen binding molecules of the invention may also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody or bispecific antigen binding molecule of the invention. The label or package insert indicates that the composition is used for treating the condition of choice. Moreover, the article of manufacture may comprise (a) a first container with a composition contained therein, wherein the composition comprises an antibody or bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Methods and Compositions for Diagnostics and Detection

In certain embodiments, any of the anti-GPRC5D antibodies provided herein is useful for detecting the presence of GPRC5D in a biological sample. The term "detecting" as used herein encompasses quantitative or qualitative detection. In certain embodiments, a biological sample comprises a cell or tissue, such as prostate tissue.

In one embodiment, an anti-GPRC5D antibody for use in a method of diagnosis or detection is provided. In a further aspect, a method of detecting the presence of GPRC5D in a biological sample is provided. In certain embodiments, the method comprises contacting the biological sample with an anti-GPRC5D antibody as described herein under conditions permissive for binding of the anti-GPRC5D antibody to GPRC5D, and detecting whether a complex is formed between the anti-GPRC5D antibody and GPRC5D. Such method may be an in vitro or in vivo method. In one embodiment, an anti-GPRC5D antibody is used to select subjects eligible for therapy with an anti-GPRC5D antibody, e.g. where GPRC5D is a biomarker for selection of patients.

Exemplary disorders that may be diagnosed using an antibody of the invention include cancer, particularly multiple myeloma.

In certain embodiments, labeled anti-GPRC5D antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

A further aspect of the invention relates to an antibody (10B10) that binds GPRC5D comprising a variable heavy chain region (VL), wherein the VL may comprises an amino acid sequence that is at least 95%, 96%, 97%, 98%, 99% or 100% identical to the sequence of SEQ ID NO: 81. The antibody may comprises a light chain variable region (VL), wherein the VL comprises an amino acid sequence that is at least 95%, 96%, 97%, 98%, 99% or 100% identical to the sequence of SEQ ID NO: 82. The antibody may comprises a VH and a VL, wherein the VL may comprises an amino acid sequence that is at least 95%, 96%, 97%, 98%, 99% or 100% identical to the sequence of SEQ ID NO: 81 and wherein the VL comprises an amino acid sequence that is at least 95%, 96%, 97%, 98%, 99% or 100% identical to the sequence of SEQ ID NO: 82. Preferably, the antibody comprises a VH comprising the amino acid sequence of SEQ ID NO: 81 and a VL comprising the amino acid sequence of SEQ ID NO: 82.

A further aspect of the invention relates to an antibody (10B10-TCB). The antibody may comprise a first light chain, wherein the first light chain comprises an amino acid sequence that is at least 95%, 96%, 97%, 98%, 99% or 100% identical to the sequence of SEQ ID NO: 67. The antibody may comprise a second light chain, wherein the second light chain comprises an amino acid sequence that is at least 95%, 96%, 97%, 98%, 99% or 100% identical to the sequence of SEQ ID NO: 68. The antibody may comprise a first heavy chain, wherein the first heavy chain comprises an amino acid sequence that is at least 95%, 96%, 97%, 98%, 99% or 100% identical to the sequence of SEQ ID NO: 69. The antibody may comprise a second heavy chain, wherein the second heavy chain comprises an amino acid sequence that is at least 95%, 96%, 97%, 98%, 99% or 100% identical to the sequence of SEQ ID NO: 70. In a preferred embodiment, the antibody comprises a first light chain comprising the amino acid sequence of SEQ ID NO: 67, a second light chain comprising the amino acid sequence of SEQ ID NO: 68, a first heavy chain comprising the amino acid sequence of SEQ ID NO: 69 and a second heavy chain comprising the amino acid sequence of SEQ ID NO: 70.

Amino Acid Sequences

| | Amino acid sequence | SEQ ID NO |
|---|---|---|
| 5E11-VH-HCDR1 | GFTFSKYAMA | 1 |
| 5E11-VH-HCDR2 | STGGVNTYYRDSVKA | 2 |
| 5E11-VH-HCDR3 | HTGDYFDY | 3 |
| 5E11-VL-LCDR1 | ASQSVSISGINLMN | 4 |
| 5E11-VL-LCDR2 | HASILAS | 5 |
| 5E11-VL-LCDR3 | QQTRESPLT | 6 |
| 5F11-VH-HCDR1 | GFSFSNYGMA | 7 |
| 5F11-VH-HCDR2 | STGGGNTYYRDSVKG | 8 |
| 5F11-VH-HCDR3 | HDRGGLY | 9 |
| 5F11-VL-LCDR1 | RSSKSLLHSNGITYVY | 10 |
| 5F11-VL-LCDR2 | RMSNLAS | 11 |
| 5F11-VL-LCDR3 | GQLLENPYT | 12 |
| 5E11-VH | ELQLEQSGGGLVQPGGSLTLSCAASGFTFSKYAMAWVRQAPTKGLEWV ASISTGGVNTYYRDSVKARFTISRDNAKNTQYLQMDSLRSEDTATYYC ATHTGDYFDYWGQGVMVTVSS | 13 |
| 5E11-VL | DIVLTQSPALAVSPGQRATISCRASQSVSISGINLMNWYQQKPGQQPK LLIYHASILASGIPTRFSGSGSGTDFTLTIDPVQADDIATYYCQQTRE SPLTFGSGTNLEIK | 14 |

-continued

Amino Acid Sequences

| | Amino acid sequence | SEQ ID NO |
|---|---|---|
| 5F11-VH | EVQLVESGGGLVQPGRSLKLSCAASGFSFSNYGMAWVRQAATKGLEWV ASISTGGGNTYYRDSVKGRFIVSRDNAKNTQYLQMDSLRSEDTATYYC TRHDRGGLYWGQGVMVTVSS | 15 |
| 5F11-VL | DIVMTQAPLSVSVTPGESASISCRSSKSLLHSNGITYVYWYFQKPGKS PQVLIYRMSNLASGVPDRFSGSGSETDFTLKISRVEAEDVGIYHCGQL LENPYTFGAGTELELK | 16 |
| 5E11-TCB-LC1(GPRC5D) | DIVLTQSPALAVSPGQRATISCRASQSVSISGINLMNWYQQKPGQQPK LLIYHASILASGIPTRFSGSGSGTDFTLTIDPVQADDIATYYCQQTRE SPLTFGSGTNLEIKRTVAAPSVFIFPPSDRKLKSGTASVVCLLNNFYP REAKVQWKVDNALQSGNSQESVTEQDSKDSTYSLSSTLTLSKADYEKH KVYACEVTHQGLSSPVTKSFNRGEC | 17 |
| 5E11-TCB-LC2(CD3) | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVY YCVRHGNFGNSYVSWFAYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | 18 |
| 5E11-TCB-HC hole | ELQLEQSGGGLVQPGGSLTLSCAASGFTFSKYAMAWVRQAPTKGLEWV ASISTGGVNTYYRDSVKARFTISRDNAKNTQYLQMDSLRSEDTATYYC ATHTGDYFDYWGQGVMVTVSSASTKGPSVFPLAPSSKSTSGGTAALGC LVEDYFPEPVTVSWNSGALTSGVHTFPAVLQSSGLYSLSSVVTVPSSS LGTQTYICNVNHKPSNTKVDEKVEPKSCDKTHTCPPCPAPEAAGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALGAPIEKTI SKAKGQPREPQVCTLPPSRDELTKNQVSLSCAVKGFYPSDIAVEWESN GQPENNYKTTPPVLDSDGSFFLVSKLTVDKSRWQQGNVFSCSVMHEAL HNHYTQKSLSLSPGK | 19 |
| 5E11-TCB-HC knob | ELQLEQSGGGLVQPGGSLTLSCAASGFTFSKYAMAWVRQAPTKGLEWV ASISTGGVNTYYRDSVKARFTISRDNAKNTQYLQMDSLRSEDTATYYC ATHTGDYFDYWGQGVMVTVSSASTKGPSVFPLAPSSKSTSGGTAALGC LVEDYFPEPVTVSWNSGALTSGVHTFPAVLQSSGLYSLSSVVTVPSSS LGTQTYICNVNHKPSNTKVDEKVEPKSCDGGGGSGGGGSQAVVTQEPS LTVSPGGTVTLTCGSSTGAVTTSNYANWVQEKPGQAFRGLIGGTNKRA PGTPARFSGSLLGGKAALTLSGAQPEDEAEYYCALWYSNLWVFGGGTK LTVLSSASTKGPSVFPLAPSSKSTSGGTAALGCLVKDYFPEPVTVSWN SGALTSGVHTFPAVLQSSGLYSLSSVVTVPSSSLGTQTYICNVNHKPS NTKVDKKVEPKSCDKTHTCPPCPAPEAAGGPSVFLFPPKPKDTLMISR TPEVTCVVVDVSHEDPEVKFNWYVDGVEVHNAKTKPREEQYNSTYRVV SVLTVLHQDWLNGKEYKCKVSNKALGAPIEKTISKAKGQPREPQVYTL PPCRDELTKNQVSLWCLVKGFYPSDIAVEWESNGQPENNYKTTPPVLD SDGSFFLYSKLTVDKSRWQQGNVFSCSVMHEALHNHYTQKSLSLSPGK | 20 |
| 5F11-TCB-LC1(GPRC5D) | DIVMTQAPLSVSVTPGESASISCRSSKSLLHSNGITYVYWYFQKPGKS PQVLIYRMSNLASGVPDRFSGSGSETDFTLKISRVEAEDVGIYHCGQL LENPYTFGAGTELELKRTVAAPSVFIFPPSDRKLKSGTASVVCLLNNF YPREAKVQWKVDNALQSGNSQESVTEQDSKDSTYSLSSTLTLSKADYE KHKVYACEVTHQGLSSPVTKSFNRGEC | 21 |
| 5F11-TCB-LC2(CD3) | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVY YCVRHGNFGNSYVSWFAYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | 22 |
| 5F11-TCB-HC hole | EVQLVESGGGLVQPGRSLKLSCAASGFSFSNYGMAWVRQAATKGLEWV ASISTGGGNTYYRDSVKGRFIVSRDNAKNTQYLQMDSLRSEDTATYYC TRHDRGGLYWGQGVMVTVSSASTKGPSVFPLAPSSKSTSGGTAALGCL VEDYFPEPVTVSWNSGALTSGVHTFPAVLQSSGLYSLSSVVTVPSSSL GTQTYICNVNHKPSNTKVDEKVEPKSCDKTHTCPPCPAPEAAGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALGAPIEKTIS KAKGQPREPQVCTLPPSRDELTKNQVSLSCAVKGFYPSDIAVEWESNG QPENNYKTTPPVLDSDGSFFLVSKLTVDKSRWQQGNVFSCSVMHEALH NHYTQKSLSLSPGK | 23 |
| 5F11-TCB-HC knob | EVQLVESGGGLVQPGRSLKLSCAASGFSFSNYGMAWVRQAATKGLEWV ASISTGGGNTYYRDSVKGRFIVSRDNAKNTQYLQMDSLRSEDTATYYC TRHDRGGLYWGQGVMVTVSSASTKGPSVFPLAPSSKSTSGGTAALGCL VEDYFPEPVTVSWNSGALTSGVHTFPAVLQSSGLYSLSSVVTVPSSSL GTQTYICNVNHKPSNTKVDEKVEPKSCDGGGGSGGGGSQAVVTQEPSL TVSPGGTVTLTCGSSTGAVTTSNYANWVQEKPGQAFRGLIGGTNKRAP | 24 |

-continued

| Amino Acid Sequences | | |
|---|---|---|
| | Amino acid sequence | SEQ ID NO |
| | GTPARFSGSLLGGKAALTLSGAQPEDEAEYYCALWYSNLWVFGGGTKL TVLSSASTKGPSVFPLAPSSKSTSGGTAALGCLVKDYFPEPVTVSWNS GALTSGVHTFPAVLQSSGLYSLSSVVTVPSSSLGTQTYICNVNHKPSN TKVDKKVEPKSCDKTHTCPPCPAPEAAGGPSVFLFPPKPKDTLMISRT PEVTCVVVDVSHEDPEVKFNWYVDGVEVHNAKTKPREEQYNSTYRVVS VLTVLHQDWLNGKEYKCKVSNKALGAPIEKTISKAKGQPREPQVYTLP PCRDELTKNQVSLWCLVKGFYPSDIAVEWESNGQPENNYKTTPPVLDS DGSFFLYSKLTVDKSRWQQGNVFSCSVMHEALHNHYTQKSLSLSPGK | |
| ET150-5-TCB-LC1(GPRC5D) | QSVLTQPPSASGTPGQRVTISCSGSRSNVGGNYVFWYQQVPGATPKLL IYRSNQRPSGVPDRFAGSKSGSSASLAISGLRSEDEADYYCATWDDSL SGFVFGTGTKVTVLGQPKAAPSVTLFPPSSKKLQANKATLVCLISDFY PGAVTVAWKADSSPVKAGVETTTPSKQSNNKYAASSYLSLTPEQWKSH RSYSCQVTHEGSTVEKTVAPTECS | 25 |
| ET150-5-TCB-LC2(CD3) | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVY YCVRHGNFGNSYVSWFAYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | 26 |
| ET150-5-TCB-HC hole | EVQLVESGGGLVKPGGSLRLSCAASGFTFSDYYMSWIRQAPGKGLEWV SYISSSGSTIYYADSVKGRFTISRDNAKNSLYLQMNSLRAEDTAVYYC ARGYGKAYDQWGQGTLVTVSSASTKGPSVFPLAPSSKSTSGGTAALGC LVEDYFPEPVTVSWNSGALTSGVHTFPAVLQSSGLYSLSSVVTVPSSS LGTQTYICNVNHKPSNTKVDEKVEPKSCDKTHTCPPCPAPEAAGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALGAPIEKTI SKAKGQPREPQVCTLPPSRDELTKNQVSLSCAVKGFYPSDIAVEWESN GQPENNYKTTPPVLDSDGSFFLVSKLTVDKSRWQQGNVFSCSVMHEAL HNHYTQKSLSLSPGK | 27 |
| ET150-5-TCB-HC knob | EVQLVESGGGLVKPGGSLRLSCAASGFTFSDYYMSWIRQAPGKGLEWV SYISSSGSTIYYADSVKGRFTISRDNAKNSLYLQMNSLRAEDTAVYYC ARGYGKAYDQWGQGTLVTVSSASTKGPSVFPLAPSSKSTSGGTAALGC LVEDYFPEPVTVSWNSGALTSGVHTFPAVLQSSGLYSLSSVVTVPSSS LGTQTYICNVNHKPSNTKVDEKVEPKSCDGGGGSGGGGSQAVVTQEPS LTVSPGGTVTLTCGSSTGAVTTSNYANWVQEKPGQAFRGLIGGTNKRA PGTPARFSGSLLGGKAALTLSGAQPEDEAEYYCALWYSNLWVFGGGTK LTVLSSASTKGPSVFPLAPSSKSTSGGTAALGCLVKDYFPEPVTVSWN SGALTSGVHTFPAVLQSSGLYSLSSVVTVPSSSLGTQTYICNVNHKPS NTKVDKKVEPKSCDKTHTCPPCPAPEAAGGPSVFLFPPKPKDTLMISR TPEVTCVVVDVSHEDPEVKFNWYVDGVEVHNAKTKPREEQYNSTYRVV SVLTVLHQDWLNGKEYKCKVSNKALGAPIEKTISKAKGQPREPQVYTL PPCRDELTKNQVSLWCLVKGFYPSDIAVEWESNGQPENNYKTTPPVLD SDGSFFLYSKLTVDKSRWQQGNVFSCSVMHEALHNHYTQKSLSLSPGK | 28 |
| CD3-VH-HCDR1 | TYAMN | 29 |
| CD3-VH-HCDR2 | RIRSKYNNYATYYADSVKG | 30 |
| CD3-VH-HCDR3 | HGNFGNSYVSWFAY | 31 |
| CD3-LH-LCDR1 | GSSTGAVTTSNYAN | 32 |
| CD3-LH-LCDR2 | GTNKRAP | 33 |
| CD3-LH-LCDR3 | ALWYSNLWV | 34 |
| CD3-VH | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVY YCVRHGNFGNSYVSWFAYWGQGTLVTVSS | 35 |
| CD3-VL | QAVVTQEPSLTVSPGGTVTLTCGSSTGAVTTSNYANWVQEKPGQAFRG LIGGTNKRAPGTPARFSGSLLGGKAALTLSGAQPEDEAEYYCALWYSN LWVFGGGTKLTVL | 36 |
| Human kappa CL domain | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC | 37 |
| Human lambda CL domain | QPKAAPSVTLFPPSSEELQANKATLVCLISDFYPGAVTVAWKADSSPV KAGVETTTPSKQSNNKYAASSYLSLTPEQWKSHRSYSCQVTHEGSTVE KTVAPTECS | 38 |

-continued

Amino Acid Sequences

| | Amino acid sequence | SEQ ID NO |
|---|---|---|
| Human IgG1 heavy chain constant region (CH1—CH2—CH3) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTC VVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSLSP | 39 |
| hCD3 | MQSGTHWRVLGLCLLSVGVWGQDGNEEMGGITQTPYKVSISGTTVILT CPQYPGSEILWQHNDKNIGGDEDDKNIGSDEDHLSLKEFSELEQSGYY VCYPRGSKPEDANFYLYLRARVCENCMEMDVMSVATIVIVDICITGGL LLLVYYWSKNRKAKAKPVTRGAGAGGRQRGQNKERPPPVPNPDYEPIR KGQRDLYSGLNQRRI | 40 |
| cynoCD3 | MQSGTRWRVLGLCLLSIGVWGQDGNEEMGSITQTPYQVSISGTTVILT CSQHLGSEAQWQHNGKNKEDSGDRLFLPEFSEMEQSGYYVCYPRGSNP EDASHHLYLKARVCENCMEMDVMAVATIVIVDICITLGLLLLVYYWSK NRKAKAKPVTRGAGAGGRQRGQNKERPPPVPNPDYEPIRKGQQDLYSG LNQRRI | 41 |
| hIgG1 Fc region | DKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNG KEYKCKVSNKALPAPIEKTISKAKGQPREPQVYTLPPSRDELTKNQVS LTCLVKGFYPSDIAVEWESNGQPENNYKTTPPVLDSDGSFFLYSKLTV DKSRWQQGNVFSCSVMHEALHNHYTQKSLSLSP | 42 |
| linker | GGGGSGGGGS | 43 |
| linker | DGGGGSGGGGS | 44 |
| Human GPRC5D | MYKDCIESTGDYFLLCDAEGPWGIILESLAILGIVVTILLLLAFLFL MRKIQDCSQWNVLPTQLLFLLSVLGLFGLAFAFIIELNQQTAPVRYF LFGVLFALCFSCLLAHASNLVKLVRGCVSFSWTTILCIAIGCSLLQI IIATEYVTLIMTRGMMFVNMTPCQLNVDFVVLLVYVLFLMALTFFVS KATFCGPCENWKQHGRLIFITVLFSIIIWVVWISMLLRGNPQFQRQP QWDDPVVCIALVTNAWVFLLLYIVPELCILYRSCRQECPLQGNACPV TAYQHSFQVENQELSRARDSDGAEEDVALTSYGTPIQPQTVDPTQEC FIPQAKLSPQQDAGGV | 45 |
| 5E11_VH1a | EVQLLESGGGLVQPGGSLRLSCAASGFTFSKYAMAWVRQAPGKGLEWV ASISTGGVNTYYRDSVKARFTISRDNSKNTLYLQMNSLRAEDTAVYYC ATHTGDYFDYWGQGTMVTVSS | 46 |
| 5E11_VH1b | ELQLLESGGGLVQPGGSLRLSCAASGFTFSKYAMAWVRQAPGKGLEWV ASISTGGVNTYYRDSVKARFTISRDNAKNTLYLQMNSLRAEDTAVYYC ATHTGDYFDYWGQGTMVTVSS | 47 |
| 5E11_VH1c | EVQLLESGGGLVQPGGSLRLSCAASGFTFSKYAMAWVRQAPGKGLEWV ASISTGGVNTYYADSVKGRFTISRDNSKNTLYLQMNSLRAEDTAVYYC ATHTGDYFDYWGQGTMVTVSS | 48 |
| 5E11_VH1d | ELQLLESGGGLVQPGGSLRLSCAASGFTFSKYAMAWVRQAPGKGLEWV ASISTGGVNTYYADSVKGRFTISRDNAKNTLYLQMNSLRAEDTAVYYC ATHTGDYFDYWGQGTMVTVSS | 49 |
| 5E11_VL1a | DIVMTQSPDSLAVSLGERATINCRASQSVSISGINLMNWYQQKPGQQP KLLIYHASILASGVPDRFSGSGSGTDFTLTISSLQAEDVAVYYCQQTR ESPLTFGQGTRLEIK | 50 |
| 5E11_VL1c | DIVMTQSPDSLAVSLGERATINCKSSQSVSISGINLMNWYQQKPGQQP KLLIYHASILASGVPDRFSGSGSGTDFTLTISSLQAEDVAVYYCQQTR ESPLTFGQGTRLEIK | 51 |
| 5E11_VL2a | EIVLTQSPGTLSLSPGERATLSCRASQSVSISGINLMNWYQQKPGQQP RLLIYHASILASGIPDRFSGSGSGTDFTLTISRLEPEDFAVYYCQQTR ESPLTFGQGTRLEIK | 52 |
| 5E11_VL2b | EIVLTQSPGTLSLSPGERATLSCRASQSVSISGINLMNWYQQKPGQQP KLLIYHASILASGIPDRFSGSGSGTDFTLTISRLEPEDFAVYYCQQTR ESPLTFGQGTRLEIK | 53 |
| 5E11_VL3a | DIQMTQSPSSLSASVGDRVTITCRASQSVSISGINLMNWYQQKPGKQP KLLIYHASILASGVPSRFSGSGSGTDFTLTISSLQPEDFATYYCQQTR ESPLTFGQGTRLEIK | 54 |

-continued

Amino Acid Sequences

| | Amino acid sequence | SEQ ID NO |
|---|---|---|
| 5E11_VL3b | DIQMTQSPSSLSASVGDRVTITCRASQSVSISGINLMNWYQQKPGQQP KLLIYHASILASGVPSRFSGSGSGTDFTLTISSLQPEDFATYYCQQTR ESPLTFGQGTRLEIK | 55 |
| 5F11_VH1a | QVQLVESGGGVVQPGRSLRLSCAASGFSFSNYGMAWVRQAPGKGLEWV ASISTGGGNTYYRDSVKGRFTISRDNSKNTLYLQMNSLRAEDTAVYYC TRHDRGGLYWGQGTMVTVSS | 56 |
| 5F11_VH1b | EVQLVESGGGVVQPGRSLRLSCAASGFSFSNYGMAWVRQAPGKGLEWV ASISTGGGNTYYRDSVKGRFTISRDNAKNTLYLQMNSLRAEDTAVYYC TRHDRGGLYWGQGTMVTVSS | 57 |
| 5F11_VH1c | QVQLVESGGGVVQPGRSLRLSCAASGFSFSNYGMAWVRQAPGKGLEWV ASISTGGGNTYYADSVKGRFTISRDNSKNTLYLQMNSLRAEDTAVYYC TRHDRGGLYWGQGTMVTVSS | 58 |
| 5F11_VH1d | EVQLVESGGGVVQPGRSLRLSCAASGFSFSNYGMAWVRQAPGKGLEWV ASISTGGGNTYYADSVKGRFTISRDNAKNTLYLQMNSLRAEDTAVYYC TRHDRGGLYWGQGTMVTVSS | 59 |
| 5F11_VH2b | EVQLVESGGGLVQPGGSLRLSCAASGFSFSNYGMAWVRQAPGKGLEWV ASISTGGGNTYYRDSVKGRFTISRDNAKNTLYLQMNSLRAEDTAVYYC TRHDRGGLYWGQGTMVTVSS | 60 |
| 5F11_VH2d | EVQLVESGGGLVQPGGSLRLSCAASGFSFSNYGMAWVRQAPGKGLEWV ASISTGGGNTYYADSVKGRFTISRDNAKNTLYLQMNSLRAEDTAVYYC TRHDRGGLYWGQGTMVTVSS | 61 |
| 5F11_VL1a | DIVMTQSPLSLPVTPGEPASISCRSSKSLLHSNGITYVYWYLQKPGQS PQVLIYRMSNLASGVPDRFSGSGSGTDFTLKISRVEAEDVGVYHCGQL LENPYTFGQGTKLEIK | 62 |
| 5F11_VL1b | DIVMTQSPLSLPVTPGEPASISCRSSKSLLHSNGITYVYWYLQKPGKS PQVLIYRMSNLASGVPDRFSGSGSGTDFTLKISRVEAEDVGVYHCGQL LENPYTFGQGTKLEIK | 63 |
| 5F11_VL2a | DIVMTQSPLSLPVTPGEPASISCRSSKSLLHSNGITYVYWYLQKPGQS PQLLIYRMSNRASGVPDRFSGSGSGTDFTLKISRVEAEDVGVYHCGQL LENPYTFGQGTKLEIK | 64 |
| 5F11_VL2b | DIVMTQSPDSLAVSLGERATINCKSSKSLLHSNGITYVYWYQQKPGQP PKLLIYRMSNLASGVPDRFSGSGSGTDFTLTISSLQAEDVAVYHCGQL LENPYTFGQGTKLEIK | 65 |
| 5F11_VL2c | EIVLTQSPGTLSLSPGERATLSCRASKSLLHSNGITYVYWYQQKPGQA PRLLIYRMSNLASGIPDRFSGSGSGTDFTLTISRLEPEDFAVYHCGQL LENPYTFGQGTKLEIK | 66 |
| 10B10 TCB_LC1 | DIQLTQSPHSLSASLGETVSIECLASEGISNYLAWFHQKPGKSPQLLI YYASSLQDGVPSRFSGSGSGTQYSLKISNMQPEDEGVYYCQQGYKYPL TFGSGTKLEIKRTVAAPSVFIFPPSDRKLKSGTASVVCLLNNFYPREA KVQWKVDNALQSGNSQESVTEQDSKDSTYSLSSTLTLSKADYEKHKVY ACEVTHQGLSSPVTKSFNRGEC | 67 |
| 10B10 TCB_LC2 | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVY YCVRHGNFGNSYVSWFAYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | 68 |
| 10B10 TCB_HC(Fc hole) | EVQLVESGGGLVQPGRSMKLSCAASGFTFTNFYMAWVRQAPTKALEWV ASINTGGGYTYYRDSVKGRFTVSRDNTRSTLYLQMDSLRSEETATYYC ARHLTYYGRYYYFDYWGQGVMVTVSSASTKGPSVFPLAPSSKSTSGGT AALGCLVEDYFPEPVTVSWNSGALTSGVHTFPAVLQSSGLYSLSSVVT VPSSSLGTQTYICNVNHKPSNTKVDEKVEPKSCDKTHTCPPCPAPEAA GGPSVFLFPPKPKDTLMISRTPEVTCVVVDVSHEDPEVKFNWYVDGVE VHNAKTKPREEQYNSTYRVVSVLTVLHQDWLNGKEYKCKVSNKALGAP IEKTISKAKGQPREPQVCTLPPSRDELTKNQVSLSCAVKGFYPSDIAV EWESNGQPENNYKTTPPVLDSDGSFFLVSKLTVDKSRWQQGNVFSCSV MHEALHNHYTQKSLSLSPGK | 69 |
| 10B10 TCB_HC(Fc knob) | EVQLVESGGGLVQPGRSMKLSCAASGFTFTNFYMAWVRQAPTKALEWV ASINTGGGYTYYRDSVKGRFTVSRDNTRSTLYLQMDSLRSEETATYYC ARHLTYYGRYYYFDYWGQGVMVTVSSASTKGPSVFPLAPSSKSTSGGT AALGCLVEDYFPEPVTVSWNSGALTSGVHTFPAVLQSSGLYSLSSVVT | 70 |

-continued

Amino Acid Sequences

| | Amino acid sequence | SEQ ID NO |
|---|---|---|
| | VPSSSLGTQTYICNVNHKPSNTKVDEKVEPKSCDGGGGSGGGGSQAVV TQEPSLTVSPGGTVTLTCGSSTGAVTTSNYANWVQEKPGQAFRGLIGG TNKRAPGTPARFSGSLLGGKAALTLSGAQPEDEAEYYCALWYSNLWVF GGGTKLTVLSSASTKGPSVFPLAPSSKSTSGGTAALGCLVKDYFPEPV TVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDT LMISRTPEVTCVVVDVSHEDPEVKFNWYVDGVEVHNAKTKPREEQYNS TYRVVSVLTVLHQDWLNGKEYKCKVSNKALGAPIEKTISKAKGQPREP QVYTLPPCRDELTKNQVSLWCLVKGFYPSDIAVEWESNGQPENNYKTT PPVLDSDGSFFLYSKLTVDKSRWQQGNVFSCSVMHEALHNHYTQKSLS LSPGK | |
| 07A04 IgG_LC | DVQMTQSPYNLAASPGESVSINCKASKSISKYLAWYQQKPGKANKLLI YDGSTLQSGIPSRFSGSGSGTDFTLTIRSLEPEDFGLYYCQQHNEYPL TFGSGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC | 71 |
| 07A04 IgG_HC | QVTLKESGPGILQPSHTLSLTCSFSGFSLSTYGMGVNWIRQPSGKGLE WLASIWWNGNTYNNPSLKSRLTVSKDTSNNQAFLKVTSVDTADTATYY CVHTRGIIRGRGLFFDYWGQGVMVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPE AAGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALG APIEKTISKAKGQPREPQVYTLPPSRDELTKNQVSLTCLVKGFYPSDI AVEWESNGQPENNYKTTPPVLDSDGSFFLYSKLTVDKSRWQQGNVFSC SVMHEALHNHYTQKSLSLSPGK | 72 |
| B72-TCB_HC1 | QTVVTQEPSLTVSPGGTVTLTCRSSTGAVTTSNYANWVQQKPGQAPRG LIGGTNKRAPGTPARFSGSLLGGKAALTLSGVQPEDEAEYYCALWYSN LWVFGGGTKLTVLSSASTKGPSVFPLAPSSKSTSGGTAALGCLVKDYF PEPVTVSWNSGALTSGVHTFPAVLQSSGLYSLSSVVTVPSSSLGTQTY ICNVNHKPSNTKVDKKVEPKSCDKTHTCPPCPAPEAAGGPSVFLFPPK PKDTLMISRTPEVTCVVVDVSHEDPEVKFNWYVDGVEVHNAKTKPREE QYNSTYRVVSVLTVLHQDWLNGKEYKCKVSNKALGAPIEKTISKAKGQ PREPQVYTLPPCRDELTKNQVSLWCLVKGFYPSDIAVEWESNGQPENN YKTTPPVLDSDGSFFLYSKLTVDKSRWQQGNVFSCSVMHEALHNHYTQ KSLSLSPGK | 73 |
| B72-TCB_LC1 | EVQLVESGGGLVQPGGSLRLSCAASGFTFNTYAMNWVRQAPGKGLEWV ARIRSKYNNYATYYAASVKGRFTISRDDSKNSLYLQMNSLKTEDTAVY YCARHGNFGNSYVSWFAYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | 74 |
| B72-TCB_HC2 | QVQLVQSGAEVKKPGASVKVSCKASGYSFTGYTMNWVRQAPGQGLEWM GLINPYNSDTNYAQKLQGRVTMTTDTSTSTAYMELRSLRSDDTAVYYC ARVALRVALDYWGQGTLVTVSSASTKGPSVFPLAPSSKSTSGGTAALG CLVEDYFPEPVTVSWNSGALTSGVHTFPAVLQSSGLYSLSSVVTVPSS SLGTQTYICNVNHKPSNTKVDEKVEPKSCDKTHTCPPCPAPEAAGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALGAPIEKT ISKAKGQPREPQVCTLPPSRDELTKNQVSLSCAVKGFYPSDIAVEWES NGQPENNYKTTPPVLDSDGSFFLVSKLTVDKSRWQQGNVFSCSVMHEA LHNHYTQKSLSLSPGK | 75 |
| B72-TCB_LC2 | DIQMTQSPSSLSASVGDRVTITCKASQNVATHVGWYQQKPGKAPKRLI YSASYRYSGVPSRFSGSGSGTEFTLTISNLQPEDFATYYCQQYNRYPY TFGQGTKLEIKRTVAAPSVFIFPPSDRKLKSGTASVVCLLNNFYPREA KVQWKVDNALQSGNSQESVTEQDSKDSTYSLSSTLTLSKADYEKHKVY ACEVTHQGLSSPVTKSFNRGEC | 76 |
| BCMA-TCB-HC1 hole | EVQLLESGGGLVQPGGSLRLSCAASGFTFSSYAMNWVRQAPGKGLEWV SAITASGGSTYYADSVKGRFTISRDNSKNTLYLQMNSLRAEDTAVYYC ARYWPMSLWGQGTLVTVSSASTKGPSVFPLAPSSKSTSGGTAALGCLV EDYFPEPVTVSWNSGALTSGVHTFPAVLQSSGLYSLSSVVTVPSSSLG TQTYICNVNHKPSNTKVDEKVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALGAPIEKTISK AKGQPREPQVCTLPPSRDELTKNQVSLSCAVKGFYPSDIAVEWESNGQ PENNYKTTPPVLDSDGSFFLVSKLTVDKSRWQQGNVFSCSVMHEALHN HYTQKSLSLSPGK | 77 |
| BCMA-TCB-LC1 | EIVLTQSPGTLSLSPGERATLSCRASQSVSAYYLAWYQQKPGQAPRLL MYDASIRATGIPDRFSGSGSGTDFTLTISRLEPEDFAVYYCQQYERWP | 78 |

-continued

| Amino Acid Sequences | | |
|---|---|---|
| | Amino acid sequence | SEQ ID NO |
| | LTFGQGTKVEIKRTVAAPSVFIFPPSDRKLKSGTASVVCLLNNFYPRE AKVQWKVDNALQSGNSQESVTEQDSKDSTYSLSSTLTLSKADYEKHKV YACEVTHQGLSSPVTKSFNRGEC | |
| BCMA-TCB-HC2 (knob) | EVQLLESGGGLVQPGGSLRLSCAASGFTFSSYAMNWVRQAPGKGLEWV SAITASGGSTYYADSVKGRFTISRDNSKNTLYLQMNSLRAEDTAVYYC ARYWPMSLWGQGTLVTVSSASTKGPSVFPLAPSSKSTSGGTAALGCLV EDYFPEPVTVSWNSGALTSGVHTFPAVLQSSGLYSLSSVVTVPSSSLG TQTYICNVNHKPSNTKVDEKVEPKSCDGGGGSGGGGSQAVVTQEPSLT VSPGGTVTLTCGSSTGAVTTSNYANWVQEKPGQAFRGLIGGTNKRAPG TPARFSGSLLGGKAALTLSGAQPEDEAEYYCALWYSNLWVFGGGTKLT VLSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNT KVDKKVEPKSCDKTHTCPPCPAPEAAGGPSVFLFPPKPKDTLMISRTP EVTCVVVDVSHEDPEVKFNWYVDGVEVHNAKTKPREEQYNSTYRVVSV LTVLHQDWLNGKEYKCKVSNKALGAPIEKTISKAKGQPREPQVYTLPP CRDELTKNQVSLWCLVKGFYPSDIAVEWESNGQPENNYKTTPPVLDSD GSFFLYSKLTVDKSRWQQGNVFSCSVMHEALHNHYTQKSLSLSPGK | 79 |
| BCMA-TCB-LC2 | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVY YCVRHGNFGNSYVSWFAYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | 80 |
| 10B10_VH | DIQLTQSPHSLSASLGETVSIECLASEGISNYLAWFHQKPGKSPQLLI YYASSLQDGVPSRFSGSGSGTQYSLKISNMQPEDEGVYYCQQGYKYPL TFGSGTKLEIK | 81 |
| 10B10_VL | EVQLVESGGGLVQPGRSMKLSCAASGFTFTNFYMAWVRQAPTKALEWV ASINTGGGYTYYRDSVKGRFTVSRDNTRSTLYLQMDSLRSEETATYYC ARHLTYYGRYYYFDYWGQGVMVTVSS | 82 |
| 5E11_P1AE5706_ PARENT-VH- HCDR1 | GFTFSKYAMA | 83 |
| 5E11_P1AE5706_ PARENT-VH- HCDR2 | SISTGGVNTYYRDSVKA | 84 |
| 5E11_P1AE5723_ P1AE5728_VH- HCDR2 | SISTGGVNTYYADSVKG | 85 |
| 5E11_P1AE5706_ PARENT-VH- HCDR3 | HTGDYFDY | 86 |
| 5E11_P1AE5706_ PARENT-VL- LCDR1 | RASQSVSISGINLMN | 87 |
| 5E11_P1AE5706_ PARENT-VL- LCDR2 | HASILAS | 88 |
| 5E11_P1AE5706_ PARENT-VL- LCDR3 | QQTRESPLT | 89 |
| 5F11_P1 AE5733_ PARENT-VH- HCDR1 | GFSFSNYGMA | 90 |
| 5F11_P1AE5733_ PARENT-VH- HCDR2 | SISTGGGNTYYRDSVKG | 91 |
| PF11_P1AE5745_ VL-HCDR2 | SISTGGGNTYYADSVKG | 92 |
| 5F11_P1AE5733_ PARENT-VH- HCDR3 | HDRGGLY | 93 |

-continued

| Amino Acid Sequences | | |
|---|---|---|
| | Amino acid sequence | SEQ ID NO |
| 5F11_P1AE5733_ PARENT-VL- LCDR1 | RSSKSLLHSNGITYVY | 94 |
| 5F11_P1 AE5733_ PARENT-VL- LCDR2 | RMSNLAS | 95 |
| 5F11_P1AE5741_ VL_LCDR2 | RMSNRAS | 96 |
| 5F11_P1AE5733_ PARENT-VL- LCDR3 | GQLLENPYT | 97 |
| CD3-C122-VH- HCDR1 | SYAMN | 98 |
| CD3-C122-VH- HCDR2 | RIRSKYNNYATYYADSVKG | 99 |
| CD3-C122-VH- HCDR3 | HTTFPSSYVSYYGY | 100 |
| CD3-C122-VH- LCDR1 | GSSTGAVTTSNYAN | 101 |
| CD3-C122-VH- LCDR2 | GTNKRAP | 102 |
| CD3-C122-VH- LCDR3 | ALWYSNLWV | 103 |
| CD3-C122-VH | EVQLLESGGGLVQPGGSLRLSCAASGFQFSSYAMNWVRQAPGKGLEWV SRIRSKYNNYATYYADSVKGRFTISRDDSKNTLYLQMNSLRAEDTAVY YCVRHTTFPSSYVSYYGYWGQGTLVTVSS | 104 |
| CD3-C122-VL | QAVVTQEPSLTVSPGGTVTLTCGSSTGAVTTSNYANWVQEKPGQAFRG LIGGTNKRAPGTPARFSGSLLGGKAALTLSGAQPEDEAEYYCALWYSN LWVFGGGTKLTVL | 105 |
| CD3-V9-VH- HCDR1 | GYSFTGYTMN | 106 |
| CD3-V9-VH- HCDR2 | LINPYKGVSTYNQKFKD | 107 |
| CD3-V9-VH- HCDR3 | SGYYGDSDWYFDV | 108 |
| CD3-V9-VH- LCDR1 | RASQDIRNYLN | 109 |
| CD3-V9-VH- LCDR2 | YTSRLES | 110 |
| CD3-V9-VH- LCDR3 | QQGNTLPWT | 111 |
| CD3-V9-VH | EVQLVESGGGLVQPGGSLRLSCAASGYSFTGYTMNWVRQAPGKGLEWV ALINPYKGVSTYNQKFKDRFTISVDKSKNTAYLQMNSLRAEDTAVYYC ARSGYYGDSDWYFDVWGQGTLVTVSS | 112 |
| CD3-V9-VL | DIQMTQSPSSLSASVGDRVTITCRASQDIRNYLNWYQQKPGKAPKLLI YYTSRLESGVPSRFSGSGSGTDYTLTISSLQPEDFATYYCQQGNTLPW TFGQGTKVEI | 113 |
| 5F11(VH 1b + VL2a)-C122-TCB- LC1(antiGPRC5D) (P1AE6623) | DIVMTQSPLSLPVTPGEPASISCRSSKSLLHSNGITYVYWYLQKPGQS PQLLIYRMSNRASGVPDRFSGSGSGTDFTLKISRVEAEDVGVYHCGQL LENPYTFGQGTKLEIKRTVAAPSVFIFPPSDRKLKSGTASVVCLLNNF YPREAKVQWKVDNALQSGNSQESVTEQDSKDSTYSLSSTLTLSKADYE KHKVYACEVTHQGLSSPVTKSFNRGEC | 114 |
| 5F11(VH1b + VL2a)-C122-TCB- | EVQLLESGGGLVQPGGSLRLSCAASGFQFSSYAMNWVRQAPGKGLEWV SRIRSKYNNYATYYADSVKGRFTISRDDSKNTLYLQMNSLRAEDTAVY | 115 |

-continued

Amino Acid Sequences

| | Amino acid sequence | SEQ ID NO |
|---|---|---|
| LC2(antiCD3) (P1AE6623) | YCVRHTTFPSSYVSYYGYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | |
| 5F11(VH1b + VL2a)-C122-TCB-HC1(Fc hole) (P1AE6623) | EVQLVESGGGVVQPGRSLRLSCAASGFSFSNYGMAWVRQAPGKGLEWV ASISTGGGNTYYRDSVKGRFTISRDNAKNTLYLQMNSLRAEDTAVYYC TRHDRGGLYWGQGTMVTVSSASTKGPSVFPLAPSSKSTSGGTAALGCL VEDYFPEPVTVSWNSGALTSGVHTFPAVLQSSGLYSLSSVVTVPSSSL GTQTYICNVNHKPSNTKVDEKVEPKSCDKTHTCPPCPAPEAAGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALGAPIEKTIS KAKGQPREPQVCTLPPSRDELTKNQVSLSCAVKGFYPSDIAVEWESNG QPENNYKTTPPVLDSDGSFFLVSKLTVDKSRWQQGNVFSCSVMHEALH NHYTQKSLSLSPGK | 116 |
| 5F11(VH1b + VL2a)-C122-TCB-HC2(Fc knob) (P1AE6623) | EVQLVESGGGVVQPGRSLRLSCAASGFSFSNYGMAWVRQAPGKGLEWV ASISTGGGNTYYRDSVKGRFTISRDNAKNTLYLQMNSLRAEDTAVYYC TRHDRGGLYWGQGTMVTVSSASTKGPSVFPLAPSSKSTSGGTAALGCL VEDYFPEPVTVSWNSGALTSGVHTFPAVLQSSGLYSLSSVVTVPSSSL GTQTYICNVNHKPSNTKVDEKVEPKSCDGGGGSGGGGSQAVVTQEPSL TVSPGGTVTLTCGSSTGAVTTSNYANWVQEKPGQAFRGLIGGTNKRAP GTPARFSGSLLGGKAALTLSGAQPEDEAEYYCALWYSNLWVFGGGTKL TVLSSASTKGPSVFPLAPSSKSTSGGTAALGCLVKDYFPEPVTVSWNS GALTSGVHTFPAVLQSSGLYSLSSVVTVPSSSLGTQTYICNVNHKPSN TKVDKKVEPKSCDKTHTCPPCPAPEAAGGPSVFLFPPKPKDTLMISRT PEVTCVVVDVSHEDPEVKFNWYVDGVEVHNAKTKPREEQYNSTYRVVS VLTVLHQDWLNGKEYKCKVSNKALGAPIEKTISKAKGQPREPQVYTLP PCRDELTKNQVSLWCLVKGFYPSDIAVEWESNGQPENNYKTTPPVLDS DGSFFLYSKLTVDKSRWQQGNVFSCSVMHEALHNHYTQKSLSLSPGK | 117 |
| 5F11(VH1c + VL1b)-C122-TCB-LC1(antiGPRC5D) (P1AE6624) | DIVMTQSPLSLPVTPGEPASISCRSSKSLLHSNGITYVYWYLQKPGKS PQVLIYRMSNLASGVPDRFSGSGSGTDFTLKISRVEAEDVGVYHCGQL LENPYTFGQGTKLEIKRTVAAPSVFIFPPSDRKLKSGTASVVCLLNNF YPREAKVQWKVDNALQSGNSQESVTEQDSKDSTYSLSSTLTLSKADYE KHKVYACEVTHQGLSSPVTKSFNRGEC | 118 |
| 5F11(VH1c + VL1b)-C122-TCB-LC2(antiCD3) (P1AE6624) | EVQLLESGGGLVQPGGSLRLSCAASGFQFSSYAMNWVRQAPGKGLEWV SRIRSKYNNYATYYADSVKGRFTISRDDSKNTLYLQMNSLRAEDTAVY YCVRHTTFPSSYVSYYGYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | 119 |
| 5F11(VH1c + VL1b)-C122-TCB-HC1(Fc hole) (P1AE6624) | QVQLVESGGGVVQPGRSLRLSCAASGFSFSNYGMAWVRQAPGKGLEWV ASISTGGGNTYYADSVKGRFTISRDNSKNTLYLQMNSLRAEDTAVYYC TRHDRGGLYWGQGTMVTVSSASTKGPSVFPLAPSSKSTSGGTAALGCL VEDYFPEPVTVSWNSGALTSGVHTFPAVLQSSGLYSLSSVVTVPSSSL GTQTYICNVNHKPSNTKVDEKVEPKSCDKTHTCPPCPAPEAAGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALGAPIEKTIS KAKGQPREPQVCTLPPSRDELTKNQVSLSCAVKGFYPSDIAVEWESNG QPENNYKTTPPVLDSDGSFFLVSKLTVDKSRWQQGNVFSCSVMHEALH NHYTQKSLSLSPGK | 120 |
| 5F11(VH1c + VL1b)-C122-TCB-HC2(Fc knob) (P1AE6624) | QVQLVESGGGVVQPGRSLRLSCAASGFSFSNYGMAWVRQAPGKGLEWV ASISTGGGNTYYADSVKGRFTISRDNSKNTLYLQMNSLRAEDTAVYYC TRHDRGGLYWGQGTMVTVSSASTKGPSVFPLAPSSKSTSGGTAALGCL VEDYFPEPVTVSWNSGALTSGVHTFPAVLQSSGLYSLSSVVTVPSSSL GTQTYICNVNHKPSNTKVDEKVEPKSCDGGGGSGGGGSQAVVTQEPSL TVSPGGTVTLTCGSSTGAVTTSNYANWVQEKPGQAFRGLIGGTNKRAP GTPARFSGSLLGGKAALTLSGAQPEDEAEYYCALWYSNLWVFGGGTKL TVLSSASTKGPSVFPLAPSSKSTSGGTAALGCLVKDYFPEPVTVSWNS GALTSGVHTFPAVLQSSGLYSLSSVVTVPSSSLGTQTYICNVNHKPSN TKVDKKVEPKSCDKTHTCPPCPAPEAAGGPSVFLFPPKPKDTLMISRT PEVTCVVVDVSHEDPEVKFNWYVDGVEVHNAKTKPREEQYNSTYRVVS VLTVLHQDWLNGKEYKCKVSNKALGAPIEKTISKAKGQPREPQVYTLP PCRDELTKNQVSLWCLVKGFYPSDIAVEWESNGQPENNYKTTPPVLDS DGSFFLYSKLTVDKSRWQQGNVFSCSVMHEALHNHYTQKSLSLSPGK | 121 |
| 5E11(VH1c + VL2b)-C122-TCB-LC1(antiGPRC5D) (P1AE6625) | EIVLTQSPGTLSLSPGERATLSCRASQSVSISGINLMNWYQQKPGQQP KLLIYHASILASGIPDRFSGSGSGTDFTLTISRLEPEDFAVYYCQQTR ESPLTFGQGTRLEIKRTVAAPSVFIFPPSDRKLKSGTASVVCLLNNFY PREAKVQWKVDNALQSGNSQESVTEQDSKDSTYSLSSTLTLSKADYEK HKVYACEVTHQGLSSPVTKSFNRGEC | 122 |

-continued

| Amino Acid Sequences | | |
|---|---|---|
| | Amino acid sequence | SEQ ID NO |
| 5E11(VH1c + VL2b)-C122-TCB-LC2(antiCD3) (P1AE6625) | EVQLLESGGGLVQPGGSLRLSCAASGFQFSSYAMNWVRQAPGKGLEWVSRIRSKYNNYATYYADSVKGRFTISRDDSKNTLYLQMNSLRAEDTAVYYCVRHTTFPSSYVSYYGYWGQGTLVTVSSASVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 123 |
| 5E11(VH1c + VL2b)-C122-TCB-HC1(Fc hole) (P1AE6625) | EVQLLESGGGLVQPGGSLRLSCAASGFTFSKYAMAWVRQAPGKGLEWVASISTGGVNTYYADSVKGRFTISRDNSKNTLYLQMNSLRAEDTAVYYCATHTGDYFDYWGQGTMVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 124 |
| 5E11(VH1c + VL2b)-C122-TCB-HC2(Fc knob) (P1AE6625) | EVQLLESGGGLVQPGGSLRLSCAASGFTFSKYAMAWVRQAPGKGLEWVASISTGGVNTYYADSVKGRFTISRDNSKNTLYLQMNSLRAEDTAVYYCATHTGDYFDYWGQGTMVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDGGGGSGGGGSQAVVTQEPSLTVSPGGTVTLTCGSSTGAVTTSNYANWVQEKPGQAFRGLIGGTNKRAPGTPARFSGSLLGGKAALTLSGAQPEDEAEYYCALWYSNLWVFGGGTKLTVLSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 125 |
| 5E11(VH1d + VL2a)-C122-TCB-LC1(antiGPRC5D) (P1AE6626) | EIVLTQSPGTLSLSPGERATLSCRASQSVSISGINLMNWYQQKPGQQPRLLIYHASILASGIPDRFSGSGSGTDFTLTISRLEPEDFAVYYCQQTRESPLTFGQGTRLEIKRTVAAPSVFIFPPSDRKLKSGTASVVCLLNNFYPREAKVQWKVDNALQSGNSQESVTEQDSKDSTYSLSSTLTLSKADYEKHKVYACEVTHQGLSSPVTKSFNRGEC | 126 |
| 5E11(VH1d + VL2a)-C122-TCB-LC2(antiCD3) (P1AE6626) | EVQLLESGGGLVQPGGSLRLSCAASGFQFSSYAMNWVRQAPGKGLEWVSRIRSKYNNYATYYADSVKGRFTISRDDSKNTLYLQMNSLRAEDTAVYYCVRHTTFPSSYVSYYGYWGQGTLVTVSSASVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 127 |
| 5E11(VH1d + VL2a)-C122-TCB-HC1(Fc hole) (P1AE6626) | ELQLLESGGGLVQPGGSLRLSCAASGFTFSKYAMAWVRQAPGKGLEWVASISTGGVNTYYADSVKGRFTISRDNAKNTLYLQMNSLRAEDTAVYYCATHTGDYFDYWGQGTMVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 128 |
| 5E11(VH1d + VL2a)-C122-TCB-HC2(Fc knob) (P1AE6626) | ELQLLESGGGLVQPGGSLRLSCAASGFTFSKYAMAWVRQAPGKGLEWVASISTGGVNTYYADSVKGRFTISRDNAKNTLYLQMNSLRAEDTAVYYCATHTGDYFDYWGQGTMVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDGGGGSGGGGSQAVVTQEPSLTVSPGGTVTLTCGSSTGAVTTSNYANWVQEKPGQAFRGLIGGTNKRAPGTPARFSGSLLGGKAALTLSGAQPEDEAEYYCALWYSNLWVFGGGTKLTVLSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 129 |
| 5F11(VH1c + VL1b)-V9-TCB-LC1(antiGPRC4D) (P1AF1336) | DIVMTQSPLSLPVTGEPASISCRSSKSLLHSNGITVYWYLQKPGKSPQVLIYRMSNLASGVPDRFSGSGSGTDFTLKISRVEAEDVGVYHCGQLLENPYTFGQGTKLEIKRTVAAPSVFIFPPSDRKLKSGTASVVCLLNNFYPREAKVQWKVDNALQSGNSQESVTEQDSKDSTYSLSSTLTLSKADYEKHKVYACEVTHQGLSSPVTKSFNRGEC | 130 |

-continued

| Amino Acid Sequences | | |
|---|---|---|
| | Amino acid sequence | SEQ ID NO |
| 5F11(VH1c + VL1b)-V9-TCB-LC2(antiCD3) (P1AF1336) | EVQLVESGGGLVQPGGSLRLSCAASGYSFTGYTMNWVRQAPGKGLEWVALINPYKGVSTYNQKFKDRFTISVDKSKNTAYLQMNSLRAEDTAVYYCARSGYYGDSDWYFDVWGQGTLVTVSSASVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 131 |
| 5F11(VH1c + VL1b)-V9-TCB-HC1(Fc hole) (P1AF1336) | QVQLVESGGGVVQPGRSLRLSCAASGFSFSNYGMAWVRQAPGKGLEWVASISTGGGNTYYADSVKGRFTISRDNSKNTLYLQMNSLRAEDTAVYYCTRHDRGGLYWGQGTMVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 132 |
| 5F11(VH1c + VL1b)-V9-TCB-HC2(Fc knob) (P1AF1336) | QVQLVESGGGVVQPGRSLRLSCAASGFSFSNYGMAWVRQAPGKGLEWVASISTGGGNTYYADSVKGRFTISRDNSKNTLYLQMNSLRAEDTAVYYCTRHDRGGLYWGQGTMVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDGGGGSGGGGSDIQMTQSPSSLSASVGDRVTITCRASQDIRNYLNWYQQKPGKAPKLLIYYTSRLESGVPSRFSGSGSGTDYTLTISSLQPEDFATYYCQQGNTLPWTFGQGTKVEIKSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 133 |

EXAMPLES

The following are examples of methods and compositions of the invention. It is understood that various other embodiments may be practiced, given the general description provided above.

Example 1

Expression of Tumor Targets

To identify the differential genes expressed by multiple myeloma over the normal plasma cells, RNAseq was performed for 10 samples derived from patients with multiple myeloma (MM) and 10 plasma cells (PCs) derived from bone marrow of healthy donors. The RNA was extracted using the RNeasy Micro kit (Qiagen) according to manufacturer's instructions. The genomic DNA was removed using the RNase free DNase set (Qiagen) during the RNA extraction. The quality of the extracted RNA was controlled on Agilent Eukaryote Total RNA pico chips (Agilent Technologies). SMARTer ultra-low RNA kit for Illumina sequencing (Clontech) was used to prepare and amplify cDNA from 1.6 ng of total RNA according to the manufacturer's instructions. Then, 1 ng of amplified cDNA was subjected to Nextera XT library preparation (Illumina) according to the manufacturer's instructions. Sequencing libraries were quantified using the Kapa Library Quantification kit (Kapa Biosystems) and quality controlled by capillary electrophoresis on a Bioanalyzer using High Sensitivity chips (Agilent Technologies). The libraries were sequenced on a HiSeq2500 sequencer (Illumina) for 2×50 cycles using version 4 cluster generation kits and version 4 sequencing reagents (Illumina).

Figure 2:
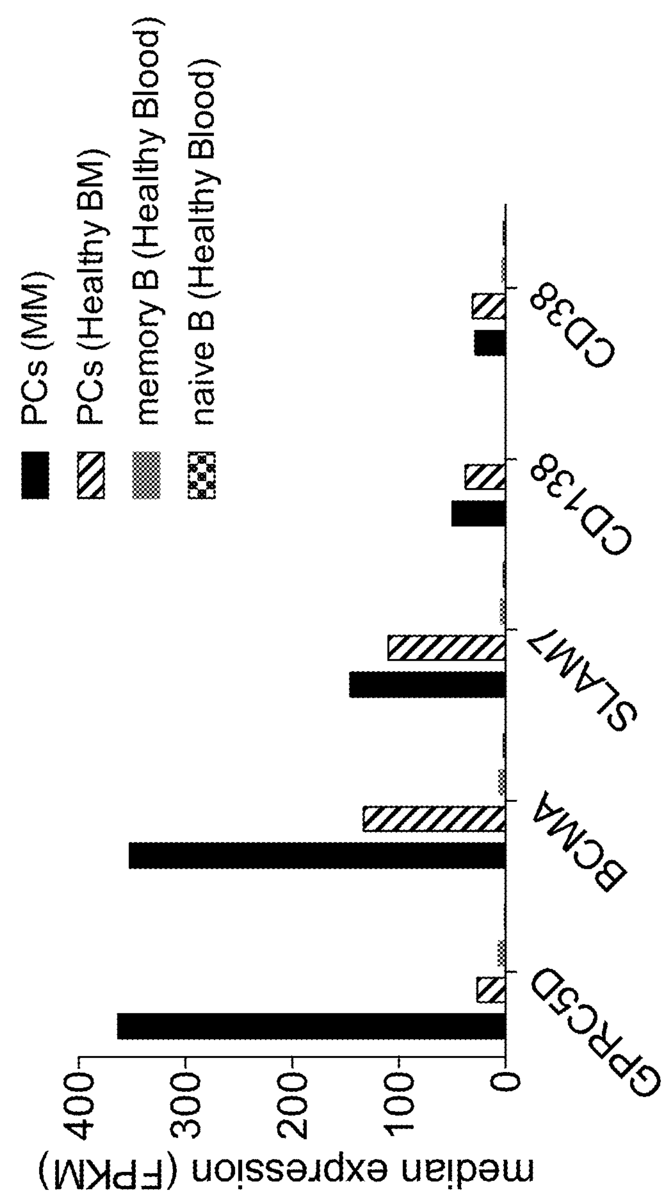
FIG. 2. Analysis of gene expression of tumor targets on plasma cells and B-cells by RNAseq.

B-cell maturation antigen (BCMA) is a cell surface protein, which is expressed on malignant plasma cells and thus recognized as multiple myeloma target (Tai Y T & Anderson K C, Targeting B-cell maturation antigen in multiple myeloma, Immunotherapy. 2015 Nov. 7(11): 1187-1199). Using the RNAseq technology, in-depth analysis indicated that GPRC5D is expressed as highly as BCMA in plasma cells from multiple myeloma patients (FIG. 2). More importantly, the differential expression of GPRC5D between plasma cells from multiple myeloma patients and healthy plasma cells is approximately 20 fold. In contrast, differential expression of BCMA between plasma cells from multiple myeloma patients and healthy plasma cells is only 2-fold. The overall expression of GPRC5D is much high than the expression of other known multiple myeloma target molecules such as SLAM7, CD138 and CD38. In addition, GPRC5D is hardly expressed by healthy naive or memory B cells.

Example 2

Figure 3:
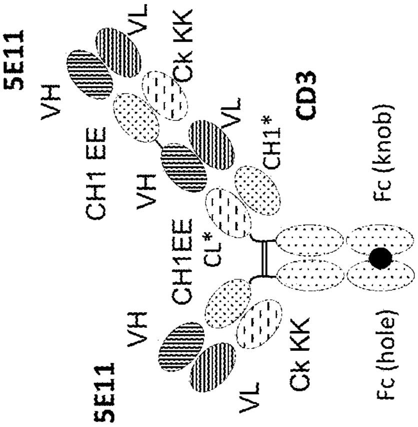
FIG. 3. Exemplary configurations of the 5E11-bispecific antigen binding molecules of the invention. Black dot: optional modification in the Fc domain promoting heterodimerization. ++, −−: amino acids of opposite charges optionally introduced in the CH1 and CL domains.

Generation of GPRC5D Binders and Preparation of T Cell Bispecific (TCB) Antibodies GPRC5D binders were generated by DNA immunization of rats, followed by hybridoma generation, screening and sequencing of hybridoma. Screening for specific binding was measured by ELISA by its binding to GPRC5D-expressing transfectant. Two GPRC5D binders were identified referred to as 5E11 (SEQ ID Nos 13 and 14) and 5F11 (SEQ ID NOs 15 and 16) in the following. Once the specific binders were identified, the IgGs were converted into T cell bispecific antibodies. The principles of converting binders into T cell bispecific antibodies are exemplified and described in the art, e.g. in PCT publication no. WO 2014/131712 A1, which is incorporated herein by reference in its entirety. The T cell bispecific antibodies comprise two GPRC5D-binding moieties and one CD3-binding moiety (anti-GPRC5D/anti-CD3 T cell bispecific antibodies) as illustrated in FIG. 3. The following anti-GPRC5D/anti-CD3 T cell bispecific antibodies were was performed on a custom-designed BD Biosciences Fortessa and analyzed using FlowJo software (Tree Star, Ashland, OR) and GraphPad Prism software.

Figure 4C:
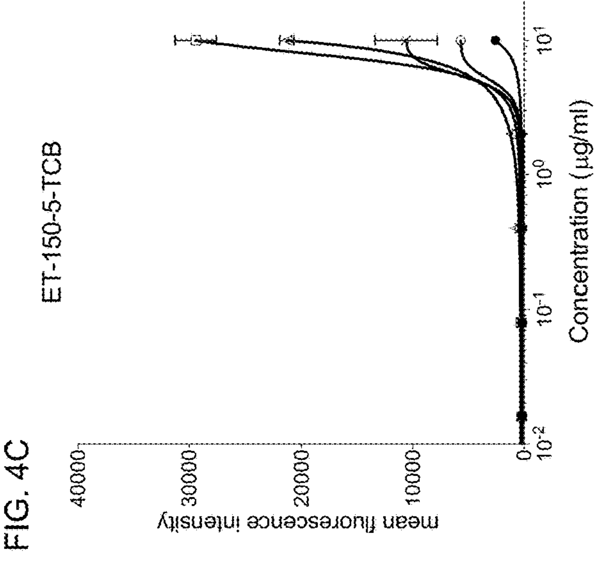
FIG. 4A-FIG. 4C. Binding analysis of bispecific antigen binding molecules 5F11-TCB (FIG. 4A) and 5E11-TCB (FIG. 4B) and control antibody ET150-5-TCB (FIG. 4C) to GPRCSD-expressing multiple myeloma cell lines AMO-1, L636, NCI-H929, RPMI-8226, OPM-2 and control cells WSU-DLCL2.
Figure 4B:
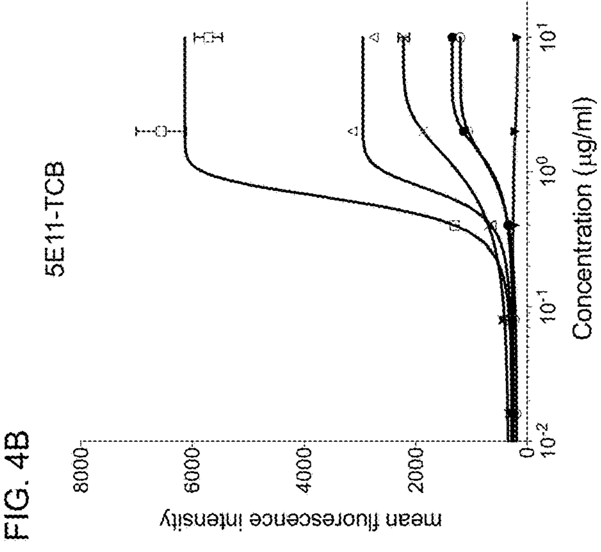
Figure 4A:
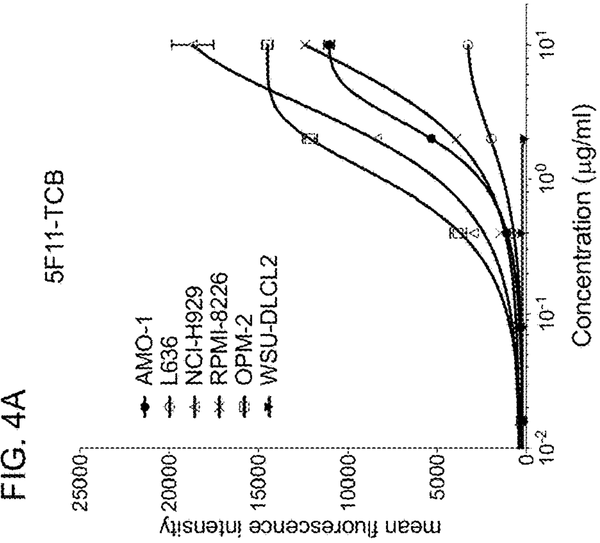

FIG. 4A-FIG. 4C show that both 5E11-TCB and 5F11-TCB bind all of the tested multiple myeloma cell lines in a dose-dependent manner. In contrast, ET150-5-TCB binds much weaker to the tested cell lines. There was no binding to WSU-DLCL2 cells (GPRC5D$^-$ cell lines of non-Hodgkin lymphoma) observed by the anti-GPRC5D-TCBs.

Example 4

Anti-GPRC5D-TCB Mediated T Cell Cytotoxicity

To measure the functionality of the anti-GPRC5D-TCB antibodies, an in-vitro T cell cytotoxicity assay was performed. Briefly, AMO-1, L363 and OPM-2 cell lines were cultured in RPMI 1640+Glutamax medium (Gibco) supplemented with 20% Heat-Inactivated Fetal Bovine Serum (FBS; Gibco) and 1% Penicillin-Streptomycin 100× (PS; Gibco). The cell line WSU-DLCL2 was cultured with the same medium supplemented with only 10% FBS. The cell lines NCI-H929 and RPMI-8226 were cultured the same medium supplemented with 50 μM Mercaptoethanol (Gibco) and 1 mM Sodium Pyruvate (Gibco). The cell lines were cultured in 75 cm$^2$ Flask (TPP) with two passages per week.

The cell lines were co-cultured at a ratio Target:Effector of 1:10 with 3.105 allogeneic T cells isolated from peripheral blood mononuclear cells (PBMCs) (Buffy coat from Blutspende Schlieren) using a human Pan T cell Isolation kit (Miltenyi Biotec) in IMDM Medium (Gibco) supplemented with 10% FBS (Gibco)+1% PS (Gibco). Anti-human GPRC5D-TCB antibodies (5E11-TCB, 5F11-TCB, ET150-5 TCB or DP47-TCB) were added to the co-culture at different concentration, in the range from 1 μg/ml to 0.000001 μg/ml with serial dilution of factor 0.1 or 0 μg/ml. After 20 hours of incubation at 37° C. with 5% $CO_2$, 75 μl of supernatant per well were transferred into a 96-well white plate (Greiner bio-one) with 25 μl per well of CytoTox-Glo Cytotoxicity Assay (Promega). Luminescence acquisition was performed on the PerkinElmer EnVision after 15 min incubation at room temperature and analyzed using GraphPad Prism and XL fit software. Data are plotted as the Luminescence signal for LDH release.

Figures 5A, 5B, 5C, 5D, 5E:
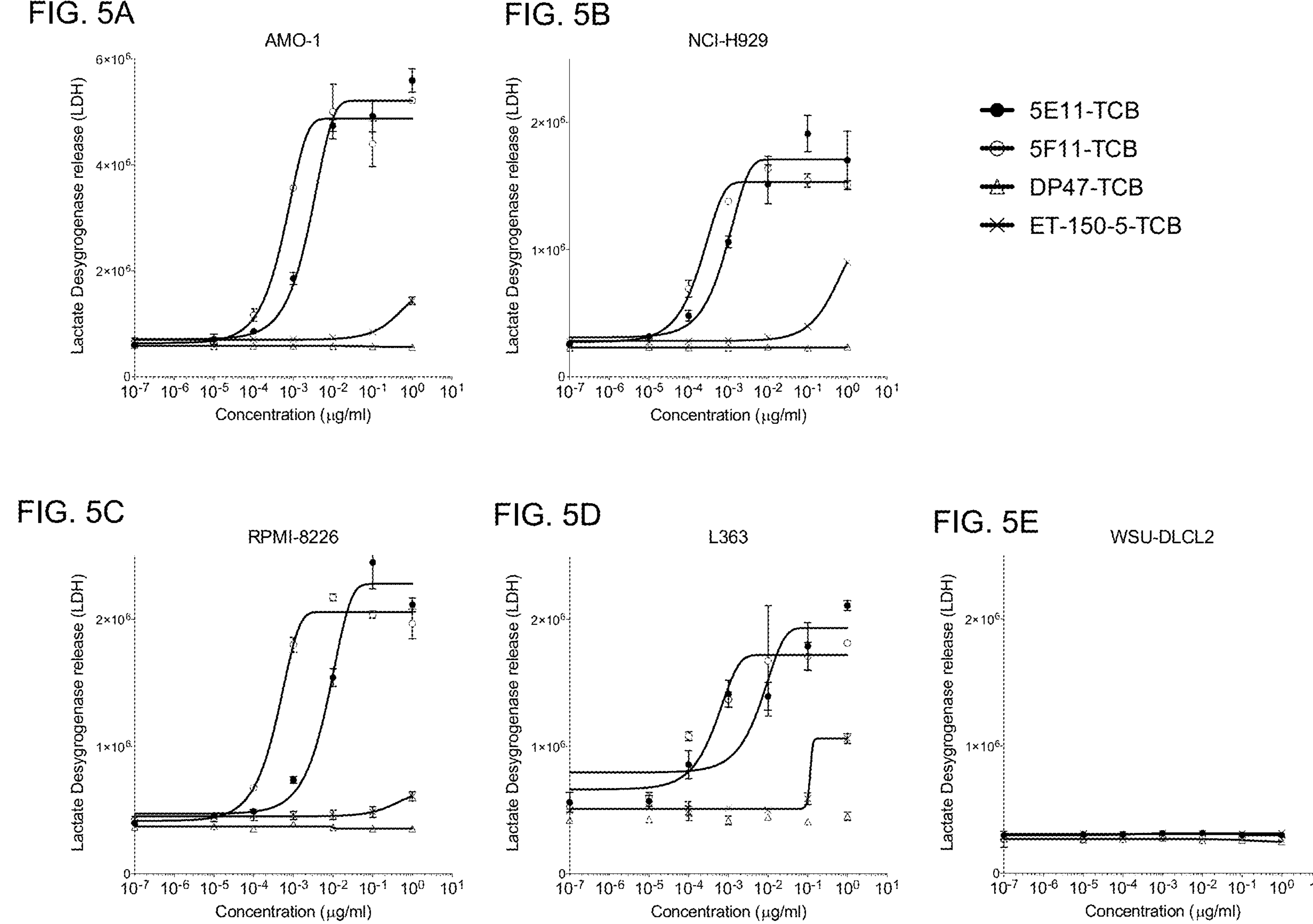
FIG. 5A-FIG. 5E. Analysis of GPRCSD-TCB mediated T cell cytotoxicity on multiple myeloma cell lines AMO-1 (FIG. 5A), NCI-H929 (FIG. 5B), RPMI-8226 (FIG. 5C) and L363 (FIG. 5D). Control cell line is WSU-DL CL2 (FIG. 5E). Tested molecules: 5E11-TCB, 5F11-TCB. Control molecules: DP47-TCB (untargeted) and ET150-5-TCB.

FIG. 5A-FIG. 5E show that both 5E11-TCB and 5F11-TCB mediated strong T cell cytotoxicity on the multiple myeloma cell lines, particularly NCI-H929 (FIG. 5B), RPMI-8226 (FIG. 5C), L363 (FIG. 5D), and AMO-1 (FIG. 5A), whereas no killing was observed on the negative control line WSU-DLCL2 (FIG. 5E). In contrast, ET150-5-TCB mediated little or significantly lower killing on the tested multiple myeloma cell lines. Table 1 summarizes the $EC_{50}$ values derived from the data shown in FIG. 5A-FIG. 5E. $EC_{50}$ value was calculated using XLfit add-on feature in Excel by plotting the raw data of the signals against the titrated TCBs.

TABLE 1

| $EC_{50}$ of anti-GPRC5D-TCB mediated killing | | | | | |
|---|---|---|---|---|---|
| | NCI-H929 | RPMI-8226 | L363 | AMO-1 | WSI-DLCL2 |
| 5E11-TCB | 0.007 nM | 0.024 nM | 0.012 nM | 0.014 nM | / |
| 5F11-TCB | 0.001 nM | 0.002 nM | 0.001 nM | 0.003 nM | / |
| ET150-5-TCB | 0.833 nM | 0.797 nM | 0.768 nM | 0.0835 nM | / |

Example 5

Anti-GPRC5D-TCB Mediated T Cell Activation

To mechanistically address the modes of action of the anti-GPRC5D-TCBs, the activation of T cells after co-culturing with target multiple myeloma cell lines in the presence of anti-GPRC5D-TCBs was measured. Similar to the experiment described in Example 4 and FIG. 5A-FIG. 5E, the cell lines were co-cultured at ratio Target:Effector of 1:10 with 3.105 allogeneic T cells isolated from PBMCs (Buffy coat from Blutspende Schlieren) using a human Pan T cell Isolation kit (Miltenyi Biotec) in IMDM Medium (Gibco) supplemented with 10% FBS (Gibco)+1% PS (Gibco). Anti-human GPRC5D-TCB antibodies (5E11-TCB, 5F11-TCB, ET150-5-TCB or DP47-TCB) were added to the co-culture at different concentration, in the range from 1 μg/ml to 0.000001 μg/ml with serial dilution of factor 0.1 or 0 μg/ml. After 20 hours of incubation at 37° C. with 5% $CO_2$, the cells were stained to evaluate T cell activation. The cells were first stained with Live blue dye (Life Technologies) diluted 1:800 in PBS (Gibco) for 20 min at 4° C. Afterwards, the cells were stained with AF700 anti-human CD4 (clone OKT4), BV711 anti-human CD8 (clone SK1), BV605 anti-human CD25 (clone BC96), APC-Cy7 anti-human CD69 (clone FN50) all from BioLegend and PE-Cy5.5 anti-human CD3 (clone SK7; eBioscience) in Flow cytometry staining buffer (eBioscience) for 30 min at 4° C. Flow cytometry acquisition was performed on a custom-designed BD Biosciences Fortessa and analyzed using FlowJo software (Tree Star, Ashland, OR) and GraphPad Prism software.

Figure 6:
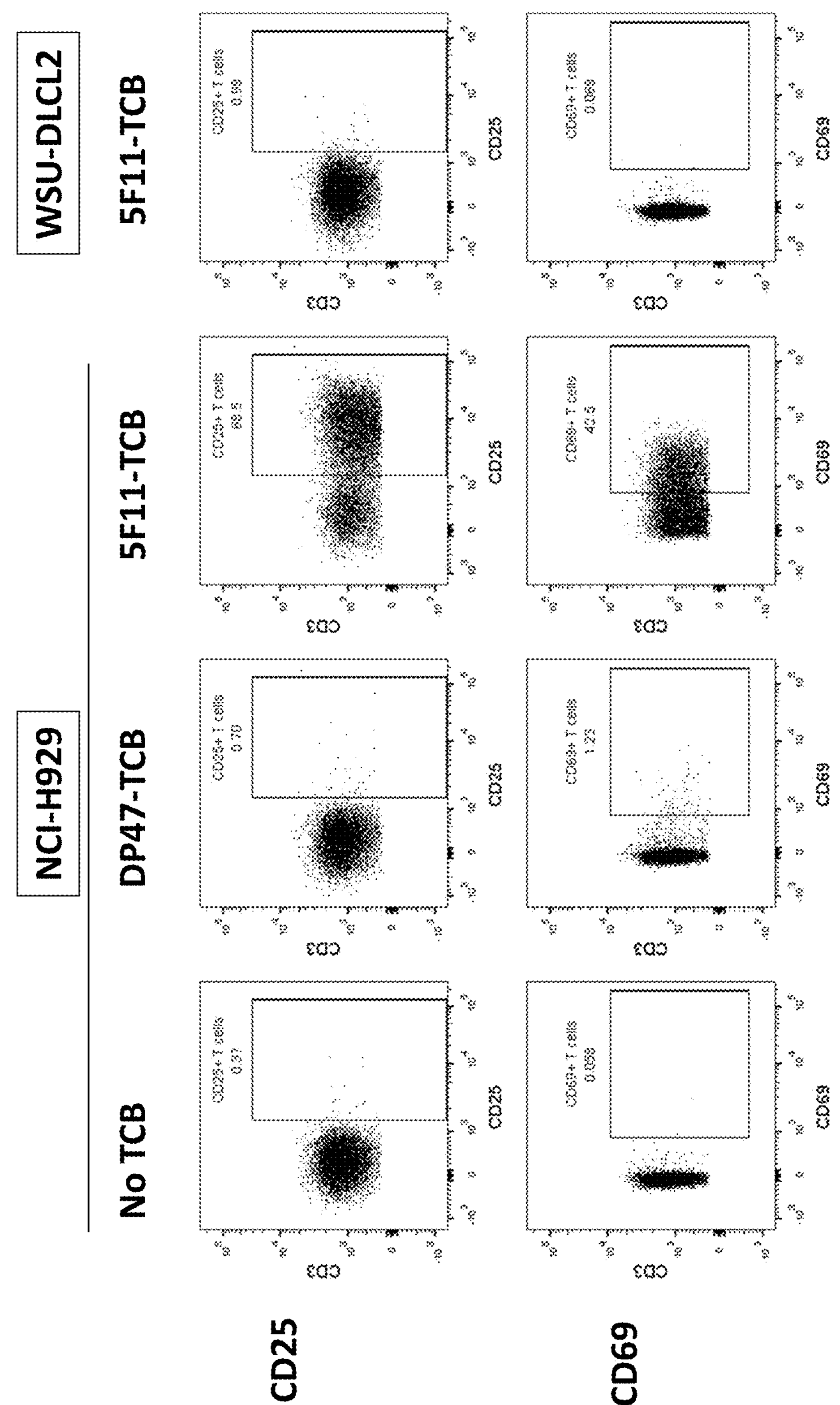
FIG. 6. Analysis of GPRCSD-TCB activated T cell engagement with multiple myeloma cell lines NCI-H929 and negative control cell line WSU-DLCL2 upregulating CD25 and CD69.
Figure 8B:
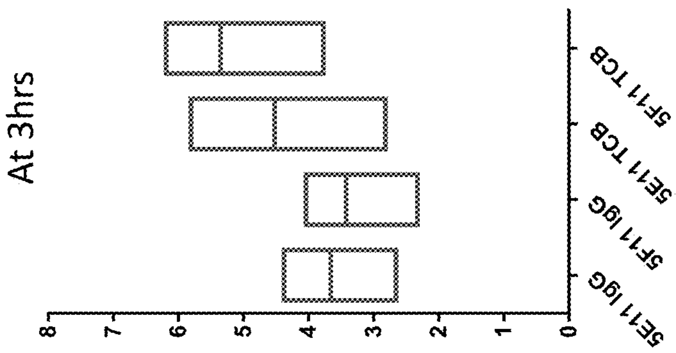
FIG. 8A-FIG. 8B. Visualization of antibody localization and internalization by Fluorescence Confocal Microscopy (FIG. 8A) and analysis of signal intensities of membrane vs cytoplasm (FIG. 8B).
Figure 8A:
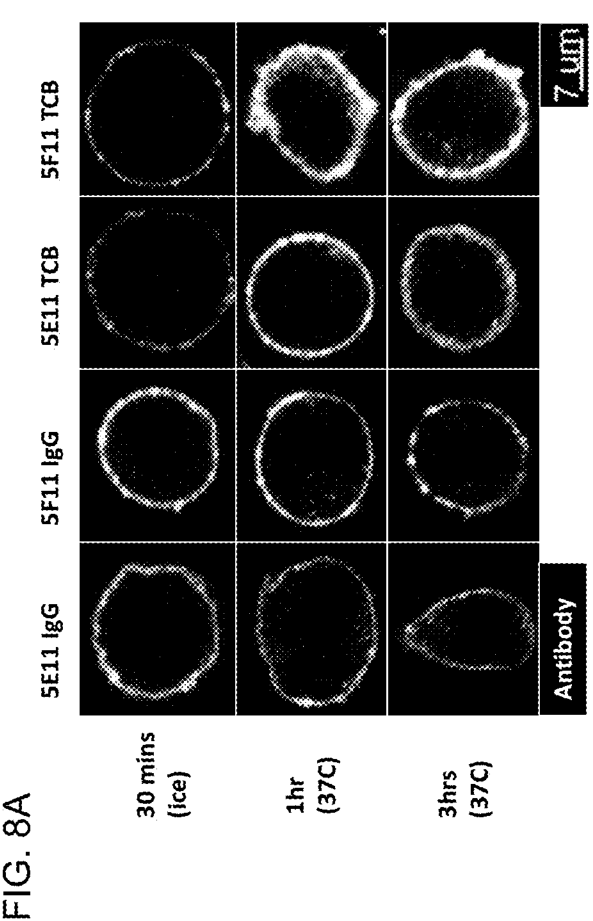

FIG. 6 shows that 5F1 I-TCB induces T cell activation in co-cultures with NCI-H929 cells by upregulating the activation marker CD25 and CD69, whereas the controls, e.g. untargeted DP47-TCB and without any TCB, did not induce T cell activation. As another negative control, 5F11-TCB treated T cells were co-cultured with WSU-DLCL2 cells, wherein T cells were also not activated. These activation profiles were consistent across multiple cell lines we studied, e.g. AMO-1, NCI-H929, RPMI-8226, L363 (FIG. 7A-FIG. 7J). In line with the poor killing potency, assay conc. starts at 30 μg/ml) to the cells for 2 hours at 4° C. After one washing step using 90 μl/well PBST (10×PBS, Roche, #11666789001+0.1% Tween 20), cells were subsequently fixed by the addition of 50 μl/well 0.05% glutaraldehyde (Sigma Cat.No: G5882 in 1×PBS) for 10 min at room temperature (RT). After three additional washing steps using 90 μl/well PBST, secondary antibodies were added for detection: for human antibodies goat anti-human Ig a chain antibody HRP conjugate (Millipore #AP502P) diluted 1:2000 in blocking buffer (lx PBS (Roche #11666789001)+2% BSA (Bovine Serum Albumin Fraction V, fatty acid free, Roche, #10735086001)+0.05% Tween 20) was used (25 μl/well). For rat antibodies a mixture of Goat anti-Rat IgG1 Antibody HRP Conjugated (Bethyl #A110-106P), Goat anti-Rat IgG2a Antibody HRP Conjugated (Bethyl #A110-109P)

and Goat anti-Rat IgG2b Antibody HRP Conjugated (Bethyl #A110-111P) was used in a 1:10000 dilution of each antibody in blocking buffer (25 μl/well). After incubation for 1 h at RT and three additional washing steps using 90 μl/well PBST, 25 μl/well TMB substrate was added (Roche order no. 11835033001) for 10 min and color development to final ODs was determined by measurement at 370 nm/492 nm.

Figure 9:
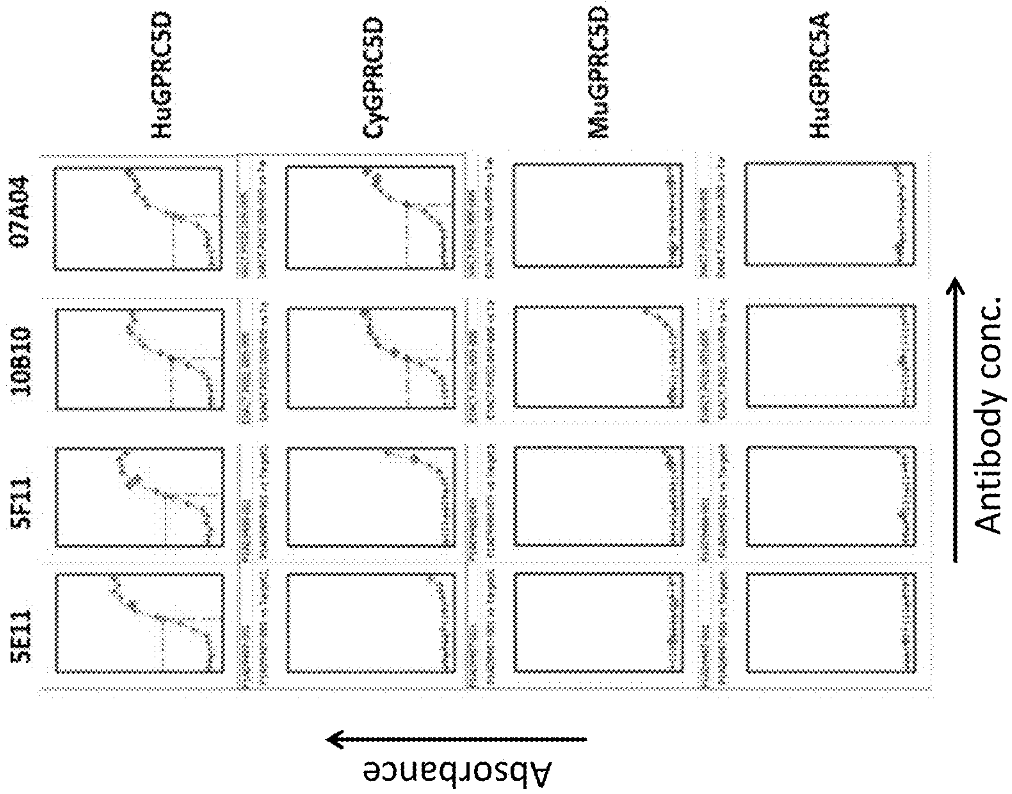
FIG. 9. Binding of different anti-GPRCSD antibodies to human, cynomolgus and murine GPRCSD was assessed by ELISA, using stably transfected CHO clones expressing either human GPRC5D (clone 12) or cynomolgus GPRC5D (clone 13), murine GPRC5D (clone 4) or human GPRC5A (clone 30).
Figures 11A, 11B, 11C, 11D, 11E, 11F:
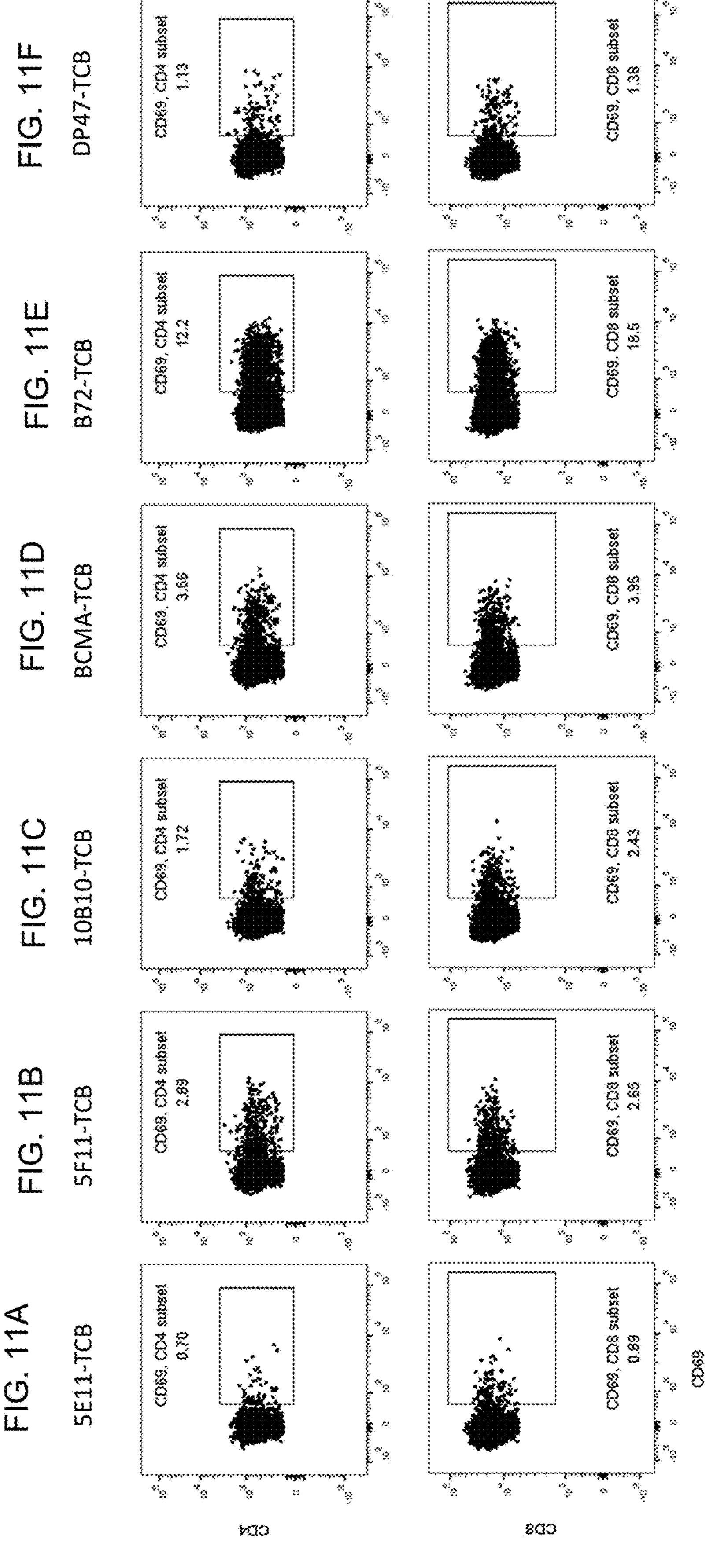
FIG. 11A-FIG. 11F. T-cell activation induced by different GPRC5D- or BCMA-targeting T-cell bispecific molecules (5E11-TCB in FIG. 11A; 5F11-TCB in FIG. 11B; 10B10-TCB in FIG. 11C; BCMA-TCB in FIG. 11D; B72-TCB in FIG. 11E; DP47-TCB in FIG. 11F) during ~20 hours of co-incubation of allogenic pan human T cells and unprocessed Bone Marrow cells from healthy donors (E:T=10:1, human pan T cells). Depicted are FACS dot plots from one representative donor, showing up-regulation of the activation marker CD69 on CD4 (upper row) or CD8 T-cells (lower row) as percent positive cells among all CD4 respective CD8 T-cells.

All tested antibodies showed positive binding to human GPRC5D with $EC_{50}$ values (reflecting avidity) in the pM range. Only the rat IgGs 10B10 and 07A04 showed cross-reactivity on CHO cells expressing the cynomolgus GPRC5D with $EC_{50}$ values comparable to the human version of the receptor (FIG. 9). Cynomolgus crossreactivity was also detected for all other antibodies but at lower levels compared to 10B10 and 07A04 (FIG. 9). No significant binding to CHO cells expressing murine GPRC5D and no binding to CHO cells expressing the human version of GPRC5A was detected (FIG. 9). The $EC_{50}$ values of binding are summarized in Table 2.

TABLE 2

ELISA based binding properties to GPRC5D across species

| | human GPRC5D+ CHO | | | | cyno GPRC5D+ CHO | | |
|---|---|---|---|---|---|---|---|
| IgG-Antibody | | EC50 (ng/ml) | | EC50 (nM) | EC50 (ng/ml) | EC50 (nM) | |
| 5E11 | | 29.57 | | 0.198 | — | — | |
| 5F11 | | 21.67 | | 0.144 | — | — | |
| 10B10 | | 16.34 | | 0.109 | 12 | 0.080 | |
| 07A04 | | 24.26 | | 0.162 | 114.54 | 0.764 | |
| 5E11-TCB | 7 | 8 | 18 | 17 | 11 | 2 | 64 |
| 10B10-TCB | 56 | 84 | 160 | 34 | 79 | 28 | 965 |
| B72-TCB | 58 | 109 | 124 | 58 | 60 | 171 | 193 |
| BCMA-TCB | 311 | 518 | 32 | 127 | 132 | 33 | 11 |

Example 9

In Vitro T Cell Activation in Healthy Human Bone Marrow Cells

Fresh unprocessed Bone Marrow of four different healthy donors (Lonza #1M-105, lot 0000739254; 0000739255; 0000739256 and 0000734008) were processed 1 or 2 days after sampling. After a quick red blood cell lysis using BD Pharm Lysis buffer (BD #555899; 1× in sterile water) for 5 minutes at room temperature; cells were washed 2 times by centrifugation and buffer exchange at 126 g and 443 g respectively. Cells were counted and resuspended at 300 000 cells/mL in RPMI 1640 Glutamax+20% HI Fetal Bovine Serum+2% human serum+1% Penicillin/Streptomycin (all from Gibco) and 100 μL of cell suspension were seeded per well in a 96-well plate round bottom (TPP). 50 μL of medium or medium supplemented with B72-TCB, 5F11-TCB, 5E11-TCB, BCMA-TCB, 10B10-TCB or DP47-TCB from 200 nM (4×) to 20 pM with serial dilution 1/10 were added per well. Finally, 50 μL of allogeneic T cell isolated using Pan T cell (Miltenyi Biotec, #130-096-535) from healthy donor PBMCs were added at 6 Mio/mL (effector T to healthy bone marrow target cell ratio of 10:1). After overnight incubation at 37° C. in a humidified incubator, cells were washed once with PBS and stained for 20 minutes at 4C with 50 μL of Live blue (Invitrogen, #L23105) diluted 1/800 in PBS. After a wash, cells were incubated for 30 minutes at 4° C. with the following mix of antibodies diluted in FACs buffer (PBS 1×, 2% Fetal Bovine Serum; 1% 0.5m EDTA PH 8; 0.25% $NaN_3$ Sodium azide (20%)): CD25 BV605, CD69 APC-Cy7, BCMA BV421, CD38 BV510, CD138 FITC, FcRH5 PE diluted 1/100 and CD8 BV711, CD3 PE-Cy5 and CD4 AlexaFluor 700 diluted 1/300 (all from BioLegend) and GPRC5D AlexaFluor 647 (in house, clone 5E11 IgG). After a wash, cells were resuspended in 100 μL of FACs buffer and acquired with Fortessa (BD Biosciences).

Figure 12B:
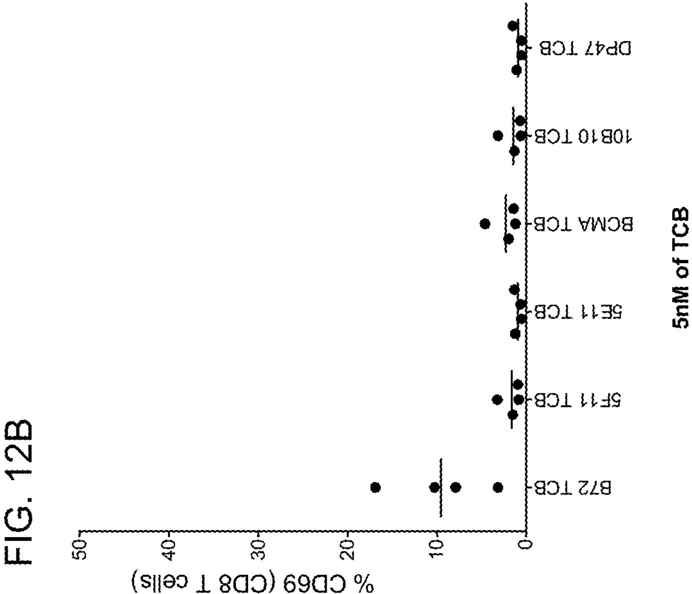
FIG. 12A-FIG. 12B. T-cell activation induced by different GPRC5D- or BCMA-targeting T-cell bispecific molecules during ~20 hours of co-incubation of allogenic pan human T cells and unprocessed Bone Marrow cells from healthy donors (E:T=10:1, human pan T cells). Depicted is the summary of all four assessed donors, showing up-regulation of the activation marker CD69 on CD8 T-cells at the selected fixed dose of either 50 nM of the TCB (FIG. 12A) or 5 nM (FIG. 12B).
Figure 12A:
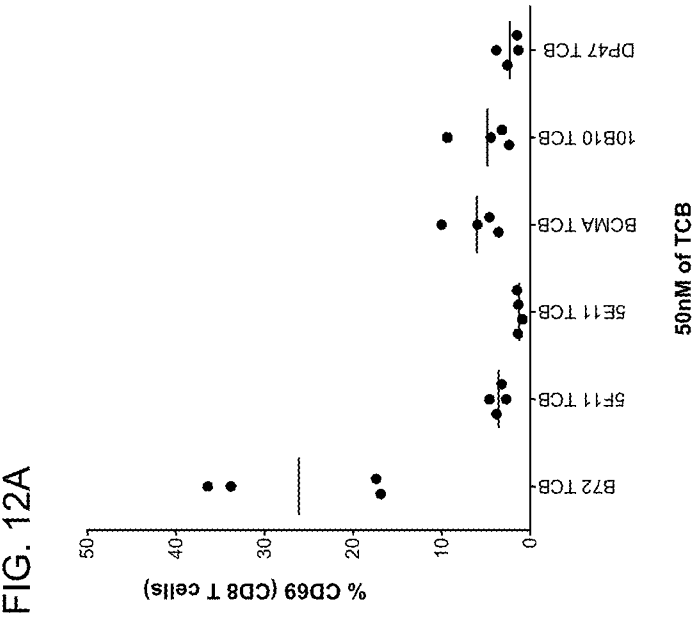

Data presented in FIG. 11A-FIG. 11F illustrate that the B72-TCB induced unspecific activation of T cells (as measured by upregulation of CD69) in the healthy bone marrow, but not by any of the other tested TCBs. As indicated, the unspecific activation induced by the B72-TCB was a concentration dependent effect and more pronounced at 50 nm than at 5 nm (FIG. 12A and FIG. 12B).

Example 10

In Vivo Efficacy of TCBs

In the efficacy study different TCB constructs (GPRC5D 5F110-TCB, 5E11-TCB, BCMA-TCB and B72-TCB) were compared in terms of tumor regression in multiple myeloma bearing fully humanized NSG mice. NCI-H929 cells were originally obtained from ATCC and OPM-2 cells from DSMZ. Both cell lines were expanded. Cells were cultured in RPMI containing 10% FCS and 2 mM L-Glutamine, 10 mM HEPES, 1 mM Sodiumpyruvate. The cells were cultured at 37° C. in a water-saturated atmosphere at 5% $CO_2$. $2.5\times10^6$ NCI-H929 and $5\times10^6$ OPM-2 cells per animal were injected subcutaneously into the right flank of the animals in RPMI cell culture medium (Gibco) and GFR matrigel (1:1, total volume of 100 ul) at a viability of >95.0%.

Female NSG (NOD·Cg-Prkdcscid Il2rgtmlWjl/SzJ) mice, age 4-5 weeks at start of the experiment (bred at Charles River, Lyon, France) were maintained under specific-pathogen-free condition with daily cycles of 12 h light/12 h darkness according to committed guidelines (GV-Solas; Felasa; TierschG). The experimental study protocol was reviewed and approved by local government (ROB-55.2-2532.Vet_03-16-10). After arrival, animals were maintained for one week to get accustomed to the new environment and for observation. Continuous health monitoring was carried out on a regular basis.

According to the protocol, female NSG mice were injected i.p. (intraperitoneal) with 15 mg/kg of Busulfan followed one day later by an i.v. injection of $1\times10^5$ human hematopoietic stem cells isolated from cord blood. At week 16-20 after stem cell injection mice were bled and blood was analyzed by flow cytometry for successful humanization. Efficiently engrafted mice were randomized according to their human T cell frequencies into the different treatment groups (n=10/group). At that time, mice were injected with tumor cells subcutaneously. as described above and treated once weekly with the compounds or PBS (Vehicle) when tumor size reached approximately 200 $mm^3$. All mice were injected intravenously with different doses of TCB molecules (see FIG. 13A-FIG. 13D and FIG. 14A-FIG. 14D).

To obtain the appropriate amount of compounds stock solutions were diluted with Histidine buffer (20 mM histidine, 140 mM NaCl, pH 6.0). Tumor growth was measured twice weekly using a caliper and tumor volume was calculated as followed:

$$T_v:(W^2/2)\times L \text{ (W: Width,L: Length)}$$

The study was terminated and all mice were sacrificed after four injections of the compounds and tumors were explanted and weighted.

FIG. 13A-FIG. 13D show the tumor growth kinetics in all animals, which had received NCl-H929 injections, after the treatment. 5F11-TCB induced complete tumor remission in all animals at either 1 mg/kg or 0.1 mg/kg (FIG. 13A), whereas B72-TCB only induced partial tumor remission when used at 1 mg/kg, with no effect at 0.1 mg/kg (FIG. 13C). BCMA-TCB also induced partial tumor remission at 1 mg/kg (FIG. 13B).

FIG. 14A-FIG. 14D show the tumor growth kinetics in all animals, which had received OPM-2 injections, after the treatment. 5F11-TCB (FIG. 14A, top panel) and 5E11-TCB (FIG. 14B, top panel) induced complete tumor remission in the majority of animals at 0.1 mg/kg whereas B72-TCB (FIG. 14C, top panel) at 0.1 mg/kg was less potent in controlling tumor growth. At 0.01 mg/kg 5F11-TCB (FIG. 14A, bottom panel) and 5E11-TCB (FIG. 14B, bottom panel) were more potent in inhibiting tumor growth as compared to B72-TCB (FIG. 14C, bottom panel).

Example 11

Humanization of Anti-GPRC5D Antibodies

Suitable human acceptor frameworks were identified by querying a BLASTp database of human V- and J-region sequences for the murine input sequences (cropped to the variable part). Selective criteria for the choice of human acceptor framework were sequence homology, same or similar CDR lengths, and the estimated frequency of the human germline, but also the conservation of certain amino acids at the VH-VL domain interface. Following the germline identification step, the CDRs of the murine input sequences were grafted onto the human acceptor framework regions. Each amino acid difference between these initial CDR grafts and the parental antibodies was rated for possible impact on the structural integrity of the respective variable region, and "back mutations" towards the parental sequence were introduced whenever deemed appropriate. The structural assessment was based on Fv region homology models of both the parental antibody and the humanization variants, created with an in-house antibody structure homology modeling protocol implemented using the BIOVIA Discovery Studio Environment, version 17R2. In some humanization variants, "forward mutations" were included, i.e., amino acid exchanges that change the original amino acid occurring at a given CDR position of the parental binder to the amino acid found at the equivalent position of the human acceptor germline. The aim is to increase the overall human character of the humanization variants (beyond the framework regions) to further reduce the immunogenicity risk.

An in silico tool developed in-house was used to predict the VH-VL domain orientation of the paired VH and VL humanization variants (as WO 2016/062734A1, which is incorporated by reference in its entirety). The results were compared to the predicted VH-VL domain orientation of the parental binders to select for framework combinations which are close in geometry to the original antibodies. The rational is to detect possible amino acid exchanges in the VH-VL interface region that might lead to disruptive changes in the pairing of the two domains that in turn might have detrimental effects on the binding properties.

Choice of Acceptor Framework and Adaptations Thereof for the GPRC5D Binder 5E11

The acceptor frameworks were chosen according to the following table 4.

TABLE 4

Acceptor frameworks for the GPRC5D binder 5E11

| | Murine (*Rattus norvegicus*) V-region germline | Choice of human acceptor V-region germline |
|---|---|---|
| VH1abcd | IGHV5S13*01 | IGHV3-23*03 |
| VL1ac | IGKV3S18*01 | IGKV4-1*01_human |
| VL2ab | | IGKV3-20*01_human |
| VL3ab | | IGKV1-39*01_human |

Post-CDR3 framework regions were adapted from human IGHJ germline IGHJ3*02 (DAFDIWGQGTMVTVSS) (SEQ ID NO: 134) and human IGKJ germline IGKJ5*01 (ITFGQGTRLEIK) (SEQ ID NO: 135).
The part relevant for the acceptor framework is indicated in bold script.

Based on structural considerations, back mutations from the human acceptor framework to the amino acid in the parental binder were introduced at certain positions of the 5E111 humanization variants (Table 5 and 6). Furthermore, some positions were identified as promising candidates for forward mutations, where the amino acid in a CDR of the parental binder is substituted by the amino acid found in the human acceptor germline. The changes are detailed in the table below.

Note: Back mutations are prefixed with b, forward mutations with f, e.g., bS49A refers to a back mutation (human germline amino acid to parental antibody amino acid) from serine to alanine at position 49. All residue indices given in Kabat numbering.

TABLE 5

List of VH/VL 5E11 humanization variants

| Variant Name | Identity to human V-region germline (BLASTp) |
|---|---|
| 5E11_VH1a (bS49A_bK94T) | 89.7 |
| 5E11_VH1b (bV2L_bS49A_bS74A_bK94T) | 87.6 |
| 5E11_VH1c (bS49A_fR60A_fA65G_bK94T) | 91.8 |
| 5E11_VH1d (bV2L_bS49A_fR60A_fA65G_bS74A_bK94T) | 89.7 |
| 5E11_VL1a (bP43Q) | 80.2 |
| 5E11_VL1c (fR24K_fA25S_bP43Q) | 82.2 |
| 5E11_VL2a (bA43Q) | 86.2 |
| 5E11_VL2b (bA43Q_bR45K) | 85.1 |
| 5E11_VL3a (bA43Q) | 83.8 |
| 5E11_VL3b (bK42Q_bA43Q) | 82.8 |

TABLE 6

Sequences of VH/VL 5E11 humanization variants

| name | aa sequence | SEQ ID NO. |
|---|---|---|
| 5E11_VH1a | EVQLLESGGGLVQPGGSLRLSCAASGFTFSKYAMAWVRQAPGKGLEWV ASISTGGVNTYYRDSVKARFTISRDNSKNTLYLQMNSLRAEDTAVYYC ATHTGDYFDYWGQGTMVTVSS | 46 |

TABLE 6-continued

| Sequences of VH/VL 5E11 humanization variants | | |
|---|---|---|
| name | aa sequence | SEQ ID NO. |
| 5E11_VH1b | ELQLLESGGGLVQPGGSLRLSCAASGFTFSKYAMAWVRQAPGKGLEWV ASISTGGVNTYYRDSVKARFTISRDNAKNTLYLQMNSLRAEDTAVYYC ATHTGDYFDYWGQGTMVTVSS | 47 |
| 5E11_VH1c | EVQLLESGGGLVQPGGSLRLSCAASGFTFSKYAMAWVRQAPGKGLEWV ASISTGGVNTYYADSVKGRFTISRDNSKNTLYLQMNSLRAEDTAVYYC ATHTGDYFDYWGQGTMVTVSS | 48 |
| 5E11_VH1d | ELQLLESGGGLVQPGGSLRLSCAASGFTFSKYAMAWVRQAPGKGLEWV ASISTGGVNTYYADSVKGRFTISRDNAKNTLYLQMNSLRAEDTAVYYC ATHTGDYFDYWGQGTMVTVSS | 49 |
| 5E11_VL1a | DIVMTQSPDSLAVSLGERATINCRASQSVSISGINLMNWYQQKPGQQP KLLIYHASILASGVPDRFSGSGSGTDFTLTISSLQAEDVAVYYCQQTR ESPLTFGQGTRLEIK | 50 |
| 5E11_VL1c | DIVMTQSPDSLAVSLGERATINCKSSQSVSISGINLMNWYQQKPGQQP KLLIYHASILASGVPDRFSGSGSGTDFTLTISSLQAEDVAVYYCQQTR ESPLTFGQGTRLEIK | 51 |
| 5E11_VL2a | EIVLTQSPGTLSLSPGERATLSCRASQSVSISGINLMNWYQQKPGQQP RLLIYHASILASGIPDRFSGSGSGTDFTLTISRLEPEDFAVYYCQQTR ESPLTFGQGTRLEIK | 52 |
| 5E11_VL2b | EIVLTQSPGTLSLSPGERATLSCRASQSVSISGINLMNWYQQKPGQQP KLLIYHASILASGPIDRFSGSGSGTDFTLTISRLEDPEFAVYYCQQTR ESPLTFGQGTRLEIK | 53 |
| 5E11_VL3a | DIQMTQSPSSLSASVGDRVTITCRASQSVSISGINLMNWYQQKPGKQP KLLIYHASILASGVPSRFSGSGSGTDFTLTISSLQPEDFATYYCQQTR ESPLTFGQGTRLEIK | 54 |
| 5E11_VL3b | DIQMTQSPSSLSASVGDRVTITCRASQSVSISGINLNNWYQQKPGQQP KLLIYHASILASGVPSRFSGSGSGTDFTLTISSLQPEDFATYYCQQTR ESPLTFGQGTRLEIK | 55 |

Choice of Acceptor Framework and Adaptations Thereof for the GPRC5D Binder 5F11

The acceptor frameworks were chosen according to the following table 7.

TABLE 7

| Acceptor frameworks for the GPRC5D binder 5F11 | | |
|---|---|---|
| | Murine (*Rattus norvegicus*) V-region germline | Choice of human acceptor V-region germline |
| VH1abcd | IGHV5S13*01 | IGHV3-30*03 |
| VH2bd | | IGHV3-23*04 |
| VL1ab, VL2a | IGKV2S17*01 | IGKV2-28*01 |
| VL2b | | IGKV4-1*01 |
| VL2c | | IGKV3-20*01 |

Post-CDR3 framework regions were adapted from human IGHJ germline IGHJ3*02 (DAFDIWGQGTMVTVSS) (SEQ ID NO: 134) and human IGKJ germline IGKJ2*01 (YTFGQGTKLEIK) (SEQ ID NO: 136). The part relevant for the acceptor framework is indicated in bold script.

Based on structural considerations, back mutations from the human acceptor framework to the amino acid in the parental binder were introduced at certain positions of the SF 11 humanization variants (Table 8 and 9). Furthermore, some positions were identified as promising candidates for forward mutations, where the amino acid in a CDR of parental binder is substituted by the amino acid found in the human acceptor germline. The changes are detailed in the table below.

Note: Back mutations are prefixed with b, forward mutations with f, e.g., bA93T refers to a back mutation (human germline amino acid to parental antibody amino acid) from alanine to threonine at position 93. All residue indices given in Kabat numbering.

TABLE 8

| List of VH/VL 5F11 humanization variants | |
|---|---|
| Variant Name | Identity to human V-region germline (BLASTp) |
| 5F11_VH1a (bA93T) | 89.8 |
| 5F11_VH1b (bQ1E_bS74A_bA93T) | 87.8 |
| 5F11_VH1c (fR60A_bA93T) | 90.8 |
| 5F11_VH1d (bQ1E_fR60A_bS74A_bA93T) | 88.8 |
| 5F11_VH2b (bS49A_bS74A_bA93T_bK94R) | 86.7 |
| 5F11_VH2d (bS49A_fR60A_bS74A_bA93T_bK94R) | 87.8 |
| 5F11_VL1a (bL46V_bY87H) | 86.0 |
| 5F11_VL1b (bQ42K_bL46V_bY87H) | 85.0 |
| 5F11_VL2a (bY87H) | 88.0 |
| 5F11_VL2b (bY87H) | 80.2 |
| 5F11_VL2c (fS25A_bY87H) | 80.0 |

TABLE 9

| Sequences of VH/VL 5F11 humanization variants | | |
|---|---|---|
| variant | aa sequence | SEQ ID NO. |
| 5F11_VH1a | QVQLVESGGGVVQPGRSLRLSCAASGFSFSNYGMAWVRQAPGKGLEWV ASISTGGGNTYYRDSVKGRFTISRDNSKNTLYLQMNSLRAEDTAVYYC TRHDRGGLYWGQGTMVTVSS | 56 |
| 5F11_VH1b | EVQLVESGGGVVQPGRSLRLSCAASGFSFSNYGMAWVRQAPGKGLEWV ASISTGGGNTYYRDSVKGRFTISRDNAKNTLYLQMNSLRAEDTAVYYC TRHDRGGLYWGQGTMVTVSS | 57 |
| 5F11_VH1c | QVQLVESGGGVVQPGRSLRLSCAASGFSFSNYGMAWVRQAPGKGLEWV ASISTGGGNTYYADSVKGRFTISRDNSKNTLYLQMNSLRAEDTAVYYC TRHDRGGLYWGQGTMVTVSS | 58 |
| 5F11_VH1d | EVQLVESGGGVVQPGRSLRLSCAASGFSFSNYGMAWVRQAPGKGLEWV ASISTGGGNTYYADSVKGRFTISRDNAKNTLYLQMNSLRAEDTAVYYC TRHDRGGLYWGQGTMVTVSS | 59 |
| 5F11_VH2b | EVQLVESGGGLVQPGGSLRLSCAASGFSFSNYGMAWVRQAPGKGLEWV ASISTGGGNTYYRDSVKGRFTISRDNAKNTLYLQMNSLRAEDTAVYYC TRHDRGGLYWGQGTMVTVSS | 60 |
| 5F11_VH2d | EVQLVESGGGLVQPGGSLRLSCAASGFSFSNYGMAWVRQAPGKGLEWV ASISTGGGNTYYADSVKGRFTISRDNAKNTLYLQMNSLRAEDTAVYYC TRHDRGGLYWGQGTMVTVSS | 61 |
| 5F11_VL1a | DIVMTQSPLSLPVTPGEPASISVRSSKSLLHSNGITYVYWYLQKPGQS PQVLIYRMSNLASGVPDRFSGSGSGTDFTLKISRVEAEDVGVYHCGQL LENPYTFGQGTKLEIK | 62 |
| 5F11_VL1b | DIVMTQSPLSLPVTPGEPASISVRSSKSLLHSNGITYVYWYLQKPGKS PQVLIYRMSNLASGVPDRFSGSGSGTDFTLKISRVEAEDVGVYHCGQL LENPYTFGQGTKLEIK | 63 |
| 5F11_VL2a | DIVMTQSPLSLPVTPGEPASISVRSSKSLLHSNGITYVYWYLQKPGQS PQLLIYRMSNRASGVPDRFSGSGSGTDFTLKISRVEAEDVGVHYCGQL LENPYTFGQGTKLEIK | 64 |
| 5F11_VL2b | DIVMTQSPDSLAVSLGERATINCKSSKSLLHSNGITYVYWYQQKPGQP PKLLIYRMSNLASGVPDRFSGSGSGTDFTLTISSLQAEDVAVYHCGQL LENPYTFGQGTKLEIK | 65 |
| 5F11_VL2c | EIVLTQSPGTLSLSPGERATLSCRASKSLLHSNGITYVYWYQQKPGQA PRLLIYRMSNLASGIPDRFSGSGSGTDFTLTISRLEPEDFAVYHCGQL LENPYTFGQGTKLEIK | 66 |

Characterization of Humanization Variants by ELISA

For the characterization of the humanization variants of the VH and VL domains of the GPRC5D binders the ELISA protocol as described above was used (see Example 7). The data are summarized in the table 10 for the humanization variants of 5E11 and in table 11 for the humanization variants of 5F11. Table 12 shows CDR sequences of the parental 5E11 and parental 5E11 and of selected humanization variants.

TABLE 10

| Characterization of humanization variants of 5E11 | | | | | | | | | | |
|---|---|---|---|---|---|---|---|---|---|---|
| | | | | | | | CHO hu GPCR5D | | CHO cy GPCR5D |
| | | Humanness | | | | | EC/IC50 | EC/IC50 | EC/IC50 |
| Tapir | Sort | VH | VL | VH huID | VL huID | Fv huID | rel (ng/ml) | rel (nM) | rel (ng/ml) |
| P1AE5706 | 1 | parental | parental | | | | 10.4 | 0.07 | na |
| P1AE5707 | 2 | VH1a | VL1a | 89.7 | 80.2 | 84.95 | 14.2 | 0.09 | na |
| P1AE5708 | 3 | VH1a | VL1c | 89.7 | 82.2 | 85.95 | 12.0 | 0.08 | na |
| P1AE5709 | 4 | VH1a | VL2a | 89.7 | 86.2 | 87.95 | 19.1 | 0.13 | na |
| P1AE5710 | 5 | VH1a | VL2b | 89.7 | 85.1 | 87.4 | 10.1 | 0.07 | na |
| P1AE5712 | 6 | VH1a | VL3a | 89.7 | 83.8 | 86.75 | 13.1 | 0.09 | na |
| P1AE5713 | 7 | VH1a | VL3b | 89.7 | 82.8 | 86.25 | 16.5 | 0.11 | na |
| P1AE5714 | 8 | VH1b | VL1a | 87.6 | 80.2 | 83.9 | 12.9 | 0.09 | na |
| P1AE5715 | 9 | VH1b | VL1c | 87.6 | 82.2 | 84.9 | 21.1 | 0.14 | na |
| P1AE5716 | 10 | VH1b | VL2a | 87.6 | 86.2 | 86.9 | 15.1 | 0.10 | na |
| P1AE5717 | 11 | VH1b | VL2b | 87.6 | 85.1 | 86.35 | 13.9 | 0.09 | na |

TABLE 10-continued

Characterization of humanization variants of 5E11

| | | | | | | | | | |
|---|---|---|---|---|---|---|---|---|---|
| P1AE5718 | 12 | VH1b | VL3a | 87.6 | 83.8 | 85.7 | 12.1 | 0.08 | na |
| P1AE5719 | 13 | VH1b | VL3b | 87.6 | 82.8 | 85.2 | 16.6 | 0.11 | na |
| P1AE5720 | 14 | VH1c | VL1a | 91.8 | 80.2 | 86 | 21.7 | 0.14 | na |
| P1AE5721 | 15 | VH1c | VL1c | 91.8 | 82.2 | 87 | 18.3 | 0.12 | na |
| P1AE5722 | 16 | VH1c | VL2a | 91.8 | 86.2 | 89 | 19.7 | 0.13 | na |
| P1AE5723 | 17 | VH1c | VL2b | 91.8 | 85.1 | 88.45 | 6.0 | 0.04 | na |
| P1AE5724 | 18 | VH1c | VL3a | 91.8 | 83.8 | 87.8 | 5.3 | 0.04 | na |
| P1AE5725 | 19 | VH1c | VL3b | 91.8 | 82.8 | 87.3 | 5.1 | 0.03 | na |
| P1AE5726 | 20 | VH1d | VL1a | 89.7 | 80.2 | 84.95 | 7.6 | 0.05 | na |
| P1AE5727 | 21 | VH1d | VL1c | 89.7 | 82.2 | 85.95 | 8.7 | 0.06 | na |
| P1AE5728 | 22 | VH1d | VL2a | 89.7 | 86.2 | 87.95 | 7.9 | 0.05 | na |
| P1AE5729 | 23 | VH1d | VL2b | 89.7 | 85.1 | 87.4 | 10.4 | 0.07 | na |
| P1AE5730 | 24 | VH1d | VL3a | 89.7 | 83.8 | 86.75 | 8.0 | 0.05 | na |
| P1AE5731 | 25 | VH1d | VL3b | 89.7 | 82.8 | 86.25 | 5.2 | 0.03 | na |

| | | Humanness | | | | | CHO hu GPCR5A EC/IC50 | |
|---|---|---|---|---|---|---|---|---|
| Tapir | Sort | VH | VL huID | VH huID | VL huID | Fv | rel (ng/ml) | CAR-J2 EC50 [ng/mL] |
| P1AE5706 | 1 | parental | parental | | | | na | 3.9 |
| P1AE5707 | 2 | VH1a | VL1a | 89.7 | 80.2 | 84.95 | na | 42.4 |
| P1AE5708 | 3 | VH1a | VL1c | 89.7 | 82.2 | 85.95 | na | 455.8 |
| P1AE5709 | 4 | VH1a | VL2a | 89.7 | 86.2 | 87.95 | na | 59.4 |
| P1AE5710 | 5 | VH1a | VL2b | 89.7 | 85.1 | 87.4 | na | 3.5 |
| P1AE5712 | 6 | VH1a | VL3a | 89.7 | 83.8 | 86.75 | na | 16.1 |
| P1AE5713 | 7 | VH1a | VL3b | 89.7 | 82.8 | 86.25 | na | 76.9 |
| P1AE5714 | 8 | VH1b | VL1a | 87.6 | 80.2 | 83.9 | na | 5.5 |
| P1AE5715 | 9 | VH1b | VL1c | 87.6 | 82.2 | 84.9 | na | 3.6 |
| P1AE5716 | 10 | VH1b | VL2a | 87.6 | 86.2 | 86.9 | na | 3.3 |
| P1AE5717 | 11 | VH1b | VL2b | 87.6 | 85.1 | 86.35 | na | 79.9 |
| P1AE5718 | 12 | VH1b | VL3a | 87.6 | 83.8 | 85.7 | na | 105.4 |
| P1AE5719 | 13 | VH1b | VL3b | 87.6 | 82.8 | 85.2 | na | 2.8 |
| P1AE5720 | 14 | VH1c | VL1a | 91.8 | 80.2 | 86 | na | 6.3 |
| P1AE5721 | 15 | VH1c | VL1c | 91.8 | 82.2 | 87 | na | 25 |
| P1AE5722 | 16 | VH1c | VL2a | 91.8 | 86.2 | 89 | na | 4.6 |
| P1AE5723 | 17 | VH1c | VL2b | 91.8 | 85.1 | 88.45 | na | 3.7 |
| P1AE5724 | 18 | VH1c | VL3a | 91.8 | 83.8 | 87.8 | na | 3.6 |
| P1AE5725 | 19 | VH1c | VL3b | 91.8 | 82.8 | 87.3 | na | 10.9 |
| P1AE5726 | 20 | VH1d | VL1a | 89.7 | 80.2 | 84.95 | na | 37.8 |
| P1AE5727 | 21 | VH1d | VL1c | 89.7 | 82.2 | 85.95 | na | 6.3 |
| P1AE5728 | 22 | VH1d | VL2a | 89.7 | 86.2 | 87.95 | na | 5.6 |
| P1AE5729 | 23 | VH1d | VL2b | 89.7 | 85.1 | 87.4 | na | 61.3 |
| P1AE5730 | 24 | VH1d | VL3a | 89.7 | 83.8 | 86.75 | na | 3.5 |
| P1AE5731 | 25 | VH1d | VL3b | 89.7 | 82.8 | 86.25 | na | 2.3 |

TABLE 11

Characterization of humanization variants of 5F11

| | Humanness | | | | | | CHO hu GPCR5D | |
|---|---|---|---|---|---|---|---|---|
| | Sort | VH | VL | VH huID | VL huID | Fv huID | EC/IC50 rel (ng/ml) | EC/IC50 rel (nM) |
| P1AE5733 | 1 | parental | parental | | | | 5.8 | 0.04 |
| P1AE5734 | 2 | VH1a | VL1a | 89.8 | 86 | 87.9 | 5.5 | 0.04 |
| P1AE5735 | 3 | VH1a | VL1b | 89.8 | 85 | 87.4 | 6.6 | 0.04 |
| P1AE5736 | 4 | VH1a | VL2a | 89.8 | 88 | 88.9 | 3.7 | 0.02 |
| P1AE5737 | 5 | VH1a | VL2b | 89.8 | 80.2 | 85 | 5.9 | 0.04 |
| P1AE5738 | 6 | VH1a | VL2c | 89.8 | 80 | 84.9 | 4.1 | 0.03 |
| P1AE5739 | 7 | VH1b | VL1a | 90.8 | 86 | 88.4 | 4.0 | 0.03 |
| P1AE5740 | 8 | VH1b | VL1b | 90.8 | 85 | 87.9 | 6.3 | 0.04 |
| P1AE5741 | 9 | VH1b | VL2a | 90.8 | 88 | 89.4 | 6.7 | 0.04 |
| P1AE5742 | 10 | VH1b | VL2b | 90.8 | 80.2 | 85.5 | 6.1 | 0.04 |
| P1AE5743 | 11 | VH1b | VL2c | 90.8 | 80 | 85.4 | 7.6 | 0.05 |
| P1AE5744 | 12 | VH1c | VL1a | 90.8 | 86 | 88.4 | 8.6 | 0.06 |
| P1AE5745 | 13 | VH1c | VL1b | 90.8 | 85 | 87.9 | 9.7 | 0.06 |
| P1AE5746 | 14 | VH1c | VL2a | 90.8 | 88 | 89.4 | 10.7 | 0.07 |
| P1AE5747 | 15 | VH1c | VL2b | 90.8 | 80.2 | 85.5 | 9.0 | 0.06 |
| P1AE5749 | 16 | VH1c | VL2c | 90.8 | 80 | 85.4 | 7.4 | 0.05 |
| P1AE5750 | 17 | VH1d | VL1a | 89.8 | 86 | 87.9 | 9.4 | 0.06 |
| P1AE5751 | 18 | VH1d | VL1b | 89.8 | 85 | 87.4 | 12.4 | 0.08 |

TABLE 11-continued

Characterization of humanization variants of 5F11

| | | | | | | | | |
|---|---|---|---|---|---|---|---|---|
| P1AE5752 | 19 | VH1d | VL2a | 89.8 | 88 | 88.9 | 6.2 | 0.04 |
| P1AE5753 | 20 | VH1d | VL2b | 89.8 | 80.2 | 85 | 10.4 | 0.07 |
| P1AE5754 | 21 | VH1d | VL2c | 89.8 | 80 | 84.9 | 9.0 | 0.06 |
| P1AE5755 | 22 | VH2b | VL1a | 90.8 | 86 | 88.4 | 7.8 | 0.05 |
| P1AE5756 | 23 | VH2b | VL1b | 90.8 | 85 | 87.9 | 7.8 | 0.05 |
| P1AE5757 | 24 | VH2b | VL2a | 90.8 | 88 | 89.4 | 2.9 | 0.02 |
| P1AE5758 | 25 | VH2b | VL2b | 90.8 | 80.2 | 85.5 | 2.6 | 0.02 |
| P1AE5759 | 26 | VH2b | VL2c | 90.8 | 80 | 85.4 | 3.1 | 0.02 |
| P1AE5760 | 27 | VH2d | VL1a | 89.8 | 86 | 87.9 | 4.0 | 0.03 |
| P1AE5761 | 28 | VH2d | VL1b | 89.8 | 85 | 87.4 | 3.7 | 0.02 |
| P1AE5762 | 29 | VH2d | VL2a | 89.8 | 88 | 88.9 | 4.6 | 0.03 |
| P1AE5763 | 30 | VH2d | VL2b | 89.8 | 80.2 | 85 | 6.0 | 0.04 |
| P1AE5764 | 31 | VH2d | VL2c | 89.8 | 80 | 84.9 | 4.5 | 0.03 |

| | | Humanness | | | | | CHO cy EC/IC50 | CHO hu GPCR5A EC/IC50 | CAR-J2 |
|---|---|---|---|---|---|---|---|---|---|
| | Sort | VH | VL | VH huID | VL huID | Fv huID | rel (ng/ml) | rel (ng/ml) | EC50 [ng/mL] |
| P1AE5733 | 1 | parental | parental | | | | na | na | 2.65 |
| P1AE5734 | 2 | VH1a | VL1a | 89.8 | 86 | 87.9 | na | na | 41.53 |
| P1AE5735 | 3 | VH1a | VL1b | 89.8 | 85 | 87.4 | na | na | 82.08 |
| P1AE5736 | 4 | VH1a | VL2a | 89.8 | 88 | 88.9 | na | na | 1.38 |
| P1AE5737 | 5 | VH1a | VL2b | 89.8 | 80.2 | 85 | na | na | 2.95 |
| P1AE5738 | 6 | VH1a | VL2c | 89.8 | 80 | 84.9 | na | na | 397.43 |
| P1AE5739 | 7 | VH1b | VL1a | 90.8 | 86 | 88.4 | na | na | 23.54 |
| P1AE5740 | 8 | VH1b | VL1b | 90.8 | 85 | 87.9 | na | na | 8.96 |
| P1AE5741 | 9 | VH1b | VL2a | 90.8 | 88 | 89.4 | na | na | 1.4 |
| P1AE5742 | 10 | VH1b | VL2b | 90.8 | 80.2 | 85.5 | na | na | 61.93 |
| P1AE5743 | 11 | VH1b | VL2c | 90.8 | 80 | 85.4 | na | na | 583.32 |
| P1AE5744 | 12 | VH1c | VL1a | 90.8 | 86 | 88.4 | na | na | 3.63 |
| P1AE5745 | 13 | VH1c | VL1b | 90.8 | 85 | 87.9 | na | na | 1.62 |
| P1AE5746 | 14 | VH1c | VL2a | 90.8 | 88 | 89.4 | na | na | 514.19 |
| P1AE5747 | 15 | VH1c | VL2b | 90.8 | 80.2 | 85.5 | na | na | 182.79 |
| P1AE5749 | 16 | VH1c | VL2c | 90.8 | 80 | 85.4 | na | na | 82.59 |
| P1AE5750 | 17 | VH1d | VL1a | 89.8 | 86 | 87.9 | na | na | 20.58 |
| P1AE5751 | 18 | VH1d | VL1b | 89.8 | 85 | 87.4 | na | na | 6.44 |
| P1AE5752 | 19 | VH1d | VL2a | 89.8 | 88 | 88.9 | na | na | 508.96 |
| P1AE5753 | 20 | VH1d | VL2b | 89.8 | 80.2 | 85 | na | na | 30.03 |
| P1AE5754 | 21 | VH1d | VL2c | 89.8 | 80 | 84.9 | na | na | 8.89 |
| P1AE5755 | 22 | VH2b | VL1a | 90.8 | 86 | 88.4 | na | na | 151.74 |
| P1AE5756 | 23 | VH2b | VL1b | 90.8 | 85 | 87.9 | na | na | 170.2 |
| P1AE5757 | 24 | VH2b | VL2a | 90.8 | 88 | 89.4 | na | na | 144.74 |
| P1AE5758 | 25 | VH2b | VL2b | 90.8 | 80.2 | 85.5 | na | na | 189.51 |
| P1AE5759 | 26 | VH2b | VL2c | 90.8 | 80 | 85.4 | na | na | 15.7 |
| P1AE5760 | 27 | VH2d | VL1a | 89.8 | 86 | 87.9 | na | na | 189.94 |
| P1AE5761 | 28 | VH2d | VL1b | 89.8 | 85 | 87.4 | na | na | 74.56 |
| P1AE5762 | 29 | VH2d | VL2a | 89.8 | 88 | 88.9 | na | na | 84.16 |
| P1AE5763 | 30 | VH2d | VL2b | 89.8 | 80.2 | 85 | na | na | 5.47 |
| P1AE5764 | 31 | VH2d | VL2c | 89.8 | 80 | 84.9 | na | na | 78.22 |

TABLE 12

CDR sequences of a selection of humanization variants

| | HCDR1 | HCDR2 | HCDR3 | LCDR1 | LCDR1 | LCDR3 |
|---|---|---|---|---|---|---|
| 5E11 parental | SEQ ID NO:83 | SEQ ID NO:84 | SEQ ID NO:86 | SEQ ID NO:87 | SEQ ID NO:88 | SEQ ID NO:89 |
| 5E11_P1AE5723 | SEQ ID NO:83 | SEQ ID NO:85 | SEQ ID NO:86 | SEQ ID NO:87 | SEQ ID NO:88 | SEQ ID NO:89 |
| 5E11_P1AE5728 | SEQ ID NO:83 | SEQ ID NO:85 | SEQ ID NO:86 | SEQ ID NO:87 | SEQ ID NO:88 | SEQ ID NO:89 |
| 5F11_parental | SEQ ID NO:90 | SEQ ID NO:91 | SEQ ID NO:93 | SEQ ID NO:94 | SEQ ID NO:95 | SEQ ID NO:97 |
| 5F11_P1AE5741 | SEQ ID NO:90 | SEQ ID NO:91 | SEQ ID NO:93 | SEQ ID NO:94 | SEQ ID NO:96 | SEQ ID NO:97 |
| 5F11_P1AE5745 | SEQ ID NO:90 | SEQ ID NO:92 | SEQ ID NO:93 | SEQ ID NO:94 | SEQ ID NO:95 | SEQ ID NO:97 |

Example 12

In Vitro Activation of CAR-J Cells in Presence of Different Humanization Variants of Selected Anti-GPRC5D IgGs The capacity of the different humanized anti-GPRC5D IgGs to activate PGLALA-CAR-J effector cells was assessed as described in the following. GPRC5D-expressing multiple Myeloma target cells L363 (Diehl et al., Blut 36: 331-338 (1978)) were co-cultured with anti-PGLALA-CAR-J effector cells (Jurkat-NFAT human acute lymphatic leukemia reporter cell line expressing a TCR directed against the PGLALA (P329G L234A L235A) mutation in the Fc part of IgG molecules and containing a NFAT promoter, as disclosed in PCT application no PCT/EP2018/086038 and PCT application No. PCT/EP2018/086067. Upon simultaneous binding of the IgG molecule to the GPRC5D on L363 cells and PGLALA-CAR-J cells, the NFAT promoter is activated and leads to expression of active firefly luciferase.

For the assay, the humanized IgG variants were diluted in RPMI 1640 medium (containing Glutamax, 15% HI Fetal Bovine Serum, 1% Penicillin-Streptomycin; all from GIBCO) and transferred into round-bottom-96 well plates (final concentration range of 0.2 μg/ml till 10 μg/ml). 20 000 L363 cells per well and anti-PGLALA-CAR-J effector cells were added to obtain a final effector (anti-PGLALA-CAR-J) to target (L363) cell ratio of 5:1 and a final volume of 200 μl per well. Cells were incubated for roughly 16 h at 37° C. in a humidified incubator. At the end of the incubation time, 100 μl/well of the supernatant were transferred to a white flat bottom 96-well plate (Costar) and incubated with another 100 μl/well of ONE-Glo luciferase substrate (Promega) for 5 min before luminescence was read using PerkinElmer Envision. The row data was plotted as relative luminescence signals (RLUs) against the IgG concentration using GraphPad Prism and the EC50 were calculated using XL-fit software.

Figures 15A, 15B:
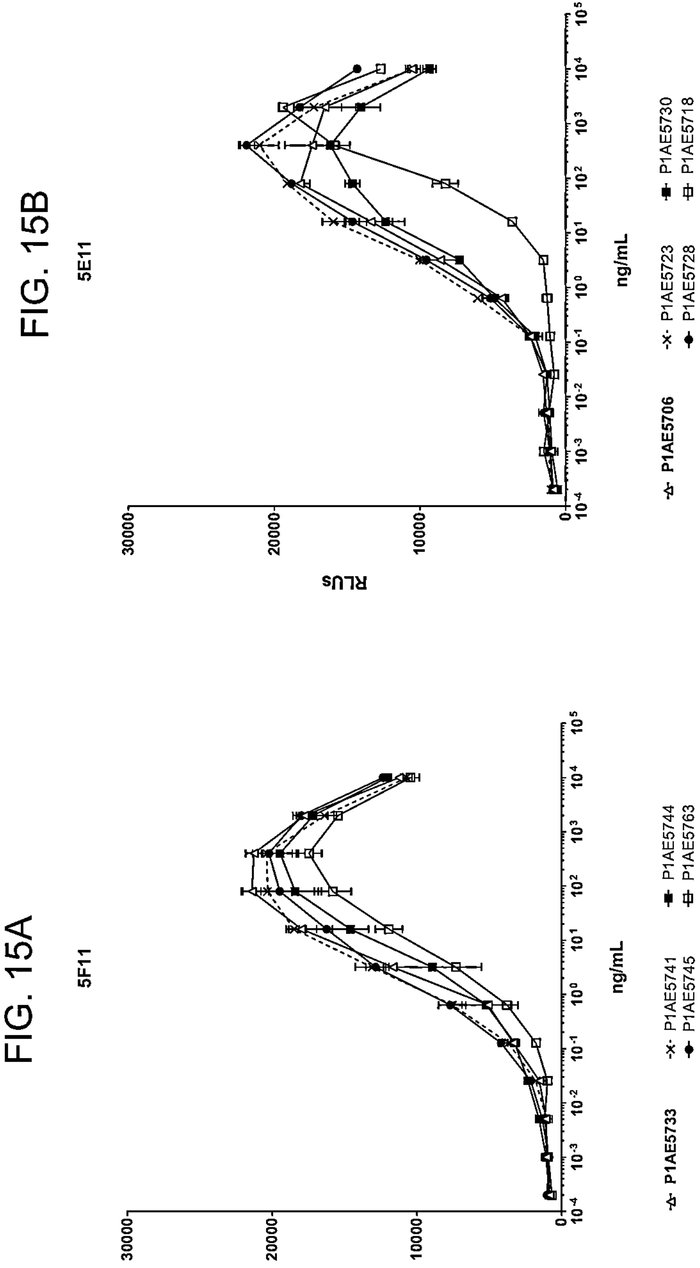
FIG. 15A-FIG. 15B. PGLALA-CAR-J activation after roughly 16 hours of incubation, as determined by luminescence. The latter is induced upon simultaneous binding of the GPRC5D IgGs (5F11-IgG in FIG. 15A; 5E11-IgG in FIG. 15B) to the GPRC5D-expressing multiple myeloma cell line L-363 and of the PGLALA-modified Fc domain to Jurkat-NFAT reporter cells, which were genetically engineered to express a TCR-directed against the PGLALA mutation in the Fc part of these IgG molecules. Depicted are duplicates with SD.

As shown in FIG. 15A-FIG. 15B and Table 13, all evaluated GPRC5D IgGs induce CAR-J activation upon simultaneous binding to GPRC5D-expressing target cells and anti-PGLALA-CAR-J cells. For both anti-GPRC5D binder 5F11 and 5E11, humanization variants could be identified with similar or even improved $EC_{50}$ values as compared to parental antibodies pre-humanization. For binder 5F11, the strongest activation could be induced by molecule P1AE5741 (FIG. 15A). For binder 5E11, the strongest activation could be induced by molecule P1AE5730 and P1AE5723 (FIG. 15B).

TABLE 13

$EC_{50}$ values of CAR-J activation

| | Binder 5F11 | | | | | Binder 5E11 | | | | |
|---|---|---|---|---|---|---|---|---|---|---|
| | P1AE5733 (parental) | P1AE5741 | P1AE5745 | P1AE5744 | P1AE5763 | P1AE5706 (parental) | P1AE5723 | P1AE5728 | P1AE5730 | P1AE5718 |
| $EC_{50}$ (ng/ml) | 2.65 | 1.4 | 1.62 | 3.63 | 5.47 | 3.9 | 3.7 | 5.6 | 3.5 | 105.4 |

Example 13

Preparation of Further T Cell Bispecific Antibodies

The principles of converting binders into T cell bispecific antibodies are exemplified and described in the art, e.g. in PCT publication no. WO 2014/131712 A1, which is incorporated herein by reference in its entirety. The T cell bispecific antibodies comprise two GPRCSD-binding moieties and one CD3-binding moiety (anti-GPRC5D/anti-CD3 T cell bispecific antibodies) as illustrated in FIG. 3. The following anti-GPRC5D/anti-CD3 T cell bispecific antibodies were prepared: i) 6623 (SEQ ID NOs 114, 115, 116 and 117); ii) 6624 (SEQ ID NOs 118, 119, 120 and 121); iii) 6625 (SEQ ID NOs 122, 123, 124 and 125); iv) 6626 (SEQ ID NOs: 126, 127, 128 and 129). DP47-TCB (the "untargeted TCB") is described in PCT publication no. WO 2014/131712 A1, which is incorporated herein by reference in its entirety. The B72 TCB derives from the GCDB72 antibody disclosed in Table 23 of WO 2018/0117786 A2 and comprises the GPRCSD binding moiety of GCDB72 (Example 7). The term "B72 TCB" also refers to the term "B72" herein. The BCMA-TCB derives from WO 2016/166629 A1 and comprises the GPRCSD binding moiety of A02_Rd4_6 nM_C01 as disclosed therein. BCMA-TCB was generated in the crossmab 2+1 Format (SEQ ID Nos 77, 78, 79, 80) as described for Example 2. The terms "5F11-TCB" and "5F11p-CH2527" are used interchangeable herein. The terms "5E11-TCB" and "5E11p-CH2527" are used interchangeable herein.

Example 14.1

Binding of T Cell Bispecific Antibodies to Multiple Myeloma Cell Lines and Jurkat-NFAT Cells To measure the binding to GPRCSD, we performed a flow cytometry-based binding assay on reported multiple myeloma cell lines (Lombardi et al., Molecular characterization of human multiple myeloma cell lines by integrative genomics: insights into the biology of the disease; Genes Chromosomes Cancer. 2007 March; 46(3):226-38.). The cell line NCI-H929 (ATCC® CRL-9068) was cultured in RPMI 1640 with Glutamax medium (Gibco) supplemented with 10% FBS, 1× Penicillin/Streptomycin (Gibco), lx Sodium Pyruvate (Gibco) and 50 μM beta-Mercaptoethanol (Gibco). Jurkat-NFAT reporter cells (a CD3-expressing human acute lymphatic leukemia reporter cell line with a NFAT promoter, GloResponse Jurkat NFAT-RE-luc2P, Promega #CS176501) were cultured in RPMI 1640, containing 2 g/l Glucose, 2 g/l $NaHCO_3$, 10% FCS, 25 mM HEPES, 2 mM L-Glutamine, 1×NEAA, 1×Sodium-pyruvate and 200 μg/ml Hygromycin B. 0.1 Mio cells per well of a 96-round-bottom-well plate were incubated with 100 nM to 1.3 pM (serial dilutions of 1:5) of the indicated GPRCSD-TCB constructs 5E11p-CH2527, 6625, 6626, 5F11p-CH2527, 6623 or 6624 or no construct for 30 min at 4° C. The cells were washed with FACS buffer (PBS, 2% Fetal Bovine Serum; 1% 0.5m EDTA pH 8; 0.25% $NaN_3$ Sodium azide (20%)) twice and stained with PE-conjugated Goat anti-human IgG, Fcγ fragment specific (Jackson Laboratories, 109-606-008) diluted 1/100 in FACS buffer, for another 30 min at 4° C.

Flow cytometry acquisition was performed on a custom-designed BD Biosciences Fortessa and analyzed using BD Diva. EC50 values were calculated, using GraphPad Prism software.

Figures 16A, 16B, 16C, 16D:
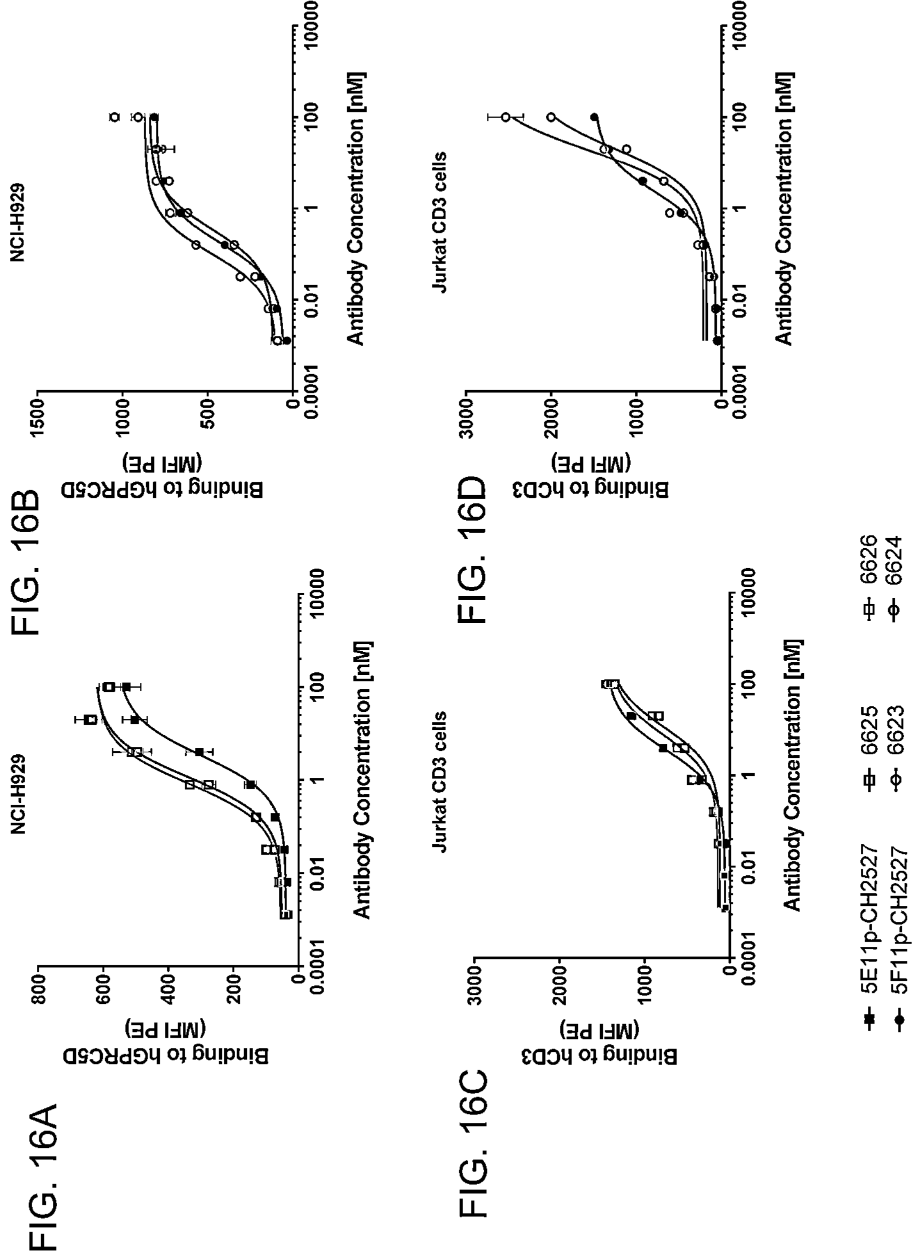
FIG. 16A-FIG. 16D. Binding of humanized TCB molecules vs. parental TCBs to human GPRC5D on NCI-H929 cells (FIG. 16A and FIG. 16B) and human CD3 on Jurkat cells (FIG. 16C and FIG. 16D) expressed on cells.

FIG. 16A-FIG. 16D show that all TCB molecules are able to bind both, human GPRCSD, as well as human CD3 in a concentration-dependent manner. Briefly, both humanized versions of the 5E11p-CH2527, namely 6625 and 6626, show enhanced binding to human GPRCSD compared to their parental TCB, which results in lower EC50 values of binding as well (FIG. 16A and Table 14.1). In addition, 6624 shows slightly enhanced binding to human GPRCSD compared to 5F11p-CH2527 and 6623 (FIG. 16B). In general, all 5F11-based molecules show better binding to human GPRCSD than the 5E11-based molecules. All 5E11-based TCB molecules show comparable concentration-dependent binding to human CD3 (FIG. 16C), whereas both humanization variants of the 5F11p-CH2527, namely the 6623 and 6624 show stronger overall binding signals at the highest antibody concentrations compared to the parental one, when incubated with human CD3-expressing Jurkat-NFAT cells (FIG. 16D).

TABLE 14.1

EC50 values (nM) for binding of the indicated GPRC5D-TCB molecules to either human GPRC5D expressed on NCI-H929 or to human CD3 expressed on Jurkat cells.

| EC50 (nM) | 5E11p-CH2527 | 6625 | 6626 | 5F11p-CH2527 | 6623 | 6624 |
|---|---|---|---|---|---|---|
| NCI-H929 | 3.36 | 1.15 | 0.85 | 0.18 | 0.36 | 0.1 |
| Jurkat | 3.67 | 11.47 | 7.8 | 2.31 | n.c. | n.c. |

Example 14.2

Binding of T Cell Bispecific Antibodies to Multiple Myeloma Cell Lines

As the data presented in Example 14.1 were falsely calculated by a factor of 10, the EC50 values are too low. Therefore and to reassess the binding to GPRC5D a, we performed a series of FACS based binding assay on reported multiple myeloma cell lines (Lombardi et al., Molecular characterization of human multiple myeloma cell lines by integrative genomics: insights into the biology of the disease; Genes Chromosomes Cancer. 2007 March; 46(3):226-38.). The cell line OPM-2 was cultured in RPMI 1640+1% Glutamax medium (Gibco) supplemented with 20% Heat-Inactivated Fetal Bovine Serum (FBS, Gibco). The cell line NCI-H929 was cultured in RPMI 1640+1% Glutamax medium (Gibco) supplemented with 10% Heat-Inactivated Fetal Bovine Serum (FBS, Gibco), 50 pM Mercaptoethanol (Gibco) and 1 mM Sodium Pyruvate (Gibco), and RPMI-8226 were cultured in RPMI 1640+1% Glutamax medium (Gibco) supplemented with 10% Heat-Inactivated Fetal Bovine Serum (FBS, Gibco). The cell lines were cultured in 75 $cm^2$ flasks (TPP) with two passages per week.

Briefly, suspension cells were harvested, counted and assessed for viability. All subsequent steps were performed at 4° C.

Cells were re-suspended in PBS at 0.5 Mio cells per ml. Next, 0.05 Mio cells were plated per well of a round-bottom 96-well-plate, centrifuged and supernatants were discarded. Cells were stained with zombie aqua viability stain (BioLegend #423102, pre-diluted 1:400), containing Fc blocking (BioLegend #422302, prediluted 1:400) for 20 minutes in a total volume of 50 ul per well. Cells were washed with FACS buffer and incubated with increasing concentrations of the 5E11(6625)-TCB, also referred to as 6625 herein, (0.7 nM-500 nM, total volume of 25 ul per well) for 30 minutes at 4° C. Assay plates were centrifuged and supernatants were discarded.

Figures 25A, 25B, 25C, 25D, 25E, 25F, 25G, 25H, 25I:
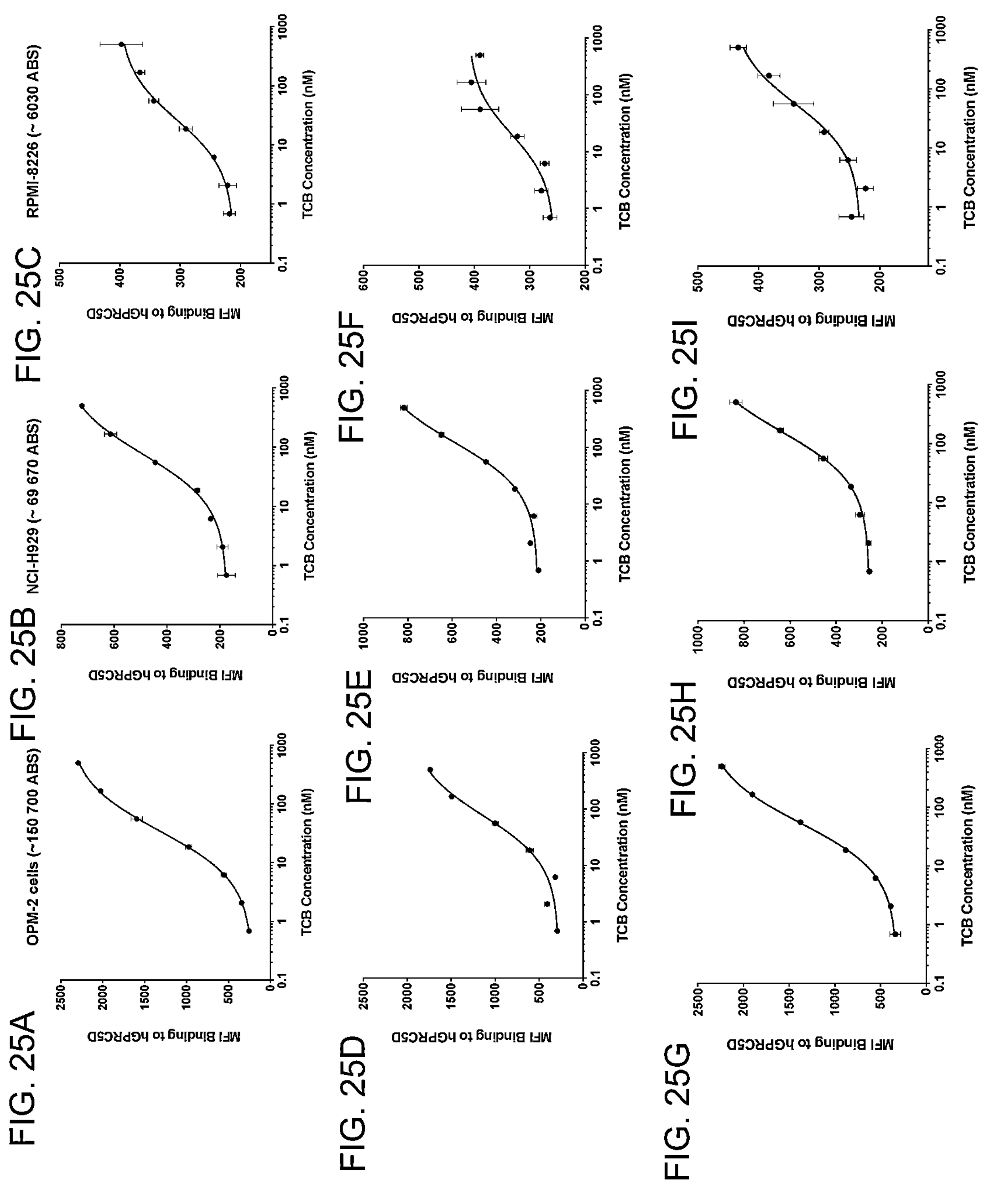
FIG. 25A-FIG. 25I. Representative Examples of the binding analysis of bispecific antigen binding molecule 5E11 (6625)-TCB to human GPRC5D-expressing multiple myeloma cell lines OPM-2 (FIG. 25A, FIG. 25D, FIG. 25G), NCI-H929 (FIG. 25B, FIG. 25E, FIG. 25H) and RPMI-8226 (FIG. 25C, FIG. 25F, FIG. 25I). The number of GPRC5D antibody binding sites (ABS) per cell line are given in brackets and were determined by QSC previously (Quantum Simply Cellular, BangsLabs). Depicted are relative median fluorescence values (MFI) from triplicates with SD. EC50 values of binding were calculated by GraphPad-Prism and are summarized in Table 14.2.

Thereafter, cells were resuspended by smooth vortexing and incubated for another 30 min at 4° C. in a total of 25 μl per well, containing 500 nM of the secondary antibody (aPGLALA mulG2b Alexa 647, produced inhouse) in FACS buffer. Cells were washed once and analyzed on a BD flow cytometer, equipped with FACS Diva. Binding curves and EC50 values were obtained using GraphPadPrism6. The EC50 values of assay replicate 1 correspond to the graphs shown in FIG. 25A, FIG. 25B and FIG. 25C. The EC50 values of assay replicate 2 correspond to the graphs shown in FIG. 25D, FIG. 25E and FIG. 25F. The EC50 values of assay replicate 3 correspond to the graphs shown in FIG. 25G, FIG. 25H and FIG. 25I.

FIG. 25 shows concentration-dependent binding of the 5E11(6625)-TCB to MM cell lines expressing various levels of human GPRCSD. The EC50 of binding ranges from 20 nM to 158 nM and shows some assay variation due to variation in target expression levels on cells.

TABLE 14.2

EC50 values Binding of 5E11(6625)-TCB to human GPRC5D expressed on different established MM cell lines

| EC50 (nM) | OPM-2 | NCI-H929 | RPMI-8226 |
|---|---|---|---|
| Assay replicate 1 | 34.5 | 75.8 | 26.8 |
| Assay replicate 2 | 75.5 | ~123.2 | 20.4 |
| Assay replicate 3 | 54.2 | ~158.2 | 55 |

Example 15

The capacity of the GPRCSD-TCBs to induce CD3-mediated activation of Jurkat-NFAT effector cells upon simultaneous binding to human CD3 and human GPRCSD, was assessed using co-cultures of RPMI-8226 (ATCC® CCL-155) cells and Jurkat-NFAT reporter cells (Promega #CS176501). Upon simultaneous binding of the TCB molecule to the human GPRCSD on RPMI-8226 cells and the human CD3 antigen on Jurkat-NFAT reporter cells, the NFAT promoter is activated and leads to expression of active firefly luciferase. The intensity of luminescence signal (obtained upon addition of luciferase substrate) is proportional to the intensity of CD3 activation and signaling.

For the assay, 20 000 RPMI8226 cells were plated per well of a 96-well-plate and the indicated TCB molecules were added to obtain a final concentration range of 50 nM to 5 fM, using serial dilution steps of 1:10 in in RPMI, containing 20% FBS and 1% Pen/Strep. 50 000 Jurkat-NFAT cells were added per well to obtain a final E:T ratio of 2.5:1. After an overnight incubation at 37° C. 5% $CO_2$, 100 μl of ONE-Glo reagent (Promega) were added to equivalent volumes of the assay supernatant and incubated for 5 minutes at room temperature, protected from light. Luminescence was analyzed using a Perkin Elmer plate reader.

Figures 17B, 17C, 17D, 17E, 17F, 17G:
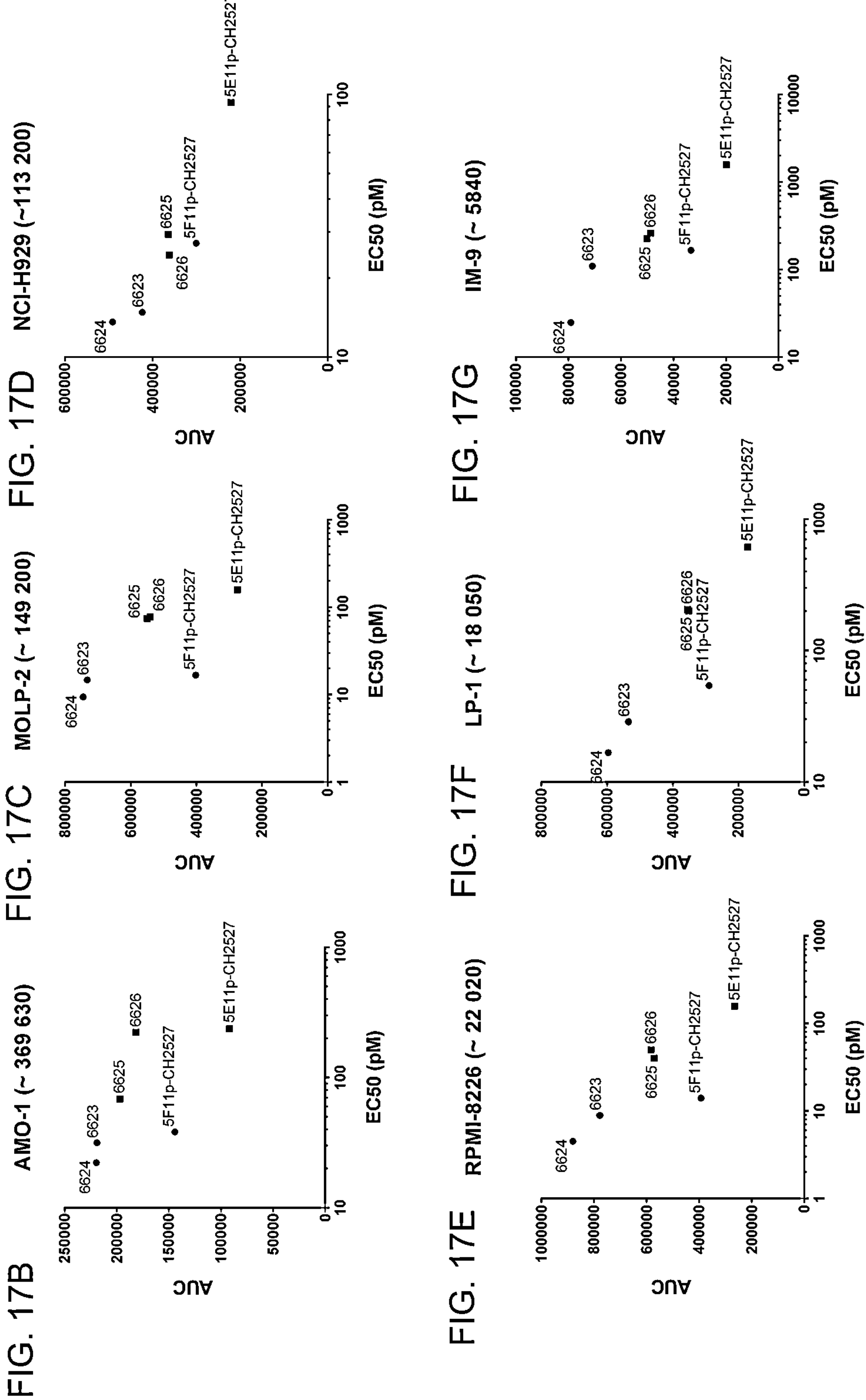
Figures 18A, 18B, 18C, 18D:
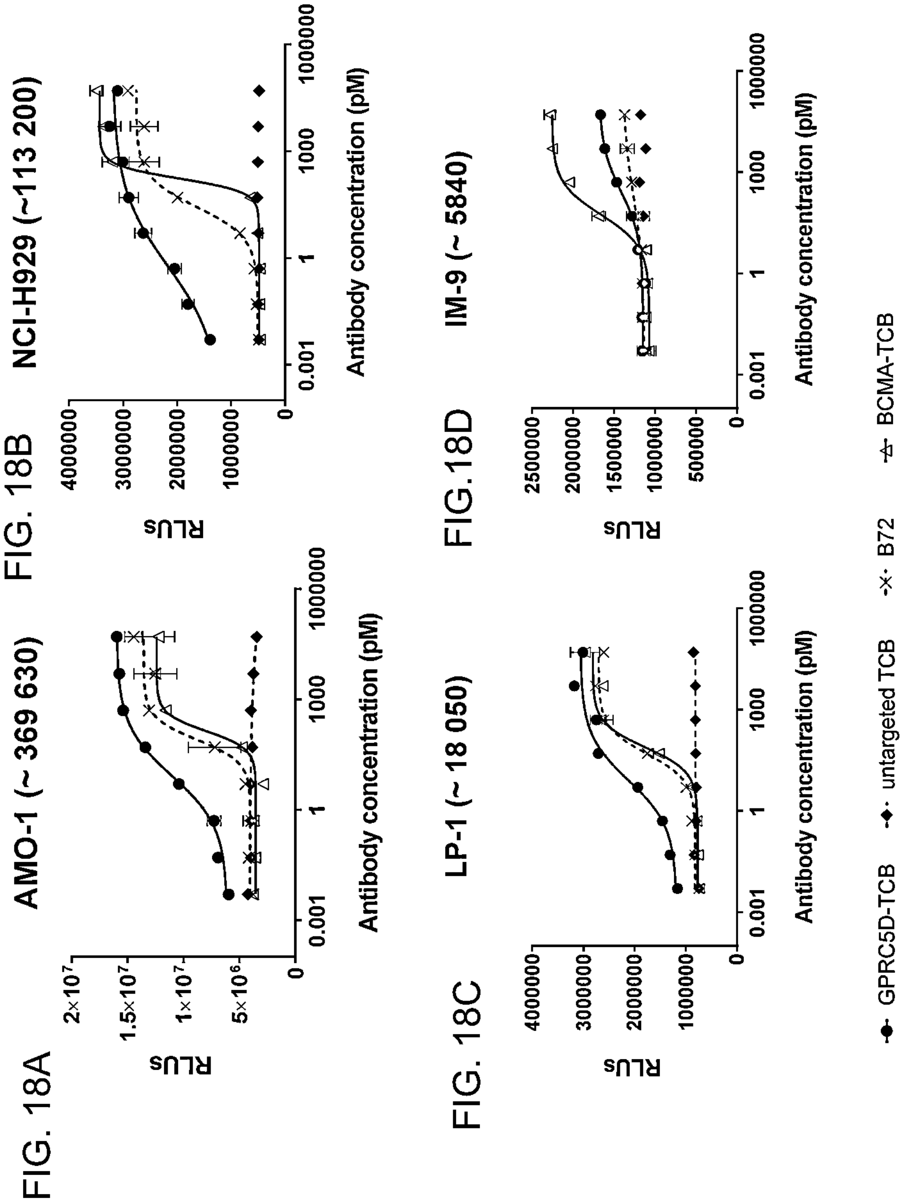
FIG. 18A-FIG. 18D. Tumor Cell Lysis assay comparing GPRC5D-TCB molecules as presented herein and molecules known in the art targeting GPRC5D or BCMA versus an untargeted reference TCB molecule.

As depicted in FIG. 17A, all evaluated GPRC5D TCB molecules induce Jurkat-NFAT activation in a dose-dependent manner, whereas no significant signal was obtained in the presence of any of the two untargeted DP47 TCB control molecules. The untargeted DP47 TCB 1 comprises a CD3 binder comprising the VH of SEQ ID NO: 104 and the VL of SEQ ID NO: 105. The untargeted DP47 TCB 2 comprises a CD3 binder comprising the VH of SEQ ID NO: 35 and the VL of SEQ ID NO: 36. The corresponding EC50 values for Jurkat activation were calculated using GraphPadPrism6, and are given in Table 15. Taking into account both EC50, as well as AUC (see Table 15) the ranking of the molecules is as follows: 6624>6623>5F11p-CH2527>6626-6625>5E11p-CH2527.

Similar assays were conducted in the presence of additional (Multiple Myeloma) cell lines, expressing various levels of human GPRC5D, as determined by flow (Quantum Simply Cellular, Bangslabs) and indicated as GPRC5D binding site numbers in brackets next to the cell line name. EC50 and AUC were calculated, using GraphPadPrism and are plotted on x- versus y-axis (FIG. 17B-FIG. 17G).

As depicted in FIG. 17B-FIG. 17G), all molecules show concentration-dependent Jurkat-activation in presence of cell lines with a broad range of relative GPRC5D expression; the ranking of the molecules is similar, independent of the target cell line present.

TABLE 15

EC50 values (pM) or area under the curve (AUC), calculated from GPRC5D-TCB-mediated activation of Jurkat-NFAT reporter cells in presence of RPMI-8226 cells, as measured by luminescence after overnight incubation (~20 h).

| | 5E11p-CH2527 | 6625 | 6626 | 5F11p-CH2527 | 6623 | 6624 |
|---|---|---|---|---|---|---|
| EC50 (pM) | 157 | 40 | 49.7 | 14.0 | 8.9 | 4.5 |
| AUC | 265 | 571 | 582 | 393 | 778 | 880 |
| | 250 | 600 | 400 | 460 | 140 | 720 |

Example 16

GPRC5D-TCB Mediated T Cell Cytotoxicity

To further measure the functionality of the anti-GPRC5D-TCB antibodies, an in-vitro tumor cell lysis assay was performed. Briefly, AMO-1 (DSMZ ACC 538), NCI-H929 ATCC® CRL-9068, LP-1 (DSMZ ACC 41) and IM-9 (ATCC® CCL-159) cell lines were co-cultured with human pan T as effector cells at a final effector to target ratio of 10:1. Human pan T cells were isolated from peripheral blood mononuclear cells (PBMCs) from healthy donors, using a human Pan T cell Isolation kit (Miltenyi Biotec). The indicated GPRC5D– (6625 and B72) or BCMA-targeting T-cell engaging bispecific molecules were added at decreasing concentrations (range from 50 nM to 5 pM, with dilution steps of 1:10). As negative control, the untargeted TCB was included.

After 20 hours of incubation at 37° C. with 5% $CO_2$, cell death was determined by quantification of the luminescence signal (CytoTox-Glo Cytotoxicity Assay, Promega), following the manufacturers' manual. Depicted are relative luminescence signals (RLUs) as direct measurement of determined cell death. EC50 and AUC were calculated, using GraphPadPrism and are summarized in Table 16.

FIG. 18A-FIG. 18D shows that all TCB molecules are able to induce concentration-dependent lysis of a wide range of tumor cell lines with varying relative expression level of human GPRC5D and BCMA, respectively. The direct comparison of the 6625 and the B72 suggests an increased efficacy and potency of the 6625 molecule. The comparison of the 6625 and the BCMA-TCB reveals better in vitro efficacy and potency of the 6625 in presence of AMO-1 (FIG. 18A), NCI-H929 (FIG. 18B) and LP-1 (FIG. 18C), whereas the BCMA-TCB is inducing stronger tumor cell lysis of IM-9 (FIG. 18D), which express rather low levels of GPRC5D. The different ranking of the 6625 and the BCMA-TCB on the tested cell lines can likely be explained by different relative expression levels of the GPRC5D versus the BCMA on these cell lines.

TABLE 16

EC50 values (pM), calculated from GPRC5D- or BCMA-TCB-mediated tumor cell lysis in presence of the indicated cell lines and as determined by luminescence after overnight incubation (~20 h).

| EC50 (pM) | Tumor Indication | 6625 | B72 | BCMA-TCB |
|---|---|---|---|---|
| AMO-1 | plasmacytoma | 8.3 | 79.9 | 137.1 |
| NCI-H929 | MM | 0.597 | 26.95 | 171 |
| LP-1 | MM | 7.99 | 48.95 | 76.36 |
| IM-9 | B lymphoblastoid from a MM patient | 266.9 | 197.5 | 55.69 |

TABLE 17

Area under the curve values, calculated from GPRC5D- or BCMA-TCB-mediated tumor cell lysis in presence of the indicated cell lines and as determined by luminescence after overnight incubation (~20 h).

| AUC | Tumor Indication | 6625 | B72 | BCMA-TCB |
|---|---|---|---|---|
| AMO-1 | plasmacytoma | 80117761 | 54494020 | 47326610 |
| NCI-H929 | MM | 17872547 | 10854134 | 10684467 |
| LP-1 | MM | 15438497 | 11504124 | 11100680 |
| IM-9 | B lymphoblastoid from a MM patient | 9268093 | 8600921 | 10994563 |

Example 17

Anti-GPRC5D-TCB Mediated T Cell Activation in Presence of a Primary MM Sample

To evaluate the activity of GPRCSD TCB molecules on primary Multiple Myeloma samples, a frozen unprocessed Bone Marrow sample (Proteogenex) was thawed and a quick red blood cell lysis was performed, using BD Pharm Lysis buffer (#555899). Thereafter, cells were washed, resuspended in RPMI 1640 Glutamax, including 20% heat-inactivated Fetal Bovine Serum, 2% human serum and 1% Penicillin/Streptomycin (all from Gibco) and 100 L of cell suspension (30 000 cells) were seeded per well in a 96-well plate round bottom (TPP). Autologous T-cells were added to obtain a final ratio of 10 T-cells per cells of the mixed BM sample. The indicated molecules were added to obtain a final concentration range of 50 nM to 0.05 nM (1:10 dilution steps) in a total volume of 200 Iii per well of a 96-well-plate.

Figure 19:
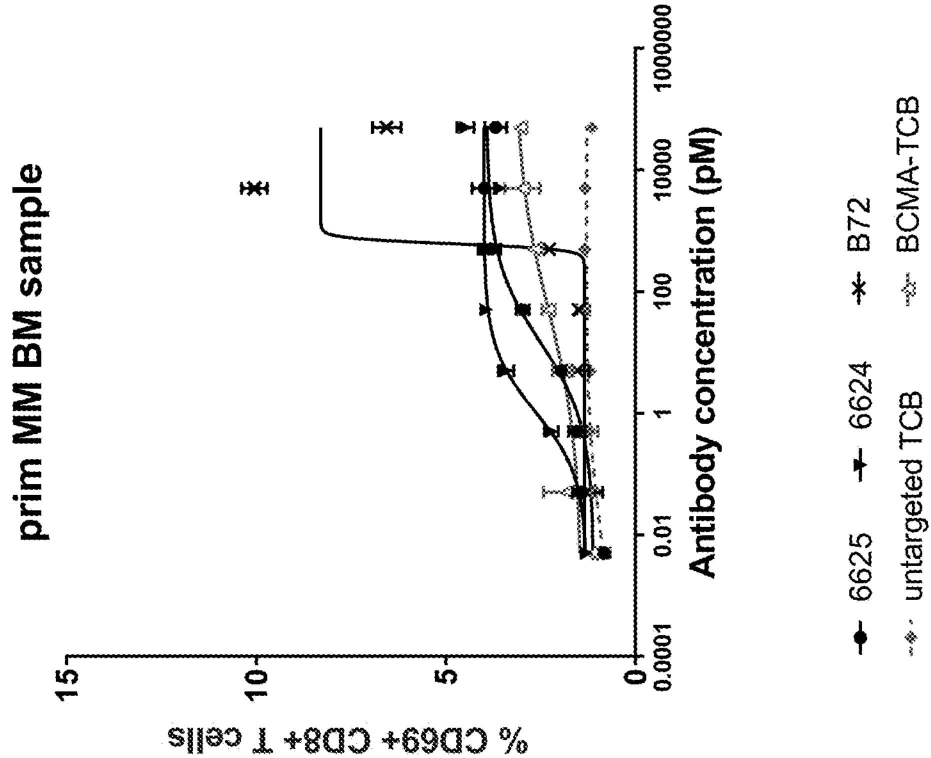
FIG. 19. Activation of autologous T-cells upon incubation of a primary MM sample with different CD3-engaging bispecific molecules. GPRC5D-TCBs as presented herein were compared to molecules known in the art targeting GPRC5D or BCMA versus an untargeted reference TCB molecule.

After overnight incubation at 37° C. in a humidified incubator, cells were washed with PBS once and stained for 20 minutes at 4° C. with 50 L of Live blue (Invitrogen, #L23105) to discriminate between live and dead cells. Surface staining was performed using a mixture of the following antibodies based on the manufacturers' suggestions: CD25 BV605, CD69 APC-Cy7, CD38 BV510, CD138 FITC, CD8 BV711, CD3 PE-Cy5 and CD4 AlexaFluor700 (all from BioLegend). For the final analysis, cells were resuspended in 100 μL of FACs buffer and acquired using a Fortessa (BD Biosciences). FIG. 19 shows percent of T-cell activation, as determined by the percent of living CD8 T cells, being positive for the early activation marker CD69. EC50 of T-cell activation was calculated by Graph Pad Prism and is summarized in Table 18. Both representative GPRC5D-targeting bispecific molecules, namely 6624 and 6625, are able to induce concentration-dependent T-cell activation with an EC50 of 1.06 pM and 14.8 pM, respectively, whereas no T-cell activation was induced in presence of an untargeted TCB control. In the depicted case, the BCMA-TCB activated T-cells to a lesser extent than both of the evaluated GPRC5D TCB molecules. A potential reason might be differences in relative expression levels of GPRC5D and BCMA (not assessed). Significant T-cell activation was induced by the B72 molecule only at much higher concentrations than it was observed with the 6624 and 6625, however the B72 led to a higher overall activation at the two highest concentrations measured. As we have observed T-cell activation at similar concentrations of the B72 in bone marrow samples of healthy donors, it is not clear, if the observed effect of B72 in presence of the primary MM samples is purely target-dependent (see FIG. 21A and FIG. 21B).

TABLE 18

EC50 values (pM), calculated from GPRC5D- or BCMA-TCB-mediated activation of autologous T-cells, incubated with a primary MM sample and quantified by flow cytometric analysis of CD69 on CD8 T cells after roughly 24 h.

| | 6624 | 6625 | B72 | BCMA-TCB |
|---|---|---|---|---|
| EC50 (pM) | 1.06 | 14.8 | ~612.5 | 52.54 |

Example 18

Depletion of B Cells Upon Incubation of PBMCs from Healthy Donors

Figures 20A, 20B, 20C, 20D:
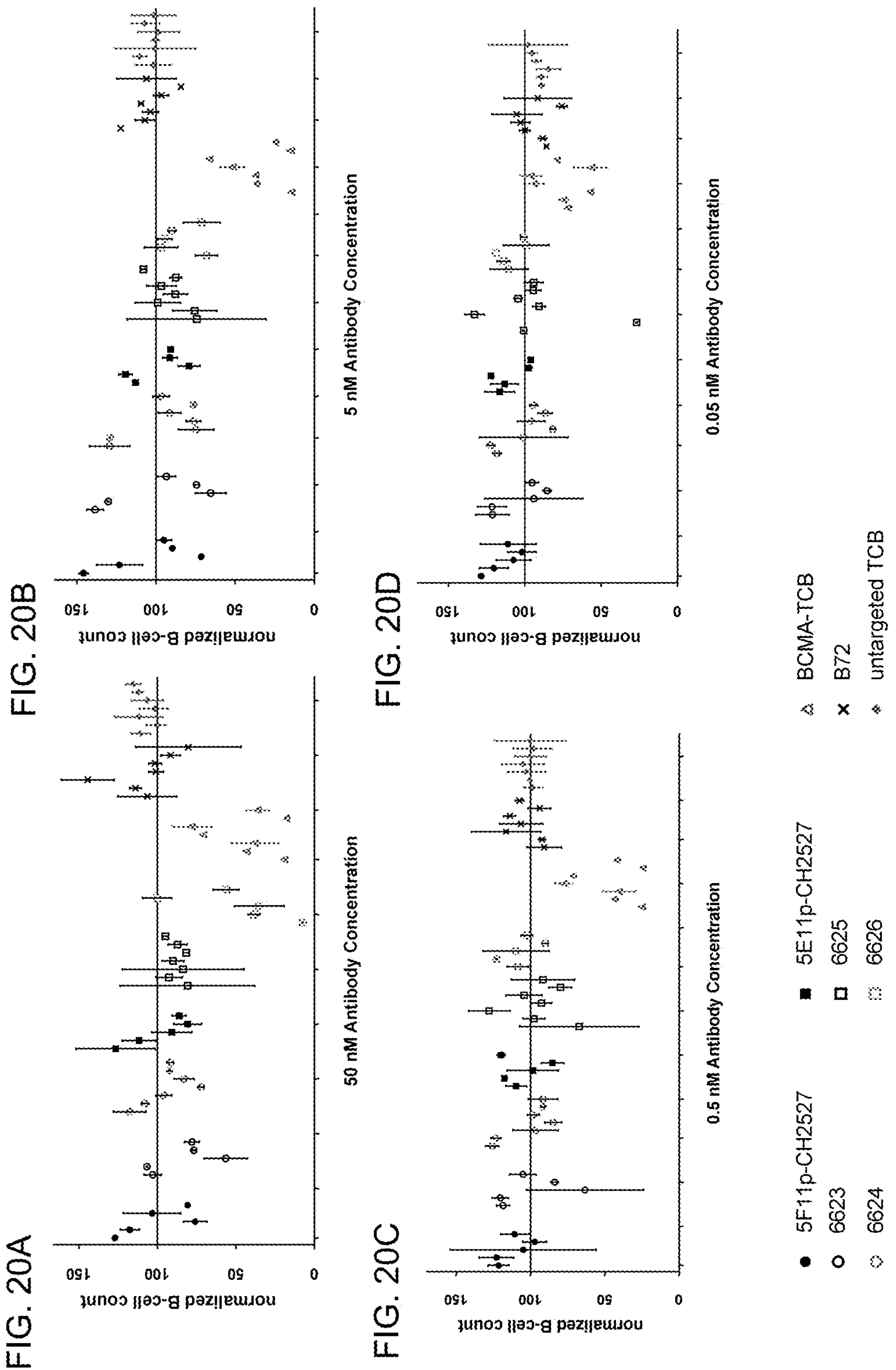
FIG. 20A-FIG. 20D. Depletion of B cells upon incubation of PBMCs from healthy donors with different CD3-engaging bispecific molecules. GPRC5D-TCBs as presented herein were compared to molecules known in the art targeting either GPRC5D or BCMA versus an untargeted reference TCB molecule. Antibodies were used at concentrations of 50 nM (FIG. 20A), 5 nM (FIG. 20B), 0.5 nM (FIG. 20C) and 0.05 nM (FIG. 20D).

Human PBMCs were isolated from the blood of healthy donors by classical density gradient centrifugation. 200 000 PBMCs were plated per well of a 96-well-plate in RPMI 1640 medium, containing 10% FBS and 1% Pen/Strep. The indicated bispecific molecules were added to have a final concentration of 50 nM, 5 nM, 0.5 nM or 0.05 nM in a total volume of 200 μl per well. After incubation for 48 h at 37° C. in a humidified incubator, cells were washed with FACS buffer and Fc receptors were blocked by incubation of cells with the Human TruStain FcX™ (Fc block, BioLegend), according to the manufacturers' protocols. Live blue (Invitrogen, #L23105) was used to discriminate between live and dead cells (see Example 17). Surface expression of the following markers was performed for 30 min at 4° C.: CD19, CD45, CD4, CD38, CD8, CD138 (all from BioLegend). For the absolute quantification of B cells per well, 10 μl per well of CountBright absolute counting beads (Invitrogen #C36950) were added prior the flow cytometric analysis with BD FACS Fortessa. FIG. 20A-FIG. 20D shows the summary of 5 different healthy donors, that have been assessed with the indicated bispecific molecules at different antibody concentrations, namely 50 nM (FIG. 20A), 5 nM (FIG. 20B), 0.05 nM (FIG. 20C) and 0.05 nM (FIG. 20D). Depicted is the B cell count, normalized to untreated controls, based on duplicates with SD (per donor). Significant depletion of healthy B cells was observed for both, the BCMA-TCB, as well as the GPRC5D-TCB 6626, whereas none of the other GPRC5D-targeting TCBs, including the B72, significantly depleted B cells in the majority of donors. The B-cell depleting effect observed with 6626 was limited to concentrations of above –5 nM, whereas the BCMA-TCB depleted healthy B-cells already at concentrations of 0.05 nM. In summary, this suggests, that GPRC5D-targeting molecules seem to have a much lower risk to deplete healthy B cells, which might be a safety advantage.

Example 19

Impact on Activation of T-Cells Upon Incubation of Bone Marrow Samples from Healthy Donors Unprocessed Bone Marrow of healthy donors (Lonza) was evaluated 1 day after sampling. After a quick red blood cell lysis using (BD Pharm Lysis buffer #555899 cells were washed, resuspended in RPMI 1640 Glutamax, including 20% heat-inactivated Fetal Bovine Serum, 2% human serum and 1% Penicillin/Streptomycin (all from Gibco) and 100 μL of cell suspension (30 000 cells) were seeded per well in a 96-well plate round bottom (TPP). The indicated molecules were added to obtain a final concentration range of 5 nM to 0.05 nM (1:10 dilution steps) in a total volume of 200 μl per well of a 96-well-plate.

Figures 21A, 21B:
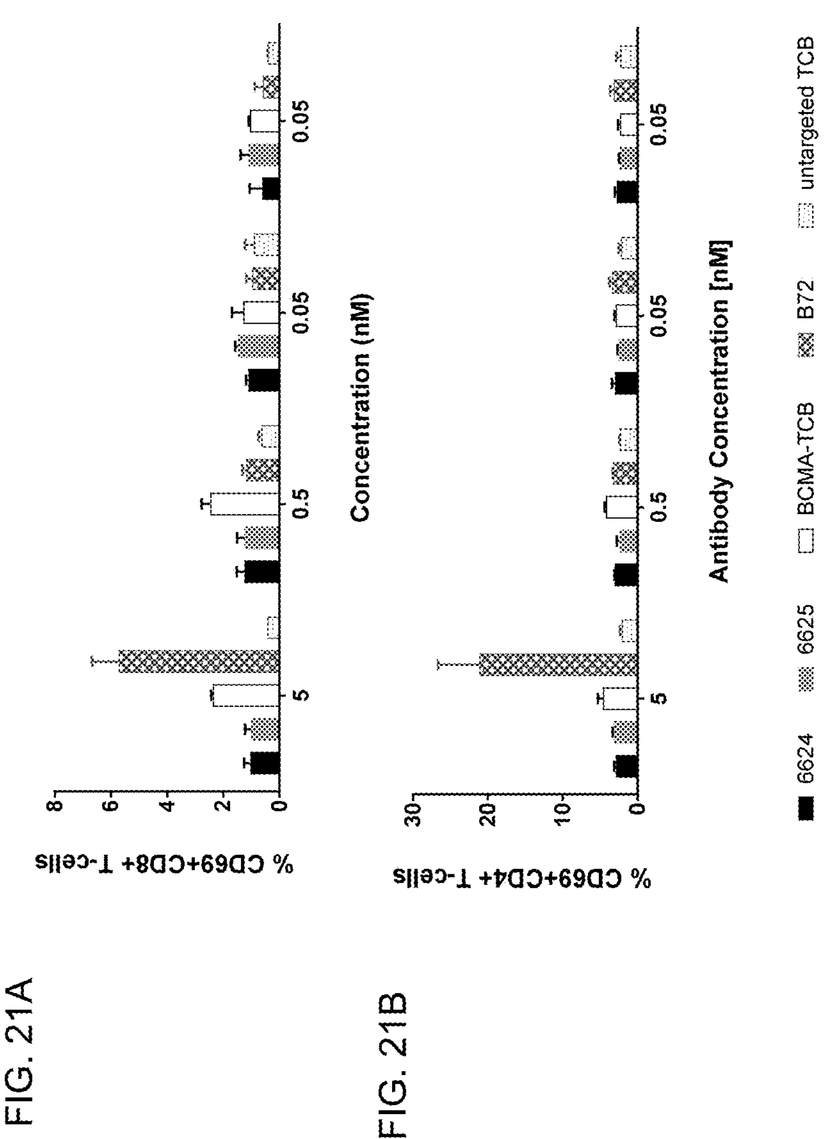
FIG. 21A-FIG. 21B. Activation of T-cells upon incubation of bone marrow samples from healthy donors with different CD3-engaging bispecific molecules. GPRC5D-TCBs as presented herein were compared to molecules known in the art. Activation was determined by detection of the percent of either $CD69^+CD8^+$ T cells (FIG. 21A) and $CD69^+CD4^+$T cells (FIG. 21B) were used among all $CD8^+$ respective $CD4^+$ T-cells.

After overnight incubation at 37° C. in a humidified incubator, cells were washed with PBS once and stained for 20 minutes at 4° C. with 50 μL of Live blue (Invitrogen, #L23105) to discriminate between live and dead cells. Surface staining was performed using a mixture of the following antibodies based on the manufacturers' suggestions: CD25 BV605, CD69 APC-Cy7, CD38 BV510, CD138 FITC, CD8 BV711, CD3 PE-Cy5 and CD4 AlexaFluor700 (all from BioLegend). For the final analysis, cells were resuspended in 100 μL of FACs buffer and acquired using a Fortessa (BD Biosciences). FIG. 21A and FIG. 21B show T-cell activation, as determined as percent of either CD69-positive $CD8^+$ (A) or $CD4^+$ T cells (B), upon the indicated treatments.

A clear concentration-dependent T-cell activation in the bone marrow sample was detected with BCMA-TCB or B72, but not with 6624 or 6625. This illustrates a potential safety advantage of molecules such as the 6624 and 6625 over BCMA-TCB or B72, when used at higher doses.

Example 20

Cytokine Release in Human Whole Blood from Healthy Donors

Figures 22A, 22B:
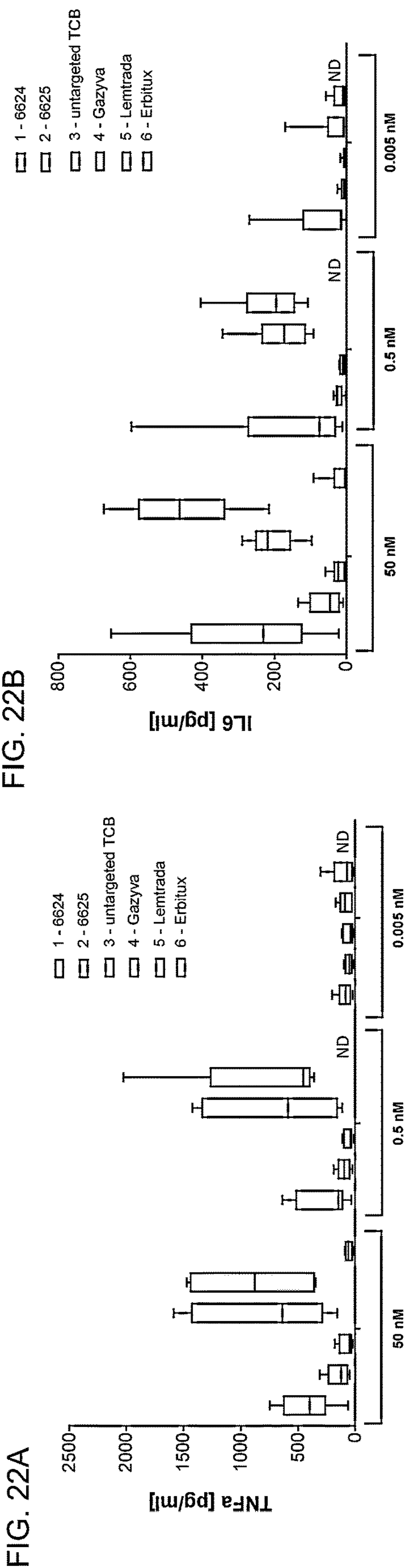
FIG. 22A-FIG. 22B. Cytokine release in human whole blood of healthy donors (TNFa readouts in FIG. 22A; IL6 readouts in FIG. 22B). GPRC5D-TCBs as described herein and positive (Gazyva, Lemtrada) and negative (Erbitux) reference molecules were compared.

Whole blood from 6 healthy donors was collected in BD Vacutainer Lithium-Heparin tubes and assayed within 3 hours. GPRC5D-TCBs 6624 and 6625, as well as the untargeted TCB control molecule were diluted in PBS (Gibco #14190) and 5 μL were added to 195 μL of whole blood in a round-bottomed 96-well plate (Corning #Costar 3799) to reach final concentrations of 50, 0.5 and 0.005 nM. The monoclonal antibodies Gazyva (obinutuzumab) and Lemtrada (alemtuzumab) were similarly assayed at 50, 0.5 and 0.005 nM, while Erbitux (cetuximab) was tested at 50 nM. PBS only served as vehicle control. After 24 h incubation at 37° C., the plate was centrifuged at 1800 g (3000 rpm) for 5 min. The plasma supernatants (-70 μl) were collected and stored at –80° C. before multiplex cytokine detection was performed using a Millipore kit (HCYTOMAG-60K) and a Luminex reader LX 200, according to the manufacturers' suggestions. As summarized in FIG. 22A (human TNFa) and FIG. 22B (human IL-6), 6624 induced secretion of low levels of TNFa and IL-6 in a similar range to Gazyva, whereas 6625 induced even lower levels of the evaluated cytokines, suggesting that 6624 may display a favourable safety profile in terms of cytokine release.

Example 21

In Vivo Efficacy of Different GPRC5D×CD3 Bispecific TCB Molecules in NCI-H929 (hNSG Mice)

To further evaluate the efficacy of the GPRC5D TCB molecules 6623, 6624, 6625 and 6626, their potential to induce tumor regression in multiple myeloma bearing fully humanized NSG mice was assessed. $2.5\times10^{6}$ NCI-H929 cells with a viability of >95.0% were re-suspended in RPMI cell culture medium (Gibco) and GFR matrigel (1:1, total volume of 100 μl) and injected subcutaneously into the right flank of humanized female NSG (NOD·Cg-Prkdcscid Il2rgtmlWjl/SzJ) mice.

Humanization of the mice was conducted as follows: aged 4-5 weeks at start of the experiment (bred at Charles River, Lyon, France) the mice were maintained under specific-pathogen-free condition with daily cycles of 12 h light/12 h darkness according to committed guidelines (GV-Solas; Felasa; TierschG). The experimental study protocol was reviewed and approved by local government (ROB-55.2-2532.Vet_03-16-10). After arrival, animals were maintained for one week to get accustomed to the new environment and for observation. Continuous health monitoring was carried out on a regular basis. According to the protocol, female NSG mice were injected i.p. (intraperitoneal) with 15 mg/kg of Busulfan followed one day later by an i.v. injection of $1\times10^{5}$ human hematopoietic stem cells isolated from cord blood. At week 16-20 after stem cell injection mice were bled and blood was analyzed by flow cytometry for successful humanization. Efficiently engrafted mice were randomized according to their human T cell frequencies into the different treatment groups (n=10/group).

At that time, mice were injected with tumor cells subcutaneously. as described above and treated once weekly with the compounds or PBS (Vehicle) when tumor size reached a median size of 308 $mm^3$ (range 92-841 mm3). All mice were injected intravenously with 0.05 mg/kg and 0.005 mg/kg of the indicated TCB molecules (see FIG. 23A and FIG. 23B).

To obtain the appropriate amount of compounds, stock solutions were diluted with Histidine buffer (20 mM histidine, 140 mM NaCl, pH 6.0). Tumor growth was measured twice weekly using a caliper and tumor volume was calculated as followed:

$$T_v:(W^2/2)\times L \text{ (W: Width,L: Length)}$$

The study was terminated at day 41 after tumor cell inoculation and all mice were sacrificed after three injections of the compounds and tumors were explanted and weighted. Statistics were performed according to Two way anova, Tukey test.

Figures 23A, 23B:
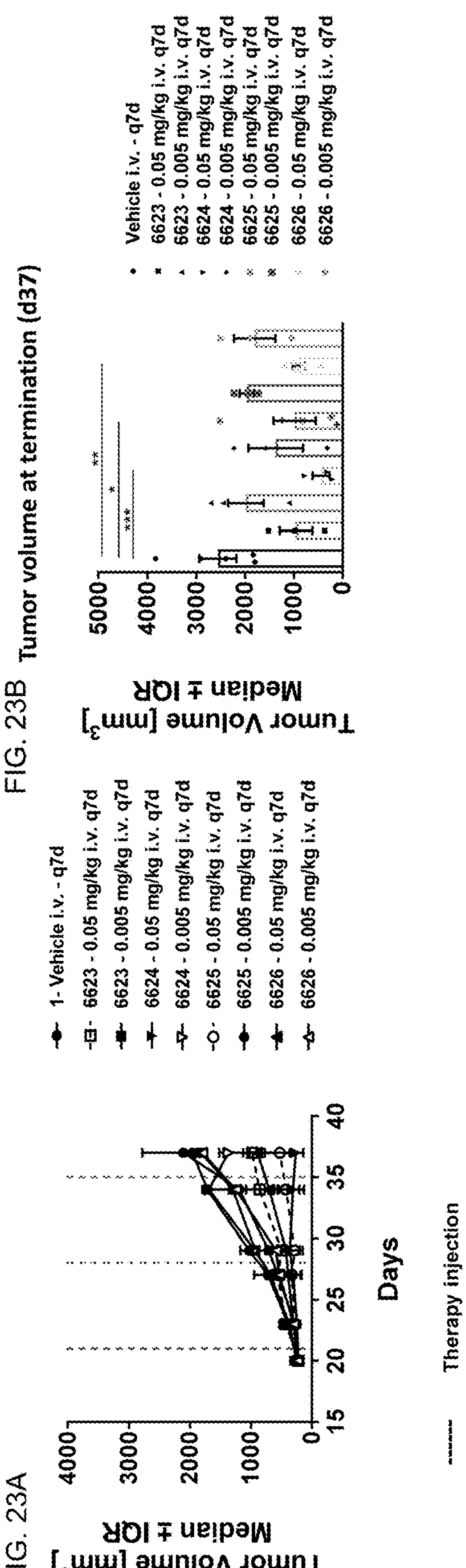
FIG. 23A-FIG. 23G. In vivo efficacy of different GPRC5D×CD3 bispecific TCB molecules in NCI-H929 (hNSG mice), including average tumor volume per treatment group over the course of therapy (FIG. 23A), tumor volume at day 37 (FIG. 23B), and tumor growth for the molecules with each line representing a single mouse (vehicle.
Figures 23C, 23D, 23E, 23F, 23G:
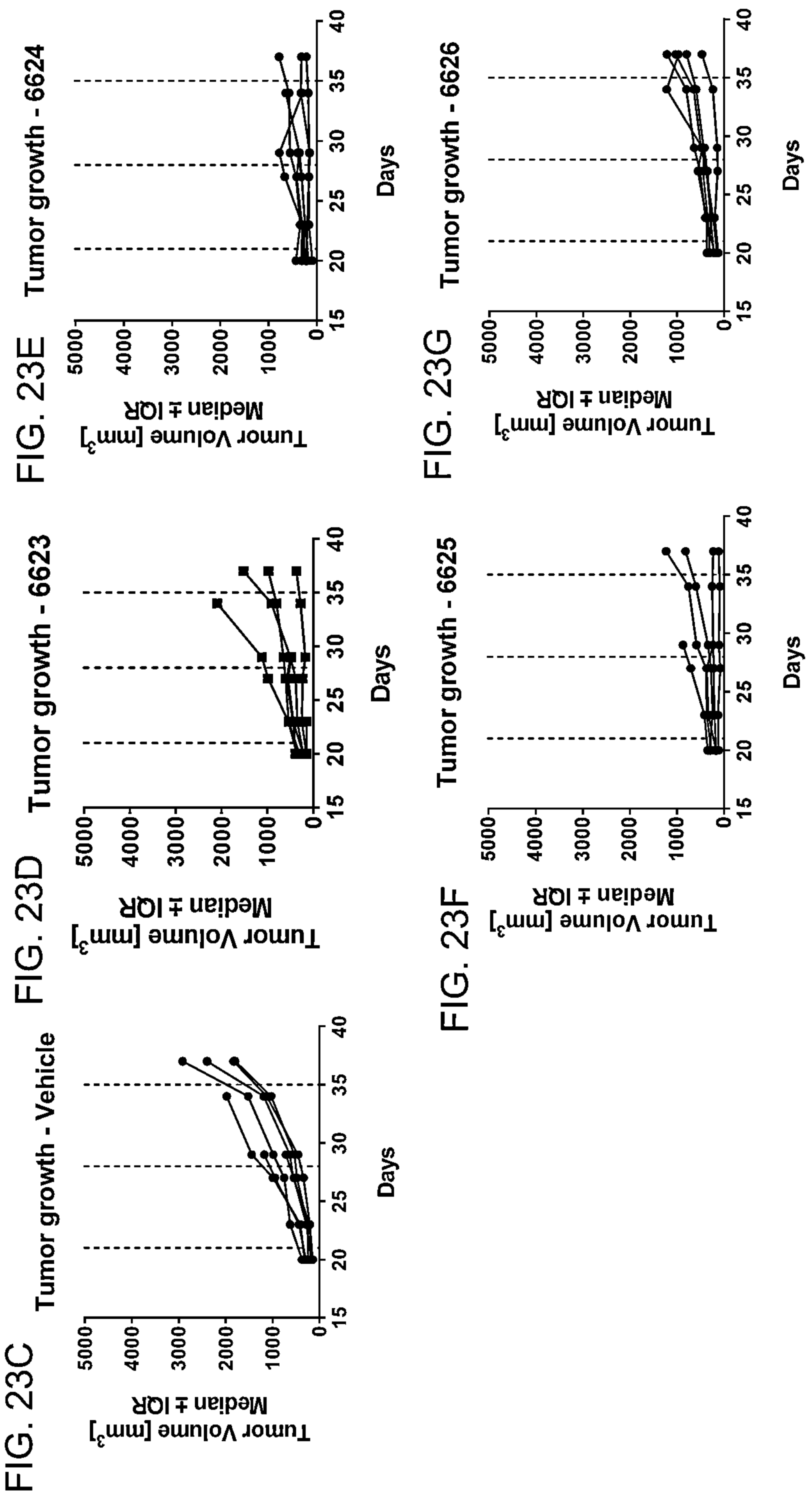

As illustrated in FIG. 23A and FIG. 23B, at the low dose of 0.005 mg/kg none of the evaluated GPRC5D-TCB molecule showed efficient tumor growth inhibition. In contrast, at 0.05 mg/kg, we saw significant anti-tumor growth responses by all four GPRC5D TCB molecules assessed compared to the vehicle group. FIG. 23C-FIG. 23G further demonstrates the tumor growth inhibition of the single mice per treatment group. There were no significant differences among the four molecules assessed though, validating the high preclinical efficacy of all four GPRC5D TCB molecules.

Example 22 in vivo SDPK in hFcRn Tg and KO mice

To evaluate PK properties of the GPRC5D TCB molecules 6623, 6624, 6625 and 6626, the respective molecules were administered intravenously (bolus) via tail vein at a dose of 1 mg/kg into either −/− huFcRn Tg line 32 (B6·Cg-Fcgrt<tmlDcr>Tg(FCGRT)32Dcr) mice or −/− muFcRn (B6.129X1-Fcgrttm1Dcr/DcrJ) (JAX laboratories, Bar harbor, USA). All studies were conducted with the approval of the local veterinary authority in strict adherence to the Swiss federal regulations on animal protection and to the rules of the Association for Assessment and Accreditation of Laboratory Animal Care International (AAALAC). Blood was collected by venous puncture (tail vein) at different time points to obtain serum for analysis at the indicated time points after dosing: 0.083, 7, 24, 48, 72, 168, 336, 504 and 672 post dose for the −/− huFcRn Tg line and 32, 0.083, 2, 7, 24, 31, 48, 72 and 96 hours post dose for the −/− muFcRn line. Blood was stored for 20 minutes at room temperature for coting and serum was obtained by centrifugation at 15 000 rpm for 5 min at 4° C. and frozen immediately. All serum samples were stored at −20° C. until they were analyzed by electro-chemiluminescence immunoassay (ECLIA), a method specific for the human Fab moiety of the administered antibody and its variants.

Briefly, samples, prediluted with assay buffer, were incubated with capture and detection molecules for 9 min at 37° C. Biotinylated mAb<H-Fab(kappa)>M-IgG-Bi was used as capture molecule and a ruthenium(II)tris(bipyridyl)32+ labeled mAb<H-Fab(CH1)>M-1.19.31-IgG-S-Ru mouse monoclonal antibody was used for detection. Streptavidin-coated magnetic microparticles were added and incubated for additional 9 min at 37° C. to allow complex formation due to biotin-streptavidin interactions. Complexes were magnetically captured on an electrode and a chemiluminescent signal generated using the co-reactant tripropylamine (TPA) was measured by a photomultiplier detector. All serum samples and positive or negative control samples were analyzed in quadruplicates and calibrated against the corresponding antibody that was administered.

Figure 24:
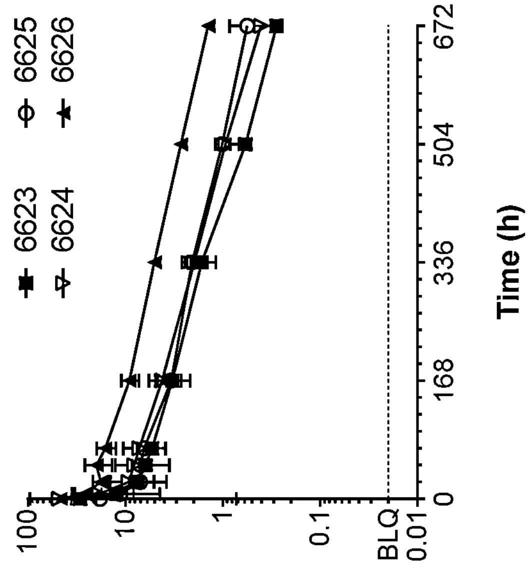
FIG. 24. in vivo SDPK in hFcRn Tg and KO mice and clearance data of the indicated TCB molecules.

As illustrated in FIG. 24 and Table 19, all four GPRC5D TCB molecules exhibit an acceptable PK profile in hFcRn tg32 mice in the range of the one from a classical IgG. The data generated in FcRn ko mice are considered to be relevant for evaluating unspecific cellular uptake, which might be linked to immunogenicity. As summarized in FIG. 10B, 6625 and 6626 show comparable clearance rates, whereas the one for 6623 and 6624 are elevated, suggesting a slightly higher potential for unspecific cellular uptake.

TABLE 19

Clearance, respective half-life calculated from SDPK studies run in hFcRn Tg32 or FcRn KO mice

| | hFcRn Tg32 mice | | FcRn KO mice | |
|---|---|---|---|---|
| Molecule | Clearance (mL/d/kg) | Half-life (d) | Clearance (mL/d/kg) | Half-life (d) |
| 6623 | 13.6 | 5.6 | 97.3 | 0.3 |
| 6624 | 22.5 | 6.2 | 143 | 0.6 |
| 6625 | 13.0 | 7.2 | 61.3 | 1.2 |
| 6626 | 9.6 | 7.3 | 57.8 | 1.1 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A bispecific antigen binding molecule, comprising (a) a first antigen binding moiety that binds to a first antigen, wherein the first antigen is GPRC5D and the first antigen binding moiety comprises:

(i) a heavy chain variable region (VH) comprising a heavy chain complementary determining region (HCDR) 1 comprising the amino acid sequence of SEQ ID NO: 83, a HCDR 2 comprising the amino acid sequence of SEQ ID NO: 84, and a HCDR 3 comprising the amino acid sequence of SEQ ID NO: 86, and a light chain variable region (VL) comprising a light chain complementarity determining region (LCDR) 1 comprising the amino acid sequence of SEQ ID NO: 87, a LCDR 2 comprising the amino acid sequence of SEQ ID NO: 88 and a LCDR 3 comprising the amino acid sequence of SEQ ID NO: 89;

(ii) a heavy chain variable region (VH) comprising a heavy chain complementary determining region (HCDR) 1 comprising the amino acid sequence of SEQ ID NO: 83, a HCDR 2 comprising the amino acid sequence of SEQ ID NO: 85, and a HCDR 3 comprising the amino acid sequence of SEQ ID NO: 86, and a light chain variable region (VL) comprising a light chain complementarity determining region (LCDR) 1 comprising the amino acid sequence of SEQ ID NO: 87, a LCDR 2 comprising the amino acid sequence of SEQ ID NO: 88 and a LCDR 3 comprising the amino acid sequence of SEQ ID NO: 89;

and (b) a second antigen binding moiety that binds to a second antigen wherein the second antigen is CD3 and the second antigen binding moiety comprises:

a heavy chain variable region (VH) comprising a heavy chain complementary determining region (HCDR) 1 comprising the amino acid sequence of SEQ ID NO: 98, a HCDR 2 comprising the amino acid sequence of SEQ ID NO: 99, and a HCDR 3 comprising the amino acid sequence of SEQ ID NO: 100, and a light chain variable region (VL) comprising a light chain complementarity determining region (LCDR) 1 comprising the amino acid sequence of SEQ ID NO: 101, a LCDR 2 comprising the amino acid sequence of SEQ ID NO: 102 and a LCDR 3 comprising the amino acid sequence of SEQ ID NO: 103.

2. The bispecific antigen binding molecule of claim 1, (i) wherein the VH of the first antigen binding moiety comprises an amino acid sequence that is at least about 95%, 96%, 97%, 98%, 99% or 100% identical to the amino acid sequence of SEQ ID NO: 13, and wherein the VL of the first antigen binding moiety comprises an amino acid sequence that is at least about 95%, 96%, 97%, 98%, 99% or 100% identical to the amino acid sequence of SEQ ID NO: 14; or (ii) wherein the VH of the first antigen binding moiety comprises an amino acid sequence that is at least about 95%, 96%, 97%, 98%, 99% or 100% identical to the amino acid sequence of SEQ ID NO: 48, and wherein the VL of the first antigen binding moiety comprises an amino acid sequence that is at least about 95%, 96%, 97%, 98%, 99% or 100% identical to the amino acid sequence of SEQ ID NO: 53.

3. The bispecific antigen binding molecule of claim 1, wherein the VH of the second antigen binding moiety comprises an amino acid sequence that is at least about 95%, 96%, 97%, 98%, 99% or 100% identical to the amino acid sequence of SEQ ID NO: 104, and the VL of the second antigen binding moiety comprises an amino acid sequence that is at least about 95%, 96%, 97%, 98%, 99% or 100% identical to the amino acid sequence of SEQ ID NO: 105.

4. The bispecific antigen binding molecule of claim 1, wherein the first and/or the second antigen binding moiety is a Fab molecule.

5. The bispecific antigen binding molecule of claim 1, wherein the second antigen binding moiety is a Fab molecule wherein the variable domains VL and VH or the constant domains CL and CH1 of the Fab light chain and the Fab heavy chain are replaced by each other.

6. The bispecific antigen binding molecule of claim 1, wherein the first antigen binding moiety is a Fab molecule wherein in the constant domain CL the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

7. The bispecific antigen binding molecule of claim 6, wherein in the constant domain CL of the first Fab the amino acid at position 124 is substituted by lysine (K) (numbering according to Kabat) and the amino acid at position 123 is substituted by arginine (R) (numbering according to Kabat), and in the constant domain CH1 of the first Fab the amino acid at position 147 is substituted by glutamic acid (E) (numbering according to Kabat EU index) and the amino acid at position 213 is substituted by glutamic acid (E) (numbering according to Kabat EU index).

8. The bispecific antigen binding molecule of claim 1, wherein the first and the second antigen binding moiety are fused to each other.

9. The bispecific antigen binding molecule of claim 8, wherein the first and the second antigen binding moiety are fused to each other via a peptide linker.

10. The bispecific antigen binding molecule of claim 1, wherein the first and the second antigen binding moiety are each a Fab molecule and wherein either (i) the second antigen binding moiety is fused at the C-terminus of the Fab heavy chain to the N-terminus of the Fab heavy chain of the first antigen binding moiety, or (ii) the first antigen binding moiety is fused at the C-terminus of the Fab heavy chain to the N-terminus of the Fab heavy chain of the second antigen binding moiety.

11. The bispecific antigen binding molecule of claim 1, comprising a third antigen binding moiety.

12. The bispecific antigen binding molecule of claim 11, wherein the third antigen moiety is identical to the first antigen binding moiety.

13. The bispecific antigen binding molecule of claim 11, comprising an Fc domain composed of a first and a second subunit, wherein the first, the second, and the third antigen binding moiety are each a Fab molecule;

wherein either (i) the second antigen binding moiety is fused at the C-terminus of the Fab heavy chain to the N-terminus of the Fab heavy chain of the first antigen binding moiety and the first antigen binding moiety is fused at the C-terminus of the Fab heavy chain to the N-terminus of the first subunit of the Fc domain, or (ii) the first antigen binding moiety is fused at the C-terminus of the Fab heavy chain to the N-terminus of the Fab heavy chain of the second antigen binding moiety and the second antigen binding moiety is fused at the C-terminus of the Fab heavy chain to the N-terminus of the first subunit of the Fc domain; and wherein the third antigen binding moiety is fused at the C-terminus of the Fab heavy chain to the N-terminus of the second subunit of the Fc domain.

14. The bispecific antigen binding molecule of claim 1, comprising an Fc domain composed of a first and a second subunit.

15. The bispecific antigen binding molecule of claim 14, wherein the first and the second antigen binding moiety are each a Fab molecule;

and wherein either (i) the second antigen binding moiety is fused at the C-terminus of the Fab heavy chain to the N-terminus of the Fab heavy chain of the first antigen binding moiety and the first antigen binding moiety is fused at the C-terminus of the Fab heavy chain to the N-terminus of the first subunit of the Fc domain, or (ii) the first antigen binding moiety is fused at the C-terminus of the Fab heavy chain to the N-terminus of the Fab heavy chain of the second antigen binding moiety and the second antigen binding moiety is fused at the C-terminus of the Fab heavy chain to the N-terminus of the first subunit of the Fc domain.

16. The bispecific antigen binding molecule of claim 14, wherein the Fc domain is an IgG Fc domain and/or a human Fc domain.

17. The bispecific antigen binding molecule of claim 14, wherein an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable.

18. The bispecific antigen binding molecule of claim 17, wherein in the first subunit of the Fc domain the threonine residue at position 366 is replaced with a tryptophan residue (T366W), and in the second subunit of the Fc domain the tyrosine residue at position 407 is replaced with a valine residue (Y407V); the threonine residue at position 366 is replaced with a serine residue (T366S); and the leucine residue at position 368 is replaced with an alanine residue (L368A) (numberings according to Kabat EU index).

19. The bispecific antigen binding molecule of claim 14, wherein the Fc domain comprises one or more amino acid substitution that reduces binding to an Fc receptor and/or effector function.

20. The bispecific antigen binding molecule of claim 19, wherein in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

21. One or more isolated polynucleotides encoding the bispecific antigen binding molecule of claim 1.

22. One or more vectors comprising the isolated polynucleotides of claim 21.

23. One or more host cells comprising the vectors of claim 22.

24. A method of producing a bispecific antigen binding molecule that binds to GPRC5D, comprising the steps of a) culturing the host cells of claim 23 under conditions suitable for the expression of the bispecific antigen binding molecule and b) recovering the bispecific antigen binding molecule.

25. A pharmaceutical composition comprising the bispecific antigen binding molecule of claim 1 and a pharmaceutically acceptable carrier.

26. The bispecific antigen binding molecule of claim 1, wherein the bispecific antigen binding molecule comprises an amino acid sequence that is at least 95%, 96%, 97%, 98%, or 99% identical to the amino acid sequence of SEQ ID NO: 122; a polypeptide comprising an amino acid sequence that is at least 95%, 96%, 97%, 98%, or 99% identical to the amino acid sequence of SEQ ID NO: 123; a polypeptide comprising an amino acid sequence that is at least 95%, 96%, 97%, 98%, or 99% identical to the amino acid sequence of SEQ ID NO: 124; and a polypeptide comprising an amino acid sequence that is at least 95%, 96%, 97%, 98%, or 99% identical to the amino acid sequence of SEQ ID NO: 125.

27. The bispecific antigen binding molecule of claim 1, wherein the first antigen binding moiety comprises a VH comprising a HCDR 1 comprising the amino acid sequence of SEQ ID NO: 83, a HCDR 2 comprising the amino acid sequence of SEQ ID NO: 85, and a HCDR 3 comprising the amino acid sequence of SEQ ID NO: 86, and a VL comprising a LCDR 1 comprising the amino acid sequence of SEQ ID NO: 87, a LCDR 2 comprising the amino acid sequence of SEQ ID NO: 88 and a LCDR 3 comprising the amino acid sequence of SEQ ID NO: 89, and the second antigen binding moiety comprises a VH comprising a HCDR 1 comprising the amino acid sequence of SEQ ID NO: 98, a HCDR 2 comprising the amino acid sequence of SEQ ID NO: 99, and a HCDR 3 comprising the amino acid sequence of SEQ ID NO: 100, and a VL comprising a LCDR 1 comprising the amino acid sequence of SEQ ID NO: 101, a LCDR 2 comprising the amino acid sequence of SEQ ID NO: 102 and a LCDR 3 comprising the amino acid sequence of SEQ ID NO: 103.

28. The bispecific antigen binding molecule of claim 1, wherein first antigen binding moiety comprises a VH comprising the amino acid sequence of SEQ ID NO: 48 and a VL comprising the amino acid sequence of SEQ ID NO: 53, and the second antigen binding moiety comprises a VH comprising the amino acid sequence of SEQ ID NO: 104 and a VL comprising the amino acid sequence of SEQ ID NO: 105.

29. The bispecific antigen binding molecule of claim 1, wherein the first antigen binding moiety comprises a VH comprising a HCDR 1 comprising the amino acid sequence of SEQ ID NO: 83, a HCDR 2 comprising the amino acid sequence of SEQ ID NO: 85, and a HCDR 3 comprising the amino acid sequence of SEQ ID NO: 86, and a VL comprising a LCDR 1 comprising the amino acid sequence of SEQ ID NO: 87, a LCDR 2 comprising the amino acid sequence of SEQ ID NO: 88 and a LCDR 3 comprising the amino acid sequence of SEQ ID NO: 89, and the second antigen binding moiety comprises a VH comprising a HCDR 1 comprising the amino acid sequence of SEQ ID NO: 98, a HCDR 2 comprising the amino acid sequence of SEQ ID NO: 99, and a HCDR 3 comprising the amino acid sequence of SEQ ID NO: 100, and a VL comprising a LCDR 1 comprising the amino acid sequence of SEQ ID NO: 101, a LCDR 2 comprising the amino acid sequence of SEQ ID NO: 102 and a LCDR 3 comprising the amino acid sequence of SEQ ID NO: 103, and wherein bispecific antigen binding molecule further comprises a third antigen binding moiety identical to the first antigen binding moiety.

30. The bispecific antigen binding molecule of claim 1, wherein first antigen binding moiety comprises a VH comprising the amino acid sequence of SEQ ID NO: 48 and a VL comprising the amino acid sequence of SEQ ID NO: 53, and the second antigen binding moiety comprises a VH comprising the amino acid sequence of SEQ ID NO: 104 and a VL comprising the amino acid sequence of SEQ ID NO:

105, and wherein bispecific antigen binding molecule further comprises a third antigen binding moiety identical to the first antigen binding moiety.

31. A bispecific antigen binding molecule comprising a polypeptide comprising the amino acid sequence of SEQ ID NO: 122, a polypeptide comprising the amino acid sequence of SEQ ID NO: 123, a polypeptide comprising the amino acid sequence of SEQ ID NO: 124 and a polypeptide comprising the amino acid sequence of SEQ ID NO: 125.

32. A bispecific antigen binding molecule, comprising:

(a) a first Fab that binds to GPRC5D comprising a VH comprising a HCDR 1 comprising the amino acid sequence of SEQ ID NO: 83, a HCDR 2 comprising the amino acid sequence of SEQ ID NO: 85, and a HCDR 3 comprising the amino acid sequence of SEQ ID NO: 86, and a VL comprising a LCDR 1 comprising the amino acid sequence of SEQ ID NO: 87, a LCDR 2 comprising the amino acid sequence of SEQ ID NO: 88 and a LCDR 3 comprising the amino acid sequence of SEQ ID NO: 89;

(b) a second Fab that binds to CD3 comprising a VH comprising a HCDR 1 comprising the amino acid sequence of SEQ ID NO: 98, a HCDR 2 comprising the amino acid sequence of SEQ ID NO: 99, and a HCDR 3 comprising the amino acid sequence of SEQ ID NO: 100, and a VL comprising a LCDR 1 comprising the amino acid sequence of SEQ ID NO: 101, a LCDR 2 comprising the amino acid sequence of SEQ ID NO: 102 and a LCDR 3 comprising the amino acid sequence of SEQ ID NO: 103; and (c) a third Fab identical to the first Fab, and wherein the bispecific antigen binding molecule comprises an $IgG_1$ Fc domain composed of a first and a second subunit.

33. The bispecific antigen binding molecule of claim 32, wherein the VH of the first Fab comprises the amino acid sequence of SEQ ID NO: 48, and the VL of the first Fab comprises the amino acid sequence of SEQ ID NO: 53, and wherein the VH of the second Fab comprises the amino acid sequence of SEQ ID NO: 104, and the VL of the second Fab comprises the amino acid sequence of SEQ ID NO: 105.

34. The bispecific antigen binding molecule of claim 32, wherein:

(i) the first Fab is fused at the C-terminus of the Fab heavy chain to the N-terminus of the Fab heavy chain of the second Fab; the second Fab is fused at the C-terminus of the Fab heavy chain to the N-terminus of the first subunit of the Fc domain; and the third Fab is fused at the C-terminus of the Fab heavy chain to the N-terminus of the second subunit of the Fc domain;

(ii) in the first subunit of the Fc domain the threonine residue at position 366 is replaced with a tryptophan residue (T366W), and in the second subunit of the Fc domain the tyrosine residue at position 407 is replaced with a valine residue (Y407V); the threonine residue at position 366 is replaced with a serine residue (T366S); and the leucine residue at position 368 is replaced with an alanine residue (L368A) (numberings according to Kabat EU index);

(iii) in the first subunit of the Fc domain the serine residue at position 354 is replaced with a cysteine residue (S354C) and in the second subunit of the Fc domain additionally the tyrosine residue at position 349 is replaced by a cysteine residue (Y349C) (numberings according to Kabat EU index); and/or (iv) in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

35. A bispecific antigen binding molecule, comprising:

(a) a first Fab that binds to GPRC5D comprising a VH comprising a HCDR 1 comprising the amino acid sequence of SEQ ID NO: 83, a HCDR 2 comprising the amino acid sequence of SEQ ID NO: 85, and a HCDR 3 comprising the amino acid sequence of SEQ ID NO: 86, and a VL comprising a LCDR 1 comprising the amino acid sequence of SEQ ID NO: 87, a LCDR 2 comprising the amino acid sequence of SEQ ID NO: 88 and a LCDR 3 comprising the amino acid sequence of SEQ ID NO: 89;

(b) a second Fab that binds to CD3 comprising a VH comprising a HCDR 1 comprising the amino acid sequence of SEQ ID NO: 98, a HCDR 2 comprising the amino acid sequence of SEQ ID NO: 99, and a HCDR 3 comprising the amino acid sequence of SEQ ID NO: 100, and a VL comprising a LCDR 1 comprising the amino acid sequence of SEQ ID NO: 101, a LCDR 2 comprising the amino acid sequence of SEQ ID NO: 102 and a LCDR 3 comprising the amino acid sequence of SEQ ID NO: 103, wherein in the second Fab, the variable domains VL and VH of the Fab light chain and the Fab heavy chain are replaced by each other; and (c) a third Fab identical to the first Fab, and wherein the bispecific antigen binding molecule comprises an $IgG_1$ Fc domain composed of a first and a second subunit, wherein the first Fab is fused at the C-terminus of the Fab heavy chain to the N-terminus of the Fab heavy chain of the second Fab; the second Fab is fused at the C-terminus of the Fab heavy chain to the N-terminus of the first subunit of the Fc domain; and the third Fab is fused at the C-terminus of the Fab heavy chain to the N-terminus of the second subunit of the Fc domain.

36. The bispecific antigen binding molecule of claim 35, wherein the VH of the first Fab comprises the amino acid sequence of SEQ ID NO: 48, and the VL of the first Fab comprises the amino acid sequence of SEQ ID NO: 53, and wherein the VH of the second Fab comprises the amino acid sequence of SEQ ID NO: 104, and the VL of the second Fab comprises the amino acid sequence of SEQ ID NO: 105.

37. The bispecific antigen binding molecule of claim 35, wherein:

(i) in the first subunit of the Fc domain the threonine residue at position 366 is replaced with a tryptophan residue (T366W), and in the second subunit of the Fc domain the tyrosine residue at position 407 is replaced with a valine residue (Y407V); the threonine residue at position 366 is replaced with a serine residue (T366S); and the leucine residue at position 368 is replaced with an alanine residue (L368A) (numberings according to Kabat EU index);

(ii) in the first subunit of the Fc domain the serine residue at position 354 is replaced with a cysteine residue (S354C) and in the second subunit of the Fc domain additionally the tyrosine residue at position 349 is replaced by a cysteine residue (Y349C) (numberings according to Kabat EU index); and/or (iii) in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

38. A bispecific antigen binding molecule, comprising:

(a) a first Fab that binds to GPRC5D comprising a VH comprising a HCDR 1 comprising the amino acid sequence of SEQ ID NO: 83, a HCDR 2 comprising the amino acid sequence of SEQ ID NO: 85, and a HCDR 3 comprising the amino acid sequence of SEQ ID NO: 86, and a VL comprising a LCDR 1 comprising the amino acid sequence of SEQ ID NO: 87, a LCDR 2 comprising the amino acid sequence of SEQ ID NO: 88 and a LCDR 3 comprising the amino acid sequence of SEQ ID NO: 89;

(b) a second Fab that binds to CD3 comprising a VH comprising a HCDR 1 comprising the amino acid sequence of SEQ ID NO: 98, a HCDR 2 comprising the amino acid sequence of SEQ ID NO: 99, and a HCDR 3 comprising the amino acid sequence of SEQ ID NO: 100, and a VL comprising a LCDR 1 comprising the amino acid sequence of SEQ ID NO: 101, a LCDR 2 comprising the amino acid sequence of SEQ ID NO: 102 and a LCDR 3 comprising the amino acid sequence of SEQ ID NO: 103, wherein in the second Fab, the variable domains VL and VH of the Fab light chain and the Fab heavy chain are replaced by each other; and (c) a third Fab identical to the first Fab, wherein in the constant domain CL of the first Fab the amino acid at position 124 is substituted by lysine (K) (numbering according to Kabat) and the amino acid at position 123 is substituted by arginine (R) (numbering according to Kabat), and in the constant domain CH1 of the first Fab the amino acid at position 147 is substituted by glutamic acid (E) (numbering according to Kabat EU index) and the amino acid at position 213 is substituted by glutamic acid (E) (numbering according to Kabat EU index), and wherein the bispecific antigen binding molecule comprises an $IgG_1$ Fc domain composed of a first and a second subunit, wherein:

(i) the first Fab is fused at the C-terminus of the Fab heavy chain to the N-terminus of the Fab heavy chain of the second Fab via a peptide linker; the second Fab is fused at the C-terminus of the Fab heavy chain to the N-terminus of the first subunit of the Fc domain; and the third Fab is fused at the C-terminus of the Fab heavy chain to the N-terminus of the second subunit of the Fc domain;

(ii) in the first subunit of the Fc domain the threonine residue at position 366 is replaced with a tryptophan residue (T366W), and in the second subunit of the Fc domain the tyrosine residue at position 407 is replaced with a valine residue (Y407V); the threonine residue at position 366 is replaced with a serine residue (T366S); and the leucine residue at position 368 is replaced with an alanine residue (L368A) (numberings according to Kabat EU index);

(iii) in the first subunit of the Fc domain the serine residue at position 354 is replaced with a cysteine residue (S354C) and in the second subunit of the Fc domain additionally the tyrosine residue at position 349 is replaced by a cysteine residue (Y349C) (numberings according to Kabat EU index); and (iv) in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

39. The bispecific antigen binding molecule of claim 38, wherein the VH of the first Fab comprises the amino acid sequence of SEQ ID NO: 48, and the VL of the first Fab comprises the amino acid sequence of SEQ ID NO: 53, and wherein the VH of the second Fab comprises the amino acid sequence of SEQ ID NO: 104, and the VL of the second Fab comprises the amino acid sequence of SEQ ID NO: 105.

* * * * *